(12) United States Patent
Liew et al.

(10) Patent No.: US 8,483,968 B2
(45) Date of Patent: Jul. 9, 2013

(54) METHOD OF DIAGNOSING MILD OSTEOARTHRITIS

(75) Inventors: Choong-Chin Liew, Toronto (CA); Hongwei Zhang, Toronto (CA); Adam Dempsey, Toronto (CA); Thomas Yager, Mississaugai (CA); Samuel Chao, Concord (CA)

(73) Assignee: GeneNews Corporation, Richmond Hill, Ontario (CA)

( * ) Notice: Subject to any disclaimer, the term of this patent is extended or adjusted under 35 U.S.C. 154(b) by 262 days.

(21) Appl. No.: 12/777,140

(22) Filed: May 10, 2010

(65) Prior Publication Data
US 2011/0020809 A1    Jan. 27, 2011

Related U.S. Application Data

(62) Division of application No. 11/347,944, filed on Feb. 6, 2006, now Pat. No. 7,713,695.

(60) Provisional application No. 60/650,685, filed on Feb. 7, 2005.

(51) Int. Cl.
*G01N 33/48*    (2006.01)

(52) U.S. Cl.
USPC .......................................................... 702/19

(58) Field of Classification Search
USPC .......................................................... 702/19
See application file for complete search history.

*Primary Examiner* — Jerry Lin
(74) *Attorney, Agent, or Firm* — Sunstein Kann Murphy & Timbers LLP

(57) ABSTRACT

The invention relates to the identification and selection of novel biomarkers and the identification and selection of novel biomarker combinations which are differentially expressed in individuals with mild osteoarthritis as compared with individuals without osteoarthritis. Polynucleotides and proteins which specifically and/or selectively hybridize to the products of the biomarkers of the invention are also encompassed within the scope of the invention as are kits containing said polynucleotides and proteins for use in diagnosing mild osteoarthritis. Further encompassed by the invention is the use of the polynucleotides and proteins which specifically and/or selectively hybridize to the product of the biomarkers of the invention to monitor disease regression in an individual and to monitor the efficacy of therapeutic regimens. The invention also provides for methods of using the products of the biomarkers of the invention in the identification of novel therapeutic targets for osteoarthritis.

16 Claims, 1 Drawing Sheet

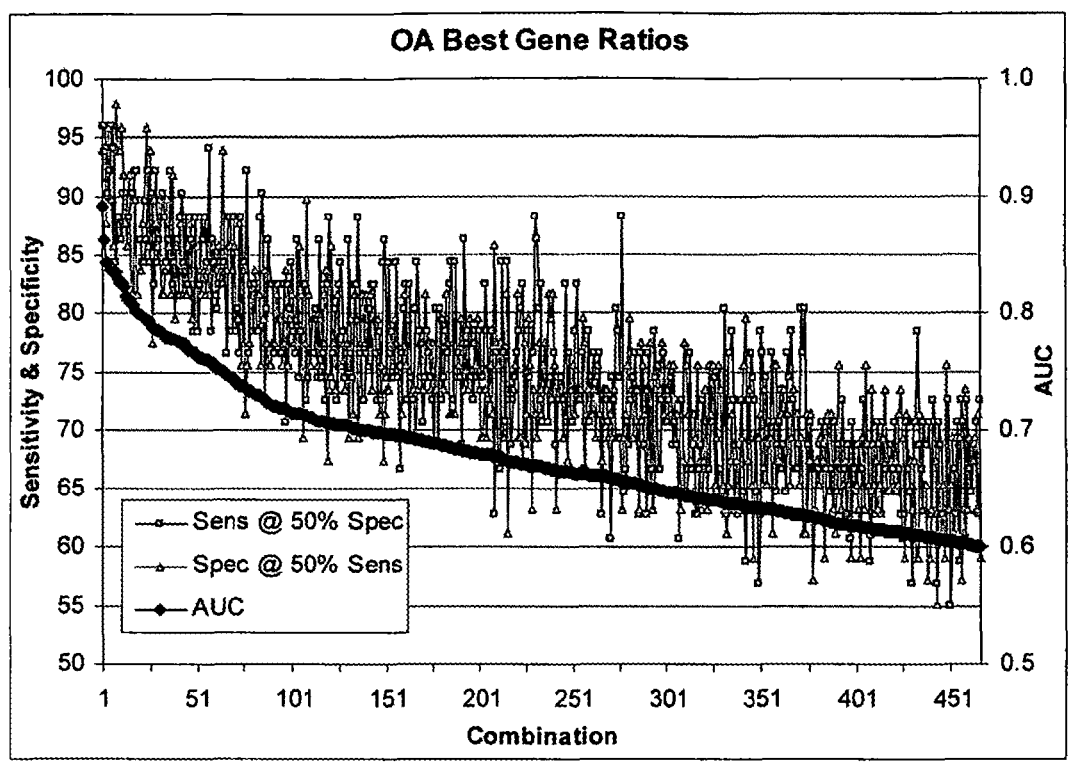

METHOD OF DIAGNOSING MILD OSTEOARTHRITIS

This application is a division of U.S. patent application Ser. No. 11/347,944 filed Feb. 6, 2006, which claims priority to U.S. Provisional Patent Application No. 60/650,685 filed Feb. 7, 2005. The contents of each of these applications are incorporated by reference in their entirety herein

1. FIELD OF THE INVENTION

The invention encompasses the identification and selection of novel mild OA biomarkers and the identification and selection of novel biomarker combinations that are differentially expressed in individuals with mild osteoarthritis as compared to individuals without osteoarthritis. The measurement of expression of the products of the biomarkers and combinations of biomarkers of the invention demonstrates particular advantage in diagnosing individuals as having OA early in the disease. As would be understood, in order to measure the products of biomarkers of the invention, polynucleotides and proteins which specifically and/or selectively hybridize/bind to the products of the biomarkers of the invention are also encompassed within the scope of the invention as are kits containing said polynucleotides and proteins for use in diagnosing individuals as having mild osteoarthritis (OA). The invention also provides for methods of using the products of the biomarkers of the invention in the identification of compounds that bind and/or modulate the activity of the biomarker genes of the invention. The compounds identified via such methods are useful for the development of assays to study osteoarthritis and osteoarthritis progression. Further, the compounds identified via such methods are useful as lead compounds in the development of prophylactic and therapeutic compositions for the prevention, treatment, management and/or amelioration of osteoarthritis or a symptom thereof.

2. BACKGROUND OF THE INVENTION

Osteoarthritis (OA) is a chronic disease in which the articular cartilage that lies on the ends of bones that forms the articulating surface of the joints gradually degenerates over time. There are many factors that are believed to predispose a patient to osteoarthritis including genetic susceptibility, obesity, accidental or athletic trauma, surgery, drugs and heavy physical demands. Osteoarthritis is thought to be initiated by damage to the cartilage of joints. The two most common injuries to joints are sports-related injuries and long term "repetitive use" joint injuries. Joints most commonly affected by osteoarthritis are the knees, hips and hands. In most cases, due to the essential weight-bearing function of the knees and hips, osteoarthritis in these joints causes much more disability than osteoarthritis of the hands. As cartilage degeneration progresses, secondary changes occur in other tissues in and around joints including bone, muscle, ligaments, menisci and synovium. The net effect of the primary failure of cartilage tissue and secondary damage to other tissues is that the patient experiences pain, swelling, weakness and loss of functional ability in the afflicted joint(s). These symptoms frequently progress to the point that they have a significant impact in terms of lost productivity and or quality of life consequences for the patient.

Articular cartilage is predominantly composed of chondrocytes, type II collagen, proteoglycans and water. Articular cartilage has no blood or nerve supply and chondrocytes are the only type of cell in this tissue. Chondrocytes are responsible for manufacturing the type II collagen and proteoglycans that form the cartilage matrix. This matrix in turn has physical-chemical properties that allow for saturation of the matrix with water. The net effect of this structural-functional relationship is that articular cartilage has exceptional wear characteristics and allows for almost frictionless movement between the articulating cartilage surfaces. In the absence of osteoarthritis, articular cartilage often provides a lifetime of pain-free weight bearing and unrestricted joint motion even under demanding physical conditions.

Like all living tissues, articular cartilage is continually undergoing a process of renewal in which "old" cells and matrix components are being removed (catabolic activity) and "new" cells and molecules are being produced (anabolic activity). Relative to most tissues, the rate of anabolic/catabolic turnover in articular cartilage is low. Long-term maintenance of the structural integrity of mature cartilage relies on the proper balance between matrix synthesis and degradation. Chondrocytes maintain matrix equilibrium by responding to chemical and mechanical stimuli from their environment. Appropriate and effective chondrocyte responses to these stimuli are essential for cartilage homeostasis. Disruption of homeostasis through either inadequate anabolic activity or excessive catabolic activity can result in cartilage degradation and osteoarthritis (Adams et al., 1995, Nature 377 Suppl:3-174). Most tissues that are damaged and have increased catabolic activity are able to mount an increased anabolic response that allows for tissue healing. Unfortunately, chondrocytes have very limited ability to up-regulate their anabolic activity and increase the synthesis of proteoglycan and type II collagen in response to damage or loss of cartilage matrix.

Currently there is no known medical treatment to reverse the effects of this cartilage damage. Rather all current therapies for osteoarthritis are directed towards treating the symptoms. In addition, because of the insidious occurrence and slow progression of osteoarthritis, identification of osteoarthritis is often done at a late stage in disease development rather than early in disease progression when potential treatments would be more likely to be effective. As a result further advances in preventing, modifying or curing the osteoarthritic disease process critically depend on identification of early diagnostic markers of disease so as to allow early intervention.

"Mild osteoarthritis" is currently very difficult to diagnose. The physician relies primarily on the patient's history and physical exam to make the diagnosis of osteoarthritis and X-rays do not show the early changes in articular cartilage. Currently there are no recognized biochemical markers used to confirm the diagnosis of mild osteoarthritis. Symptoms, such as episodic joint pain, are a common manifestation of early osteoarthritis. Joints become tender during an episode, which can last days to weeks and remit spontaneously. These symptoms, however, often do not correlate well with the pathological stages of damage to the cartilage. A more reliable measure of "mild" osteoarthritis can be obtained by determining the extent of cartilage damage, however there is currently no method for measuring cartilage deterioration which is relatively non-invasive.

3. SUMMARY OF THE INVENTION

The invention encompasses the identification and selection of novel mild OA biomarkers and the identification and selection of novel mild OA biomarker combinations which are differentially expressed in individuals with mild osteoarthritis as compared with individuals without OA, as well as a means of selecting the novel biomarker combinations. The measurement of expression of the products of the biomarkers and combinations of biomarkers of the invention demonstrates particular advantage in diagnosing individuals as having mild OA. As would be understood, in order to measure the products of biomarkers of the invention, polynucleotides and proteins which specifically and/or selectively hybridize/bind to the products of the biomarkers, and derivatives thereof, of the invention are also encompassed within the scope of the invention as are kits containing said polynucleotides and proteins for use in diagnosing individuals as having a mild OA. Further encompassed by the invention is the use of the polynucleotides and proteins which specifically and/or selectively hybridize to the product of the biomarkers of the invention to monitor disease progression in an individual and to monitor the efficacy of therapeutic regimens. The invention also provides for the identification of methods of using the products of the biomarkers of the invention in the identification of novel therapeutic targets for osteoarthritis. The invention also provides for the identification of methods of using the products of the biomarkers of the invention in the identification of compounds that bind and/or modulate the activity of the genes of the invention. The compounds identified via such methods are useful for the development of assays to study osteoarthritis and osteoarthritis progression. Further, the compounds identified via such methods are useful as lead compounds in the development of prophylactic and therapeutic compositions for the prevention, treatment, management and/or amelioration of osteoarthritis or a symptom thereof.

The present invention includes a composition comprising at least two isolated polynucleotides, wherein each isolated polynucleotide selectively hybridizes to a biomarker selected from the biomarkers set out in Table 1 or Table 4 and wherein the composition permits the measurement of the level of expression of at least two of said biomarkers.

The isolated polynucleotides can be single or double stranded RNA or DNA.

The invention also includes a composition comprising at least two isolated polynucleotides, wherein each isolated polynucleotide selectively hybridizes to an RNA product of a biomarker selected from the biomarkers set out in Table 1 or Table 4, and/or a polynucleotide sequence complementary to the RNA product, wherein the composition permits the measurement of the level of RNA expression of at least two of said biomarkers.

The invention further features a composition comprising a collection of two or more isolated polynucleotides, wherein each isolated polynucleotide selectively hybridizes to an RNA sequences set out in Table 3 or Table 5; and/or a polynucleotide sequences complementary to the RNA sequence.

The invention also includes a composition comprising at least two biomarker specific primers as set out in Table 6 and/or Table 8. The invention also includes a composition comprising at least two polynucleotide probes as set out in Table 8.

The invention also includes a composition comprising a collection of two or more isolated proteins, wherein each isolated protein binds selectively to a protein product of a biomarker selected from the biomarkers set out in Table 1 or Table 4 and wherein said composition is used to measure the level of expression of at least two of said biomarkers. Examples of isolated proteins within the scope of the invention are set out in Table 7.

The isolated proteins can be ligands, wherein the ligand includes antibodies and fragments thereof. Both monoclonal and polyclonal antibodies are within the scope of the invention.

A composition comprising at least two antibodies, is also contemplated within scope of the invention, wherein each antibody binds selectively to a protein product of a biomarker selected from the biomarkers set out in Table 1 or Table 4 and wherein said composition permits the measurement of the level of expression of at least two of said biomarkers. Examples of antibodies included in the invention are set out in Table 7.

The antibodies can include monoclonal and polyclonal antibodies.

The present invention features a method of diagnosing or detecting mild OA in an individual comprising: determining the level of an RNA product of one or more biomarker including the biomarkers set out in Table 1 and/or Table 4 in a blood sample from the individual; and comparing the level of RNA product in the blood sample from said individual with the level of the same RNA product in a control, wherein differential expression of the RNA products between the individual and the control is indicative of a mild OA in the individual. The blood sample can be whole blood, a drop of whole blood, or blood that has been lysed.

The method can also include a step of isolating RNA from the blood sample.

The step of determining the level of said RNA products can be performed using quantitative RT-PCR (QRT-PCR), optionally including the step of hybridizing primers which hybridize to said one or more RNA products or the complement thereof to the RNA product or complement thereof. The primers can be between about 4-40 nucleotides in length, preferably 8-35, preferably 10-30 and still more preferably, the primers are 15-25 nucleotides in length. In addition, the step of determining the level of each of the RNA products is performed by hybridizing a first plurality of isolated polynucleotides that correspond to one or more RNA transcripts to an array comprising a second plurality of isolated polynucleotides. The first population of polynucleotides optionally includes RNA, DNA, cDNA, PCR products, or ESTs. The second plurality of isolated polynucleotides on the array can include polynucleotides corresponding to one or more of the biomarkers of Table 1 and/or Table 4.

In another embodiment, the step of determining the level of an RNA product can be performed by hybridizing said isolated RNA to an array comprising a plurality of isolated polynucleotides. The array can optionally include a plurality of isolated polynucleotides comprising RNA, DNA, cDNA, PCR products or ESTs. The plurality of isolated polynucleotides on said array can also include polynucleotides corresponding to one or more of the biomarkers of Table 1 and/or Table 4.

In one embodiment, the control is derived from an individual that does not have mild OA.

The invention also includes a kit for diagnosing or detecting mild OA comprising any one of the foregoing compositions and instructions for use.

The invention further includes a kit for diagnosing or detecting mild OA comprising at least two sets of biomarker specific primers wherein each set of biomarker specific primers produces double stranded DNA complementary to a unique biomarker selected from Table 1 and/or Table 4; wherein each first primers of said sets contains a sequence which can selectively hybridize to RNA, cDNA or an EST complementary to one of said biomarkers to create an extension product and each said second primers of said sets is capable of selectively hybridizing to said extension product. The kit can also include an enzyme with reverse transcriptase activity, an enzyme with thermostable DNA polymerase activity, or a labeling means.

The present invention also features a method for diagnosing or detecting mild OA in an individual comprising: determining the level of protein product of one or more biomarker selected from the group consisting of the biomarkers set out in Table 1 and/or Table 4 in a blood sample from an individual; and comparing the level of protein products in the blood sample with a control, wherein differential expression of the protein products between the individual and the control is indicative of mild OA in the individual. The level of protein product can be determined using antibodies or fragments thereof, including the antibodies set out in Table 7. The antibodies can include monoclonal or polyclonal antibodies.

The invention also includes a composition comprising at least two isolated polynucleotides, wherein each isolated polynucleotide selectively hybridizes to a biomarker shown in Table 1, Table 2 and/or Table 4 and wherein the composition permits measurement of the level of expression of at least two biomarkers, at least one of which is selected from Table 1 or Table 4.

The invention also includes a composition comprising at least two isolated polynucleotides, wherein each isolated polynucleotide selectively hybridizes to an RNA product of a biomarker selected from the biomarkers set out in Table 1, Table 2 or Table 4, and/or a polynucleotide sequence complementary to the RNA product, wherein the composition permits the measurement the level of RNA expression of at least two of the biomarkers, and wherein at least one of the biomarkers is selected from Table 1 or Table 4.

The invention further includes a composition comprising at least two antibodies, wherein each antibody binds selectively to a protein product of a biomarker selected from the biomarkers set out in Table 1, Table 2 or Table 4 and wherein the composition permits the measurement of the level of expression of at least two of the biomarkers, and wherein at least one of the biomarkers is selected from Table 1 or Table 4.

The invention also features a composition comprising a collection of two or more isolated polynucleotides, wherein each isolated polynucleotide selectively hybridizes to a biomarker selected from the biomarkers set out in Table 1 or Table 4. The composition is permits the measurement of the level of expression of at least two of the biomarkers, where the biomarkers are capable of determining whether an individual has mild OA as determined using a ROC curve analysis. Preferably, the Area Under the ROC curve is greater than 0.5, preferably greater than about 0.6, 0.7, 0.8, or greater than about 0.9.

The invention also features a method for detecting whether an individual has mild OA comprising determining the level of an RNA product or protein product of one or more biomarkers including the biomarkers set out in Table 1, Table 2 and/or Table 4 in a blood sample from the individual; performing a ROC curve analysis, and measuring the Area Under the ROC curve, wherein if the Area Under the ROC curve is greater than about 0.5, preferably greater than about 0.6, 0.7, 0.8, or preferably greater than about 0.9, mild OA is concluded to have been detected in the individual.

The present invention provides a method for identifying a compound to be tested for an ability to prevent, treat, manage or ameliorate osteoarthritis or a symptom thereof. The method includes the steps of contacting a protein product of one or more biomarkers of the invention or a fragment thereof, or a RNA product of one or more biomarkers of the invention or a portion thereof with a test compound; and determining the ability of the test compound to bind to the protein product or RNA product so that if a compound binds to the protein product, or RNA product, the compound is identified as one to be tested for an ability to prevent, treat, manage or ameliorate osteoarthritis.

The present invention also provides a method for identifying a compound to be tested for an ability to prevent, treat, manage or ameliorate osteoarthritis or a symptom thereof. The method includes the steps of contacting a cell expressing a protein or RNA product of one or more biomarkers of the invention with a test compound; after an incubation period, determining the amount of the protein or RNA product present the cells contacted with the test compound using any of the compositions described hereinabove; and comparing the amount or protein or RNA product to that present in a corresponding control cell that has not been contacted with the test compound, so that if the amount of the protein or RNA product is altered relative to the amount in the control, the compound is identified as one to be tested for an ability to prevent, treat, manage or ameliorate osteoarthritis or a symptom thereof.

The present invention also provides a method for identifying a compound to be tested for an ability to prevent, treat, manage or ameliorate osteoarthritis or a symptom thereof. The method includes the steps of contacting a cell-free extract (e.g., a chondrocyte extract) with a nucleic acid sequence encoding a protein or RNA product of one or more biomarkers of the invention and a test compound; determining the amount of the protein or RNA product present in the cell free extract; and comparing the amount of RNA or protein product to that present in a corresponding control that has not been contacted with the test compound, so that if the amount of the protein or RNA product is altered relative to the amount in the control, the compound is identified as one to be tested for an ability to prevent, treat, manage or ameliorate osteoarthritis or symptoms thereof.

3.1 Definitions

The following definitions are provided for specific terms which are used in the following written description.

As used herein, the term "3' end" refers to the end of an mRNA up to the last 1000 nucleotides or ⅓ of the mRNA, where the 3' terminal nucleotide is that terminal nucleotide of the coding or untranslated region that adjoins the poly-A tail, if one is present. That is, the 3' end of an mRNA does not include the poly-A tail, if one is present. The "3' region" of a gene refers to a polynucleotide (double-stranded or single-stranded) located within or at the 3' end of a gene, and includes, but is not limited to, the 3' untranslated region, if that is present, and the 3' protein coding region of a gene. The 3' region is not shorter than 8 nucleotides in length and not longer than 1000 nucleotides in length. Other possible lengths of the 3' region include but are not limited to 10, 20, 25, 50, 100, 200, 400, and 500 nucleotides.

As used herein, the term "5' end" refers to the end of an mRNA up to the first 1000 nucleotides or ⅓ of the mRNA (where the full length of the mRNA does not include the poly A tail), starting at the first nucleotide of the mRNA. The "5' region" of a gene refers to a polynucleotide (double-stranded or single-stranded) located within or at the 5' end of a gene, and includes, but is not limited to, the 5' untranslated region, if that is present, and the 5' protein coding region of a gene. The 5' region is not shorter than 8 nucleotides in length and not longer than 1000 nucleotides in length. Other possible lengths of the 5' region include but are not limited to 10, 20, 25, 50, 100, 200, 400, and 500 nucleotides.

As used herein, the term "amplified" refers to a process whereby one or more copies of one or more nucleic acid sequences are generated from template nucleic acid, preferably by the method of polymerase chain reaction (Mullis and Faloona, 1987, Methods Enzymol. 155:335). "Polymerase chain reaction" or "PCR" refers to an in vitro method for amplifying one or more nucleic acid template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and nucleic acid template. The PCR reaction comprises providing at least one set of polynucleotide primers wherein a first primer contains a sequence complementary to a region in one strand of the nucleic acid template sequence to be amplified and primes the synthesis of a complementary DNA strand, and a second primer contains a sequence complementary to a region in a second strand of the particular target nucleic acid sequence to be amplified and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product, and with an optional denaturation step. "A set of polynucleotide primers" or "a set of PCR primers" can comprise two, three, four or more primers. In one embodiment, an exo-DNA polymerase is used to amplify a nucleic acid template in PCR reaction. Other methods of amplification include, but are not limited to, ligase chain reaction (LCR), polynucleotide-specific based amplification (NSBA), or any other nucleic acid amplification method known in the art.

As used herein, the term "amino terminal" region of a polypeptide refers to the polypeptide sequences encoded by polynucleotide sequences (double-stranded or single-stranded) located within or at the 5' end of a gene, and includes, but is not limited to, the 5' protein coding region of a gene. As used herein, the term "amino terminal" region refers to the amino terminal end of a polypeptide up to the first 300 amino acids or ⅓ of the polypeptide, starting at the first amino acid of the polypeptide. The "amino terminal" region of a polypeptide is not shorter than 3 amino acids in length and not longer than 350 amino acids in length. Other possible lengths of the "amino terminal" region of a polypeptide include but are not limited to 5, 10, 20, 25, 50, 100 and 200 amino acids.

As used herein, the term "analog" in the context of proteinaceous agent (e.g., proteins, polypeptides, peptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length.

The determination of percent identity between two sequences can also be accomplished using a mathematical algorithm. A preferred, non-limiting example of a mathematical algorithm utilised for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilised as described in Altschul et al., 1997, Nucleic Acids Res. 25:3389-3402. Alternatively, PSI-BLAST can be used to perform an iterated search which detects distant relationships between molecules (Id.). When utilising BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilised for the comparison of sequences is the algorithm of Myers and Miller, 1988, CABIOS 4:11-17. Such an algorithm is incorporated in the ALIGN program (version 2.0) which is part of the GCG sequence alignment software package. When utilising the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possess a similar or identical function as a first organic or inorganic molecule and is structurally similar to the first organic or inorganic molecule.

As used herein, the term "biomarker" refers to a gene that is differentially expressed as between individuals with mild OA and individuals not having OA.

The term "biomarker specific primers" as used herein refers to a primer that can prime the synthesis of DNA complementary to a portion of an RNA products of the biomarker of the invention. For example, the primers can include a first primer which is a sequence that can selectively hybridize to RNA, cDNA or EST complementary to a region of the biomarker of the invention to create an extension product and a second primer capable of selectively hybridizing to the extension product, which are used to produce double stranded DNA complementary to a region of the biomarker of the invention. The invention includes primers useful for measuring the expression of RNA products of the biomarkers of the invention. Table 8 provides representative species of primers.

The term "biomarker specific probe" as used herein refers to a nucleic acid probe that can selectively hybridize to the sequence of a biomarker of the invention or an RNA cDNA, or EST complementary thereto. For example, a probe can be affixed to an array including a microarray or the probes can be used in conjunction with a biomarker specific primer so as to permit quantitative real time RT-PCR (for example TaqMan® or Molecular Beacon® probes. Table 8 provides representative species of TaqMan® probes and corresponding primers which can be utilized in the invention. A biomarker specific probe can selectively hybridize to a portion of the sequence of a biomarker or complement thereof (for example, at least about 8 contiguous nucleic acid residues), up to and including the entire sequence of a biomarker. For example, the biomarker specific probe can selectively hybridize to at least about 8, 10, 15, 20, 25, 30, 35, 40, 45, 50, 55, 60, 65, 70, 75, 80, 85, 90, 95, or 100 or more, up to and including the entire sequence of a biomarker or the complement thereof.

As used herein, the term "data" or "biomarker data" generally refers to data reflective of the abundance of a product of a biomarker found in a blood sample.

As used herein, the term "patient sample", refers to a biological sample from a patient from which a biomarker for mild OA can be detected. Patient samples include, but are not limited to samples of blood, serum, saliva, urine, synovial fluid, tissue, and the like. Preferably, a patient sample is a blood sample.

As used herein, the term "blood nucleic acid sample" refers to nucleic acid obtained from blood and can include nucleic acids obtained from whole blood, centrifuged lysed blood, serum free whole blood or fractionated blood including peripheral blood leukocytes (PBLs) or other fractions of blood as described herein. By whole blood is meant unfractionated blood, for example, a drop of blood wherein a drop of blood includes volumes of 5 µl, 10 µl, 15 µl, 20 µl, 25 µl, 30 µl. By centrifuged lysed blood or 'lysed blood' is meant whole blood that is mixed with lysis buffer and centrifuged as described herein (see Example 2). By serum free blood is meant whole blood wherein the serum or plasma is removed by centrifugation as described herein (see Example 2). Preferably, a blood nucleic acid sample is whole blood or centrifuged lysed blood and is total RNA, mRNA or is a nucleic acid corresponding to mRNA, for example, cDNA isolated from said blood. A blood nucleic acid sample can also include a PCR product obtained from total RNA, mRNA or cDNA.

As used herein, the term "carboxy terminal" region of a polypeptide refers to the polypeptide sequences encoded by polynucleotide sequences (double-stranded or single-stranded) located within or at the 3' end of a gene, and includes, but is not limited to, the 3' protein coding region of a gene. As used herein, the "carboxy terminal" region refers to the carboxy terminal end of a polypeptide up to 300 amino acids or ⅓ of the polypeptide from the last amino acid of the polypeptide. The "3' end" does not include the polyA tail, if one is present. The "carboxy terminal" region of a polypeptide is not shorter than 3 amino acids in length and not longer than 350 amino acids in length. Other possible lengths of the "carboxy terminal" region of a polypeptide include, but are not limited to, 5, 10, 20, 25, 50, 100 and 200 amino acids.

As used herein, the term "cartilage nucleic acid sample" refers to nucleic acids derived from cartilage. Preferably, a cartilage nucleic acid sample is total RNA, mRNA or is a nucleic acid corresponding to RNA, for example, cDNA. A cartilage nucleic acid sample can also include a PCR product derived from total RNA, mRNA or cDNA.

As used herein, the term "combination of the biomarkers of the invention" refers to any one or more biomarkers as disclosed in Table 1 or Table 4 and any combinations of any two or more biomarkers as disclosed in Table 1 and/or Table 2 so long as at least one of the biomarkers of said combination is from Table 1. The term "combination of the biomarkers of the invention" refers to any combinations of any two or more biomarkers as disclosed in Table 4 and/or Table 2 so long as at least one of the biomarkers of said combination is from Table 4. The term "combination of the biomarkers of the invention" refers to any combinations of any two or more biomarkers as disclosed in Table 1 and Table 4 and/or Table 2 so long as at least one of the biomarkers of said combination is from either Table 1 or Table 4.

As used herein, the terms "compound" and "agent" are used interchangeably.

As used herein, "consisting essentially of" refers to the maximum number of biomarker genes that are useful to diagnose mild osteoarthritis. In one embodiment, a biomarker for the diagnosis of mild osteoarthritis consists essentially of at least any of up to 1, 2, 3, 4, 5, 6, 7, 8, 9, 10, 11, 12, 13, 14, 15, 16, 17, 18, 19, 20, 25, 30, 35, 40, 45, 50, 100, 150 or up to all of the biomarkers of Table 1 and/or Table 4. In another embodiment, a biomarker for the diagnosis of mild osteoarthritis consists essentially of at least any of up to 1, 2, 3, 4, 5, 6, 7, 8, 9, 10, 11, 13, 15, 20, 25, 30, 35, 40, 45, 50, 100, 150 of the biomarkers of Table 1 and/or Table 4 in combination with at least any of up to 1, 2, 3, 4, 5, 6, 7, 8, 9, or 10, 15, 20, 30, 40, 50 or up to all of the biomarkers as disclosed in application Ser. No. 10/915,680 and which are provided in Table 2. In one embodiment, a biomarker for the diagnosis of mild osteoarthritis consists essentially of at least any of up to 1, 2, 3, 4, 5, 6, 7, 8, 9, 10, 11, 12, 13, 14, 15, 16, 17, 18, 19, 20, 25, 30 or up to all of the biomarkers of Table 4.

As used herein, the term "control" or "control sample" in the context of diagnosing mild osteoarthritis refers to one or more samples isolated from an individual or group of individuals who have been determined to not having osteoarthritis (i.e. "normal control") or who have been determined to mild osteoarthritis (i.e. "mild OA control") using means other than the biomarkers of the invention. The term control or control sample can also refer to the compilation of data derived from samples of one or more individuals classified as not having osteoarthritis (i.e. "normal control") or having mild osteoarthritis (i.e. "mild OA control"). As used herein, the term "control" in the context of screening for a prophylactic or therapeutic agent refers to a standard or reference for an assay or methodology to which other conditions can be compared.

As used herein, the term "derivative" in the context of proteinaceous agent (e.g., proteins, polypeptides, peptides, and antibodies) refers to a proteinaceous agent that comprises an amino acid sequence which has been altered by the introduction of one or more amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "classifier" is used to describe the output of a mathematical model generated on its ability to differentiate between two or more phenotypic traits—for example individuals having or not having mild OA.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein "Diagnosis of mild OA" or "Mild OA diagnosis", according to one aspect of the invention refers to a process of determining if an individual is afflicted with mild OA. In a specific embodiment, "diagnosis of mild OA" or "mild OA diagnosis" refers to a determination as between two options, that an individual has mild OA or that an individual does not have mild OA. In another specific embodiment, "diagnosis" refers to a determination as between three options, an individual has mild OA, an individual does not have mild OA, or it cannot be determined with sufficient degree of certainty whether an individual has mild OA or does not have mild OA. As would be understood by a person skilled in the art, in this context a "sufficient degree of certainty" depends upon the sensitivity and specificity required for the diagnosis. More particularly the sufficient degree of certainty includes greater than 50% sensitivity and/or specificity, greater than 60% sensitivity and/or specificity, greater than 70% sensitivity and/or specificity, greater than 80% sensitivity and/or specificity, greater than 90% sensitivity and/or specificity and 100% sensitivity and/or specificity.

As used herein, the term "differential expression" refers to a difference in the level of expression of the RNA and/or protein products of one or more biomarkers of the invention, as measured by the amount or level of RNA or protein. In reference to RNA, it can include difference in the level of expression of mRNA, and/or one or more spliced variants of mRNA of the biomarker in one sample as compared with the level of expression of the same one or more biomarkers of the invention as measured by the amount or level of RNA, including mRNA and/or one or more spliced variants of mRNA in a second sample. "Differentially expressed" or "differential expression" can also include a measurement of the protein, or one or more protein variants encoded by the biomarker of the invention in a sample or population of samples as compared with the amount or level of protein expression, including one or more protein variants of the biomarker or biomarkers of the invention. Differential expression can be determined as described herein and as would be understood by a person skilled in the art. The term "differentially expressed" or "changes in the level of expression" refers to an increase or decrease in the measurable expression level of a given product of the biomarker as measured by the amount of RNA and/or the amount of protein in a sample as compared with the measurable expression level of a given product of the biomarker in a second sample. The first sample and second sample need not be from different patients, but can be samples from the same patient taken at different time points. The term "differentially expressed" or "changes in the level of expression" can also refer to an increase or decrease in the measurable expression level of a given biomarker in a population of samples as compared with the measurable expression level of a biomarker in a second population of samples. As used herein, "differentially expressed" when referring to a single sample can be measured using the ratio of the level of expression of a given biomarker in said sample as compared with the mean expression level of the given biomarker of a control population wherein the ratio is not equal to 1.0. Differentially expressed can also be used to include comparing a first population of samples as compared with a second population of samples or a single sample to a population of samples using either a ratio of the level of expression or using p-value. When using p-value, a nucleic acid transcript including hnRNA and mRNA is identified as being differentially expressed as between a first and second population when the p-value is less than 0.1, less than 0.05, less than 0.01, less than 0.005, less than 0.001 etc. When determining differential expression on the basis of the ratio of the level of gene product expression, an RNA or protein gene product is differentially expressed if the ratio of the level of its RNA or protein product in a first sample as compared with that in a second sample is greater than or less than 1.0. For instance, a ratio of greater than 1, for example 1.2, 1.5, 1.7, 2, 3, 4, 10, 20, or a ratio of less than 1, for example 0.8, 0.6, 0.4, 0.2, 0.1. 0.05, of RNA or protein product of a gene would be indicative of differential expression. In another embodiment of the invention, a nucleic acid transcript including hnRNA and mRNA is differentially expressed if the ratio of the mean level of expression of a first transcript in a nucleic acid population as compared with its mean level of expression in a second population is greater than or less than 1.0. For instance, a ratio of greater than 1, for example 1.2, 1.5, 1.7, 2, 3, 4, 10, 20, or a ratio less than 1, for example 0.8, 0.6, 0.4, 0.2, 0.1. 0.05 would be indicative of differential expression. In another embodiment of the invention a nucleic acid transcript including hnRNA, and mRNA is differentially expressed if the ratio of its level of expression in a first sample as compared with the mean of the second population is greater than or less than 1.0 and includes for example, a ratio of greater than 1, for instance 1.2, 1.5, 1.7, 2, 3, 4, 10, 20, or a ratio less than 1, for example 0.8, 0.6, 0.4, 0.2, 0.1. 0.05. "Differentially increased expression" refers to 1.1 fold, 1.2 fold, 1.4 fold, 1.6 fold, 1.8 fold, or more, relative to a standard, such as the mean of the expression level of the second population. "Differentially decreased expression" refers to less than 1.0 fold, 0.8 fold, 0.6 fold, 0.4 fold, 0.2 fold, 0.1 fold or less, relative to a standard, such as the mean of the expression level of the second population.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the reduction of the symptoms of osteoarthritis or the prevention of osteoarthritis progression as described in the present specification. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

As used herein, the term "effective amount" refers to the amount of a compound which is sufficient to reduce or ameliorate the progression, severity and/or duration of osteoarthritis or one or more symptoms thereof, prevent the development, recurrence or onset of osteoarthritis or one or more symptoms thereof, prevent the advancement of osteoarthritis or one or more symptoms thereof, or enhance or improve the prophylactic or therapeutic effect(s) of another therapy.

As used herein, the term "fragment" in the context of a proteinaceous agent refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a polypeptide or a protein. In a specific embodiment, a fragment of a protein or polypeptide retains at least one function of the protein or polypeptide. In another embodiment, a fragment of a protein or polypeptide retains at least one, two, three, four, or five functions of the protein or polypeptide. Preferably, a fragment of an antibody retains the ability to immunospecifically bind to an antigen.

As used herein, the term "fusion protein" refers to a polypeptide that comprises an amino acid sequence of a first protein or polypeptide or fragment thereof, or functional fragment thereof, or an analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used herein, the terms "gene expression pattern", "gene expression profile" and "nucleic acid array expression profile" are used interchangeably and comprise the pattern of hybridization of a plurality of target nucleic acid sequences hybridized to a plurality of nucleic acid probes on an array for mild OA individuals as compared with non OA individuals or normal individuals. "Gene expression pattern", "gene expression profile" and "nucleic acid array expression profile" can also refer to a pattern of the level of abundance of RNAs and/or proteins corresponding to two or more biomarkers of the invention as is determined by any methodology known in the art for measuring the levels of said RNAs and/or proteins. For example, the pattern can be a mathematical representation of the pattern e.g. a mathematical equation, vector etc.

As used herein, the terms "hybridizing to" and "hybridization" refer to the sequence specific non-covalent binding interactions with a complementary nucleic acid, for example, interactions between a target nucleic acid sequence and a nucleic acid member on an array.

As used herein, the term "immunoglobulin" refers to a protein consisting of one or more polypeptides substantially encoded by immunoglobulin genes or antigen binding fragment thereof. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, the term "in combination" in reference to therapy refers to the use of more than one therapies (e.g., more than one prophylactic agent and/or therapeutic agent). The use of the term "in combination" does not restrict the order in which therapies (e.g., prophylactic and/or therapeutic agents) are administered to a subject. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject.

As used herein, "indicative of disease or condition" when referring to an expression pattern indicates an expression pattern which is diagnostic of disease or condition (e.g. presence of mild OA); or indicative of a risk of having mild OA such that the expression pattern is found significantly more often in patients with said disease or condition than in patients without the disease or condition (as determined using routine statistical methods setting confidence levels at a minimum of 70%, 75%, 80%, 85%, 90%, 95% and the like). Preferably, an expression pattern which is indicative of disease is found in at least 70%, at least 75%, at least 80%, at least 85%, at least 90%, at least 95% or more in patients who have the disease and is found in less than 10%, less than 8%, less than 5%, less than 2.5%, or less than 1% of patients who do not have the disease. "Indicative of disease" also indicates an expression pattern which is diagnostic of disease such that the expression pattern more properly categorizes with control expression patterns of individuals with disease as compared with control expression patterns of individuals without disease using statistical algorithms for class prediction as would be understood by a person skilled in the art and see for example commercially available programs such as those provided by Silicon Genetics (e.g. GeneSpring™).

As used herein, the term "internal coding region" of a gene refers to a polynucleotide (double-stranded or single-stranded) located between the 5' region and the 3' region of a gene as defined herein. The "internal coding region" is not shorter than 8 nucleotides in length and can be as long or longer than 1000 nucleotides in length. Other possible lengths of the "internal coding region" include but are not limited to 10, 20, 25, 50, 100, 200, 400, and 500 nucleotides. The 5', 3' and internal regions are non-overlapping and may, but need not be contiguous, and may, but need not, add up to the full length of the corresponding gene.

As used herein, the term "internal polypeptide region" of a polypeptide refers to the polypeptide sequences located between the amino terminal region and the carboxy terminal region of a polypeptide, as defined herein. The "internal polypeptide region" of a polypeptide is not shorter than 3 amino acids in length and can be as long as or longer than 350 amino acids in length. Other possible lengths of the "internal polypeptide region" of a polypeptide include, but are not limited to, 5, 10, 20, 25, 50, 100 and 200 amino acids.

The amino terminal, carboxy terminal and internal polypeptide regions of a polypeptide are non-overlapping and may, but need not be contiguous, and may, but need not, add up to the full length of the corresponding polypeptide.

As used herein, "isolated" or "purified" when used in reference to a nucleic acid means that a naturally occurring sequence has been removed from its normal cellular (e.g., chromosomal) environment or is synthesised in a non-natural environment (e.g., artificially synthesised). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein, the terms "isolated" and "purified" in the context of a proteinaceous agent (e.g., a peptide, polypeptide, protein or antibody) refer to a proteinaceous agent which is substantially free of cellular material and in some embodiments, substantially free of heterologous proteinaceous agents (i.e., contaminating proteins) from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous proteinaceous agent (e.g., protein, polypeptide, peptide, or antibody; also referred to as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. Preferably, proteinaceous agents disclosed herein are isolated.

As used herein, the term "level of expression" refers to the measurable quantity of a given nucleic acid or protein as determined by methods known to a person skilled in the art and as described herein. In reference to RNA, hnRNA, mRNA or spliced variants of mRNA corresponding to a biomarker of the invention, level of expression can be determined by hybridization or more quantitative measurements such as quantitative real-time RT PCR, which includes use of SYBR® green, TaqMan® and Molecular Beacons technology.

As used herein, a "ligand" is a molecule that specifically binds to a polypeptide encoded by one of the genes of a biomarker of the invention. A ligand can be a nucleic acid (RNA or DNA), polypeptide, peptide or chemical compound. A ligand of the invention can be a peptide ligand, e.g., a scaffold peptide, a linear peptide, or a cyclic peptide. In a preferred embodiment, the polypeptide ligand is an antibody. The antibody can be a human antibody, a chimeric antibody, a recombinant antibody, a humanized antibody, a monoclonal antibody or antigen binding fragment thereof, or a polyclonal antibody. The antibody can be an intact immunoglobulin, e.g., an IgA, IgG, IgE, IgD, IgM or subtypes thereof. The antibody can be conjugated to a functional moiety (e.g., a compound which has a biological or chemical function (which may be a second different polypeptide, a therapeutic drug, a cytotoxic agent, a detectable moiety, or a solid support. A polypeptide ligand (e.g. antibody polypeptide) of the invention interacts with a polypeptide, encoded by one of the genes of a biomarker, with high affinity and specificity. For example, the polypeptide ligand binds to a polypeptide, encoded by one of the genes of a biomarker, with an affinity constant of at least $10^7$ $M^{-1}$, preferably, at least $10^8$ $M^{-1}$, $10^9$ $M^{-1}$, or $10^{10}$ $M^{-1}$.

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

As used herein, the terms "manage", "managing" and "management" refer to the beneficial effects that a subject derives from a therapy (e.g., a prophylactic or therapeutic agent) which does not result in a cure of osteoarthritis. In certain embodiments, a subject is administered one or more therapies to "manage" osteoarthritis so as to prevent the progression or worsening of the osteoarthritis.

As used herein, "mRNA integrity" refers to the quality of mRNA extracts from either cartilage samples or blood samples. mRNA extracts with good integrity do not appear to be degraded when examined by methods well known in the art, for example, by RNA agarose gel electrophoresis (e.g., Ausubel et al., John Weley & Sons, Inc., 1997, Current Protocols in Molecular Biology). Preferably, the mRNA samples have good integrity (e.g., less than 10%, preferably less than 5%, and more preferably less than 1% of the mRNA is degraded) to truly represent the gene expression levels of the cartilage or blood samples from which they are extracted.

As used herein, the terms "non-responsive" and "refractory" describe patients treated with a currently available therapy (e.g., prophylactic or therapeutic agent) for osteoarthritis, which is not clinically adequate to relieve one or more symptoms associated therewith. Typically, such patients suffer from severe, persistently active disease and require additional therapy to ameliorate the symptoms associated with their osteoarthritis.

As used herein, "normal" refers to an individual or group of individuals who have not shown any OA symptoms, including joint pain, and have not been diagnosed with cartilage injury or OA. Preferably said normal individual(s) is not on medication affecting OA and has not been diagnosed with any other disease. More preferably normal individuals have similar sex, age and body mass index (BMI) as compared with the test samples. "Normal", according to the invention, also refers to a samples isolated from normal individuals and includes total RNA or mRNA isolated from normal individuals. A sample taken from a normal individual can include RNA isolated from a cartilage tissue sample wherein RNA is isolated from a whole or a piece of cartilage isolated from cartilage tissue from an individual who was not diagnosed with OA and does not show any symptoms of OA at the time of tissue removal. In one embodiment of the invention, the "normal" cartilage sample is isolated at 14 hours post-mortem and the integrity of mRNA samples extracted is confirmed. A sample taken from a normal individual can also include RNA isolated from a blood sample wherein the blood is from an individual who has not been diagnosed with OA and does not show any symptoms of OA at the time the blood is isolated.

As used herein, "nucleic acid(s)" is interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As defined herein, a "nucleic acid array" refers a plurality of unique nucleic acids (or "nucleic acid members") attached to a support where each of the nucleic acid members is attached to a support in a unique pre-selected region. In one embodiment, the nucleic acid member attached to the surface of the support is DNA. In a preferred embodiment, the nucleic acid member attached to the surface of the support is either cDNA or oligonucleotides. In another preferred embodiment, the nucleic acid member attached to the surface of the support is cDNA synthesised by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein, a "nucleic acid probe" includes nucleic acids capable of binding to a complementary sequence of a nucleic acid member on an array through sets of non-covalent bonding interactions, including complementary base pairing interactions. As used herein, a nucleic acid probe may include natural (i.e., A, G, C, or T) or modified bases (7-deazaguanosine, inosine, etc.). In addition, the bases in nucleic acid probes may be joined by a linkage other than a phosphodiester bond, so long as it does not interfere with hybridization (i.e., the nucleic acid probe still specifically binds to its complementary sequence under standard stringent or selective hybridization conditions). Thus, nucleic acid probes may be peptide nucleic acids in which the constituent bases are joined by peptide bonds rather than phosphodiester linkages.

As used herein "nucleic acid target" or "nucleic acid member" is defined as a nucleic acid capable of binding to an array. The nucleic acid target can either be an isolated nucleic acid sequence corresponding to a gene or portion thereof, or the nucleic acid target can be total RNA or mRNA isolated from a sample. Preferably, the nucleic acid target or nucleic acid markers are derived from human cartilage, blood, or synovial fluid extracts. More preferably, the nucleic acid targets are single- or double-stranded DNA, RNA, or DNA-RNA hybrids, from human cartilage, blood, or synovial fluid total RNA extracts, and preferably from mRNA extracts.

In one embodiment, a conventional nucleic acid array of 'target' sequences bound to the array can be representative of the entire human genome, e.g. Affymetrix chip, and the isolated biomarker consisting of or comprising two or more biomarker specific probes corresponding to the genes described in Table 1, Table 4 and/or Table 2 so long as at least one biomarker specific probes is from Table 1 or Table 4 are applied to the conventional array.

In another embodiment, sequences bound to the array can be an isolated oligonucleotide, cDNA, EST or PCR product corresponding to a biomarker of the invention total cellular RNA is applied to the array.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oligonucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

As used herein, "osteoarthritis" refers to a particular form of arthritis, and in particular a chronic disease in which the articular cartilage that lies on the ends of bones that form the articulating surface of the joints gradually degenerates over time.

As used herein, the term "mild osteoarthritis (OA)" refers to a specific advancement or progression of OA in an individual or a specific level of pathology of OA as defined in accordance with the scoring system of Marshall (Marshall W., 1996, The Journal of Rheumatology, 23:582-584, incorporated by reference). According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A designation of mild OA is indicative of the cumulative score of a score applied to each articular surface to reflect the cartilage severity grade for that surface. For example, if the medial femoral condyle has a grade I lesion as its most severe cartilage damage a value of 1 is assigned. A total score for the patient is then derived from the sum of the scores on the 6 articular surfaces. Based on the total score, each patient is placed into one of 4 OA groups: "mild" (early) is defined as having a Marshall score of 1-6, "moderate" is defined as having a Marshall score of 7-12, "marked" is defined as having a Marshall score of 13-18 and "severe" is defined as having a Marshall score of greater than 18.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, "polynucleotide" encompasses double-stranded DNA, single-stranded DNA and double-stranded or single-stranded RNA of more than 8 nucleotides in length.

As used herein, "polypeptide sequences encoded by" or "protein products of the biomarkers" refers to the amino acid sequences obtained after translation of the protein coding region of a biomarker, as defined herein. The mRNA nucleotide sequence for each of the biomarkers of the invention is identified by its RNA Accession number (see Table 3 or Table 5) and the corresponding polypeptide sequence is identified by a Protein Accession number (see Table 3 or Table 5).

When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand. "Antigenic fragments" may be up to any one of 5000, 1000, 500, 400, 300, 200, 100, 50 or 25 or 20 or 10 or 5 amino acids in length.

As used herein, "pre-selected region", "predefined region", or "unique position" refers to a localised area on a substrate which is, was, or is intended to be used for the deposit of a nucleic acid and is otherwise referred to herein in the alternative as a "selected region" or simply a "region." The pre-selected region may have any convenient shape, e.g., circular, rectangular, elliptical, wedge-shaped, etc. In some embodiments, a pre-selected region is smaller than about 1 $cm^2$, more preferably less than 1 $mm^2$, still more preferably less than 0.5 $mm^2$, and in some embodiments less than 0.1 $mm^2$. A nucleic acid member at a "pre-selected region", "predefined region", or "unique position" is one whose identity (e.g., sequence) can be determined by virtue of its position at the region or unique position.

As used herein, the terms "prevent", "preventing" and "prevention" refer to the prevention of the development, recurrence or onset of mild osteoarthritis or one or more symptoms thereof resulting from the administration of one or more compounds identified in accordance the methods of the invention or the administration of a combination of such a compound and another therapy.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J., and White, T. J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

As used herein, the term "probe" means oligonucleotides and analogs thereof and refers to a range of chemical species that recognise polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

The oligonucleotides and analogs thereof may be RNA or DNA, or analogs of RNA or DNA, commonly referred to as antisense oligomers or antisense oligonucleotides. Such RNA or DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)—Oligonucleotide Analogues with an Achiral Peptide Backbone, (1992)).

Probes may also be mixtures of any of the oligonucleotide analog types together or in combination with native DNA or RNA. At the same time, the oligonucleotides and analogs thereof may be used alone or in combination with one or more additional oliognucleotides or analogs thereof.

As used herein, the terms "prophylactic agent" and "prophylactic agents" refer to any compound(s) which can be used in the prevention of osteoarthritis. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression of osteoarthritis or one or more symptoms thereof.

As used herein, the phrase "prophylactically effective amount" refers to the amount of a therapy (e.g., a prophylactic agent) which is sufficient to result in the prevention of the development, recurrence or onset of osteoarthritis or one or more symptoms thereof.

As used herein, the terms "protein" and "polypeptide" and "proteinaceous agent" are used interchangeably to refer to a chain of amino acidslinked together by peptide bonds which optionally can comprise natural or non-natural amino acids. Optionally, the protein or peptide can comprise other molecules in addition to amino acids. Said chain can be of any length. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds.

As used herein, "a plurality of" or "a set of" refers to more than two, for example, 3 or more, 10 or more, 100 or more, or 1000 or more, or 10,000 or more.

As used herein, the terms "RNA portion" and "a portion thereof" in context of RNA products of a biomarker of the invention refer to an RNA transcript comprising a nucleic acid sequence of at least 6, at least 9, at least 15, at least 18, at least 21, at least 24, at least 30, at least 60, at least 90, at least 99, or at least 108, or more nucleotides of a RNA product of a biomarker of the invention.

As used herein the term "product of the biomarker of the invention" refers to the RNA and/or the protein expressed by the gene corresponding to the biomarker of the invention. The "RNA product of a biomarker of the invention" includes one or more products which can include heteronuclear RNA ("hnRNA"), mRNA, and all or some of the spliced variants of mRNA whose measure of expression can be used as a biomarker in accordance with the teachings disclosed herein. The "protein product of a biomarker of the invention" includes one or more of the products of the biomarker which can include proteins, protein variants, and any post-translationally modified proteins.

As used herein, the term "selectively amplified" or "selective amplification", refers to a process whereby one or more copies of a particular target nucleic acid sequence is selectively generated from a template nucleic acid. Selective amplification or selectively amplified is to be compared with amplification in general which can be used as a method in combination with, for example, random primers and an oligodT primer to amplify a population of nucleic acid sequences (e.g. mRNA). Selective amplification is preferably done by the method of polymerase chain reaction (Mullis and Faloona, 1987, Methods Enzymol. 155:335).

As used herein, the term "selectively binds" in the context of proteins encompassed by the invention refers to the specific interaction of any two of a peptide, a protein, a polypeptide, and an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognises and binds to a structure on the second molecule, rather than to other proteins. "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein "selective hybridization" in the context of this invention refers to a hybridization which occurs as between a polynucleotide encompassed by the invention and an RNA, and its complement thereof, or protein product of the biomarker of the invention, wherein the hybridization is such that the polynucleotide preferentially binds to the RNA products of the biomarker of the invention relative to the RNA products of other genes in the genome in question. In a preferred embodiment a polynucleotide which "selectively hybridizes" is one which hybridizes with a selectivity of greater than 70%, greater than 80%, greater than 90% and most preferably of 100% (i.e. cross hybridization with other RNA species preferably occurs at less than 30%, less than 20%, less than 10%). As would be understood to a person skilled in the art, a polynucleotide which "selectively hybridizes" to the RNA product of a biomarker of the invention can be determined taking into account the length and composition.

As used herein, "specifically hybridizes", "specific hybridization" refers to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, Nucleic acids Res., 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature ($T_M$) than do shorter ones, and are less likely to be repeated within a given target sequence, thereby minimizing non-specific hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As used herein, the term "specifically binds" refers to the interaction of two molecules, e.g., a ligand and a protein or peptide, or an antibody and a protein or peptide wherein the interaction is dependent upon the presence of particular structures on the respective molecules. For example, when the two molecules are protein molecules, a structure on the first molecule recognises and binds to a structure on the second molecule, rather than to proteins in general. "Specific binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As herein used, the term "standard stringent conditions" and "stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: $Tm=81.5+16.6(\log [Na+])+0.41(\text{fraction G+C})-(600/N)$ where N is the length of the oligonucleotide.

For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature of the annealing nucleic acid strands may be calculated using the equation $Tm=81.5+16.6(\log [Na^+])+0.41 (\text{fraction G+C})-(0.63\% \text{ formamide})-(600/N)$, where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. Hybridization conditions are considered to be "moderate stringency" conditions when hybridization fluids are comprised of above 25% formamide and "low stringency" conditions when hybridization fluids are comprised of below 25% formamide. A specific example of "moderate stringency" hybridization conditions is when the above hybridization is conducted at 30% formamide. A specific example of "low stringency" hybridization conditions is when the above hybridization is conducted at 10% formamide. Hybridization conditions are considered to be "high stringency", where the conditions include, for example, hybridization in 6×SSC at about 45° C., followed by one or more washes in 0.2×SSC, 0.1% SDS at 65° C.

As used herein, the terms "subject" and "patient" and "individual" are used interchangeably to refer to an animal (e.g., a mammal, a fish, an amphibian, a reptile, a bird and an insect). In a specific embodiment, a subject is a mammal (e.g., a non-human mammal and a human). In another embodiment, a subject is a pet (e.g., a dog, a cat, a guinea pig, a monkey and a bird), a farm animal (e.g., a horse, a cow, a pig, a goat and a chicken) or a laboratory animal (e.g., a mouse and a rat). In another embodiment, a subject is a primate (e.g., a chimpanzee and a human). In another embodiment, a subject is a human.

As used herein, the term "synergistic" refers to a combination of a compound identified using one of the methods described herein, and another therapy (e.g., agent), which is more effective than the additive effects of the therapies. Preferably, such other therapy has been or is currently being to prevent, treat, manage or ameliorate osteoarthritis or a symptom thereof. A synergistic effect of a combination of therapies (e.g., prophylactic or therapeutic agents) permits the use of lower dosages of one or more of the therapies and/or less frequent administration of said therapies to a subject with osteoarthritis. The ability to utilize lower dosages of a therapy (e.g., a prophylactic or therapeutic agent) and/or to administer said therapy less frequently reduces the toxicity associated with the administration of said agent to a subject without reducing the efficacy of said therapies in the prevention, treatment, management or amelioration of osteoarthritis. In addition, a synergistic effect can result in improved efficacy of therapies (e.g., agents) in the prevention, treatment, management or amelioration of osteoarthritis. Finally, a synergistic effect of a combination of therapies (e.g., prophylactic or therapeutic agents) may avoid or reduce adverse or unwanted side effects associated with the use of either therapy alone.

As used herein, "synovial fluid" refers to fluid secreted from the "synovial sac" which surrounds each joint. Synovial fluid serves to protect the joint, lubricate the joint and provide nourishment to the articular cartilage. Synovial fluid useful according to the invention contains cells from which RNA can be isolated according to methods well known in the art as described herein.

As used herein, the terms "therapeutic agent" and "therapeutic agents" refer to any compound(s) which can be used in the treatment, management or amelioration of osteoarthritis or one or more symptoms thereof. In a specific embodiment, the term "therapeutic agent" refers to a compound that increases or decreases the expression of a polynucleotide sequence that is differentially expressed in a chondrocyte from mild osteoarthritis, relative to that in a chondrocyte from a normal individual, as defined herein. A therapeutic agent according to the invention also refers to a compound that increases or decreases the anabolic activity of a chondrocyte. The invention provides for a "therapeutic agent" that 1) prevents the onset of osteoarthritis; 2) reduces, delays, or eliminates osteoarthritis symptoms such as pain, swelling, weakness and loss of functional ability in the afflicted joints; 3) reduces, delays, or eliminates cartilage degeneration, and/or enhances chondrocyte metabolic activity and cell division rates; and/or 4) restores one or more expression profiles of one or more disease-indicative nucleic acids of a patient to a profile more similar to that of a normal individual when administered to a patient. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to treat, manage or ameliorate osteoarthritis or one or more symptoms thereof.

As used herein, the term "therapeutically effective amount" refers to that amount of a therapy (e.g., a therapeutic agent) sufficient to result in the amelioration of osteoarthritis or one or more symptoms thereof, prevent advancement of osteoarthritis, cause regression of osteoarthritis, or to enhance or improve the therapeutic effect(s) of another therapy (e.g., therapeutic agent). In a specific embodiment, a therapeutically effective amount refers to the amount of a therapy (e.g., a therapeutic agent) that reduces joint pain or swelling of the joint. Preferably, a therapeutically effective of a therapy (e.g., a therapeutic agent) reduces the swelling of the joint by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control such as phosphate buffered saline ("PBS").

As used herein, the terms "treat", "treatment" and "treating" refer to the reduction or amelioration of the progression, severity and/or duration of osteoarthritis or one or more symptoms thereof resulting from the administration of one or more compounds identified in accordance the methods of the invention, or a combination of one or more compounds identified in accordance with the invention and another therapy.

As used herein, the term "up regulated" or "increased level of expression" in the context of this invention refers to a sequence corresponding to a gene which is expressed wherein the measure of the quantity of the sequence demonstrates an increased level of expression of the gene, as can be determined using array analysis or other similar analysis, in cartilage or blood isolated from an individual having osteoarthritis or an identified disease state of osteoarthritis as determined by osteoarthritis staging as compared with the same gene in cartilage or blood isolated from normal individuals or from an individual with a different identified disease state of osteoarthritis as determined by osteoarthritis staging. An "increased level of expression" according to the present invention, is an increase in expression of at least 1%, 2%, 3%, 4%, 5%, 6%, 7%, 8%, 9%, 10% or more, for example, 20%, 30%, 40%, or 50%, 60%, 70%, 80%, 90% or more, or greater than 1-fold, up to 2-fold, 3-fold, 4-fold, 5-fold, 10-fold, 50-fold, 100-fold or more as measured, for example, by the intensity of hybridization according to methods of the present invention. For example, up regulated sequences includes sequences having an increased level of expression in cartilage or blood isolated from individuals characterised as having mild, moderate, marked or severe OA as compared with cartilage isolated from normal individuals. Up regulated sequences can also include sequences having an increased level of expression in cartilage or blood isolated from individuals characterised as having one stage of osteoarthritis as compared to another stage of osteoarthritis (e.g. marked OA v. severe OA).

4. BRIEF DESCRIPTION OF THE FIGURES AND TABLES

FIG. 1 depicts the results of the analysis of all possible combinations of ratios of the genes listed in Table 4 where the ROC was greater than 0.6 for diagnosing mild OA. Shown is a graphical depiction of ROC area, sensitivity (assuming specificity is set at the 50% threshold) and specificity (assuming sensitivity is set at the 50% threshold). Further details are described in Example 8.

The objects and features of the invention can be better understood with reference to Tables 1, Table 2, Table 3, Table 4, Table 5, and Table 6, Table 7 and Table 8 as well as FIG. 1 which are included after the Examples Section of the instant specification.

Table 1 is a table showing, in one embodiment, the genes of the invention and in particular identifying the genes on the basis of their locus link ID.

Table 2 is a table showing, specific embodiments of the biomarkers as disclosed in application Ser. No. 10/915,680.

Table 3 is a table showing, in one embodiment, RNA products corresponding to the biomarkers identified in Table 1 and the nucleic acid reference accession numbers and protein reference accession numbers for each of the RNA products.

Table 4 is a table showing, in one embodiment, a selection of biomarkers of the invention which are each individually indicative of mild OA and are useful in combinations as indicative of mild OA. Table 4 identifies each biomarker by gene ID (formerly Locus Link ID) and includes Gene Symbol, Alternate Gene Symbol and Gene Description as identifiers of the biomarkers. In addition specific p value and fold change results as further described in Example 9 are shown.

Table 5 is a table showing, in one embodiment, representative examples of RNA and Protein variants corresponding to the biomarkers of Table 4.

Table 6 is a table showing, in one embodiment, a selection of primers used for quantitative real time RT-PCR on selected RNA species of the biomarkers listed in Table 4.

Table 7 is a table showing, in one embodiment, commercially available antibodies specific for protein products of the biomarkers of Table 4.

Table 8 provides, in one embodiment, representative species of primers and TaqMan® probes which are useful for to measure the RNA products of the biomarkers listed in Table 4.

5. DETAILED DESCRIPTION OF THE INVENTION

The practice of the present invention employs in part conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entireties.

The invention as disclosed herein identifies biomarkers and biomarker combinations useful in diagnosing mild and/or useful in differentiating as between mild OA and non OA. In order to use these biomarkers, the invention teaches the identification of the products of these biomarkers including the RNA products and the protein products. The invention further discloses the oligonucleotides, cDNA, DNA, RNA, PCR products, synthetic DNA, synthetic RNA, and fragments thereof, or other combinations of naturally occurring modified nucleotides that specifically and/or selectively hybridize to the RNA products of the biomarkers of the invention. The invention further discloses proteins, peptides, antibodies, ligands, and fragments thereof including antigen binding fragments that specifically and/or selectively hybridize to the protein products of the biomarkers of the invention. The measuring of the expression of the RNA product(s) of the biomarkers and combination of biomarkers of the invention, can be done by using those polynucleotides which are specific and/or selective for the RNA product(s) of the biomarkers of the invention to quantitate the expression of the RNA product(s). In a specific embodiment of the invention, the polynucleotides which are specific and/or selective for the RNA products are probes or primers. In one embodiment, these polynucleotides are in the form of a nucleic acid probes which can be hybridized to a manufactured array. In another embodiment, commercial arrays can be used to measure the expression of the RNA product and the invention teaches which combination of genes to analyze. In another embodiment, the polynucleotides which are specific and/or selective for the RNA products of the biomarkers of the invention are used in the form of probes and primers in techniques such as quantitative real-time RT PCR, using for example SYBR®Green, or using TaqMan® or Molecular Beacon techniques, where the polynucleotides used are used in the form of a forward primer, a reverse primer, a TaqMan labelled probe or a Molecular Beacon labelled probe. In one specific embodiment, the results generated from measuring the level of expression of the RNA products of the invention can be input into a model of the invention which is used to identify the combinations of biomarkers to determine a diagnosis as defined by the model. In a preferred embodiment, the same method is used to generate the expression data used to generate the mathematical model as is used to diagnose the test individual.

The invention further contemplates the use of proteins or polypeptides as disclosed herein and would be known by a person skilled in the art to measure the protein products of the biomarkers of the invention. Techniques known to persons skilled in the art (for example, techniques such as Western Blotting, Immunoprecipitation, protein microarray analysis and the like) can then be used to measure the level of protein products corresponding to the biomarkers of the invention. As would be understood to a person skilled in the art, the measure of the level of expression of the protein products of the biomarkers of the invention requires a protein which specifically or selectively binds to one or more of the protein products corresponding to each biomarker of the invention. Data representative of the level of expression of the protein products of the biomarker of the invention can then be input into the model generated to identify the combination in order to determine a diagnosis as defined by the model. In a preferred embodiment, the same method is used to generate the expression data used to generate the mathematical model as is used to diagnose the test individual.

5.1 Samples for Use in the Invention

Unless otherwise indicated herein, any tissue sample (e.g., a cartilage, synovial fluid or blood sample) or cell sample (e.g., chondrocyte sample or a blood cell sample) obtained from any subject may be used in accordance with the methods of the invention. Examples of subjects from which such a sample may be obtained and utilized in accordance with the methods of the invention include, but are not limited to, asymptomatic subjects, subjects manifesting or exhibiting 1, 2, 3, 4 or more symptoms of osteoarthritis, subjects clinically diagnosed as having osteoarthritis, subjects predisposed to osteoarthritis (e.g., subjects with a family history of osteoarthritis, subjects with a genetic predisposition to osteoarthritis, and subjects that lead a lifestyle that predisposes them to osteoarthritis or increases the likelihood of contracting osteoarthritis), subjects suspected of having osteoarthritis, subjects undergoing therapy for osteoarthritis, subjects with osteoarthritis and at least one other condition (e.g., subjects with 2, 3, 4, 5 or more conditions), subjects not undergoing therapy for osteoarthritis, subjects determined by a medical practitioner (e.g., a physician) to be healthy or osteoarthritis-free (i.e., normal), subjects that have been cured of osteoarthritis, subjects that are managing their osteoarthritis, and subjects that have not been diagnosed with osteoarthritis. In a specific embodiment, the subjects from which a sample may be obtained and utilized have osteoarthritis of the hands, feet, spine, knee, hip and/or wrist.

In another embodiment, the subjects from which a sample may be obtained and utilized have mild OA. In a further embodiment, the subject from which a sample may be obtained is a test individual wherein it is unknown whether the person has osteoarthritis, and/or it is unknown what stage of osteoarthritis the test individual has.

In order to classify an individual according to disease state, a scoring system based on cartilage may be used, whereby subjective decisions by the arthroscopist are minimized. An example of a scoring system which defines disease states described herein is that of Marshall, 1996, The Journal of Rheumatology 23:582-584, incorporated herein by reference. According to this method, each of the 6 articular surfaces (patella, femoral trochlea, medial femoral condyle, medial tibial plateau, lateral femoral condyle and lateral tibial plateau) is assigned a cartilage grade based on the worst lesion present on that specific surface. A scoring system is then applied in which each articular surface receives an osteoarthritis severity number value that reflects the cartilage severity grade for that surface, as described in Table 9.

TABLE 9

Articular Cartilage Grading System

| Grade | Articular Cartilage | Points |
|---|---|---|
| 0 | Normal | 0 |
| I | Surface intact-softening, edema | 1 |
| II | Surface-disrupted-partial thickness lesions (no extension to bone) | 2 |
| III | Full thickness lesions-extensions to intact bone | 3 |
| IV | Bone erosion or eburnation | 4 |

For example, if the medial femoral condyle has a grade I lesion as its most severe cartilage damage, a value of 1 is assigned. A total score for the patient is then derived from the sum of the scores of the 6 articular surfaces. Based on the total score, each patient is placed into one of 4 osteoarthritis groups: mild (1-6), moderate (7-12), marked (13-18) and severe (>18).

In certain embodiments, the sample obtained from a subject is a cartilage sample (including a sample of cells from cartilage). In other embodiments, the sample obtained from a subject is a synovial fluid sample (including a sample of cells from synovial fluid). In yet other embodiments, the sample obtained from a subject is a blood sample (including a sample of cells from blood).

5.1.1 Cartilage

In one aspect, a cartilage sample is obtained from a normal individual who is alive or is obtained from cartilage tissue less than 14 hours post mortem, according to methods known in the art and described below. Normal articular cartilage from human adults are obtained using any known method. In a specific embodiment, cartilage is obtained from individuals undergoing arthroscopy or total knee replacements and samples are stored in liquid nitrogen until needed. Typically, truly normal cartilage cannot generally be sampled from live donors due to ethical considerations. Thus, preferably, normal cartilage samples are obtained from deceased donors, within a fourteen-hour post-mortem window after cessation of perfusion to the sampled joint, to minimize the degradation of RNA observed beyond the window. In other embodiments, the "normal" tissue is obtained less than 14 hours post-mortem, such as less than or equal to 13, 12, 11, 10, 9, 8, 7, 6, 5, 4, 3, 2, or 1 hour post-mortem. Preferably, the normal cartilage is obtained less than 12 hours post-mortem.

In another aspect, cartilage is obtained from a subject diagnosed with mild osteoarthritis. Human cartilage samples from osteoarthritic individuals are obtained using any known method. Preferably, the cartilage samples are stored in liquid nitrogen until needed. In a specific embodiment, a minimum of 0.05 g of cartilage sample is isolated to obtain 2 μg total RNA extract. In another embodiment, a minimum of 0.025 g cartilage sample is isolated to obtain 1 μg total RNA extract. A cartilage sample that is useful according to the invention is in an amount that is sufficient for the detection of one or more nucleic acid sequences or amino acid sequences according to the invention.

The cartilage collected is optionally but preferably stored at refrigerated temperatures, such 4° C., prior to use in accordance with the methods of the invention. In some embodiments, a portion of the cartilage sample is used in accordance with the methods of the invention at a first instance of time whereas one or more remaining portions of the sample is stored for a period of time for later use. This period of time can be an hour or more, a day or more, a week or more, a month or more, a year or more, or indefinitely. For long term storage, storage methods well known in the art, such as storage at cryo temperatures (e.g., below −60° C.) can be used. In some embodiments, in addition to storage of the cartilage or instead of storage of the cartilage, isolated nucleic acid or protein are stored for a period of time (e.g., an hour or more, a day or more, a week or more, a month or more, a year or more, or indefinitely) for later use.

In some embodiments of the present invention, chrondrocytes present in the cartilage are separated using techniques known in the art and used in accordance with the methods of the invention. Chondrocytes may be obtained from a subject having mild OA, not having OA or a test subject. Chondrocytes can be frozen by standard techniques prior to use in the present methods.

5.1.2 Synovial Fluid

In one aspect, a sample of synovial fluid is obtained from a subject according to methods well known in the art. For example, arthrocentesis may be performed. During arthrocentesis, a sterile needle is used to remove synovial fluid from a joint. Synovial fluid may be collected from a knee, elbow, wrist, finger, hip, spine or any other joint using arthrocentesis. In a specific embodiment, synovial fluid is collected from the joint affected or suspected to be affected by osteoarthritis. Synovial fluid may be obtained from a subject having mild OA, not having OA or from a test subject.

A synovial fluid sample that is useful according to the invention is in an amount that is sufficient for the detection of one or more nucleic acid or amino acid sequences according to the invention. In a specific embodiment, a synovial fluid sample useful according to the invention is in an amount ranging from 0.1 ml to 20 ml, 0.1 ml to 15 ml, 0.1 ml to 10 ml, 0.1 ml to 5 ml, 0.1 to 2 ml, 0.5 ml to 20 ml, 0.5 ml to 15 ml, 0.5 ml to 10 ml, 0.5 ml to 5 ml, or 0.5 ml to 2 ml. In another embodiment, a synovial fluid sample useful according to the invention is 0.1 ml or more, 0.5 ml or more, 1 ml or more, 2 ml or more, 3 ml or more, 4 ml or more, 5 ml or more, 6 ml or more, 7 ml or more, 8 ml or more, 9 ml or more, 10 ml or more, 11 ml or more, 12 ml or more, 13 ml or more, 14 ml or more, 15 ml or more, 16 ml or more, 17 ml or more, 18 ml or more, 19 ml or more, or 20 ml or more.

The synovial fluid collected is optionally but preferably stored at refrigerated temperatures, such 4° C., prior to use in accordance with the methods of the invention. In some embodiments, a portion of the synovial fluid sample is used in accordance with the methods of the invention at a first instance of time whereas one or more remaining portions of the sample is stored for a period of time for later use. This period of time can be an hour or more, a day or more, a week or more, a month or more, a year or more, or indefinitely. For long term storage, storage methods well known in the art, such as storage at cryo temperatures (e.g., below −60° C.) can be used. In some embodiments, in addition to storage of the synovial fluid or instead of storage of the synovial fluid, isolated nucleic acid or protein are stored for a period of time (e.g. an hour or more, a day or more, a week or more, a month or more, a year or more, or indefinitely) for later use.

In some embodiments of the present invention, cells present in the synovial fluid are separated using techniques known in the art and used in accordance with the methods of the invention. Generally, the following cells are found in synovial fluid: lymphocytes (B and T lymphocytes), monocytes, neutrophils, synoviocytes and macrophages. In synovial fluid from patients with a pathological condition, such as osteoarthritis, the following cells may also be found: chondrocytes, osteoblasts and osteoclasts. Such cells may be isolated and used in accordance with the methods of the invention. In a specific embodiment, lymphocytes (B and T lymphocytes) are isolated from the synovial fluid sample and used in accordance with the methods of the invention. In another embodiment, monocytes or neutrophils are isolated from the synovial fluid sample and used in accordance with the methods of the invention. Cells isolated from the synovial fluid can be frozen by standard techniques prior to use in the present methods.

5.1.3 Blood

In one aspect of the invention, a sample of blood is obtained from a subject according to methods well known in the art. A sample of blood may be obtained from a subject having mild OA, not having OA or from a test individual where it is unknown whether the individual has osteoarthritis, or has a stage of osteoarthritis. In some embodiments, a drop of blood is collected from a simple pin prick made in the skin of a subject. In such embodiments, this drop of blood collected from a pin prick is all that is needed. Blood may be drawn from a subject from any part of the body (e.g., a finger, a hand, a wrist, an arm, a leg, a foot, an ankle, a stomach, and a neck) using techniques known to one of skill in the art, in particular methods of phlebotomy known in the art. In a specific embodiment, venous blood is obtained from a subject and utilised in accordance with the methods of the invention. In another embodiment, arterial blood is obtained and utilised in accordance with the methods of the invention. The composition of venous blood varies according to the metabolic needs of the area of the body it is servicing. In contrast, the composition of arterial blood is consistent throughout the body. For routine blood tests, venous blood is generally used.

Venous blood can be obtained from the basilic vein, cephalic vein, or median vein. Arterial blood can be obtained from the radial artery, brachial artery or femoral artery. A vacuum tube, a syringe or a butterfly may be used to draw the blood. Typically, the puncture site is cleaned, a tourniquet is applied approximately 3-4 inches above the puncture site, a needle is inserted at about a 15-45 degree angle, and if using a vacuum tube, the tube is pushed into the needle holder as soon as the needle penetrates the wall of the vein. When finished collecting the blood, the needle is removed and pressure is maintained on the puncture site. Usually, heparin or another type of anticoagulant is in the tube or vial that the blood is collected in so that the blood does not clot. When collecting arterial blood, anesthetics can be administered prior to collection.

The amount of blood collected will vary depending upon the site of collection, the amount required for a method of the invention, and the comfort of the subject. However, an advantage of one embodiment of the present invention is that the amount of blood required to implement the methods of the present invention can be so small that more invasive procedures are not required to obtain the sample. For example, in some embodiments, all that is required is a drop of blood. This drop of blood can be obtained, for example, from a simple pinprick. In some embodiments, any amount of blood is collected that is sufficient to detect the expression of one, two, three, four, five, ten or more genes listed in Table 1. As such, in some embodiments, the amount of blood that is collected is 1 µl or less, 0.5 µl or less, 0.1 µl or less, or 0.01 µl or less. However, the present invention is not limited to such embodiments. In some embodiments more blood is available and in some embodiments, more blood can be used to effect the methods of the present invention. As such, in various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In another embodiment, 0.001 ml to 15 ml, 0.01 ml to 10 ml, 0.1 ml to 10 ml, 0.1 ml to 5 ml, 1 to 5 ml of blood is collected from a subject.

In some embodiments of the present invention, blood is stored within a K3/EDTA tube. In another embodiment, one can utilize tubes for storing blood which contain stabilizing agents such as disclosed in U.S. Pat. No. 6,617,170 (which is incorporated herein by reference). In another embodiment the PAXgene™ blood RNA system: provided by PreAnalytiX, a Qiagen/BD company may be used to collect blood. In yet another embodiment, the Tempus™ blood RNA collection tubes, offered by Applied Biosystems may be used. Tempus™ collection tubes provide a closed evacuated plastic tube containing RNA stabilizing reagent for whole blood collection.

The collected blood collected is optionally but preferably stored at refrigerated temperatures, such 4° C., prior to use in accordance with the methods of the invention. In some embodiments, a portion of the blood sample is used in accordance with the invention at a first instance of time whereas one or more remaining portions of the blood sample is stored for a period of time for later use. This period of time can be an hour or more, a day or more, a week or more, a month or more, a year or more, or indefinitely. For long term storage, storage methods well known in the art, such as storage at cryo temperatures (e.g. below −60° C.) can be used. In some embodiments, in addition to storage of the blood or instead of storage of the blood, isolated nucleic acid or proteins are stored for a period of time for later use. Storage of such molecular markers can be for an hour or more, a day or more, a week or more, a month or more, a year or more, or indefinitely.

In one aspect, whole blood is obtained from a normal individual or from an individual diagnosed with, or suspected of having osteoarthritis according the methods of phlebotomy well known in the art. Whole blood includes blood which can be used directly, and includes blood wherein the serum or plasma has been removed and the RNA or mRNA from the remaining blood sample has been isolated in accordance with methods well known in the art (e.g., using, preferably, gentle centrifugation at 300 to 800×g for 5 to 10 minutes). In a specific embodiment, whole blood (i.e., unseparated blood) obtained from a subject is mixed with lysing buffer (e.g., Lysis Buffer (1 L): 0.6 g EDTA; 1.0 g $KHCO_2$, 8.2 g $NH_4Cl$ adjusted to pH 7.4 (using NaOH)), the sample is centrifuged and the cell pellet retained, and RNA or mRNA extracted in accordance with methods known in the art ("lysed blood") (see for example Sambrook et al.). The use of whole blood is preferred since it avoids the costly and time-consuming need to separate out the cell types within the blood (Kimoto, 1998, Mol. Gen. Genet 258:233-239; Chelly J et al., 1989, Proc. Nat. Acad. Sci. USA 86:2617-2621; Chelly J et al., 1988, Nature 333:858-860).

In some embodiments of the present invention, whole blood collected from a subject is fractionated (i.e., separated into components). In specific embodiments of the present invention, blood cells are separated from whole blood collected from a subject using techniques known in the art. For example, blood collected from a subject can be subjected to Ficoll-Hypaque (Pharmacia) gradient centrifugation. Such centrifugation separates erythrocytes (red blood cells) from various types of nucleated cells and from plasma. In particular, Ficoll-Hypaque gradient centrifugation is useful to isolate peripheral blood leukocytes (PBLs) which can be used in accordance with the methods of the invention.

By way of example but not limitation, macrophages can be obtained as follows. Mononuclear cells are isolated from peripheral blood of a subject, by syringe removal of blood followed by Ficoll-Hypaque gradient centrifugation. Tissue culture dishes are pre-coated with the subject's own serum or with AB+ human serum and incubated at 37° C. for one hour. Non-adherent cells are removed by pipetting. Cold (4° C.) 1 mM EDTA in phosphate-buffered saline is added to the adherent cells left in the dish and the dishes are left at room temperature for fifteen minutes. The cells are harvested, washed with RPMI buffer and suspended in RPMI buffer. Increased numbers of macrophages can be obtained by incubating at 37° C. with macrophage-colony stimulating factor (M-CSF). Antibodies against macrophage specific surface markers, such as Mac-1, can be labeled by conjugation of an affinity compound to such molecules to facilitate detection and separation of macrophages. Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods, affinity chromatography, and panning.

Blood cells can be sorted using a using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150-165. Laser excitation of fluorescent moieties in the individual particles results in a small electrical charge allowing electromagnetic separation of positive and negative particles from a mixture. An antibody or ligand used to detect a blood cell antigenic determinant present on the cell surface of particular blood cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate blood cells in some embodiments of the present invention. For example, blood cells can be sorted using a using a magnetic activated cell sorting (MACS) technique, a method for separating particles based on their ability to bind magnetic beads (0.5-100 m diameter). A variety of useful modifications can be performed on the magnetic microspheres, including covalent addition of an antibody which specifically recognizes a cell-solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate blood cells by a method called panning. Separate dishes can be coated with antibody specific to particular blood cells. Cells can be added first to a dish coated with blood cell specific antibodies of interest. After thorough rinsing, the cells left bound to the dish will be cells that express the blood cell markers of interest. Examples of cell surface antigenic determinants or markers include, but are not limited to, CD2 for T lymphocytes and natural killer cells, CD3 for T lymphocytes, CD11a for leukocytes, CD28 for T lymphocytes, CD19 for B lymphocytes, CD20 for B lymphocytes, CD21 for B lymphocytes, CD22 for B lymphocytes, CD23 for B lymphocytes, CD29 for leukocytes, CD14 for monocytes, CD41 for platelets, CD61 for platelets, CD66 for granulocytes, CD67 for granulocytes and CD68 for monocytes and macrophages.

Whole blood can be separated into cells types such as leukocytes, platelets, erythrocytes, etc. and such cell types can be used in accordance with the methods of the invention. Leukocytes can be further separated into granulocytes and agranulocytes using standard techniques and such cells can be used in accordance with the methods of the invention. Granulocytes can be separated into cell types such as neutrophils, eosinophils, and basophils using standard techniques and such cells can be used in accordance with the methods of the invention. A granulocytes can be separated into lymphocytes (e.g., T lymphocytes and B lymphocytes) and monocytes using standard techniques and such cells can be used in accordance with the methods of the invention. T lymphocytes can be separated from B lymphocytes and helper T cells separated from cytotoxic T cells using standard techniques and such cells can be used in accordance with the methods of the invention. Separated blood cells (e.g., leukocytes) can be frozen by standard techniques prior to use in the present methods.

A blood sample that is useful according to the invention is in an amount that is sufficient for the detection of one or more nucleic acid or amino acid sequences according to the invention. In a specific embodiment, a blood sample useful according to the invention is in an amount ranging from 1 µl to 100 ml, preferably 10 µl to 50 ml, more preferably 10 µl to 25 ml and most preferably 10 µl to 1 ml.

5.1.4 RNA Preparation

In one aspect of the invention, RNA is isolated from an individual in order to measure the RNA products of the biomarkers of the invention. RNA is isolated from cartilage samples as described herein. Samples can be from a single patient or can be pooled from multiple patients.

In another aspect, RNA is isolated directly from synovial fluid of persons with osteoarthritis as described herein. Samples can be from a single patient or can be pooled from multiple patients.

In another aspect, RNA is isolated directly from blood samples of persons with osteoarthritis as described herein. Samples can be from a single patient or can be pooled from multiple patients.

Total RNA is extracted from the cartilage samples according to methods well known in the art. In one embodiment, RNA is purified from cartilage tissue according to the following method. Following the removal of a tissue of interest from an individual or patient, the tissue is quick frozen in liquid nitrogen, to prevent degradation of RNA. Upon the addition of a volume of tissue guanidinium solution, tissue samples are ground in a tissuemizer with two or three 10-second bursts. To prepare tissue guanidinium solution (1 L) 590.8 g guanidinium isothiocyanate is dissolved in approximately 400 ml DEPC-treated $H_2O$. 25 ml of 2 M Tris-Cl, pH 7.5 (0.05 M final) and 20 ml $Na_2EDTA$ (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18:5294).

Alternatively, RNA is isolated from cartilage tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 µl DEPC-treated water or DEPC-treated 0.5% SDS (Chomczynski and Sacchi, 1987, *Anal. Biochem.*, 162: 156).

Preferably, the cartilage samples are finely powdered under liquid nitrogen and total RNA is extracted using TRIzol® reagent (GIBCO/BRL).

Alternatively, RNA is isolated from blood by the following protocol. Lysis Buffer is added to blood sample in a ratio of 3 parts Lysis Buffer to 1 part blood (Lysis Buffer (1 L) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

Alternatively, RNA is isolated from synovial fluid using TRIzol® reagent (GIBCO/BRL) as above.

Purity and integrity of RNA is assessed by absorbance at 260/280 nm and agarose gel electrophoresis followed by inspection under ultraviolet light.

5.2 Biomarkers of the Invention

In one embodiment, the invention provides biomarkers and biomarker combinations wherein the measure of the level of expression of the product or products of said biomarkers is indicative of the existence of mild osteoarthritis. In another embodiment, the invention provides biomarkers and biomarker combinations, wherein the measure of the level of expression of the product or products of said biomarkers can be used to diagnose whether an individual has either mild OA or does not have OA.

Table 1 provides a list of the gene names and the associated locus link ID for the biomarkers of the invention wherein the measure of the level of expression of the biomarkers, either individually, or in combination, can be used to diagnose an individual as having either mild osteoarthritis; or determining whether an individual has osteoarthritis or does not have osteoarthritis. As would be understood by a person skilled in the art, the locus link ID can be used to determine the sequence of all the RNA transcripts and all of the proteins which correspond to the biomarkers of the invention.

Table 2 provides biomarkers disclosed in application Ser. No. 10/915,680 which can be used in combination with one or more of the biomarkers disclosed in Table 1 as taught herein to diagnose mild OA; or to differentiate as between mild OA and non OA.

Table 3 in particular shows reference accession numbers corresponding to the RNA products of the biomarkers and reference accession numbers corresponding to the protein products of the biomarkers listed in Table 1. The invention thus encompasses the use of those methods known to a person skilled in the art and outlined herein to measure the expression of these biomarkers and combinations of biomarkers for each of the purposes outlined above.

Table 4 provides a list of the gene names and the associated locus link ID (gene ID) for a selection of biomarkers of the invention wherein the measure of the level of expression of the biomarkers, either individually, or in combination, can be used to diagnose an individual as having either mild osteoarthritis or does not have osteoarthritis. As would be understood by a person skilled in the art, the locus link ID can be used to determine the sequence of all the RNA transcripts and all of the proteins products which correspond to the biomarkers of the invention.

Table 5 in particular discloses reference accession numbers corresponding to the RNA products of the biomarkers and reference accession numbers corresponding to the protein products of the biomarkers listed in Table 1. The invention thus encompasses the use of those methods known to a person skilled in the art and outlined herein to measure the expression of these biomarkers and combinations of biomarkers for each of the purposes outlined above.

5.3 Combinations of Biomarkers

Combinations of Biomarkers

In one embodiment, combinations of biomarkers of the present invention includes any combination of any number up to 2, 3, 4, 5, 6, 7, 8, 10, 20, 30, 40, 50, 100 or all of the biomarkers listed in Table 1. In another embodiment of the invention, combinations of biomarkers of the present invention include any combination of any one or any number up to 1, 2, 3, 4, 5, 6, 7, 8, 10, 20, 30, 40, 50, 100 or all of the biomarkers listed in Table 2 in combination with any one or any number up to 1, 2, 3, 4, 5, 6, 7, 8, 10, 20, 30, 40, 50, 100 or all of the biomarkers listed in Table 1, the measurement of expression of the products of which can be used for diagnosing whether an individual has mild osteoarthritis or does not have osteoarthritis. In another embodiment, combinations of biomarkers of the present invention includes any combination of any number up to 2, 3, 4, 5, 6, 7, 8, 10, 20, 30, 40, 50, 100 or all of the RNA and/or protein products listed in Table 3. In another embodiment of the invention, combinations of biomarkers of the present invention include any combination of any one or any number up to 1, 2, 3, 4, 5, 6, 7, 8, 10, 20, 30, 40, 50, 100 or all of the biomarkers listed in Table 2 in combination with any one or any number up to 1, 2, 3, 4, 5, 6, 7, 8, 10, 20, 30, 40, 50, 100 or all of the RNA and/or protein products listed in Table 3, the measurement of expression of the products of which can be used for diagnosing whether an individual has mild osteoarthritis or does not have osteoarthritis. In one embodiment, combinations of biomarkers of the present invention includes any combination of any number up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or all of the biomarkers listed in Table 4. In another embodiment of the invention, combinations of biomarkers of the present invention include any combination of any one or any number up to 1, 2, 3, 4, 5, 6, 7, 8, 10, 20, 30, 40, 50, 100 or all of the biomarkers listed in Table 2 in combination with any one or any number up to all of the biomarkers listed in Table 4.

For instance, the number of possible combinations of a subset m of n genes is described in Feller, *Intro to Probability Theory*, Third Edition, volume 1, 1968, ed. J. Wiley, using the general formula:

$$m!/(n)!(m-n)!$$

In one embodiment, where n is 2 and m is 19, there are:

$$\frac{19!}{2!(19-2)!} = \frac{19 \times 18 \times 17 \times 16 \times 15 \times 14 \times 13 \times 12 \times 11 \times 10 \times 9 \times 8 \times 7 \times 6 \times 5 \times 4 \times 3 \times 2 \times 1}{(2 \times 1)(19 \times 18 \times 17 \times 16 \times 15 \times 14 \times 13 \times 12 \times 11 \times 10 \times 9 \times 8 \times 7 \times 6 \times 5 \times 4 \times 3 \times 2 \times 1)}$$

$$= \frac{1.21610^{17}}{7.1110^{14}}$$

$$= 171$$

unique two-gene combinations. The measurement of the gene expression of each of these two-gene combinations can independently be used to determine whether a patient has osteoarthritis. In another specific embodiment in which m is 19 and n is three, there are 19!/3!(19−3)! unique three-gene combinations. Each of these unique three-gene combinations can independently serve as a model for determining whether a patient has osteoarthritis.

5.4 Particularly Useful Combinations of Biomarkers

Although all of the combinations of the biomarkers as listed in Table 1 and Table 4 of the invention are useful for diagnosing mild OA as are combinations of biomarkers which select biomarkers from Table 2 along with at least one or more biomarkers from Table 1 and/or Table 4, the invention further provides a means of selecting and evaluating combinations of biomarkers particularly useful for diagnosing mild OA.

In order to identify useful combinations of biomarkers a mathematical model of the invention is used to create one or more classifiers, each classifier using data representative of each biomarker within a specific combination of biomarkers to separate as between individuals having mild osteoarthritis (a first phenotypic subgroup) and individuals not having osteoarthritis (a second phenotypic subgroup) of a training population used for input into the model.

The classifier generated can be subsequently evaluated or scored as outlined in section 5.9 by determining the ability of the classifier to correctly call each individual of the training population as described in Section 5.5. The classifier generated can also be evaluated or scored by determining the ability of the classifier to correctly call one or more individuals of a "scoring population". The scoring population is similar to the training population described in Section 5.5 below, however the scoring population is made up of one or more individuals not used to generate the classifier. As such the scoring population is comprised of individuals who have already been diagnosed as having mild osteoarthritis (the first phenotypic subgroup) and individuals not having osteoarthritis (the second phenotypic subgroup). In one embodiment, the scoring population includes members of the training population in addition to one or more members not used in the training population. In some embodiments, five percent or less, ten percent or less, twenty percent or less, thirty percent or less, fifty percent or less, or ninety percent or less of the members of the training population are common to the scoring population.

As would be understood by a person skilled in the art, this allows one to predict the ability of the classifiers to properly characterize an individual whose phenotypic characterization is unknown.

The data which is input into the mathematical model can be any data which is representative of the expression level of the product of each biomarker of the biomarker combination being evaluated. In one embodiment of the invention, each possible combination of the biomarkers in Table 1 are evaluated. In another embodiment of the invention, each possible combination of any of up to 2, 3, 4, 5, 10, 20, 30, etc of Table 1 are evaluated. In another embodiment of the invention, biomarkers in Table 1 are ranked on the basis of individual p value wherein the p value is indicative of each biomarkers ability to differentiate between members having mild OA and members having non OA, and then the top 40, 30, 20, or 10 ranked biomarkers are evaluated. In another embodiment of the invention, each possible combination of the biomarkers found in Table 1 and Table 2 are evaluated and biomarker combinations selected wherein the combinations include at least one of the biomarkers as listed in Table 1. In another embodiment of the invention, each possible combination of 2, 3, 4, 5, 10, 20, 30, etc biomarkers found in Table 1 and Table 2 are evaluated and biomarker combinations selected wherein the combinations include at least one of the biomarkers as listed in Table 1. In another embodiment of the invention, biomarkers in Table 1 and Table 2 are ranked on the basis of individual p value wherein the p value is indicative of each biomarkers ability to individually differentiate between members having mild OA and members having non OA, and then the top 40, 30, 20, or 10 ranked biomarkers are evaluated and biomarker combinations selected wherein the combinations include at least one of the biomarkers as listed in Table 1. In another embodiment of the invention, each possible combination of the biomarkers in Table 4 are evaluated. In another embodiment of the invention, each possible combination of any of up to 2, 3, 4, 5, 10, 20, 30, etc of Table 4 are evaluated. In another embodiment of the invention, biomarkers in Table 4 are ranked on the basis of individual p value wherein the p value is indicative of each biomarkers ability to differentiate between members having mild OA and members having non OA, and then the top 30, 20, or 10 ranked biomarkers are evaluated. In another embodiment of the invention, each possible combination of the biomarkers found in Table 4 and Table 2 are evaluated and biomarker combinations selected wherein the combinations include at least one of the biomarkers as listed in Table 4. In another embodiment of the invention, each possible combination of 2, 3, 4, 5, 10, 20, 30, etc biomarkers found in Table 4 and Table 2 are evaluated and biomarker combinations selected wherein the combinations include at least one of the biomarkers as listed in Table 4. In another embodiment of the invention, biomarkers in Table 4 and Table 2 are ranked on the basis of individual p value wherein the p value is indicative of each biomarkers ability to individually differentiate between members having mild OA and members having non OA, and then the top 40, 30, 20, or 10 ranked biomarkers are evaluated and biomarker combinations selected wherein the combinations include at least one of the biomarkers as listed in Table 4. In one embodiment of the invention, the mathematical model used is selected from the following: a regression model, a logistic regression model, a neural network, a clustering model, principal component analysis, nearest neighbour classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, a projection pursuit, and weighted voting.

The resulting classifiers can be used to diagnosis an unknown or test individual to determine whether said test individual has mild OA. In one embodiment, the diagnosis results from one or more classifiers generated by the mathematical model (for eg. logistic regression) is one of two results, having or not having mild OA. In yet another embodiment of the invention, the answer may be an answer of non determinable. It is important to note that each classifier uses a combination of biomarkers, and the classifier is generated using data representative of the level of expression of each biomarker. Thus, for example when the mathematical model used is logistic regression, a resulting classifier uses data representative of the level of expression of each of the 10 genes combined with a weighting factor. In one embodiment, the classifier itself is useful in diagnosing as described above. In another embodiment however, the combination identified (e.g. the 10 genes) can be used independently of the classifier which identified the genes. For example, the profile resulting from the 10 genes can be monitored to evaluate a test individual wherein the profile of the test individual is compared to the profile of the 10 genes from individuals having mild OA and a profile of the 10 genes in individuals not having OA.

5.5 Data for Input into Mathematical Models to Identify Biomarker Combinations for Diagnosis of Mild Osteoarthritis For example, in order to identify those biomarkers which are useful in diagnosing an individual as having mild osteoarthritis, or not having osteoarthritis, data reflective of the level of expression of one or more of the mRNA products of the biomarkers of Table 1, Table 2, and/or Table 4 are used from a population of individuals having mild osteoarthritis, and a second population of individuals not having osteoarthritis (the "training population"). For purposes of characterizing the training population into the prescribed phenotypic subgroups, any method of OA diagnosis can be used. In a preferred embodiment, the scoring method of Marshall as described herein is used.

In another embodiment, in order to identify those combinations of biomarkers which are useful in diagnosing an individual as having mild osteoarthritis, or not having osteoarthritis, data reflective of the level of expression of one or more of the mRNA products of the biomarkers of Table 1 as noted in Table 3 from individuals within the training population are used. In yet another embodiment, in order to identify those combinations biomarkers which are useful in diagnosing an individual as having mild osteoarthritis, or not having osteoarthritis, data reflective of the level of expression of one or more of the mRNA products of the biomarkers of Table 4 as noted in Table 5 from individuals within the training population are used.

In another embodiment data reflective of the level of expression of one or more protein products of the biomarkers of Table 1, Table 2 and/or Table 4 from individuals within the training population are used. Species of protein products of the biomarkers of Table 1 and Table 4 are noted in Table 3 and Table 5 respectively.

5.6 The Training Population

In some embodiments, the reference or training population includes between 10 and 30 subjects. In another embodiment the training population contains between 30-50 subjects. In still other embodiments, the reference population includes two or more populations each containing between 50 and 100, 100 and 500, between 500 and 1000, or more than 1000 subjects.

For example, in order to identify those biomarkers which are useful in diagnosing an individual as having mild osteoarthritis, or not having osteoarthritis, data reflective of the level of expression of one or more of the mRNA products of the biomarkers of Table 1 (e.g. as noted in Table 3) and/or Table 4 (e.g. as noted in Table 5) are used from a training population comprised of a first phenotypic subgroup (individuals having mild osteoarthritis), and a second phenotypic subgroup (individuals not having osteoarthritis). In some embodiments, data reflective of the level of expression of one or more of the mRNA products of the biomarkers of Table 2 are also utilized. In one embodiment, the distribution of other phenotypic traits (including age, sex, body mass index, co-morbidity status, medications etc) within each phenotypic subgroup of the training population is the same or similar. For example, the age distribution of individuals within the first and second phenotypic subgroup are the same or similar. In a preferred embodiment, the phenotypic characteristics of the two populations used in the training set are similar but for having or not having OA.

In another embodiment, in order to identify those biomarkers combinations which are useful in diagnosing an individual as having mild osteoarthritis, or not having osteoarthritis, data reflective of the level of expression of any one or more of the mRNA products of the biomarkers of Table 1 including those noted in Table 3, and/or Table 4 as noted in Table 5, optionally along with any one or more of up to 1, 2, 3, 4, 5, 6, 7, 8, 9, 10, 20, 30 40 or all of the biomarkers in Table 2 are used.

In another embodiment, in order to identify those biomarkers which are useful in diagnosing an individual as having mild osteoarthritis, or not having osteoarthritis, data reflective of the level of expression of any number or all of the RNA products of any number or all of the biomarkers of Table 1 including those noted in Table 3 and/or Table 4 including those noted in Table 5 which are expressed in blood resulting from a population of individuals having mild osteoarthritis, and a second population of individuals not having osteoarthritis are used.

5.7 Regression Models

In some embodiments the expression data for each combination of biomarkers to be tested are used in within a regression model, preferably a logistic regression model. Such a regression model will determine an equation for each possible combination of biomarkers tested, each equation providing a coefficient to be multiplied by the data reflective of the expression level of each individual biomarker represented by the model.

In general, the multiple regression equation of interest can be written $$Y = \alpha + \beta_1 X_1 + \beta_2 X_2 + \ldots + \beta_k X_k + \epsilon$$

where Y, the dependent variable, is presence (when Y is positive) or absence (when Y is negative) of the first phenotypic trait of (e.g., having mild osteoarthritis). This model says that the dependent variable Y depends on k explanatory variables (the measured values representative of the level of the gene product in the tissue of interest for the k select genes from subjects in the first and second phenotypic subgroups in the training population), plus an error term that encompasses various unspecified omitted factors. In the above-identified model, the parameter $\beta_1$ gauges the effect of the first explanatory variable $X_1$ on the dependent variable Y, holding the other explanatory variables constant. Similarly, $\beta_2$ gives the effect of the explanatory variable $X_2$ on Y, holding the remaining explanatory variables constant.

The logistic regression model is a non-linear transformation of the linear regression. The logistic regression model is termed the "logit" model and can be expressed as $$\ln [p/(1-p)] = \alpha + \beta_1 X_1 + \beta_2 X_2 + \ldots + \beta_k X_k + \epsilon \text{ or}$$

$$[p/(1-p)] = \exp^{\alpha} \exp^{\beta_1 X_1} \exp^{\beta_2 X_2} \times \ldots \times \exp^{\beta_k X_k} \exp^{\epsilon}$$

where,
ln is the natural logarithm, $\log^{exp}$, where exp= 2.71828...,
p is the probability that the event Y occurs, p(Y=1),
p/(1−p) is the "odds ratio",
ln [p/(1−p)] is the log odds ratio, or "logit", and
all other components of the model are the same as the general regression equation described above. It will be appreciated by those of skill in the art that the term for a and can be folded into the same constant. Indeed, in preferred embodiments, a single term is used to represent $\alpha$ and $\epsilon$. The "logistic" distribution is an S-shaped distribution function. The logit distribution constrains the estimated probabilities (p) to lie between 0 and 1.

In some embodiments of the present invention, the logistic regression model is fit by maximum likelihood estimation (MLE). In other words, the coefficients (e.g., $\alpha$, $\beta_1$, $\beta_2$, ...) are determined by maximum likelihood. A likelihood is a conditional probability (e.g., P(Y|X), the probability of Y given X). The likelihood function (L) measures the probability of observing the particular set of dependent variable values $(Y_1, Y_2, \ldots, Y_n)$ that occur in the sample data set. It is written as the probability of the product of the dependent variables:

$$L = Prob(Y_1 * Y_2 * * * Y_n)$$

The higher the likelihood function, the higher the probability of observing the Ys in the sample. MLE involves finding the coefficients ($\alpha$, $\beta_1$, $\beta_2$, ...) that makes the log of the likelihood function (LL<0) as large as possible or −2 times the log of the likelihood function (−2LL) as small as possible. In MLE, some initial estimates of the parameters $\alpha$, $\beta_1$, $\beta_2$, ... are made. Then the likelihood of the data given these parameter estimates is computed. The parameter estimates are improved the likelihood of the data is recalculated. This process is repeated until the parameter estimates do not change much (for example, a change of less than 0.01 or 0.001 in the probability). Examples of logistic regression and fitting logistic regression models are found in Hastie, *The Elements of Statistical Learning*, Springer, New York, 2001, pp. 95-100 which is incorporated herein in its entirety.

5.8 Neural Networks

In another embodiment, the expression measured for each of the biomarkers of the present invention can be used to train a neural network. A neural network is a two-stage regression or classification model. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. As such a neural network can be applied to allow identification of biomarkers which differentiate as between more than two populations. In one specific example, a neural network can be trained using expression data from the products of the biomarkers in Table 1 including those noted in Table 3 to identify those combinations of biomarkers which are specific for mild osteoarthritis as compared with any individuals not having osteoarthritis. As a result, the trained neural network can be used to directly identify combination of biomarkers useful to diagnose mild osteoarthritis. In some embodiments, the back-propagation neural network (see, for example Abdi, 1994, "A neural network primer", J. Biol. System. 2, 247-283) containing a single hidden layer of ten neurons (ten hidden units) found in EasyNN-Plus version 4.0 g software package (Neural Planner Software Inc.) is used.

Neural networks are described in Duda et al., 2001, *Pattern Classification*, Second Edition, John Wiley & Sons, Inc., New York; and Hastie et al., 2001, *The Elements of Statistical Learning*, Springer-Verlag, New York which is incorporated herein in its entirety.

5.9 Other Mathematical Models

The pattern classification and statistical techniques described above are merely examples of the types of models that can be used to construct a model for mild OA classification, for example clustering as described on pages 211-256 of Duda and Hart, *Pattern Classification and Scene Analysis*, 1973, John Wiley & Sons, Inc., New York, incorporated herein by reference in its entirety; Principal component analysis, (see for Jolliffe, 1986, *Principal Component Analysis*, Springer, New York, incorporated herein by reference); nearest neighbour classifier analysis, (see for example Duda, *Pattern Classification*, Second Edition, 2001, John Wiley & Sons, Inc; and Hastie, 2001, *The Elements of Statistical Learning*, Springer, New York); linear discriminant analysis, (see for example Duda, *Pattern Classification*, Second Edition, 2001, John Wiley & Sons, Inc; and Hastie, 2001, *The Elements of Statistical Learning*, Springer, New York; Venables & Ripley, 1997, *Modern Applied Statistics with s-plus*, Springer, New York); Support Vector Machines (see, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York, all of which are incorporated herein by reference.)

5.10 Evaluation of Classifiers

Once one or more classifiers have been computed using a mathematical model, the classifiers can be evaluated to determine which of the classifiers are effective for the desired purpose. For example, each classifier is evaluated or scored for its ability to properly characterize each individual of the training population as having mild OA or not having OA. For example one can evaluate the classifiers using cross validation Leave One out Cross Validation, n-fold cross validation, jackknife analysis using standard statistical methods and disclosed. As used herein the process of evaluating the classifiers is termed as "scoring. In some embodiments, scoring is done using the training population. In other embodiments, scoring is done using a "scoring population" as described herein. In one embodiment, the scoring population includes members of the training population in addition to one or more members not used in the training population. In some embodiments, five percent or less, ten percent or less, twenty percent or less, thirty percent or less, fifty percent or less, or ninety percent or less of the members of the training population are common to the scoring population.

In some embodiments, the Percent Correct Predictions statistic is used to score each classifier. The "Percent Correct Predictions" statistic assumes that if the estimated p is greater than or equal to 0.5, then the event is expected to occur and to not occur otherwise. By assigning these probabilities zeros and ones, a comparison can be made to the values of the samples in the training population to determine what percentage of the training population was sampled correctly.

In one embodiment, the method used to evaluate the classifier for its ability to properly characterize each individual of the training population is a method which evaluates the classifiers sensitivity (TPF, true positive fraction) and 1-specificity (TNF, true negative fraction). For example, in one embodiment the Receiver Operating Characteristic ("ROC") is utilised. The ROC provides several parameters to evaluate both the sensitivity and specificity of the diagnostic result of the equation generated. For example, in one embodiment the ROC area (area under the curve) is used to evaluate the equations. In a preferred embodiment, an ROC area greater than 0.5, 0.6, 0.7, 0.8, 0.9 is preferred. A perfect ROC area score of 1.0 on the other hand indicates with both 100% sensitivity and 100% specificity.

As would be understood by those of skill in the relevant arts, area under the curve converts the two dimensional information contained in the ROC curve into one dimensional information. In other embodiments, information from the two dimensional aspect of the ROC curve is utilized directly. For example, the ROC curve also provides information with respect to the sensitivity and specificity of the classifier. In some embodiments, classifiers are selected on the basis of either sensitivity or specificity. This can be an important scoring indicator. For example, a diagnostic classifier with high specificity (i.e. smaller number of false negatives) may be important in situations where it is safer to misdiagnosis an individual as having disease rather than misdiagnosing a person as normal. Therefore in some embodiments, a cutoff can be set for either sensitivity or specificity and the classifier ranked or scored on the basis of the remaining variable. In some embodiments, ROC curves are generated for each classifier using any known method to generate data. In some embodiments data is generated using microarray. In some embodiments data is generated utilizing quantitative RT-PCR.

In some embodiments, a classifier is a weighted logistic regression model characterized by a multicategory logit model. For example, in some embodiments, a classifier discriminates between two different trait groups. In other embodiments, a classifier discriminates between more than two different trait groups. Logit models, including multicategory logit models are described in Agresti, *An Introduction to Categorical Data Analysis*, John Wiley & Sons, Inc., 1996, New York, Chapters 7 and 8, which is hereby incorporated by reference. Table 10 illustrates the data that is used to form an ROC curve based on expression data applied to a mathematical model that uses the logit:

$$\ln [p/(1-p)] = \alpha + \beta_1 X_1 + \beta_2 X_2 + \epsilon.$$

TABLE 10

Values for the logit $\ln[p/(1-p)] = \alpha + \beta_1 X_1 + \beta_2 X_2 + \epsilon$ using data set 44

| $\ln[p/(1-p)]$ | Presence/Absence of a Trait |
|---|---|
| 0.98 | Y |
| 0.97 | Y |
| 0.95 | Y |
| 0.93 | Y |
| 0.91 | N |
| 0.11 | Y |
| 0.07 | N |
| 0.03 | N |

Each row in Table 10 corresponds to a different specimen in the scoring population. The left column represents the results of the logit for the classifier being sampled. The specimens in Table 10 are ranked by the logit score listed in the left hand column. The right hand column details the presence or absence of the trait that is being considered by the regression equation. Table 10 can be used to compute a ROC curve in which each row in Table 10 is considered a threshold cutoff value in order to compute ROC curve datapoints. Then, the area under the ROC curve can be computed in order to assess the predictive quality of the classifier.

5.11 Products of the Biomarkers of the Invention

As would be understood by a person skilled in the art, the identification of one or more of a combination of biomarkers which are differentially expressed as between mild OA and non OA allows the diagnosis of mild OA for a test individual using data reflective of the expression of the products of the biomarkers (gene) of the combination identified.

The products of each of the biomarkers of the invention includes both RNA and protein. RNA products of the biomarkers of the invention are transcriptional products of the biomarkers of the invention and include populations of hnRNA, mRNA, and one or more spliced variants of mRNA. To practice the invention, measurement of one or more of the populations of the RNA products of the biomarkers of the invention can be used for purposes of diagnosis. More particularly, measurement of those populations of RNA products of the biomarkers which are differentially expressed as between mild OA and non OA are encompassed herein.

In one embodiment of the invention, the RNA products of the biomarkers of the invention which are measured is the population of RNA products including the hnRNA, the mRNA, and all of the spliced variants of the mRNA. In another embodiment, the RNA products of the biomarkers of the invention which are measured are the population of mRNA. In another embodiment of the invention the RNA products of the biomarkers of the invention which are measured is the population of mRNA which is expressed in blood or in chondrocytes or in synovial fluid. In yet another embodiment of the invention, RNA products of the biomarkers of the invention which are measured are the population of one or more spliced variants of the mRNA. In yet another embodiment of the invention, RNA products of the biomarkers of the invention which are measured is the population of one or more spliced variants of the mRNA which are expressed in blood or in chondrocytes or in synovial fluid. In yet another embodiment of the invention, RNA products of the biomarkers of the invention are those RNA products which are listed in Table 3 and Table 5.

Protein products of the biomarkers of the invention are also included within the scope of the invention and include the entire population of protein products arising from a biomarker of the invention. As would be understood by a person skilled in the art, the entire population of proteins arising from a biomarker of the invention include proteins, protein variants arising from spliced mRNA variants, and post translationally modified proteins. In one embodiment the protein products of the biomarkers of the invention are all proteins corresponding to the locus link (Gene ID) identified in Table 1 and Table 4. In another embodiment of the invention the protein products of the biomarkers of the invention which are measured are the proteins corresponding to the locus link in Table 1 and Table 4 which are expressed in blood. In yet another embodiment of the invention, protein products of the biomarkers of the invention are those products which are listed in Table 3 and Table 5. To practice the invention, measurement of one or more of the populations of the protein products of the biomarkers of the invention can be used for purposes of diagnosis. More particularly, measurement of those populations of protein products of the biomarkers which are differentially expressed as between individuals with mild OA and individuals without OA are useful for purposes of diagnosis and are encompassed herein.

In one embodiment of the invention the protein products of the biomarkers of the invention which are measured are the entire population of protein products translated from the RNA products of the biomarkers of the invention. In another embodiment, the protein products of the biomarkers of the invention are those protein products which are expressed in blood and/or chondrocytes and/or synovial fluid. In yet another embodiment of the invention, the protein products of any one or more of the biomarkers of the invention are any one or more of the protein products translated from any one or more of the mRNA spliced variants. In yet another embodiment of the invention, the protein products of the biomarkers of the invention are any one or more of the protein products translated from any one or more of the mRNA spliced variants expressed in blood and/or chondrocytes and/or synovial fluid.

5.12 Use of the Combinations Identified to Diagnose Mild OA

As described herein, the application of a mathematical model (e.g. logistic regression etc.) using the data corresponding to the level of expression of each biomarker of the tested biomarker combination creates a classifier. Classifiers are mathematical functions which convert data representative of each of the biomarkers of the tested biomarker combination into a diagnostic determination as between whether an individual has mild OA or does not have OA. Classifiers can be scored using methods described herein to determine the classifiers ability to properly call (i.e. diagnose) individuals within the test population and/or the scoring population as either having mild OA or not having OA. Classifiers can be used directly to diagnose an individual as having mild OA or not having OA, by providing data for a test individual for input into the classifier resulting in a diagnostic determination. For example, where the classifier is developed using logistic regression the classifier takes the form as follows:

$$Y = \alpha + \beta_1 X_1 + \beta_2 X_2 + \ldots + \beta_k X_k + \epsilon$$

where $X_1, X_2, \ldots X_k$ of the equation represent the measured values representative of the level of the gene product in the tissue of interest for the k select biomarkers of the combination used to generate the classifier. Thus to diagnose a test individual, measurement values for each biomarker of the equation are input and the value of Y determines the diagnosis of said test individual.

The combinations identified can also be used independently of the classifier. For example, if a classifier is chosen (e.g. has an ROC area under the curve score of 0.9 indicating high sensitivity and high specificity) which uses three biomarkers then one can measure the abundance of the products for each of the three biomarkers in a test individual and compare the measurement of the abundance of each of the three biomarkers with one or more individuals from a control population of individuals having mild OA and/or one or more individuals form a control population of individuals not having OA so as to determine whether the pattern of expression of the test individual is more similar to the controls having mild OA or the controls not having OA. In a preferred embodiment, one would use the classifier generated so as to diagnose an individual, e.g., by the measure of the level of expression of the RNA and/or protein products of the biomarkers of the combination identified in a test individual for input into the classifier. In one embodiment, the same method is used to generate the expression data used to generate the mathematical model as is used to diagnose the test individual.

5.13 Use of the Combinations Identified to Monitor Regression of OA

The invention teaches the ability to identify useful combinations of biomarkers and classifiers for those combinations for the purposes of diagnosing an individual as having a mild OA or not having OA. It would be understood by a person skilled in the art that combinations and classifiers which are diagnostic for a mild OA and non OA are also useful in determining whether an individual has progressed or regressed with regards to the severity of their OA, for example, in response to treatment. For example, an individual can be diagnosed as having mild OA prior to treatment using one or more of the combinations identified. Subsequent to treatment the individual could again be tested to determine whether said individual still has mild OA. In the event that the individual can no longer be identified the stage prior to treatment, this may in itself suggest treatment is effective. In addition, the treatment may lead to regression of the stage of OA such that the individual now is diagnosed as not having OA. As such, one or more of the combinations identified as specific to diagnosing a stage of OA is useful so as to monitor regression of OA in response to treatment.

5.14 Polynucleotides Used to Measure the Products of the Biomarkers of the Invention As a means of measuring the expression of the RNA products of the biomarkers of the invention, one can use one or more of the following as would be understood by a person skilled in the art in combination with one or more methods to measure RNA expression in a sample of the invention: oligonucleotides, cDNA, DNA, RNA, PCR products, synthetic DNA, synthetic RNA, or other combinations of naturally occurring of modified nucleotides which specifically hybridize to one or more of the RNA products of the biomarkers of the invention. In another specific embodiment, the oligonucleotides, cDNA, DNA, RNA, PCR products, synthetic DNA, synthetic RNA, or other combinations of naturally occurring of modified nucleotides oligonucleotides which selectively hybridize to one or more of the RNA products of the biomarker of the invention are used. In a preferred embodiment, the oligonucleotides, cDNA, DNA, RNA, PCR products, synthetic DNA, synthetic RNA, or other combinations of naturally occurring of modified nucleotides oligonucleotides which both specifically and selectively hybridize to one or more of the RNA products of the biomarker of the invention are used.

5.15 Techniques to Measure the RNA Products of the Biomarkers of the Invention

Array Hybridization

In one embodiment of the invention, the polynucleotide used to measure the RNA products of the invention can be used as nucleic acid members stably associated with a support to comprise an array according to one aspect of the invention. The length of a nucleic acid member can range from 8 to 1000 nucleotides in length and are chosen so as to be specific for the RNA products of the biomarkers of the invention. In one embodiment, these members are specific and/or selective for RNA products of the biomarkers of the invention. In yet another embodiment these members are specific and/or selective for the mRNA products of the biomarkers of the invention. In a preferred embodiment, these members are specific and/or selective for all of the variants of the mRNA products of the biomarkers of the invention. In yet another preferred embodiment, these members are specific and/or selective for one or more variants of the mRNA products of the biomarkers of the invention. The nucleic acid members may be single or double stranded, and/or may be oligonucleotides or PCR fragments amplified from cDNA. Preferably oligonucleotides are approximately 20-30 nucleotides in length. ESTs are preferably 100 to 600 nucleotides in length. It will be understood to a person skilled in the art that one can utilize portions of the expressed regions of the biomarkers of the invention as a probe on the array. More particularly oligonucleotides complementary to the genes of the invention and or cDNA or ESTs derived from the genes of the invention are useful. In some embodiments of the invention the polynucleotides capable of specifically and/or selectively hybridizing to RNA products of the biomarkers of the invention can be spotted onto an array for use in the invention. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784. In one embodiment, the array consists of sequences of between 10-1000 nucleotides in length capable of hybridizing to one or more of the products of each of the biomarkers of the invention as disclosed in Table 1 and/or Table 4 including those specific transcripts noted in Table 3 and/or Table 5.

The target nucleic acid samples that are hybridized to and analyzed with an array of the invention are preferably from human cartilage, blood or synovial fluid. A limitation for this procedure lies in the amount of RNA available for use as a target nucleic acid sample. Preferably, at least 1 microgram of total RNA is obtained for use according to this invention. Lesser quantities of RNA can be used in combination with PCR and primers directed to the mRNA subspecies (e.g. poly T oligonucleotides).

Construction of a Nucleic Acid Array

In the subject methods, an array of nucleic acid members stably associated with the surface of a support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/cm$^2$, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In a preferred embodiment, the nucleic acid attached to the surface of the support is cDNA or RNA.

In another preferred embodiment, the nucleic acid attached to the surface of the support is cDNA synthesised by polymerase chain reaction (PCR). Preferably, a nucleic acid member in the array, according to the invention, is at least 10, 25 or 50 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length.

In the arrays of the invention, the nucleic acid compositions are stably associated with the surface of a support, where the support may be a flexible or rigid solid support. By "stably associated" is meant that each nucleic acid member maintains a unique position relative to the solid support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like.

Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of target nucleic acid sequences during the assay in which the array is employed. Generally, the amount of each nucleic acid member stably associated with the solid support of the array is at least about 0.001 ng, preferably at least about 0.02 ng and more preferably at least about 0.05 ng, where the amount may be as high as 1000 ng or higher, but will usually not exceed about 20 ng. Preferably multiple samples corresponding to a single gene are spotted onto the array so as to ensure statistically significant results. Where the nucleic acid member is "spotted" onto the solid support in a spot comprising an overall circular dimension, the diameter of the "spot" will generally range from about 10 to 5,000 µm, usually from about 20 to 2,000 µm and more usually from about 100 to 200 µm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Substrate

An array according to the invention comprises of a substrate sufficient to provide physical support and structure to the associated nucleic acids present thereon under the assay conditions in which the array is employed, particularly under high throughput handling conditions.

The substrate may be biological, non-biological, organic, inorganic, or a combination of any of these, existing as particles, strands, precipitates, gels, sheets, tubing, spheres, beads, containers, capillaries, pads, slices, films, plates, slides, chips, etc. The substrate may have any convenient shape, such as a disc, square, sphere, circle, etc. The substrate is preferably flat or planar but may take on a variety of alternative surface configurations. The substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure.

In a preferred embodiment the substrate is flat glass or single-crystal silicon. According to some embodiments, the surface of the substrate is etched using well-known techniques to provide for desired surface features. For example, by way of formation of trenches, v-grooves, mesa structures, or the like, the synthesis regions may be more closely placed within the focus point of impinging light, be provided with reflective "mirror" structures for maximization of light collection from fluorescent sources, etc.

Surfaces on the substrate will usually, though not always, be composed of the same material as the substrate. Alternatively, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which are carboxyl, amino, hydroxyl, or the like. Most preferably, the surface will be optically transparent and will have surface Si—OH functionalities, such as are found on silica surfaces.

The surface of the substrate is preferably provided with a layer of linker molecules, although it will be understood that the linker molecules are not required elements of the invention. The linker molecules are preferably of sufficient length to permit nucleic acids of the invention and on a substrate to hybridize to other nucleic acid molecules and to interact freely with molecules exposed to the substrate.

Often, the substrate is a silicon or glass surface, (poly) tetrafluoroethylene, (poly)vinylidenedifluoride, polystyrene, polycarbonate, a charged membrane, such as nylon 66 or nitrocellulose, or combinations thereof. In a preferred embodiment, the support is glass. Preferably, at least one surface of the substrate will be substantially flat. Preferably, the surface of the support will contain reactive groups, including, but not limited to, carboxyl, amino, hydroxyl, thiol, or the like. In one embodiment, the surface is optically transparent. In a preferred embodiment, the substrate is a poly-lysine coated slide or Gamma amino propyl silane-coated Corning Microarray Technology-GAPS or CMT-GAP2 coated slides.

Any support to which a nucleic acid member may be attached may be used in the invention. Examples of suitable support materials include, but are not limited to, silicates such as glass and silica gel, cellulose and nitrocellulose papers, nylon, polystyrene, polymethacrylate, latex, rubber, and fluorocarbon resins such as TEFLON™.

The support material may be used in a wide variety of shapes including, but not limited to slides and beads. Slides provide several functional advantages and thus are a preferred form of support. Due to their flat surface, probe and hybridization reagents are minimized using glass slides. Slides also enable the targeted application of reagents, are easy to keep at a constant temperature, are easy to wash and facilitate the direct visualization of RNA and/or DNA immobilized on the support. Removal of RNA and/or DNA immobilized on the support is also facilitated using slides.

The particular material selected as the support is not essential to the invention, as long as it provides the described function. Normally, those who make or use the invention will select the best commercially available material based upon the economics of cost and availability, the expected application requirements of the final product, and the demands of the overall manufacturing process.

Spotting Method

In one aspect, the invention provides for arrays where each nucleic acid member comprising the array is spotted onto a support.

Preferably, spotting is carried out as follows. PCR products (~40 µl) of cDNA clones from osteoarthritis, fetal or normal cartilage cDNA libraries, in the same 96-well tubes used for amplification, are precipitated with 4 µl (1/10 volume) of 3M sodium acetate (pH 5.2) and 100 µl (2.5 volumes) of ethanol and stored overnight at −20° C. They are then centrifuged at 3,300 rpm at 4° C. for 1 hour. The obtained pellets are washed with 50 µl ice-cold 70% ethanol and centrifuged again for 30 minutes. The pellets are then air-dried and resuspended well in 20 µl 3×SSC or in 50% dimethylsulfoxide (DMSO) overnight. The samples are then spotted, either singly or in duplicate, onto slides using a robotic GMS 417 or 427 arrayer (Affymetrix, Ca).

The boundaries of the spots on the microarray may be marked with a diamond scriber (as the spots become invisible after post-processing). The arrays are rehydrated by suspending the slides over a dish of warm particle free $ddH_2O$ for approximately one minute (the spots will swell slightly but will not run into each other) and snap-dried on a 70-80° C. inverted heating block for 3 seconds. Nucleic acid is then UV crosslinked to the slide (Stratagene, Stratalinker, 65 mJ—set display to "650" which is 650×100 uJ) or the array is baked at 80 C for two to four hours prior to hybridization. The arrays are placed in a slide rack. An empty slide chamber is prepared and filled with the following solution: 3.0 grams of succinic anhydride (Aldrich) was dissolved in 189 ml of 1-methyl-2-pyrrolidinone (rapid addition of reagent is crucial); immediately after the last flake of succinic anhydride is dissolved, 21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. $ddH_2O$ for 2 minutes, followed by plunging five times in 95% ethanol. The slides are then air dried by allowing excess ethanol to drip onto paper towels. The arrays are stored in the slide box at room temperature until use.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference, for teaching methods of polymer attachment.

Alternatively, spotting may be carried out using contact printing technology as is known in the art.

Use of a Microarray

Nucleic acid arrays according to the invention can be used in high throughput techniques that can assay a large number of nucleic acids in a sample comprising one or more target nucleic acid sequences. The arrays of the subject invention find use in a variety of applications, including gene expression analysis, diagnosis of osteoarthritis and prognosis of osteoarthritis, monitoring a patient's response to therapy, drug screening, and the like.

The arrays are also useful in broad scale expression screening for drug discovery and research, such as the effect of a particular active agent on the expression pattern of genes of the invention, where such information is used to reveal drug efficacy and toxicity, environmental monitoring, disease research and the like.

Arrays can be made using at least one, more preferably a combination of these sequences, as a means of diagnosing mild osteoarthritis, or for purposes of monitoring efficacy of treatment.

The choice of a standard sample would be well understood by a person skilled in the art, and would include a sample complementary to RNA isolated from one or more normal individuals, wherein a normal individual is an individual not suffering from osteoarthritis. In the case of monitoring efficacy of treatment or identifying stage specific osteoarthritis including mild OA, it would be understood by a person skilled in the art that a control would include samples from persons suffering various degrees of osteoarthritis and/or persons responding to treatment. Standard samples would also include a sample complementary to RNA isolated from chondrocytes, or from blood, or from synovial fluid.

Target Preparation

The targets for the arrays according to the invention are preferably derived from human cartilage, blood or synovial fluid.

A target nucleic acid is capable of binding to a nucleic acid probe or nucleic acid member of complementary sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable target nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid targets used herein are preferably derived from human cartilage, blood or synovial fluid. Preferably, the targets are nucleic acids derived from human cartilage, blood or synovial fluid extracts. Nucleic acids can be single- or double-stranded DNA, RNA, or DNA-RNA hybrids synthesised from human cartilage, blood or synovial fluid mRNA extracts using methods known in the art, for example, reverse transcription or PCR.

In the simplest embodiment, such a nucleic acid target comprises total mRNA or a nucleic acid sample corresponding to mRNA (e.g., cDNA) isolated from cartilage, blood, or synovial fluid samples. In another embodiment, total mRNA is isolated from a given sample using, for example, an acid guanidinium-phenol-chloroform extraction method and polyA+mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the target nucleic acid sample prior to hybridization, for example, when synovial fluid is used. One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989, *Genomics*, 4:560; Landegren, et al., 1988, *Science*, 241:1077 and Barringer, et al., 1990, *Gene*, 89:117, transcription amplification (Kwoh, et al., 1989, *Proc. Natl. Acad. Sci. USA*, 86: 1173), and self-sustained sequence replication (Guatelli, et al., 1990, *Proc. Nat. Acad. Sci. USA*, 87: 1874).

In a particularly preferred embodiment, the target nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, *Proc. Natl. Acad. Sci. USA*, 87: 1663-1667 who demonstrate that in vitro amplification according to this method preserves the relative frequencies of the various RNA transcripts. Moreover, Eberwine et al. *Proc. Natl. Acad. Sci. USA*, 89: 3010-3014 provide a protocol that uses two rounds of amplification via in vitro transcription to achieve greater than 106 fold amplification of the original starting material thereby permitting expression monitoring even where biological samples are limited.

Labelling of Target or Nucleic Acid Probe

Either the target or the probe can be labelled.

Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labelled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, 35S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labelled primers or labelled nucleotides will provide a labelled amplification product. In a preferred embodiment, transcription amplification, as described above, using a labelled nucleotide (e.g. fluorescein-labelled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labelled RNA) by kinasing of the nucleic acid and subsequent attachment (ligation) of a nucleic acid linker joining the sample nucleic acid to a label (e.g., a fluorophore).

In a preferred embodiment, the fluorescent modifications are by cyanine dyes e.g. Cy-3/Cy-5 dUTP, Cy-3/Cy-5 dCTP (Amersham Pharmacia) or alexa dyes (Khan, et al., 1998, *Cancer Res.* 58:5009-5013).

In a preferred embodiment, the two target samples used for comparison are labelled with different fluorescent dyes which produce distinguishable detection signals, for example, targets made from normal cartilage are labelled with Cy5 and targets made from mild osteoarthritis cartilage are labelled with Cy3. The differently labelled target samples are hybridized to the same microarray simultaneously. In a preferred embodiment, the labelled targets are purified using methods known in the art, e.g., by ethanol purification or column purification.

In a preferred embodiment, the target will include one or more control molecules which hybridize to control probes on the microarray to normalize signals generated from the microarray. Preferably, labelled normalization targets are nucleic acid sequences that are perfectly complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes, thereby normalizing the measurements.

Preferred normalization targets are selected to reflect the average length of the other targets present in the sample, however, they are selected to cover a range of lengths. The normalization control(s) also can be selected to reflect the (average) base composition of the other probes in the array, however, in a preferred embodiment, only one or a few normalization probes are used and they are selected such that they hybridize well (i.e., have no secondary structure and do not self hybridize) and do not match any target molecules.

Normalization probes are localised at any position in the array or at multiple positions throughout the array to control for spatial variation in hybridization efficiency. In a preferred embodiment, normalization controls are located at the corners or edges of the array as well as in the middle.

Hybridization Conditions

Nucleic acid hybridization involves providing a denatured probe or target nucleic acid member and target nucleic acid under conditions where the probe or target nucleic acid member and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., *Laboratory Techniques in Biochemistry and Molecular Biology*, Vol. 24: *Hybridization With Nucleic acid Probes*, P. Tijssen, ed. Elsevier, N.Y., (1993)).

Following hybridization, non-hybridized labelled or unlabeled nucleic acid is removed from the support surface, conveniently by washing, thereby generating a pattern of hybridized target nucleic acid on the substrate surface. A variety of wash solutions are known to those of skill in the art and may be used. The resultant hybridization patterns of labelled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labelled target nucleic acids to obtain a count or absolute value of the copy number of each end-labelled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two cartilage samples to be compared, where each sample is labelled with a different fluorescent dye.

Each element of the microarray is scanned for the first fluorescent color. The intensity of the fluorescence at each array element is proportional to the expression level of that gene in the sample.

The scanning operation is repeated for the second fluorescent label. The ratio of the two fluorescent intensities provides a highly accurate and quantitative measurement of the relative gene expression level in the two tissue samples.

In a preferred embodiment, fluorescence intensities of immobilized target nucleic acid sequences were determined from images taken with a custom confocal microscope equipped with laser excitation sources and interference filters appropriate for the Cy3 and Cy5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each target are as described (Khan, et al., 1998, *Cancer Res*. 58:5009-5013. Chen, et al., 1997, *Biomed. Optics* 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy 3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A linear regression approach is used for normalization and assumes that a scatter plot of the measured Cy5 versus Cy3 intensities should have a slope of one. The average of the ratios is calculated and used to rescale the data and adjust the slope to one. A ratio of expression not equal to 1 is used as an indication of differential gene expression.

In a particularly preferred embodiment, where it is desired to quantify the transcription level (and thereby expression) of one or more nucleic acid sequences in a sample, the target nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear and still provide meaningful results. Thus, for example, an assay where a 5 fold difference in concentration of the target mRNA results in a 3- to 6-fold difference in hybridization intensity is sufficient for most purposes. Where more precise quantification is required, appropriate controls are run to correct for variations introduced in sample preparation and hybridization as described herein. In addition, serial dilutions of "standard" target mRNAs are used to prepare calibration curves according to methods well known to those of skill in the art. Of course, where simple detection of the presence or absence of a transcript is desired, no elaborate control or calibration is required.

For example, if an nucleic acid member on an array is not labelled after hybridization, this indicates that the gene comprising that nucleic acid member is not expressed in either sample. If a nucleic acid member is labelled with a single color, it indicates that a labelled gene was expressed only in one sample. The labeling of a nucleic acid member comprising an array with both colors indicates that the gene was expressed in both samples. Even genes expressed once per cell are detected (1 part in 100,000 sensitivity). A difference in expression intensity in the two samples being compared is indicative of differential expression, the ratio of the intensity in the two samples being not equal to 1.0, preferably less than 0.7 or greater than 1.2, more preferably less than 0.5 or greater than 1.5.

RT-PCR

In aspect of the invention, the level of the expression of the RNA products of the biomarkers of the invention can be measured by amplifying the RNA products of the biomarkers from a sample using reverse transcription (RT) in combination with the polymerase chain reaction (PCR). In accordance with one embodiment of the invention, the RT can be quantitative as would be understood to a person skilled in the art.

Total RNA, or mRNA from a sample is used as a template and a primer specific to the transcribed portion of a biomarker of the invention is used to initiate reverse transcription. Methods of reverse transcribing RNA into cDNA are well known and described in Sambrook et al., 1989, supra. Primer design can be accomplished utilizing commercially available software (e.g., Primer Designer 1.0, Scientific Software etc.). using methods that are standard and well known in the art.

One embodiment of a protocol used to design and select primers encompassed by the invention describes the principle and steps involved in the design of primers for use in real-time PCR with SYBR-Green assay. Preferably, this protocol uses The National Center for Biotechnology Information (NCBI) search engine and application of PrimerQuest primer design software. The PrimerQuest is web-base software developed for Integrated DNA Technologies, Inc. (IDT). This software is based on Primer3 developed by the Whitehead Institute for Biomedical Research.

Preferred guidelines used for designing primers encompassed by the invention are that the product or amplicon length preferably be 100-150 bases, that the optimum Tm preferably be 60° C., with the preferable ranges from 58-62° C. also being acceptable, and that the most preferable GC content be 50%, with preferable ranges from 45-55% also being acceptable. It is preferable that complementary strings of the three bases at the 3'-end of each primer to itself or the other primer be avoided in order to reduce "primer-dimer" formation. Also it is preferable that complementary sequences within a primer sequence and between the primers of a pair be avoided. Preferably, runs of 3 or more G's or C's at the 3'-end are avoided, as well as single base repeats greater than 3 bases. Unbalanced distribution of G/C- and A/T rich domains preferably are avoided, and preferably the primer has a G or C is the 3'-end. It is preferable that the 3'-end of the primers not be a T since primers with a T at the 3'-end have a greater tolerance to mismatch. It is preferable to avoid mismatches, especially at the 3'-end; and it is preferable to position at least 7 unique bases at the 3'-end. Preferably, genomic amplification is avoided, and as such, it is preferable that any one primers should span an intron. Preferably, primers should be designed so that one half or at least 7 nucleotides of the primer hybridizes to the 3' end of one exon and the remaining to the 5' end of the adjacent exon.

Primer Software programs can be used to aid in the design and selection of primers encompassed by the instant invention, such as "The Primer Quest software" which is available through the following web site link: biotools.idtdna.com/primerquest/.

The following website links are useful when searching and updating sequence information from the Human Genome Database for use in biomarker primer design: 1) the NCBI LocusLink Homepage: www.ncbi.nlm.nih.gov/LocusLink/, and 2) Ensemble Human Genome Browser: www.ensembl.org/Homo_sapiens, preferably using pertinant biomarker information such as Gene or Sequence Description, Accession or Sequence ID, Gene Symbol, RefSeq #, and/or UniGene #.

Once the correct target DNA Sequence has been obtained from which the primers will be generated, it is preferable to note the Exon-Intron Boundaries from links of the LocusLink or from the Ensembl Gene Browser for the Gene Interest. One preferable means to optimize primer design is to use the three options of BASIC, STANDARD and ADVANCE, in the PrimerQuest software.

A preferable use of the BASIC Function of PrimerQuest software is first, under Sequence Information, to enter the name of the primer into the [Name] box and Cut and paste the target sequence into [Sequence] box, selecting to design a PCR Primer using the parameter settings of Real-Time PCR. Under the standard sequence design, it is preferable to select 50 as the Number of Primer Set to Return and human as the Mispriming Library to use. It is preferable to enter the following selections under the Advanced Function of Standard Primer Design: Optimum Primer Size: 20 (nt), Optimum Primer Tm: 60 (° C.), Optimum Primer GC %: 50(%), Product Size Range: 100-150. Further, under the standard function, the following options preferably can be fine-tuned; the primer selection; Targets, Excluded Regions, Included Regions and Start Codon Position.

Once the required parameters are entered or selected, the Primer Quest search for the possible primer selections is initiated producing a detail description on potential forward and reverse primers, including the actual sequence, its start position, length, Tm, GC %, product size penalties values, and a means to predict secondary structure—mFold. The following two criteria are most useful: preferably delta G should be greater than $-3.0$ kcal·mol$-1$, and preferably the TM should be less than 50° C. and not greater than 55° C. The dot plot is a little more difficult to interpret, but in general it is preferable not to select a primer that produces a long diagonal line of black dots in the dot plot since it is most likely to form a hairpin.

Preferably, the primer should be unique to the target sequence and not match to a pseudogene, which can be verified by using [BLAST] to examine the specificity of the primer. Preferably, the OligoAnalyzer 3.0 provided by IDT BioTools can be used to examine the possibility of Self-Dimer and Hetero-Dimer formation. Preferably, the information and guidelines provided by IDT BioTools or Primer3 can be used for the selection of the best possible primer pair(s) for the investigation of the Biomarkers of the instant invention. It is preferable that only those primers that produced a single amplicon with the size matched to the expected product, as determined by the melting curve analysis and agarose gel electrophoresis separation be used in the biomarker investigation.

The following related references are hereby incorporated by reference; Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155, Innis, M. A., and Gelfand, D. H. (1990) Optimization of PCRs. In: PCR protocols, A Guide to Methods and Applications (Eds. Innis, M. A., Gelfand, D. H., Sninsky, J. J., and White, T. J.) Academic Press, San Diego, 3-12, Sharrocks, A. D. (1994) The design of primers for PCR. In: PCR Technology, Current Innovations (Eds. Griffin, H. G., and Griffin, A. M, Ed.) CRC Press, London, 5-11.

The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, Methods Enzymol., 155: 335, which is incorporated herein by reference. PCR is performed using template DNA (at least 1 fg; more usefully, 1-1000 ng) and at least 25 pmol of oligonucleotide primers. A typical reaction mixture includes: 2 µl of DNA, 25 pmol of oligonucleotide primer, 2.5 µl of 10H PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

QRT-PCR, which is quantitative in nature, can also be performed to provide a quantitative measure of gene expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a fluorescence proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the flourescense increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880), isothermal amplification method (see, e.g., Walker et al. (1992) PNAS 89:382-396), strand displacement amplification (SDA), repair chain reaction, Asymmetric Quantitative PCR (see, e.g., U.S. Publication No. US200330134307A1) and the multiplex microsphere bead assay described in Fuja et al., 2004, Journal of Biotechnology 108:193-205.

The level of gene expression can be measured by amplifying RNA from a sample using transcription based amplification systems (TAS), including nucleic acid sequence amplification (NASBA) and 3SR. See, e.g., Kwoh et al (1989) PNAS USA 86:1173; International Publication No. WO 88/10315; and U.S. Pat. No. 6,329,179. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 1989. Several techniques for detecting PCR products quantitatively without electrophoresis may also be used according to the invention (see for example *PCR Protocols, A Guide to Methods and Applications*, Innis et al., Academic Press, Inc. N.Y., (1990)). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

Amplification products must be visualized in order to confirm amplification of the nucleic acid sequences of interest. One typical visualization method involves staining of a gel with ethidium bromide and visualization under LTV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe preferably is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 1989, supra. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Nuclease Protection Assays

In another embodiment of the invention, Nuclease protection assays (including both ribonuclease protection assays and S1 nuclease assays) can be used to detect and quantitate the RNA products of the biomarkers of the invention. In nuclease protection assays, an antisense probe (labelled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 µg of sample RNA, compared with the 20-30 µg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Northern Blots

A standard Northern blot assay can also be used to ascertain an RNA transcript size, identify alternatively spliced RNA transcripts, and the relative amounts of RNA products of the biomarker of the invention, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labelled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labelled probe, e.g., a radiolabelled cDNA, either containing the full-length, single stranded DNA or a fragment of that DNA sequence may be any length up to at least 20, at least 30, at least 50, or at least 100 consecutive nucleotides in length. The probe can be labelled by any of the many different methods known to those skilled in this art. The labels most commonly employed for these studies are radioactive elements, enzymes, chemicals that fluoresce when exposed to ultraviolet light, and others. A number of fluorescent materials are known and can be utilised as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labelled with a radioactive element or with an enzyme. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilised colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilised. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

5.16 Techniques to Measure the Protein Products of the Biomarkers of the Invention Protein Products Standard techniques can also be utilised for determining the amount of the protein or proteins of interest present in a sample. For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, preferably an antibody with a detectable label.

For such detection methods, protein from the sample to be analyzed can easily be isolated using techniques which are well known to those of skill in the art. Protein isolation methods can, for example, be such as those described in Harlow and Lane (Harlow, E. and Lane, D., *Antibodies: A Laboratory Manual*, Cold Spring Harbor Laboratory Press, Cold Spring Harbor, N.Y. (1988)).

Preferred methods for the detection of the protein or proteins of interest involve their detection via interaction with a protein-specific antibody. For example, antibodies directed a protein of interest can be utilised as described herein. Antibodies can be generated utilising standard techniques well known to those of skill in the art. See, e.g., Section 5.19.1 of this application and Section 5.2 of U.S. Publication No. 20040018200 for a more detailed discussion of such antibody generation techniques, which is incorporated herein by reference. Briefly, such antibodies can be polyclonal, or more preferably, monoclonal. An intact antibody, or an antigen binding antibody fragment (e.g., Fab or $F(ab')_2$) can, for example, be used. Preferably, the antibody is a human or humanized antibody.

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labelled antibody thereto that is directed to a protein. The antibody (or fragment) is preferably applied by overlaying the labelled antibody (or fragment) onto a biological sample. Through the use of such a procedure, it is possible to determine not only the presence of the protein of interest, but also its distribution, its presence in cells (e.g., chondrocytes and lymphocytes) within the sample. A wide variety of well-known histological methods (such as staining procedures) can be utilised in order to achieve such in situ detection.

Immunoassays for a protein of interest typically comprise incubating a biological sample of a detectably labelled antibody capable of identifying a protein of interest, and detecting the bound antibody by any of a number of techniques well-known in the art. As discussed in more detail, below, the term "labelled" can refer to direct labeling of the antibody via, e.g., coupling (i.e., physically linking) a detectable substance to the antibody, and can also refer to indirect labeling of the antibody by reactivity with another reagent that is directly labelled. Examples of indirect labeling include detection of a primary antibody using a fluorescently labelled secondary antibody.

For example, the biological sample can be brought in contact with and immobilized onto a phase support or carrier such as nitrocellulose, or other support which is capable of immobilizing cells, cell particles or soluble proteins. The support can then be washed with suitable buffers followed by treatment with the detectably labelled fingerprint gene-specific antibody. The phase support can then be washed with the buffer a second time to remove unbound antibody. The amount of bound label on support can then be detected by conventional means.

By "phase support or carrier" in the context of proteinaceous agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a specific antibody can be detectably labelled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labelled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labelled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Protein Arrays

Polypeptides which specifically and/or selectively bind to the protein products of the biomarkers of the invention can be immobilized on a protein array. The protein array can be used as a diagnostic tool, e.g., to screen medical samples (such as isolated cells, blood, synovial fluid, sera, biopsies, and the like) for the presence of the polypeptides protein products of the biomarkers of the invention. The protein array can also include antibodies as well as other ligands, e.g., that bind to the polypeptides encoded by the biomarkers of the invention.

Methods of producing polypeptide arrays are described, e.g., in De Wildt et al., 2000, Nature Biotech. 18:989-994; Lueking et al., 1999, Anal. Biochem. 270:103-111; Ge, 2000, Nuc. Acids Res. 28:e3; MacBeath and Schreiber, 2000, Science 289:1760-1763; International Publication Nos. WO 01/40803 and WO 99/51773A1; and U.S. Pat. No. 6,406,921. Polypeptides for the array can be spotted at high speed, e.g., using commercially available robotic apparatus, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g. acrylamide, agarose, or another polymer.

For example, the array can be an array of antibodies, e.g., as described in De Wildt, supra. Cells that produce the polypeptide ligands can be grown on a filter in an arrayed format. Polypeptide production is induced, and the expressed antibodies are immobilized to the filter at the location of the cell. Information about the extent of binding at each address of the array can be stored as a profile, e.g., in a computer database.

In one embodiment the array is an array of protein products comprising of any number of up to 1, 2, 3, 4, 5, 6, 7, 8, 9, 10, 15, 20, 25, 30, 35, 40, 45, 50, all or any combination of the biomarkers of the invention. In another embodiment the array is an array of protein products consisting essentially of any number of up to 1, 2, 3, 4, 5, 6, 7, 8, 9, 10, 15, 20, 25, 30, 35, 40, 45, 50, all or any combination of the biomarkers of the invention. In another embodiment the array is an array of protein products consisting essentially of any one or more of the protein products of the biomarkers of Table 1 including those noted in Table 3 along with any one or more of up to 1, 2, 3, 4, 5, 6, 7, 8, 9, 10, 20, 30 40 or all of the protein products of the biomarkers in Table 2. In another embodiment the array is an array of protein products comprising of any one or more of the protein products of the biomarkers of Table 1 including those noted in Table 3 along with any one or more of up to 1, 2, 3, 4, 5, 6, 7, 8, 9, 10, 20, 30 40 or all of the protein products of the biomarkers in Table 2.

In one aspect, the invention provides for antibodies or antigen binding fragments thereof, that are bound to an array which selectively bind to the protein products of the biomarkers of the invention.

5.17 Protein Production

Standard recombinant nucleic acid methods can be used to express a polypeptide or antibody of the invention (e.g., a protein product of a biomarker of the invention). Generally, a nucleic acid sequence encoding the polypeptide is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesised using automated organic synthetic methods. Polypeptides comprising the 5' region, 3' region or internal coding region of a biomarker of the invention, are expressed from nucleic acid expression vectors containing only those nucleotide sequences corresponding to the 5' region, 3' region or internal coding region of a biomarker of the invention. Methods for producing antibodies directed to protein products of a biomarker of the invention, or polypeptides encoded by the 5' region, 3' region or internal coding regions of a biomarker of the invention.

The expression vector for expressing the polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters. In specific embodiments, the promoter is an inducible promoter. In other embodiments, the promoter is a constitutive promoter. In yet other embodiments, the promoter is a tissue-specific promoter.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention provides host cells genetically engineered to contain the polynucleotides of the invention. For example, such host cells may contain nucleic acids of the invention introduced into the host cell using known transformation, transfection or infection methods. The present invention also provides host cells genetically engineered to express the polynucleotides of the invention, wherein such polynucleotides are in operative association with a regulatory sequence heterologous to the host cell which drives expression of the polynucleotides in the cell.

The present invention further provides host cells containing the vectors of the present invention, wherein the nucleic acid has been introduced into the host cell using known transformation, transfection or infection methods. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)). Cell-free translation systems can also be employed to produce such proteins using RNAs derived from the DNA constructs of the present invention.

Any host/vector system can be used to express one or more of the genes listed in Table 2 or splice variants. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety. The most preferred host cells are those which do not normally express the particular polypeptide or which expresses the polypeptide at low natural level.

In a specific embodiment, the host cells are engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesised by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The host of the present invention may also be a yeast or other fungi. In yeast, a number of vectors containing constitutive or inducible promoters may be used. For a review see, Ausubel et al. (eds), *Current Protocols in Molecular Biology*, Vol. 2, Greene Publish. Assoc. & Wiley Interscience, Ch. 13 (1988); Grant et al., 1987, "Expression and Secretion Vectors for Yeast", Methods Enzymol. 153:516-544; Glover, DNA Cloning, Vol. II, IRL Press, Wash., D.C., Ch. 3 (1986); Bitter, 1987, "Heterologous Gene Expression in Yeast", Methods Enzymol. 152:673-684; and Strathern et al. (eds), *The Molecular Biology of the Yeast Saccharomyces*, Cold Spring Harbor Press, Vols. I and II (1982).

Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli*, enterobacteriaceae such as *Serratia marescans*, bacilli such as *Bacillus subtilis, Salmonella typhimurium*, pseudomonads or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

Various mammalian cell culture systems can also be employed to express recombinant protein. Examples of mammalian expression systems include the monkey COS cells such as COS-7 lines of monkey kidney fibroblasts, described by Gluzman, 1981, Cell 23:175 (1981), Chinese Hamster Ovary (CHO) cells, human kidney 293 cells, human epidermal A431 cells, human Colo205 cells, 3T3 cells, CV-1 cells, normal diploid cells, cell strains derived from in vitro culture of primary tissue, primary explants, HeLa cells, mouse L cells, BHK, HL-60, U937, HaK, C127, 3T3, or Jurkat cells, and other cell lines capable of expressing a compatible vector. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

Microbial cells employed in expression of proteins can be disrupted by any convenient method, including freeze-thaw cycling, sonication, mechanical disruption, or use of cell lysing agents. Recombinant polypeptides produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine.

Recombinant proteins can be isolated using an technique well-known in the art. Scopes (*Protein Purification: Principles and Practice*, Springer-Verlag, New York (1994)), for example, provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography.

Variations, modifications, and other implementations of what is described herein will occur to those of ordinary skill in the art without departing from the spirit and scope of the invention.

In order that the invention described herein may be more fully understood, the following example is set forth. It should be understood that this example is for illustrative purposes only and are not to be construed as limiting this invention in any manner.

5.18 Methods for Identifying Compounds for Use in the Prevention, Treatment, Management or Amelioration of Osteoarthritis or a Symptom Thereof

5.18.1 Methods for Identifying Compounds that Modulate the Expression or Activity of a Biomarker The present invention provides methods of identifying compounds that bind to the products of the biomarkers of the invention. The present invention also provides methods for identifying compounds that modulate the expression and/or activity of the products of the biomarkers of the invention. The compounds identified via such methods are useful for the development of one or more animal models to study osteoarthritis. Further, the compounds identified via such methods are useful as lead compounds in the development of prophylactic and therapeutic compositions for prevention, treatment, management and/or amelioration of osteoarthritis or a symptom thereof. Such methods are particularly useful in that the effort and great expense involved in testing potential prophylactics and therapeutics in vivo is efficiently focused on those compounds identified via the in vitro and ex vivo methods described herein.

The present invention provides a method for identifying a compound to be tested for an ability to prevent, treat, manage or ameliorate osteoarthritis or a symptom thereof, said method comprising: (a) contacting a cell expressing a protein product of one or more biomarkers of the invention or a fragment thereof, or a RNA product of one or more biomarkers of the invention or a fragment thereof with a test compound; and (b) determining the ability of the test compound to bind to the protein product, protein fragment, RNA product, or RNA portion so that if a compound binds to the protein product, protein fragment, RNA product, RNA portion, a compound to be tested for an ability to prevent, treat, manage or ameliorate osteoarthritis or a symptom thereof is identified. The cell, for example, can be a yeast cell or a cell of mammalian origin. Determining the ability of the test compound to bind to the protein product, protein fragment, RNA product, or RNA portion can be accomplished, for example, by coupling the test compound with a radioisotope or enzymatic label such that binding of the test compound to the protein product, protein fragment, RNA product, or RNA portion can be determined by detecting the labelled compound in a complex. For example, test compounds can be labelled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labelled with, for example, horseradish peroxidase, alkaline phosphatase, or luciferase, and the enzymatic label detected by determination of conversion of an appropriate substrate to product. In a specific embodiment, the assay comprises contacting a cell which expresses a protein product of one or more biomarkers of the invention or a fragment thereof, or a RNA product of one or more biomarkers of the invention or a fragment thereof, with a known compound which binds the protein product, protein fragment, RNA product, or RNA portion to form an assay mixture, contacting the assay mixture with a test compound, and determining the ability of the test compound to interact with the protein product, protein fragment, RNA product, or RNA portion, wherein determining the ability of the test compound to interact with the protein product, protein fragment, RNA product, or RNA portion comprises determining the ability of the test compound to preferentially bind to the protein product, protein fragment, RNA product, or RNA portion as compared to the known compound.

The present invention provides a method for identifying a compound to be tested for an ability to prevent, treat, manage or ameliorate osteoarthritis or a symptom thereof, said method comprising: (a) contacting a protein product of one or more biomarkers of the invention or a fragment thereof, or a RNA product of one or more biomarkers of the invention or a portion thereof with a test compound; and (b) determining the ability of the test compound to bind to the protein product, protein fragment, RNA product, or RNA portion so that if a compound binds to the protein product, protein fragment, RNA product, or RNA portion, a compound to be tested for an ability to prevent, treat, manage or ameliorate osteoarthritis or a symptom thereof is identified. Binding of the test compound to the protein product or protein fragment can be determined either directly or indirectly. In a specific embodiment, the assay includes contacting a protein product of one or more biomarkers of the invention or a fragment thereof, or a RNA product of one or more biomarkers of the invention or a portion thereof with a known compound which binds the protein product, protein fragment, RNA product, or RNA portion to form an assay mixture, contacting the assay mixture with a test compound, and determining the ability of the test compound to interact with the protein product, protein fragment, RNA product, or RNA portion, wherein determining the ability of the test compound to interact with the protein product, protein fragment, RNA product, or RNA portion comprises determining the ability of the test compound to preferentially bind to the protein product, protein fragment, RNA product, or RNA portion as compared to the known compound. Techniques well known in the art can be used to determine the binding between a test compound and a protein product of a biomarker of the invention or a fragment thereof, or a RNA product of a biomarker of the invention or a portion thereof.

In some embodiments of the above assay methods of the present invention, it may be desirable to immobilize a RNA product of a biomarker of the invention or a portion thereof, or its target molecule to facilitate separation of complexed from uncomplexed forms of the RNA product or RNA portion, the target molecule or both, as well as to accommodate automation of the assay. In more than one embodiment of the above assay methods of the present invention, it may be desirable to immobilize either a protein product of a biomarker of the invention or a fragment thereof, or its target molecule to facilitate separation of complexed from uncomplexed forms of one or both of the proteins, as well as to accommodate automation of the assay. Binding of a test compound to a protein product of a biomarker of the invention or a fragment thereof can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-5-transferase (GST) fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or a protein product of a biomarker of the invention or a fragment thereof, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding of a protein product of a biomarker of the invention or a fragment thereof can be determined using standard techniques.

Other techniques for immobilizing proteins on matrices can also be used in the screening assays of the invention. For example, either a protein product of a biomarker of the invention or a fragment thereof, or a target molecule can be immobilized utilising conjugation of biotin and streptavidin. A biotinylated protein product of a biomarker of the invention or a target molecule can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a protein product of a biomarker of the invention or a fragment thereof can be derivatized to the wells of the plate, and protein trapped in the wells by antibody conjugation. Methods for detecting such complexes, in addition to those described above for the GST-immobilized complexes, include immunodetection of complexes using antibodies reactive with a protein product of a biomarker of the invention, as well as enzyme-linked assays which rely on detecting an enzymatic activity associated with a protein product of a biomarker of the invention or a fragment thereof, or target molecule.

The interaction or binding of a protein product of a biomarker of the invention or a fragment thereof to a test compound can also be determined using such proteins or protein fragments as "bait proteins" in a two-hybrid assay or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and International Publication No. WO 94/10300).

The present invention provides a method for identifying a compound to be tested for an ability to prevent, treat, manage or ameliorate osteoarthritis or a symptom thereof, said method comprising: (a) contacting a cell expressing a protein or RNA product of one or more biomarkers of the invention with a test compound; (b) after an incubation period, determining the amount of the protein or RNA product present in (a); and (c) comparing the amount in (a) to that present in a corresponding control cell that has not been contacted with the test compound, so that if the amount of the protein or RNA product is altered relative to the amount in the control, a compound to be tested for an ability to prevent, treat, manage or ameliorate osteoarthritis or a symptom thereof is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control as determined by utilising an assay described herein (e.g., a microarray or RT-PCR) or an assay well known to one of skill in the art. In alternate embodiments, such a method comprises determining the amount of the protein or RNA product of any of at least 2, at least 3, at least 4, at least 5, at least 6, at least 7, at least 8, at least 9, at least 10, at least 12, at least 15, at least 20, at least 25, at least 30, at least 35, at least 40, at least 45, at least 50, 1 to 5, 1-10, 5-10, 5-25, or 10-40, all or any combination of the biomarkers of the invention as listed in Table 1 (including those specific products noted in Table 3), or as listed in Table 1 (including those specific products noted in Table 3) in combination with any one or more of the products of the biomarkers listed in Table 2, present in the cell and comparing the amounts to those present in the control.

The cells utilised in the cell-based assays described herein can be engineered to express a biomarker of the invention utilising techniques known in the art. See, e.g., Section III entitled "Recombinant Expression Vectors and Host Cells" of U.S. Pat. No. 6,245,527, which is incorporated herein by reference. Alternatively, cells that endogenously express a biomarker of the invention can be used. For example, chondrocytes may be used.

In a specific embodiment, chondrocytes are isolated from a "normal" individual, or an individual with mild, moderate, marked or severe osteoarthritis and are incubated in the presence and absence of a test compound for varying amounts of time (i.e., 30 min, 1 hr, 5 hr, 24 hr, 48 hr and 96 hrs). When screening for prophylactic or therapeutic agents, a clone of the full sequence of a biomarker of the invention or functional portion thereof is used to transfect chondrocytes. The transfected chondrocytes are cultured for varying amounts of time (i.e., 1, 2, 3, 5, 7, 10, or 14 days) in the presence or absence of test compound. Following incubation, target nucleic acid samples are prepared from the chondrocytes and hybridized to a nucleic acid probe corresponding to a nucleic acid sequence which is differentially expressed in a chondrocyte derived from at least any two of the following of: normal, mild osteoarthritic, moderate osteoarthritic and severe osteoarthritic. The nucleic acid probe is labelled, for example, with a radioactive label, according to methods well-known in the art and described herein. Hybridization is carried out by northern blot, for example as described in Ausubel et al., supra or Sambrook et al., supra). The differential hybridization, as defined herein, of the target to the samples on the array from normal relative to RNA from any one of mild osteoarthritic, moderate osteoarthritic, marked osteoarthritic and severe osteoarthritic is indicative of the level of expression of RNA corresponding to a differentially expressed chondrocyte specific nucleic acid sequence. A change in the level of expression of the target sequence as a result of the incubation step in the presence of the test compound, is indicative of a compound that increases or decreases the expression of the corresponding chondrocyte specific nucleic acid sequence.

The present invention also provides a method for identifying a compound to be tested for an ability to prevent, treat, manage or ameliorate osteoarthritis or a symptom thereof, said method comprises: (a) contacting a cell-free extract (e.g., a chondrocyte extract) with a nucleic acid sequence encoding a protein or RNA product of one or more biomarkers of the invention and a test compound; (b) determining the amount of the protein or RNA product present in (a); and (c) comparing the amount(s) in (a) to that present to a corresponding control that has not been contacted with the test compound, so that if the amount of the protein or RNA product is altered relative to the amount in the control, a compound to be tested for an ability to prevent, treat, manage or ameliorate osteoarthritis or a symptom thereof is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control sample determined by utilising an assay described herein (e.g., a microarray or RT-PCR) or an assay well known to one of skill in the art. In alternate embodiments, such a method comprises determining the amount of a protein or RNA product of at least 2, at least 3, at least 4, at least 5, at least 6, at least 7, at least 8, at least 9, at least 10, at least 12, at least 15, at least 20, at least 25, at least 30, at least 35, at least 40, at least 45, at least 50, 1 to 5, 1-10, 5-10, 5-25, or 10-40, all or any combination of the biomarkers of the invention present in the extract and comparing the amounts to those present in the control.

In certain embodiments, the amount of RNA product of a biomarker of the invention is determined, in other embodiments, the amount of protein product of a biomarker of the invention is determined, while in still other embodiments, the amount of RNA and protein product of a biomarker of the invention is determined. Standard methods and compositions for determining the amount of RNA or protein product of a biomarker of the invention can be utilised. Such methods and compositions are described in detail above.

In specific embodiments, in a screening assay described herein, the amount of protein or RNA product of a biomarker of the invention is determined utilising kits. Such kits comprise materials and reagents required for measuring the expression of any number up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more protein or RNA products of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention. In specific embodiments, the kits may further comprise one or more additional reagents employed in the various methods, such as: (1) reagents for purifying RNA from blood, chondrocytes or synovial fluid; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA transcript (preferably, mRNA) for use as a control.

In some embodiments, the kits are RT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In a specific embodiment, kits for measuring a RNA product of a biomarker of the invention comprise materials and reagents that are necessary for measuring the expression of the RNA product. For example, a microarray or RT-PCR kit may be used and contain only those reagents and materials necessary for measuring the levels of RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention. Alternatively, in some embodiments, the kits can comprise materials and reagents that are not limited to those required to measure the levels of RNA products of any number of up to 1, 2, 3, 4, 5, 6, 7, 8, 9, 10, 15, 20, 25, 30, 35, 40, 45, 50, all or any combination of the biomarkers of the invention. For example, a microarray kit may contain reagents and materials necessary for measuring the levels of RNA products any number of up to 1, 2, 3, 4, 5, 6, 7, 8, 9, 10, 15, 20, 25, 30, 35, 40, 45, 50, all or any combination of the biomarkers of the invention, in addition to reagents and materials necessary for measuring the levels of the RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than the biomarkers of the invention. In a specific embodiment, a microarray or RT-PCR kit contains reagents and materials necessary for measuring the levels of RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention, and any number of up to 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, 500, 1000, 5000, 15,000 20,000 or more genes that are not biomarkers of the invention, or any number of 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000, 1000-5000, 5000-10, 000, 10,000-20,000 or more genes that are not biomarkers of the invention.

For nucleic acid micoarray kits, the kits generally comprise probes attached to a support surface. The probes may be labeled with a detectable label. In a specific embodiment, the probes are specific for the 5' region, the 3' region, the internal coding region, an exon(s), an intron(s), an exon junction(s), or an exon-intron junction(s), of any number of up to 1, 2, 3, 4, 5, 6, 7, 8, 9, 10, 15, 20, 25, 30, 35, 40, 45, 50, all or any combination of the biomarkers of the invention. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of any number of up to 1, 2, 3, 4, 5, 6, 7, 8, 9, 10, 15, 20, 25, 30, 35, 40, 45, 50, all or any combination of the biomarkers of the invention. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for any number of up to 1, 2, 3, 4, 5, 6, 7, 8, 9, 10, 15, 20, 25, 30, 35, 40, 45, 50, all or any combination of the biomarkers of the invention. The probes may or may not be labeled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay.

For antibody based kits, the kit can comprise, for example: (1) a first antibody (which may or may not be attached to a support) which binds to protein of interest (e.g., a protein product of any number of up to 1, 2, 3, 4, 5, 6, 7, 8, 9, 10, 15, 20, 25, 30, 35, 40, 45, 50, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

Reporter gene-based assays may also be conducted to identify a compound to be tested for an ability to prevent, treat, manage or ameliorate osteoarthritis or a symptom thereof. In a specific embodiment, the present invention provides a method for identifying a compound to be tested for an ability to prevent, treat, manage or ameliorate osteoarthritis or a symptom thereof, said method comprising: (a) contacting a compound with a cell expressing a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control cell that has not been contacted with the test compound, so that if the amount of expressed reporter gene is altered relative to the amount in the control cell, a compound to be tested for an ability to prevent, treat, manage or ameliorate osteoarthritis or a symptom thereof is identified. In accordance with this embodiment, the cell may naturally express the biomarker or be engineered to express the biomarker. In another embodiment, the present invention provides a method for identifying a compound to be tested for an ability to prevent, treat, manage or ameliorate osteoarthritis or a symptom thereof, said method comprising: (a) contacting a compound with a cell-free extract and a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control that has not been contacted with the test compound, so that if the amount of expressed reporter gene is altered relative to the amount in the control, a compound to be tested for an ability to prevent, treat, manage or ameliorate osteoarthritis or a symptom thereof is identified.

Any reporter gene well-known to one of skill in the art may be used in reporter gene constructs used in accordance with the methods of the invention. Reporter genes refer to a nucleotide sequence encoding a RNA transcript or protein that is readily detectable either by its presence (by, e.g., RT-PCR, Northern blot, Western Blot, ELISA, etc.) or activity. Non-limiting examples of reporter genes are listed in Table 5, infra. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesised or obtained from a suitable source (e.g., a cDNA library, or a cDNA library generated from, or nucleic acid, preferably poly A+RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

TABLE 11

Reporter Genes and the Properties of the Reporter Gene Products

| Reporter Gene | Protein Activity & Measurement |
| --- | --- |
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

In accordance with the invention, cells that naturally or normally express one or more, all or any combination of the biomarkers of the invention can be used in the methods described herein. Alternatively, cells can be engineered to express any one or more, all or any combination of the biomarkers of the invention, or a reporter gene using techniques well-known in the art and used in the methods described herein. Examples of such techniques include, but are not to, calcium phosphate precipitation (see, e.g., Graham & Van der Eb, 1978, Virol. 52:546), dextran-mediated transfection, calcium phosphate mediated transfection, polybrene mediated transfection, protoplast fusion, electroporation, encapsulation of the nucleic acid in liposomes, and direct microinjection of the nucleic acid into nuclei.

In a specific embodiment, the cells used in the methods described herein are chondrocytes, lymphocytes (T or B lymphocytes), monocytes, neutrophils, macrophages, eosinophils, basophils, erythrocytes or platelets. In a preferred embodiment, the cells used in the methods described herein are chondrocytes. In another preferred embodiment, the cells used in the methods described herein are lymphocytes. In another embodiment, the cells used in the methods described herein are immortalized cell lines derived from a source, e.g., a tissue.

Any cell-free extract that permits the translation, and optionally but preferably, the transcription, of a nucleic acid can be used in accordance with the methods described herein. The cell-free extract may be isolated from cells of any species origin. For example, the cell-free translation extract may be isolated from human cells, cultured mouse cells, cultured rat cells, Chinese hamster ovary (CHO) cells, *Xenopus oocytes*, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a specific embodiment, the human cells are HeLa cells, lymphocytes, or chondrocytes.

In addition to the ability to modulate the expression levels of RNA and/or protein products a biomarker of the invention, it may be desirable, at least in certain instances, that compounds modulate the activity of a protein product of a biomarker of the invention. Thus, the present invention provides methods of identifying compounds to be tested for an ability to prevent, treat, manage or ameliorate osteoarthritis or a symptom thereof, comprising methods for identifying compounds that modulate the activity of a protein product of one or more biomarkers of the invention. Such methods can comprise: (a) contacting a cell expressing a protein product of one or more biomarkers of the invention with a test compound; (b) after an incubation period determining the activity level of the protein product; and (c) comparing the activity level to that in a corresponding control cell that has not been contacted with the test compound, so that if the level of activity in (a) is altered relative to the level of activity in the control cell, a compound to be tested for an ability to prevent, treat, manage or ameliorate osteoarthritis or a symptom thereof is identified. In a specific embodiment, the activity level(s) is altered by up to 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilising an assay described herein (e.g., a microarray or RT-PCR) or an assay well known to one of skill in the art. In alternate embodiments, such a method comprises determining the activity level of a protein product of any number of up to at least 2, at least 3, at least 4, at least 5, at least 6, at least 7, at least 8, at least 9, at least 10, at least 12, at least 15, at least 20, at least 25, at least 30, at least 35, at least 40, at least 45, at least 50, 1 to 5, 1-10, 5-10, 5-25, or 10-40, all or any combination of the biomarkers of the invention present in the cell and comparing the activity levels to those present in the control.

The present invention provides methods of identifying compounds to be tested for an ability to prevent, treat, manage or ameliorate osteoarthritis or a symptom thereof, comprising: (a) contacting a cell-free extract with a nucleic acid encoding a protein product of one or more biomarkers of the invention and a test compound; (b) after an incubation period, determining the activity level of the protein product; and (c) comparing the activity level to that in a corresponding control that has not been contacted with the test compound, so that if the level of activity in (a) is altered relative to the level of activity in the control, a compound to be tested for an ability to prevent, treat, manage or ameliorate osteoarthritis or a symptom thereof is identified. In a specific embodiment, the activity level(s) is altered by 1% ? 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilising an assay described herein (e.g., a microarray or RT-PCR) or an assay well known to one of skill in the art. In alternate embodiments, such a method comprises determining the activity level of a protein product of any number of up to at least 1, at least 2, at least 3, at least 4, at least 5, at least 6, at least 7, at least 8, at least 9, at least 10, at least 12, at least 15, at least 20, at least 25, at least 30, at least 35, at least 40, at least 45, at least 50, 1 to 5, 1-10, 5-10, 5-25, or 10-40, all or any combination of the biomarkers of the invention present in the sample and comparing the activity levels to those present in the control.

Standard techniques can be utilised to determine the level of activity of a protein product of a biomarker of the invention.

5.18.2 Biological Activity of the Compounds

Upon identification of compounds to be tested for an ability to prevent, treat, manage or ameliorate osteoarthritis or a symptom thereof (for convenience referred to herein as a "lead" compound), the compounds can be further investigated. For example, the compounds identified via the present methods can be further tested in vivo in accepted animal models of inflammation, preferably, arthritis and more preferably, osteoarthritis. Further, the compounds identified via the methods can be analyzed with respect to their specificity. In particular, the compounds can be tested for an effect on manufacture of type II collagen and proteoglycans by chondrocytes. by methods well known to those of skill in the art, see for example, Nelson et al. J. Clin. Invest. Volume 102, Number 12, December 1998, 2115-2125 *Evidence for Altered Synthesis of Type II Collagen in Patients with Osteoarthritis*, and Venkatesan, N. et al. (December 2004) PNAS 101(52): 18087-92 *Stimulation of proteoglycan synthesis by glucuronosyltransferase-I gene delivery: A strategy to promote cartilage repair*, both of which are hereby incorporated by reference. For Techniques for such additional compound investigation are well known to one of skill in the art.

In one embodiment, the effect of a lead compound can be assayed by measuring the cell growth or viability of the target cell. Such assays can be carried out with representative cells of cell types involved in osteoarthritis (e.g., chondrocytes). Alternatively, instead of culturing cells from a patient, a lead compound may be screened using cells of a cell line.

Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or ($^3$H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and RNA (e.g., mRNA) and activity can be determined by any method well known in the art. For example, protein can be quantitated by known immunodiagnostic methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

One example of a chondrocyte proliferation assay is as follows: Chondrocytes are retrieved from human severe OA cartilage slices as previously described. (Doherty P J, Zhang H, Trembley L, Manolopoulos V and Marshall K W., 1998, Osteoarthritis and Cartilage 6:153-160). Cells are then washed, counted and seeded at $1 \times 10^4$ cells/well in a flat-bottomed 96-well plate (Corning) in DMEM++. After cells attach to the plate, they are washed with DMEM only, and then incubated in DMEM with or without 10% FCS along with different concentrations of lead compound for 48 hours. The cell number in each well is then determined by adding 10 µl of WST-1 (a tetrazolium salt that can be cleaved to formazan by mitochondrial dehydrogenases in live cells, Roche) to each well, mixing thoroughly for 1 min. and incubating at 37° for 1.5 hours. Then the plate is scanned by a microplate autoreader (BIO-TEK Instruments) at an absorbance of 450 nm. The number of viable cells is reflected by the amount of formazan formed which is quantified by measuring absorbance at 450 nm. (Lang I, Hoffmann C, Olip H, Pabst M A, Hahn T, Dohr G, Desoye G., 2001, Differential mitogenic responses of human macrovascular and microvascular endothelial cells to cytokines underline their phenotypic heterogeneity. Cell Prolif 34:143-55).

The effect on manufacture of type II collagen and proteoglycans by chondrocytes exposed to a lead compound can be determined using techniques well known in the art. Further, any assay well known in the art for assessing the efficacy of a therapy for prevention, treatment, management or amelioration of a condition, in particular osteoarthritis, can be performed using the lead compounds.

Animal Models

Compounds can be tested in suitable animal model systems prior to use in humans. Such animal model systems include but are not limited to rats, mice, chicken, cows, monkeys, pigs, dogs, rabbits, etc. Any animal system well-known in the art may be used. In certain embodiments, compounds are tested in a mouse model. Compounds can be administered repeatedly.

Accepted animal models can be utilised to determine the efficacy of the compounds identified via the methods described above for the prevention, treatment, management and/or amelioration of osteoarthritis or a symptom thereof. Such models can include the various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

In one embodiment, the efficacy of a compound for the prevention, treatment, management and/or amelioration of osteoarthritis or a symptom thereof is determined using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," Inflammation, 24(2): 141-155, (2000). Also commonly used are zymosan-induced inflammation animal models as known and described in the art.

The anti-inflammatory activity of the compounds can be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test compound is expressed as the percent inhibition of the increase in hind paw weight of the test group relative to the vehicle dosed control group.

In another embodiment, the efficacy of a compound for the prevention, treatment, management and/or amelioration of osteoarthritis or a symptom thereof is determined using a collagen-induced arthritis (CIA) model. CIA is an animal model for the human autoimmune disease rheumatoid arthritis (RA) (Trenthom et al., 1977, J. Exp. Med., 146:857). This disease can be induced in many species by the administration of heterologous type II collagen (Courtenay et al., 1980, Nature 283:665; Cathcart et at, 1986, Lab. Invest., 54:26). With respect to animal models of arthritis see, in addition, e.g., Holmdahl, R., 1999, Curr. Biol. 15:R528-530.

In another embodiment, the efficacy of a compound for the prevention, treatment, management and/or amelioration of osteoarthritis or a symptom thereof is determined using assays that determine bone formation and/or bone loss. Animal models such as ovariectomy-induced bone resorption mice, rat and rabbit models are known in the art for obtaining dynamic parameters for bone formation. Using methods such as those described by Yositake et al. or Yamamoto et al., bone volume is measured in vivo by microcomputed tomography analysis and bone histomorphometry analysis. Yoshitake et al., "Osteopontin-Deficient Mice Are Resist ant to Ovariectomy-Induced Bone Resorption," Proc. Natl. Acad. Sci. 96:8156-8160, (1999); Yamamoto et al., "The Integrin Ligand Echistatin Prevents Bone Loss in Ovariectomized Mice and Rats," Endocrinology 139(3):1411-1419, (1998), both incorporated herein by reference in their entirety.

Toxicity

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilised. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxicol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to the proteins of interest (i.e., the protein products of a biomarker of the invention) using the above-described screens for biologic activity. Alternatively, lead compounds with little or no biologic activity, as ascertained in the screen, can also be used to design analogs and congeners of the compound that have biologic activity.

5.18.3 Compounds

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal, plant or animal extracts.

Compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Furthermore, diversity libraries of test compounds, including small molecule test compounds, may be utilised. Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a specific embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available For example, libraries may be commercially obtained from, e.g., Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), Asinex (Moscow, Russia), ComGenex (Princeton, N.J.), Ru, Tripos, Inc. (St. Louis, Mo.), ChemStar, Ltd (Moscow, Russia), 3D Pharmaceuticals (Exton, Pa.), and Martek Biosciences (Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesised. There is a great interest in synthetic methods directed toward the creation of large collections of small organic compounds, or libraries, which could be screened for pharmacological, biological or other activity. The synthetic methods applied to create vast combinatorial libraries are performed in solution or in the phase, i.e., on a support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesised using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesised in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multi-step solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesised on solid supports. In one embodiment, a split synthesis method, a protocol of separating and mixing supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

In some embodiments of the present invention, compounds can be attached to solid supports via linkers. Linkers can be integral and part of the solid support, or they may be nonintegral that are either synthesised on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds. Examples of such techniques include, but are not limited to, mass spectrometry, NMR spectroscopy, X-ray crytallography and vibrational spectroscopy.

5.19 Use of Identified Compounds to Prevent, Treat, Manage or Ameliorate Osteoarthritis or a Symptom Thereof The present invention provides methods of preventing, treating, managing or ameliorating osteoarthritis or a symptom thereof, said methods comprising administering to a subject in need thereof one or more compounds identified in accordance with the methods of the invention. In a preferred embodiment, the subject is human.

In one embodiment, the invention provides a method of preventing, treating, managing or ameliorating osteoarthritis or a symptom thereof, said method comprising administering to a subject in need thereof a dose of a prophylactically or therapeutically effective amount of one or more compounds identified in accordance with the methods of the invention. In a specific embodiment, a compound identified in accordance with the methods of the invention is not administered to prevent, treat, or ameliorate osteoarthritis or a symptom thereof, if such compound has been used previously to prevent, treat, manage or ameliorate osteoarthritis or a symptom thereof. In another embodiment, a compound identified in accordance with the methods of the invention is not administered to prevent, treat, or ameliorate osteoarthritis or a symptom thereof, if such compound has suggested to be used to prevent, treat, manage or ameliorate osteoarthritis or a symptom thereof. In another embodiment, a compound identified in accordance with the methods of the invention specifically binds to and/or alters the expression and/or activity level of a protein or RNA product of only one biomarker of the invention. In yet another embodiment, a compound identified in accordance with the methods of the invention binds to and/or alters the expression and/or activity level of a protein or RNA product of any number of up to at least 2, at least 3, at least 4, at least 5, at least 10, at least 15, at least 20, at least 25, at least 30, at least 35, at least 40 or more biomarkers of the invention.

In a specific embodiment, a compound identified in accordance with the methods of the invention increases or decreases the anabolic and/or the catabolic activity of a chondrocyte. Preferably, such a compound increases or decreases the anabolic and/or catabolic activity of a chondrocyte by greater than 1.0-fold, more preferably, 1.5-5-fold, and most preferably, 5-100-fold, as compared to an untreated chondrocyte. In another embodiment, a compound identified in accordance with the methods of the invention ameliorates at least one of the symptoms and/or changes associated with osteoarthritis including cartilage degeneration, or pain, swelling, weakness and/or loss of functional ability in the afflicted joints, associated with cartilage degeneration. In a particular embodiment, the prophylactic or therapeutic agent administered to prevent, treat, manage or ameliorate osteoarthritis or a symptom thereof is a synthetic compound or a natural product (e.g. a plant extract or culture supernatant), or a mixture of compounds.

The invention also provides methods of preventing, treating, managing or ameliorating osteoarthritis or a symptom thereof, said methods comprising administering to a subject in need thereof one or more of the compounds identified utilising the screening methods described herein, and one or more other therapies (e.g., prophylactic or therapeutic agents and surgery). In a specific embodiment, such therapies are currently being used, have been used or are known to be useful in the prevention, treatment, management or amelioration of osteoarthritis or a symptom thereof (including, but not limited to the prophylactic or therapeutic agents listed in Section 1.21.2?? hereinbelow). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in an assay described herein is administered to a subject, preferably a human, to prevent, treat, manage or ameliorate osteoarthritis or a symptom thereof. In accordance with the invention, the pharmaceutical composition may also comprise one or more prophylactic or therapeutic agents. Preferably, such agents are currently being used, have been used or are known to be useful in the prevention, treatment, management or amelioration of osteoarthritis or a symptom thereof.

A compound identified in accordance with the methods of the invention may be used as a first, second, third, fourth or fifth line of therapy for osteoarthritis. The invention provides methods for treating, managing or ameliorating osteoarthritis or a symptom thereof in a subject refractory to conventional therapies for osteoarthritis, said methods comprising administering to said subject a dose of a prophylactically or therapeutically effective amount of a compound identified in accordance with the methods of the invention.

The invention provides methods for treating, managing or ameliorating osteoarthritis or a symptom thereof in a subject refractory to existing single agent therapies for osteoarthritis, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating or managing a osteoarthritis by administering a compound identified in accordance with the methods of the invention in combination with any other therapy (e.g., surgery) to patients who have proven refractory to other therapies but are no longer on these therapies. The invention also provides methods for the treatment or management of a patient having osteoarthritis and immunosuppressed by reason of having previously undergone other therapies. The invention also provides alternative methods for the treatment or management of osteoarthritis where hormonal therapy and/or biological therapy/immunotherapy has proven or may prove too toxic, i.e., results in unacceptable or unbearable side effects, for the subject being treated or managed.

5.19.1 Compounds for Use in Preventing, Treating, Managing or Ameliorating Osteoarthritis or a Symptom Thereof Representative, non-limiting examples of compounds that can used in accordance with the methods of the invention to prevent, treat, manage and/or ameliorate osteoarthritis or a symptom thereof are described in detail below.

First, such compounds can include, for example, antisense, ribozyme, or triple helix compounds that can downregulate the expression or activity of a protein or RNA product of a biomarker of the invention. Such compounds are described in detail in the subsection below.

Second, such compounds can include, for example, antibody compositions that can modulate the expression of a protein or RNA product of a biomarker of the invention, or the activity of a protein product of a biomarker of the invention. In a specific embodiment, the antibody compositions downregulate the expression a protein or RNA product of a biomarker of the invention, or the activity of a protein product of a biomarker of the invention. Such compounds are described in detail in the subsection below.

Third, such compounds can include, for example, protein products of a biomarker of the invention. The invention encompasses the use of peptides or peptide mimetics selected to mimic a protein product of a biomarker of the invention to prevent, treat, manage or ameliorate osteoarthritis or a symptom thereof. Further, such compounds can include, for example, dominant-negative polypeptides that can modulate the expression a protein or RNA product of a biomarker of the invention, or the activity of a protein product of a biomarker of the invention.

The methods also encompasses the use derivatives, analogs and fragments of a protein product of a biomarker of the invention to prevent, treat, manage or ameliorate osteoarthritis or a symptom thereof. In particular, the invention encompasses the use of fragments of a protein product of a biomarker of the invention comprising one or more domains of such a protein(s) to prevent, treat, manage or ameliorate osteoarthritis or a symptom thereof. In another specific embodiment, the invention encompasses the use of a protein product of a biomarker of the invention, or an analog, derivative or fragment of such a protein which is expressed as a fusion, or chimeric protein product (comprising the protein, fragment, analog, or derivative joined via a peptide bond to a heterologous protein sequence).

In specific embodiments, an antisense oligonucleotide of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of biomarkers of the invention are administered to prevent, treat, manage or ameliorate osteoarthritis or a symptom thereof. In other embodiments, one or more of protein products of a biomarker of the invention or a fragment, analog, or derivative thereof are administered to prevent, treat, manage or ameliorate osteoarthritis or a symptom thereof. In other embodiment, one or more antibodies that specifically bind to a protein product of the invention are administered to prevent, treat, manage or ameliorate osteoarthritis or a symptom thereof. In other embodiments, one or more dominant-negative polypeptides are administered to prevent, treat, manage or ameliorate osteoarthritis or a symptom thereof.

Antisense, Ribozyme, Triple-Helix Compositions

Standard techniques can be utilised to produce antisense, triple helix, or ribozyme molecules for use as part of the methods described herein. First, standard techniques can be utilised for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, any number of up to about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesised using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue, e.g., a joint (e.g., a knee, hip, elbow, and knuckle), site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or chondrocyte, surface, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660: 27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, Nucleic Acids Res. 24(17):3357-63. For example, a DNA chain can be synthesised on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesised with a 5' DNA segment and a 3' PNA segment (Peterser et al., 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Antibody Compositions

In one embodiment, antibodies that specifically bind to one or more protein products of one or more biomarkers of the invention are administered to a subject, preferably a human, to prevent, treat, manage or ameliorate osteoarthritis or a symptom thereof. In another embodiment, any combination of antibodies that specifically bind to one or more protein products of one or more biomarkers of the invention are administered to a subject, preferably a human, to prevent, treat, manage or ameliorate osteoarthritis or a symptom thereof. In a specific embodiment, one or more antibodies that specifically bind to one or more protein products of one or more biomarkers of the invention are administered to a subject, preferably a human, in combination with other types of therapies (e.g., NSAIDS) to prevent, treat, manage or ameliorate osteoarthritis or a symptom thereof. In certain embodiments, antibodies known in the art that specifically bind to one or more protein products of one or more biomarkers of the invention are administered to a subject, preferably a human, alone or in combination with other types of therapies (e.g., NSAIDS) to prevent, treat, manage or ameliorate osteoarthritis or a symptom thereof. In other embodiments, antibodies known in the art that specifically bind to one or more protein products of one or more biomarkers of the invention are not administered to a subject, preferably a human, alone or in combination with other types of therapies (e.g., NSAIDS) to prevent, treat, manage or ameliorate osteoarthritis or a symptom thereof.

One or more antibodies that specifically bind to one or more protein products of one or more biomarkers of the invention can be administered to a subject, preferably a human, using various delivery systems are known to those of skill in the art. For example, such antibodies can be administered by encapsulation in liposomes, microparticles or microcapsules. See, e.g., U.S. Pat. Nos. 5,762,904, 6,004,534, and International Publication No. WO 99/52563. In addition, such antibodies can be administered using recombinant cells capable of expressing the antibodies, or retroviral, other viral vectors or non-viral vectors capable of expressing the antibodies.

Antibodies that specifically bind one or more protein products of one or more biomarkers of the invention can be obtained from any known source. Alternatively, antibodies that specifically bind to one or more protein products of one or more biomarkers of the invention can be produced by any method known in the art for the synthesis of antibodies, in particular, by chemical synthesis or preferably, by recombinant expression techniques.

Antibodies include, but are not limited to, polyclonal antibodies, monoclonal antibodies, bispecific antibodies, multispecific antibodies, human antibodies, humanized antibodies, camelised antibodies, chimeric antibodies, single-chain Fvs (scFv) (see e.g., Bird et al. (1988) *Science* 242:423-426; and Huston et al. (1988) *Proc. Natl. Acad. Sci. USA* 85:5879-5883), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and antigen binding and/or epitope-binding fragments of any of the above. The term "antibody", as used herein, refers to immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, IgA, and $IgA_2$) or subclass. Examples of immunologically active fragments of immunoglobulin molecules include F(ab) fragments (a monovalent fragment consisting of the VL, VH, CL and CH1 domains) and F(ab')2 fragments (a bivalent fragment comprising two Fab fragments linked by a disulfide bridge at the hinge region) which can be generated by treating the antibody with an enzyme such as pepsin or papain. Immunologically active fragments also include, but are not limited to, Fd fragments (consisting of the VH and CH1 domains), Fv fragments (consisting of the VL and VH domains of a single arm of an antibody), dAb fragments (consisting of a VH domain; Ward et al., (1989) Nature 341:544-546), and isolated complementarity determining regions (CDRs). Antibodies that specifically bind to an antigen can be produced by any method known in the art for the synthesis of antibodies, in particular, by chemical synthesis or preferably, by recombinant expression techniques.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

The term "monospecific antibody" refers to an antibody that displays a single binding specificity and affinity for a particular target, e.g., epitope. This term includes monoclonal antibodies. Monoclonal antibodies can be prepared using a wide variety of techniques known in the art including the use of hybridoma, recombinant, and phage display technologies, or a combination thereof. See, e.g., U.S. Pat. Nos. RE 32,011, 4,902,614, 4,543,439, 4,411,993 and 4,196,265; Kennett et al (eds.), *Monoclonal Antibodies, Hybridomas: A New Dimension in Biological Analyses*, Plenum Press (1980); and Harlow and Lane (eds.), *Antibodies. A Laboratory Manual*, Cold Spring Harbor Laboratory Press (1988), which are incorporated herein by reference. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). Other techniques that enable the production of antibodies through recombinant techniques (e.g., techniques described by William D. Huse et al., 1989, Science, 246: 1275-1281; L. Sastry et al., 1989, Proc. Natl. Acad. Sci. USA, 86: 5728-5732; and Michelle Alting-Mees et al., Strategies in Molecular Biology, 3: 1-9 (1990) involving a commercial system available from Stratacyte, La Jolla, Calif.) may also be utilised to construct monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a protein product of a biomarker of the invention, and once an immune response is detected, e.g., antibodies specific for the protein are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997, Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, preferably, the hybridoma is generated by fusing splenocytes isolated from a mouse immunized with a protein product of a biomarker of the invention, with myeloma cells and then screening the hybridomas resulting from the fusion for hybridoma clones that secrete an antibody able to bind to the protein or protein fragment.

Antibody fragments which recognise specific-epitopes of a protein product of a biomarker of the invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labelled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilising cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Antibodies can also be produced by a transgenic animal. In particular, human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

U.S. Pat. No. 5,849,992, for example, describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab').sub.2, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., 2002, J. Immunol. 169:1119-25, Caldas et al., 2000, Protein Eng. 13(5):353-60, Morea et al., 2000, Methods 20(3):267-79, Baca et al., 1997, J. Biol. Chem. 272(16): 10678-84, Roguska et al., 1996, Protein Eng. 9(10):895-904, Couto et al., 1995, Cancer Res. 55 (23 Supp):5973s-5977s, Couto et al., 1995, Cancer Res. 55(8):1717-22, Sandhu J S, 1994, Gene 150(2):409-10, and Pedersen et al., 1994, J. Mol. Biol. 235(3):959-73. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to an antigen can, in turn, be utilised to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8): 2429-2438). Such antibodies can be used, alone or in combination with other therapies, in the prevention, treatment, management or amelioration of osteoarthritis or a symptom thereof.

The invention encompasses polynucleotides comprising a nucleotide sequence encoding an antibody or fragment thereof that specifically binds to an antigen. The invention also encompasses polynucleotides that hybridize under high stringency, intermediate or lower stringency hybridization conditions to polynucleotides that encode an antibody of the invention.

The polynucleotides may be obtained, and the nucleotide sequence of the polynucleotides determined, by any method known in the art. The nucleotide sequences encoding known antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesised oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesised or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

Once a polynucleotide encoding an antibody molecule, heavy or light chain of an antibody, or fragment thereof (preferably, but not necessarily, containing the heavy or light chain variable domain) of the invention has been obtained, the vector for the production of the antibody molecule may be produced by recombinant DNA technology using techniques well-known in the art.

In one preferred embodiment, monoclonal antibodies are produced in mammalian cells. Preferred mammalian host cells for expressing the clone antibodies or antigen-binding fragments thereof include Chinese Hamster Ovary (CHO cells) (including dhfr− CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fc☐ receptors and complement C1q (Burton and Woof, 1992, Adv. Immunol. 51:1-84; Jefferis et al., 1998, Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Once an antibody molecule has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or fragments thereof may be fused to heterologous polypeptide sequences known in the art to facilitate purification.

Gene Therapy Techniques

Gene therapy refers to therapy performed by the administration to a subject of an expressed or expressible nucleic acid. Any of the methods for gene therapy available in the art can be used according to the present invention. Exemplary methods are described below.

In specific embodiments, one or more antisense oligonucleotides for one or more biomarkers of the invention are administered to prevent, treat, manage or ameliorate osteoarthritis or a symptom thereof, by way of gene therapy. In other embodiments, one or more nucleic acid molecules comprising nucleotides encoding one or more antibodies that specifically bind to one or more protein products of one or more biomarkers of the invention are administered to prevent, treat, manage or ameliorate osteoarthritis or a symptom thereof, by way of gene therapy. In other embodiments, one or more nucleic acid molecules comprising nucleotides encoding protein products of one or more biomarkers of the invention or analogs, derivatives or fragments thereof, are administered to prevent, treat, manage or ameliorate osteoarthritis or a symptom thereof, by way of gene therapy. In yet other embodiments, one or more nucleic acid molecules comprising nucleotides encoding one or more dominant-negative polypeptides of one or more protein products of one or more biomarker of the invention are administered to prevent, treat, manage or ameliorate osteoarthritis or a symptom thereof, by way of gene therapy.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition of the invention comprises nucleic acid sequences encoding one or more antibodies that specifically bind to one or more protein products of one or more biomarkers of the invention, said nucleic acid sequences being part of expression vectors that express one or more antibodies in a suitable host. In particular, such nucleic acid sequences have promoters operably linked to the antibodies, said promoter being inducible or constitutive, and, optionally, tissue-specific.

In another aspect, a composition of the invention comprises nucleic acid sequences encoding dominant-negative polypeptides of one or protein products of one or more biomarkers of the invention, said nucleic acid sequences being part of expression vectors that express dominant-negative polypeptides in a suitable host. In particular, such nucleic acid sequences have promoters operably linked to the dominant-negative polypeptides, said promoter being inducible or constitutive, and, optionally, tissue-specific. In another particular embodiment, nucleic acid molecules are used in which the dominant-negative coding sequences and any other desired sequences are flanked by regions that promote homologous recombination at a desired site in the genome, thus providing for intrachromosomal expression of the dominant-negative nucleic acids (Koller and Smithies, 1989, Proc. Natl. Acad. Sci. USA 86:8932-8935; Zijlstra et al., 1989, Nature 342: 435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequence is directly administered in vivo, where it is expressed to produce the encoded product. This can be accomplished by any of numerous methods known in the art, e.g., by constructing it as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

For example, a retroviral vector can be used. These retroviral vectors have been modified to delete retroviral sequences that are not necessary for packaging of the viral genome and integration into host cell DNA. The nucleic acid sequences encoding the antibodies of interest, or proteins of interest or fragments thereof to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) and/or chondrocytes are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, chondrocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, nucleic acid sequences encoding antibodies of interest, or proteins of interest or fragments thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., International Publication No. WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

Promoters that may be used to control the expression of nucleic acid sequences encoding antibodies of interest, proteins of interest or fragments thereof may be constitutive, inducible or tissue-specific. Non-limiting examples include the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilised in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.19.2 Anti-Inflammatory Therapies

Anti-inflammatory agents have exhibited success in the treatment, management and amelioration of osteoarthritis and are now a common and a standard therapy for such disorder. Any anti-inflammatory agent well-known to one of skill in the art can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

5.20 Pharmaceutical Compositions

Biologically active compounds identified using the methods of the invention or a pharmaceutically acceptable salt thereof can be administered to a patient, preferably a mammal, more preferably a human, suffering from osteoarthritis. In a specific embodiment, a compound or pharmaceutically acceptable salt thereof is administered to a patient, preferably a mammal, more preferably a human, suffering from the following stage of osteoarthritis: mild, moderate, marked or severe. In another embodiment, a compound or a pharmaceutically acceptable salt thereof is administered to a patient, preferably a mammal, more preferably a human, as a preventative measure against osteoarthritis. In accordance with these embodiments, the patient may be a child, an adult or elderly, wherein a "child" is a subject between the ages of 24 months of age and 18 years of age, an "adult" is a subject 18 years of age or older, and "elderly" is a subject 65 years of age or older.

When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In a specific embodiment, a compound is administered locally to a joint affected by osteoarthritis.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

The compounds described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of interest. Such methods comprise formulating a pharmaceutically acceptable carrier with an agent that modulates expression or activity of a polypeptide or nucleic acid of interest. Such compositions can further include additional active agents. Thus, the invention further includes methods for preparing a pharmaceutical composition by formulating a pharmaceutically acceptable carrier with an agent that modulates expression or activity of a polypeptide or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Intravenous administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (more preferably, 0.1 to 20 mg/kg, 0.1-10 mg/kg, or 0.1 to 1.0 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. (1997, J. Acquired Immune Deficiency Syndromes and Human Retrovirology 14:193).

In a specific embodiment, an effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 0.1 to 1.0 mg/kg, 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In addition to those compounds described above, the present invention encompasses the use of small molecules that modulate expression or activity of a nucleic acid or polypeptide of interest. Non-limiting examples of small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to a subject (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

5.21 Kits

The present invention provides kits for measuring the expression of the protein and RNA products of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention. Such kits comprise materials and reagents required for measuring the expression of such protein and RNA products. In specific embodiments, the kits may further comprise one or more additional reagents employed in the various methods, such as: (1) reagents for purifying RNA from blood, chondrocytes or synovial fluid; (2) primers for generating test nucleic acids; (3) dNTPs and/or rNTPs (either premixed or separate), optionally with one or more uniquely labelled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g. hybridization and washing buffers; (7) labelled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA isolated from a sample (e.g., blood or chondrocytes or synovial fluid) for use as a control.

In some embodiments, the kits are RT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In some embodiments, the kits are Quantitative RT-PCR kits. In one embodiment, the quantitative RT-PCR kit includes the following: (a) primers used to amplify each of a combination of biomarkers of the invention; (b) buffers and enzymes including an reverse transcripate; (c) one or more thermos table polymerases; and (d) Sybr® Green. In a preferred embodiment, the kit of the invention also includes (a) a reference control RNA and (b) a spiked control RNA.

The invention provides kits that are useful for (a) diagnosing individuals as having arthritis, (b) differentiating between two stages of osteoarthritis (OA) and (c) diagnosing individuals as having a particular stage of osteoarthritis (OA). For example, in a particular embodiment of the invention a kit is comprised a forward and reverse primer wherein the forward and reverse primer are designed to quantitate expression of all of the species of mRNA corresponding to each of the biomarkers as identified in accordance with the invention useful in determining whether an individual has mild OA or does not have OA. In certain embodiments, at least one of the primers is designed to span an exon junction.

The invention provides kits that are useful for detecting, diagnosing, monitoring and prognosing osteoarthritis based upon the expression of protein or RNA products of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention in a sample. In certain embodiments, such kits do not include the materials and reagents for measuring the expression of a protein or RNA product of a biomarker of the invention that has been suggested by the prior art to be associated with osteoarthritis. In other embodiments, such kits include the materials and reagents for measuring the expression of a protein or RNA product of a biomarker of the invention that has been suggested by the prior art to be associated with osteoarthritis and at least 1, at least 2, at least 3, at least 4, at least 5, at least 6, at least 7, at least 8, at least 9, at least 10, at least 15, at least 20, at least 25, at least 30, at least 35, at least 40, at least 45 or more genes other than the biomarkers of the invention.

The invention provides kits useful for monitoring the efficacy of one or more therapies that a subject is undergoing based upon the expression of a protein or RNA product of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention in a sample. In certain embodiments, such kits do not include the materials and reagents for measuring the expression of a protein or RNA product of a biomarker of the invention that has been suggested by the prior art to be associated with osteoarthritis. In other embodiments, such kits include the materials and reagents for measuring the expression of a protein or RNA product of a biomarker of the invention that has been suggested by the prior art to be associated with osteoarthritis and any number of up to at least 1, at least 2, at least 3, at least 4, at least 5, at least 6, at least 7, at least 8, at least 9, at least 10, at least 15, at least 20, at least 25, at least 30, at least 35, at least 40, at least 45 or more genes other than the biomarkers of the invention.

The invention provides kits using for determining whether a subject will be responsive to a therapy based upon the expression of a protein or RNA product of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention in a sample. In certain embodiments, such kits do not include the materials and reagents for measuring the expression of a protein or RNA product of a biomarker of the invention that has been suggested by the prior art to be associated with osteoarthritis. In other embodiments, such kits include the materials and reagents for measuring the expression of a protein or RNA product of a biomarker of the invention that has been suggested by the prior art to be associated with osteoarthritis and any number of up to at least 1, at least 2, at least 3, at least 4, at least 5, at least 6, at least 7, at least 8, at least 9, at least 10, at least 15, at least 20, at least 25, at least 30, at least 35, at least 40, at least 45 or more genes other than the biomarkers of the invention.

The invention provides kits for measuring the expression of a RNA product of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention in a sample. In a specific embodiment, such kits comprise materials and reagents that are necessary for measuring the expression of a RNA product of a biomarker of the invention. For example, a microarray or RT-PCR kit may be produced for osteoarthritis and contain only those reagents and materials necessary for measuring the levels of RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention. Alternatively, in some embodiments, the kits can comprise materials and reagents that are not limited to those required to measure the levels of RNA products of any number of up to 1, 2, 3, 4, 5, 6, 7, 8, 9, 10, 15, 20, 25, 30, 35, 40, 45, 50, all or any combination of the biomarkers of the invention. For example, a microarray kit may contain reagents and materials necessary for measuring the levels of RNA products of not necessarily associated with or indicative of osteoarthritis, in addition to reagents and materials necessary for measuring the levels of the RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention. In a specific embodiment, a microarray or RT-PCR kit contains reagents and materials necessary for measuring the levels of RNA products of any number of up to at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, all or any combination of the biomarkers of the invention, and any number of up to 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes other than the biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, 500-1000 other genes than the biomarkers of the invention.

For nucleic acid micoarray kits, the kits generally comprise probes attached to a solid support surface. The probes may be labelled with a detectable label. In a specific embodiment, the probes are specific for an exon(s), an intron(s), an exon junction(s), or an exon-intron junction(s)), of RNA products of any number of up to 1, 2, 3, 4, 5, 6, 7, 8, 9, 10, 15, 20, 25, 30, 35, 40, 45, 50, all or any combination of the biomarkers of the invention. The microarray kits may comprise instructions for performing the assay and methods for interpreting and analyzing the data resulting from the performance of the assay. In a specific embodiment, the kits comprise instructions for diagnosing osteoarthritis. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For RT-PCR kits, the kits generally comprise pre-selected primers specific for particular RNA products (e.g., an exon(s), an intron(s), an exon junction(s), and an exon-intron junction(s)) of any number of up to 1, 2, 3, 4, 5, 6, 7, 8, 9, 10, 15, 20, 25, 30, 35, 40, 45, 50, all or any combination of the biomarkers of the invention. The RT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The RT-PCR kits may also comprise probes specific for RNA products of any number of up to 1, 2, 3, 4, 5, 6, 7, 8, 9, 10, 15, 20, 25, 30, 35, 40, 45, 50, all or any combination of the biomarkers of the invention. The probes may or may not be labelled with a detectable label (e.g., a fluorescent label). Each component of the RT-PCR kit is generally in its own suitable container. Thus, these kits generally comprise distinct containers suitable for each individual reagent, enzyme, primer and probe. Further, the RT-PCR kits may comprise instructions for performing the assay and methods for interpreting and analyzing the data resulting from the performance of the assay. In a specific embodiment, the kits contain instructions for diagnosing osteoarthritis.

In a specific embodiment, the kit is a real-time RT-PCR kit. Such a kit may comprise a 96 well plate and reagents and materials necessary for SYBR Green detection. The kit may comprise reagents and materials so that beta-actin can be used to normalize the results. The kit may also comprise controls such as water, phosphate buffered saline, and phage MS2 RNA. Further, the kit may comprise instructions for performing the assay and methods for interpreting and analyzing the date resulting from the performance of the assay. In a specific embodiment, the instructions state that the level of a RNA product of any number of up to 1, 2, 3, 4, 5, 6, 7, 8, 9, 10, 15, 20, 25, 30, 35, 40, 45, 50, all or any combination of the biomarkers of the invention should be examined at two concentrations that differ by, e.g., 5 fold to 10-fold.

For antibody based kits, the kit can comprise, for example: (1) a first antibody (which may or may not be attached to a solid support) which binds to protein of interest (e.g., a protein product of any number of up to 1, 2, 3, 4, 5, 6, 7, 8, 9, 10, 15, 20, 25, 30, 35, 40, 45, 50, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for diagnosing osteoarthritis.

6. EXAMPLES

The examples below are non-limiting and are merely representative of various aspects and features of the present invention

Example 1

Microarray Construction

An array according to one aspect of the invention was constructed as follows.

PCR products (~40 ul) of cDNA clones from OA cartilage cDNA libraries, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets were washed with 50 ul ice-cold 70% ethanol and centrifuged again for 30 minutes. The pellets are then air-dried and resuspended well in 50% dimethylsulfoxide (DMSO) or 20 ul 3×SSC overnight. The samples are then deposited either singly or in duplicate onto Gamma Amino Propyl Silane (Corning CMT-GAPS or CMT-GAP2, Catalog No. 40003, 40004) or polylysine-coated slides (Sigma Cat. No. P0425) using a robotic GMS 417 or 427 arrayer (Affymetrix, CA). The boundaries of the DNA spots on the microarray are marked with a diamond scriber. The invention provides for arrays where 10-20,000 PCR products are spotted onto a solid support to prepare an array.

The arrays are rehydrated by suspending the slides over a dish of warm particle free ddH$_2$O for approximately one minute (the spots will swell slightly but not run into each other) and snap-dried on a 70-80° C. inverted heating block for 3 seconds. DNA is then UV crosslinked to the slide (Stratagene, Stratalinker, 65 mJ—set display to "650" which is 650×100 uJ) or baked at 80 C for two to four hours. The arrays are placed in a slide rack. An empty slide chamber is prepared and filled with the following solution: 3.0 grams of succinic anhydride (Aldrich) is dissolved in 189 ml of 1-methyl-2-pyrrolidinone (rapid addition of reagent is crucial); immediately after the last flake of succinic anhydride dissolved, 21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. ddH$_2$O for 2 minutes, followed by plunging five times in 95% ethanol. The slides are then air dried by allowing excess ethanol to drip onto paper towels. The arrays are then stored in the slide box at room temperature until use.

Example 2

RNA Isolation

From Whole Blood 100 ul whole blood is obtained in a microcentrifuge tube and spun at 2,000 rpm (800 g) for 5 min at 4° C. and the supernatant removed. Pelleted cells are homogenized using TRIzol® (GIBCO/BRL) in a ratio of approximately 6 µl of TRIzol® for every 10 µl of the original blood sample and vortexed well. Samples are left for 5 minutes at room temperature. RNA is extracted using 12 µl of chloroform per 10 µl of TRIzol®. Sample is centrifuged at 12,000×g for 5 minutes at 4° C. and upper layer is collected. To upper layer, isopropanol is added in ratio of 5 µl per 10 µl of TRIzol®. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

From Centrifuged Lysed Blood 10 ml whole blood is obtained in a Vacutainer and spun at 2,000 rpm (800 g) for 5 min at 4° C. and the plasma layer optionally removed. Lysis Buffer is added to blood sample in a ratio of 3 parts Lysis Buffer to 1 part blood (Lysis Buffer (1 L) 0.6 g EDTA; 1.0 g KHCO$_2$, 8.2 g NH$_4$Cl adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

From Serum Free Whole Blood 10 ml whole blood is obtained in a Vacutainer and spun at 2,000 rpm (800 g) for 5 min at 4° C. and the plasma layer removed. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

Example 3

Target Nucleic Acid Preparation and Hybridization

Preparation of Fluorescent DNA Probe from mRNA

Fluorescently labelled target nucleic acid samples of RNA are prepared for analysis with an array of the invention.

1 µg Oligo-dT primers are annealed to 10 ug of total RNA isolated from blood from patient diagnosed with mild osteoarthritis or suspected of having mild osteoarthritis in a total volume of 10 ul, by heating to 70° C. for 10 min, and cooled on ice. The mRNA is reverse transcribed by incubating the sample at 42° C. for 40 min in a 25 µl volume containing a final concentration of 50 mM Tris-HCl (pH 8.3), 75 mM KCl, 3 mM MgCl$_2$, 25 mM DTT, 25 mM unlabeled dNTPs, 400 units of Superscript II (200 U/uL, Gibco BRL), and 15 mM of Cy3 or Cy5 (Amersham). The reaction is stopped by the addition of 2.5 µl of 500 mM EDTA and 5 µl of 1M NaOH, and incubation at 65° C. for 10 min. The reaction mixture is neutralized by addition of 12.5 µl of 1M Tris HCl (pH7.6).

The labelled target nucleic acid sample is purified by centrifugation in a Centricon-30 micro-concentrator (Amicon). If two different target nucleic acid samples (e.g., two samples derived from different patients) are being analyzed and compared by hybridization to the same array, each target nucleic acid sample is labelled with a different fluorescent label (e.g., Cy3 and Cy5) and separately concentrated. The separately concentrated target nucleic acid samples (Cy3 and Cy5 labelled) are combined into a fresh centricon, washed with 500 µl TE, and concentrated again to a volume of less than 7 µl. 1 µL of 10 µg/µl polyA RNA (Sigma, #P9403) and 1 µl of 10 µg/ul tRNA (Gibco-BRL, #15401-011) is added and the volume is adjusted to 9.5 µl with distilled water. For final target nucleic acid preparation 2.1 µl 20×SSC (1.5M NaCl, 150 mM NaCitrate (pH8.0)) and 0.35 µl 10% SDS is added.

Hybridization

Labelled nucleic acid is denatured by heating for 2 min at 100° C., and incubated at 37° C. for 20-30 min before being placed on a nucleic acid array under a 22 mm×22 mm glass cover slip. Hybridization is carried out at 65° C. for 14 to 18 hours in a custom slide chamber with humidity maintained by a small reservoir of 3×SSC. The array is washed by submersion and agitation for 2-5 min in 2×SSC with 0.1% SDS, followed by 1×SSC, and 0.1×SSC. Finally, the array is dried by centrifugation for 2 min in a slide rack in a Beckman GS-6 tabletop centrifuge in Microplus carriers at 650 RPM for 2 min.

Example 4

Real Time RT PCR

Real time RT PCR can be performed on the RNA products of the biomarkers disclosed in The term "biomarker specific primers" as used herein refers to a set of primers which can produce double stranded DNA complementary to a portion of one or more RNA products of the biomarker of the invention. For example, the primers can include a first primer which is a sequence that can selectively hybridize to RNA, cDNA or EST complementary to a region of the biomarker of the invention to create an extension product and a second primer capable of selectively hybridizing to the extension product, which are used to produce double stranded DNA complementary to a region of the biomarker of the invention. The invention includes primers useful for measuring the expression of RNA products of the biomarkers of the invention. Table 5 and Table 8 provide representative species of primers and probes of the invention.

including those noted in Table 3 using, for example, the SYBR® Green Kit from Qiagen (Product Number 204143).

Either a one step (reverse transcription and PCR combined) or a two step (reverse transcription first and then subsequent PCR) can be used. In the case of the two step protocol, reverse transcription was first performed using the High-Capacity cDNA Archive Kit from Applied Biosystems (Product number 4322171) and following the protocol utilized therein.

More specifically purified RNA as described previously herein was incubated with Reverse Transcriptase buffer, dNTPs, Random primers and Reverse transcriptase and incubated for 25° C. for 10 minutes and subsequently for 37° C. for two hours and the resulting mixture utilized as the starting product for quantitative PCR.

cDNA resulting from reverse transcription can be incubated with the QuantiTect SYBR® Green PCR Master Mix as provided and no adjustments made for magnesium concentration. Uracil-N-Glycosylase is optional. 5 µM of both forward primer and reverse primer specific to the genes of the invention are added and the reaction incubated and monitored in accordance with the standard protocol utilizing the ABI PRISM 7700/ABI GeneAmp 5700/iCycler/DNA Engine Opticon.

Example 5

TAQMAN®

Quantitative real time RT PCR can be performed using the QuantiTect™ Probe RT-PCR system from Qiagen (Product Number 204343) in conjunction with a TaqMan® dual labelled probe and primers corresponding to the gene of interest. The TaqMan® probe and primers can be ordered from Applied Biosystems Assays-On-Demand™.

The dual labelled probe contains both a fluorophore and a quencher molecule. The proximity of the fluorescent reporter with the quencher prevents the reporter from fluorescing, but during the PCR extension step, the 5'-3' exonuclease activity of the Taq DNA polymerase releases the fluorophore which allows it to fluoresce. As such, the amount of fluorescence correlates with the amount of PCR product generated.

Example 6

Statistical Analysis of Real Time PCR Results

Real Time PCR analysis on blood samples isolated from individuals categorized as normal or having mild OA are statistically analyzed using known methods in order to obtain data corresponding the level of abundance of the biomarkers of the invention in a training population.

Preferably individuals having similar age and body mass index (BMI) are selected for further analysis. Selection of samples for which comparisons can be made on the basis of age and BMI are determined using KW One Way Analysis of Variance on Ranks as would be understood by a person skilled in the art.

Delta CT value and MW Rank Sum tests can be utilized on age and BMI matched sample sets of approximately 20 to 50 in size. As would be clear to a person skilled in the art, similar analysis can be performed for any of the sequences identified herein.

Example 7

Analysis of Gene Expression Profiles of Blood Samples from Individuals Having Mild Osteoarthritis as Compared with Gene Expression Profiles from Normal Individuals USING the RNA Products of the Biomarkers Described in FIG. 1

This example demonstrates the use of the claimed invention to diagnose mild osteoarthritis by detecting differential gene expression in blood samples taken from patients with mild OA as compared to blood samples taken from healthy patients.

Blood samples are taken from patients who are clinically diagnosed with mild osteoarthritis as defined herein; patients who are clinically diagnosed as not having osteoarthritis as defined herein and one or more test patients. Gene expression profiles of combinations of biomarkers of the invention are then analyzed and the test individuals profile compared with the two control profiles.

Total mRNA from lysed whole blood is taken from each patient is first isolated using TRIzol® reagent (GIBCO) and fluorescently labelled probes for each blood sample are then generated, denatured and hybridized to a microarray containing full length cDNA sequences for each of the 19 genes as described in FIG. 1. Detection of specific hybridization to the array is then measured by scanning with a GMS Scanner 418 and processing of the experimental data with Scanalyzer software (Michael Eisen, Stanford University), followed by GeneSpring software (Silicon Genetics, CA) analysis. Differential expression of the RNA products in blood samples corresponding to the biomarkers as between the two control populations and the test individual is determined by statistical analysis using the Wilcox Mann Whitney rank sum test (Glantz SA. Primer of Biostatistics. 5th ed. New York, USA: McGraw-Hill Medical Publishing Division, 2002).

Example 8

Application of Logistic Regression to Identify Classifiers and Combinations Useful in Differentiating Mild Oa from Non Oa Using the RNA Products of the Biomarkers Described in FIG. 1

RNA is isolated from blood samples of 82 patients with mild osteoarthritis as classified using the system of Marshall (supra) and 82 normal subjects. Data corresponding to the level of RNA products for 4 biomarkers as selected from Table 1 for each of the 164 patients are collected using primers designed to amplify the mRNA products noted in Table 3 of the 4 biomarkers. A Reference dataset consisting of ΔCt values arising from the QRT-PCR for the four biomarkers are utilized for input into logistic regression to determine the diagnostic capabilities of different combinations of ΔCt values from these 4 candidate biomarkers. Of the $2^4-1$ possible biomarker combinations, each combination is evaluated in maximum-likelihood logistic regression to determine the discrimination ability (ROC Area>0.5) of "mild osteoarthritis" vs. "control".

Example 9

Identification of Combinations of Biomarkers and Classifiers which Differentiate Mild Osteoarthritis from Non Osteoarthritis Using Logistic Regression Initial analysis of samples derived from patients diagnosed as having mild OA and patients diagnosed as not having OA were each analyzed by hybridization of labelled samples onto an Affymetrix U133Plus 2.0 GeneChips (Affymetrix; Santa Clara, Calif.). Briefly, hybridization signals were scaled in the Affymetrix GCOS software (version 1.1.1), using a scaling factor determined by adjusting the global trimmed mean signal intensity value to 500 for each array, and imported into GeneSpring version 7.2 (Silicon Genetics; Redwood City, Calif.). Signal intensities were then centered to the $50^{th}$ percentile of each chip, and for each individual gene, to the median intensity of the whole sample set. Only genes called present or marginal by the GCOS software in at least 80% of each group of samples were used for further analysis. Differentially expressed genes were identified using one of a variety of statistical tests including (a) the non-parametric Wilcoxon-Mann-Whitney non-parametric test (P<0.05), 2) or (b) parametric t test (P<0.05), Results from numerous microarray experiments were analyzed (data not shown) and a selection of genes subsequently analyzed using real time RT-PCR methods on additional samples as further described below.

A total of 100 individuals were analyzed using real time RT-PCR. Patients diagnosed with mild OA were recruited from the Toronto Western Hospital, University Health Network (UHN), at the University of Toronto. The UHN Research Ethics Board approved the research and participants provided written informed consent. Patients were diagnosed and graded with OA adventitiously, while undergoing arthroscopy as a consequence of meniscal tearing, anterior cruciate ligament (ACL) injury and/or patellar maltracking. Severity was graded with an established arthroscopic scoring method as described in Marshall K W. (The case for a simple method of grading osteoarthritis severity at arthroscopy. J Rheumatol 1996; 23:582-5). Briefly, this system assigns a score of 0-4 to the worst lesion on each of six articular surfaces. Grade 0 is normal (0 points), Grade I cartilage is soft or swollen but the articular surface is intact (1 point). In Grade II lesions, the cartilage surface is not intact but the lesion does not extend down to subchondral bone (2 points). Grade III damage extends to subchondral bone but the bone is neither eroded nor eburnated (3 points). In Grade IV lesions, there is eburnation of, or erosion into, bone (4 points). The score from all surfaces is summed to produce a global score, which is used to categorize OA severity as mild (early): 1-6; moderate: 7-12; marked: 13-18; and severe: 19-24.

51 individuals were diagnosed as having mild OA and compared with 49 samples from control subjects who had no knee symptoms and no history of previous knee injury.

Ten ml of peripheral whole blood was collected from each individual into EDTA Vacutainer tubes (Becton Dickinson, Franklin Lakes, N.J.) and stored on ice until processing (within 6 hours). Upon centrifugation, blood samples separated into plasma, buffy coat and red blood cell layers. The plasma was removed and a hypotonic buffer (1.6 mM EDTA, 10 mM $KHCO_3$, 153 mM $NH_4Cl$, pH 7.4) was added to lyse the red blood cells at a 3:1 volume ratio. The mixture was centrifuged to yield a cell pellet, which was dissolved and homogenized into 1.0 ml of TRIzol® Reagent (Invitrogen Corp., Carlsbad, Calif.) and 0.2 ml of chloroform according to the manufacture's instructions. After centrifugation, isopropanol was added to the aqueous phase at a 1:1 ratio and allowed to precipitate at −20° C. Subsequent centrifugation yielded an RNA pellet that was resuspended in water for experimental use. RNA quality was assessed on Agilent 2100 Bioanalyzer RNA 6000 Nano Chips as specified by the manufacturer, and RNA quantity was determined by absorbance at 260 μm in a Beckman-Coulter DU640 Spectrophotometer.

Quantitative real time RT PCR (QRT-PCR) was performed using the SYBR® Green Kit from Qiagen (Product Number 204143). Amplicons were detected in real time using a Prism 7500 instrument (Applied Biosystems). Reverse transcription was first performed using the High-Capacity cDNA Archive Kit from Applied Biosystems (Product number 4322171) and following the protocol utilized therein.

More specifically purified RNA as described previously herein was incubated with Reverse Transcriptase buffer, dNTPs, Random primers and Reverse transcriptase and incubated for 25° C. for 10 minutes and subsequently for 37° C. for two hours and the resulting mixture utilized as the starting product for quantitative PCR. cDNA resulting from reverse transcription was incubated with the QuantiTect SYBR® Green PCR Master Mix as provided and no adjustments were made for magnesium concentration. Uracil-N-Glycosylase was not added. 5 μM of both forward primer and reverse primer specific to the selected genes were added and the reaction was incubated and monitored in accordance with the standard protocol utilizing the ABI PRISM 7700/ABI GeneAmp 5700/iCycler/DNA Engine Opticon. Genes were selected which demonstrated a pvalue of at least <0.2, but preferentially those were selected with a p value of less than 0.05. We have previously found that genes demonstrating a p value of between 0.05 and 0.2, although not significant as an individual biomarker are able to contribute significantly to a combination of genes for purposes of diagnosis (data not shown). A selection of 32 genes was identified which had a pvalue of <0.2 to differentiate as between mild OA and non OA. These genes are identified in Table 4.

A reference (training) data set was constructed containing ΔCt values for genes identified in Table 4 using the primers as shown in Table 5. All possible combinations of biomarkers identified in Table 4 can be tested and diagnostic classifiers derived for each combination of biomarkers using techniques as described herein and subsequently scored as further described to aid in selection of the most useful combinations and classifiers. Discussed below is representative classifiers identified for selected combinations tested.

Logistic regression was used to analyze the dependence of the binary diagnostic variable Y (0=control, 1=disease) on the ΔCt values from the reference data set. If P=probability that a patient sample is identified as "diseased", then a function X=Logit (p) can be defined as follows:

$$X=\text{Logit}(P)=\ln(P/(1-P))=b_0+b_1\Delta Ct_1+b_2\Delta Ct_2+\ldots +b_n\Delta Ct_n \quad \text{(Eq 1)}$$

If X≧threshold then Y=1 (diagnosis="has mild OA"), and if X<threshold then Y=0 (diagnosis=does not have OA). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. Classifiers were derived for all two gene ratio's of the biomarkers identified in Table 4 using quantitative real time RT-PCR for the genes identified in Table 4 using the primers in Table 6 across the 51 individuals having mild OA and 49 individuals not having OA. Two gene ratio's result in the following equation form:

$$X = \text{Logit}(P) = \ln(P/(1-P)) = b_0 + b_1(\Delta Ct_1 - \Delta Ct_2) \quad \text{(Eq 2)}$$

Of the possible 861 two gene ratios, 465 of these had an area under the curve (AUC) of greater than 0.60 with differing sensitivity and specificity depending upon the combination tested. Graphically the results of this analysis can be seen in FIG. 1. 19 combinations had an AUC of greater than 0.80. Note that an AUC of less than of 0.7 is still valuable and can still provide significant clinically useful combinations. For example a combination having a specificity of 95% and a sensitivity of 75% can still result in an Area Under the Curve of only 0.7. Results for these 19 combinations are shown below in Table A:

TABLE A

| AUC | Sens @ 50% Spec | Spec @ 50% Sens | Two Gene Combination | Constant B0) | Coeff (B1) |
|---|---|---|---|---|---|
| 0.892 | 96.08 | 93.88 | CPT1A/IL13RA1 | −9.44E−02 | −2.1336 |
| 0.8619 | 96.08 | 93.88 | IL13RA1/ILF1 | 4.1019 | 2.6663 |
| 0.8439 | 94.12 | 87.76 | IL13RA1/KIAA0010 | 0.79656 | 2.2328 |
| 0.8439 | 90.2 | 95.92 | PDK4/PF4 | 10.911 | −1.3515 |
| 0.8371 | 92.16 | 89.8 | B2M/IL13RA1 | −18.274 | −2.5853 |
| 0.8359 | 96.08 | 89.8 | IL13RA1/PDK4 | 8.2667 | 1.2839 |
| 0.8355 | 94.12 | 85.71 | CPT1A/LAMCA | −9.0048 | −1.6535 |
| 0.8355 | 84.31 | 97.96 | IL13RA1/LOC286286 | 10.652 | 1.3885 |
| 0.8295 | 88.24 | 93.88 | HDGF/IL13RA1 | −0.54205 | −1.8387 |
| 0.8255 | 88.24 | 93.88 | IL13RA1/NOV | 3.9782 | 1.4352 |
| 0.8255 | 86.27 | 95.92 | CLIC5/IL13RA1 | 8.2454 | −1.5523 |
| 0.8231 | 90.2 | 91.84 | IL13RA1/PRG1 | −12.426 | 2.188 |
| 0.8143 | 88.24 | 87.76 | CKLFSF7/CPT1A | −9.46E−02 | 1.8735 |
| 0.8123 | 90.2 | 85.71 | ASAHL/IL13RA1 | −1.6458 | −1.412 |
| 0.8115 | 88.24 | 91.84 | LAMCA/PDK4 | 1.398 | 1.303 |
| 0.8087 | 90.2 | 81.63 | ATP1B1/IL13RA1 | 5.3727 | −1.2825 |
| 0.8071 | 90.2 | 81.63 | CPT1A/PF4 | 1.7992 | −1.1558 |
| 0.8015 | 92.16 | 89.8 | PDK4/SERPINE1 | 0.17073 | −1.1786 |
| 0.8007 | 92.16 | 81.63 | IL13RA1/PBEF1 | −8.1824 | 1.5323 |

Note the AUC is the area under the curve, and the Sensitivity is listed where specificity is set at 50%. Similarly the Specificity is indicated where the Sensitivity is set at 50%. The Constant ($B_0$) and the Coefficient ($B_1$) for the equation noted in Eq2 are shown.

Classifiers were also derived for selected combinations of 4 sets of two gene ratio's (e.g. combinations of eight biomarkers, each in ratios of two biomarkers) for the biomarkers identified in Table 4 using quantitative real time RT-PCR for the genes identified in Table 4 using the primers in Table 5 across the 51 individuals having mild OA and 49 individuals not having OA. Results are in the following equation form:

$$X = \text{Logit}(P) = \ln(P/(1-P)) = b_0 + b_1(\Delta Ct_1 - \Delta Ct_2) + b_2(\Delta Ct_3 - \Delta Ct_4) + b_3(\Delta Ct_5 - \Delta Ct_6) + b_4(\Delta Ct_7 - \Delta Ct_8) \quad \text{(Eq 3)}$$

Note Table B below shows the AUC (area under the curve), and the Sensitivity is listed where specificity is set at 90%. Similarly the Specificity is indicated where the Sensitivity is set at 90%. The Constant ($B_0$) and the Coefficient $B_1$, Coefficient B2, Coefficient B3, and Coefficient B4 for the equation noted in Eq3 are shown.

TABLE B

| AUC | Sens @ 90% Spec | Spec @ 90% Sens | Delat Ct1/Ct2 | Delta Ct3/Ct4 | Delta Ct5/Ct6 |
|---|---|---|---|---|---|
| 0.9796 | 98.04 | 95.92 | G2AN/IL1RN | IL13RA1/ILF1 | FLJ11142/NOV |
| 0.9780 | 92.16 | 91.84 | CPT1A/G2AN | IL13RA1/ILF1 | ASAHL/LAMCA |
| 0.9728 | 94.12 | 91.84 | IL13RA1/ILF1 | CPTIALAMCA | ASAHL/PF4 |
| 0.9720 | 90.20 | 95.92 | IL13RA1/ILF1 | FLJ11142/NOV | CPTIAPF4 |
| 0.9716 | 92.16 | 93.88 | HDGF/IL13RA1 | GDF15/PDK4 | LRPPRC-B-NS/PF4 |
| 0.9712 | 90.20 | 91.84 | HDGF/IL13RA1 | ASGR1/LOC286286 | G2AN/PBEF1 |
| 0.9712 | 90.20 | 91.84 | ASGR1/KIAA0010 | CPTIAPF4 | IL13RA1/TNFSF10S |
| 0.9704 | 94.12 | 93.88 | CPT1A/ILF1 | IL13RA1/ILF1 | IL1RN/PF4 |
| 0.9704 | 92.16 | 91.84 | CKLFSF7/CPT1A | HDGF/IL13RA1 | HDGF/IL1RN |
| 0.9704 | 86.27 | 87.76 | ASGR1/HDGF | ASAHL/LAMCA | BMP6/LOC286286 |
| 0.9700 | 96.08 | 93.88 | IL13RA1/ILF1 | CPTIAPF4 | PDK4/RPS6KA2 |
| 0.9696 | 94.12 | 91.84 | CKLFSF3/CPT1A | IL13RA1/ILF1 | KIAA0010/PF4 |
| 0.9696 | 88.24 | 89.80 | CKLFSF3/CPT1A | IL13RA1/ILF1 | NOV/PF4 |
| 0.9696 | 88.24 | 87.76 | CKLFSF3CPT1A | DNAPTP6/G2AN | IL13RA1/ILF1 |
| 0.9692 | 82.35 | 87.76 | ASGR1/CPT1A | FLJ11142/IKBKAP | IL13RA1/ILF1 |
| 0.9684 | 94.12 | 91.84 | CKLFSF3/HDGF | IL13RA1/KIAA0010 | ATP1B1/PF4 |
| 0.9680 | 92.16 | 91.84 | ASGR1/ATP1B1 | HDGF/IL13RA1 | ASGR1/PDK4 |
| 0.9680 | 92.16 | 91.84 | ATP1B1/CKLF | CPTIAIL13RA1 | ASGR1/LOC286286 |
| 0.9680 | 88.24 | 83.67 | ASGR1/BMPR2 | IL13RA1/KIAA0010 | PDK4/PF4 |
| 0.9672 | 94.12 | 93.88 | IL13RA1/ILF1 | CPTIALAMCA | CLECSF6/PF4 |
| 0.9672 | 88.24 | 87.76 | IL13RA1/KIAA0010 | ATP1B1/LAMCA | IKBKAP/NOV |
| 0.9668 | 88.24 | 89.80 | CPT1A/IL1RN | IL13RA1/ILF1 | F2RL1_F/NOV |
| 0.9668 | 86.27 | 87.76 | CPT1A/IL13RA1 | GDF15/ILF1 | LOC283337/PF4 |
| 0.9668 | 88.24 | 85.71 | CKLFSF3/CPT1A | HSPCA/IKBKAP | IL13RA1/ILF1 |
| 0.9664 | 90.20 | 91.84 | ASGR1/CYBRD1 | CPTIAIL13RA1 | CPTIAILF1 |
| 0.9660 | 88.24 | 85.71 | BMPR2/CKLFSF3 | CPTIAIL13RA1 | ASGR1/LOC286286 |
| 0.9660 | 84.31 | 83.67 | BMPR2/CPT1A | IL13RA1/ILF1 | DNAPTP6/LAMCA |
| 0.9656 | 90.20 | 91.84 | ASGR1/FLJ11142 | CKLFSF3/KIAA0010 | IL13RA1/PDK4 |

TABLE B-continued

| | | | | | |
|---|---|---|---|---|---|
| 0.9656 | 88.24 | 89.80 | HDGF/LAMCA | ASGR1/LOC286286 | CPT1ASETBP1 |
| 0.9656 | 88.24 | 89.80 | CPT1A-/PF4 | KIAA0010/SETBP1 | IL13RA1/TNFSF10S |
| 0.9656 | 84.31 | 87.76 | HDGF/IL13RA1 | BMPR2/IL1RN | CKLFSF3/KIAA0010 |
| 0.9652 | 94.12 | 93.88 | CPT1A/IL13RA1 | CKLFSF3/ILF1 | IL1RN/ILF1 |
| 0.9648 | 88.24 | 89.80 | CPT1A/IL13RA1 | G2AN/LOC286286 | LAMCA/PBEF1 |
| 0.9644 | 94.12 | 91.84 | CPT1A/ILF1 | IL13RA1/ILF1 | BMP6/LOC286286 |

| AUC | Delta Ct7/Ct8 | Constant (B0) | Coeff B1 | Coeff B2 | Coeff B3 | Coeff B4 |
|---|---|---|---|---|---|---|
| 0.9796 | CPTIAPF4 | 10.752 | 2.1522 | 7.1374 | 1.036 | −2.7848 |
| 0.9780 | PBEF1/SERPINE1 | −23.019 | −2.6623 | 6.0707 | −1.7348 | −1.5536 |
| 0.9728 | ASAHL/WASF2 | −6.6422 | 5.5159 | −2.0784 | −1.4765 | −0.41881 |
| 0.9720 | B2M/RPS6KA2 | 0.79507 | 5.7281 | 0.7486 | −2.066 | −0.95786 |
| 0.9716 | NOV/PF4 | 18.277 | −3.8357 | 2.4527 | −1.4383 | −1.2075 |
| 0.9712 | CKLFSF7/PDK4 | 21.745 | −4.3857 | 2.1262 | 1.0588 | 2.5306 |
| 0.9712 | ILF1/TNFSF10S | 5.9169 | 1.6859 | −2.0491 | 5.3561 | −4.4945 |
| 0.9704 | IL13RA1/SETBP1 | −2.7173 | −2.9259 | 7.841 | −1.6725 | −1.6814 |
| 0.9704 | LOC286286/SETBP1 | 6.46E−02 | 2.9078 | −3.9019 | 0.85305 | −1.6729 |
| 0.9704 | IL13RA1/PDK4 | 8.8334 | 2.7625 | −1.8465 | 1.7467 | 2.816 |
| 0.9700 | CKLF_A_NS/WASF2 | 9.9077 | 5.4365 | −2.0623 | −0.79232 | −0.32047 |
| 0.9696 | PDK4/SERPINE1 | 10.631 | 2.1326 | 4.5517 | −1.4928 | −0.86575 |
| 0.9696 | LAMCA/TNFAIP6 | 10.319 | 1.9704 | 4.5866 | −1.0143 | 0.44853 |
| 0.9696 | PF4/PRG1(45) | 4.2496 | 2.2554 | −0.48072 | 6.2534 | 2.0314 |
| 0.9692 | B2M/PF4 | −6.3408 | 2.0089 | 0.67327 | 5.8672 | −2.1416 |
| 0.9684 | NOV/RPS6KA2 | 8.8752 | 2.6989 | 3.6492 | −1.6935 | −1.4434 |
| 0.9680 | LOC286286/SERPINE1 | 16.272 | 1.4204 | −4.0948 | 2.2948 | −1.6186 |
| 0.9680 | LAMCA/TNFSF10S | 1.2999 | −0.89257 | −3.2649 | 1.5093 | 1.607 |
| 0.9680 | ASAHL/SETBP1 | 3.8103 | 2.4261 | 2.965 | −1.9102 | −1.7 |
| 0.9672 | ASAHL/WASF2 | −8.0027 | 5.9124 | −1.9042 | −1.3612 | −0.82483 |
| 0.9672 | PF4/PRG1 | −4.3813 | 4.7389 | −1.9183 | 1.5604 | 1.1841 |
| 0.9668 | CPTIAPF4 | 13.105 | 0.3154 | 4.9576 | 0.72056 | −2.564 |
| 0.9668 | SETBP1/TNFSF10S | −5.0587 | −4.103 | 2.0898 | −1.2855 | 1.5378 |
| 0.9668 | PF4/PRG1(45) | 1.9013 | 1.9932 | 1.33E−02 | 5.6783 | 1.8445 |
| 0.9664 | HDGF/SERPINE1 | −4.6434 | 1.2305 | −4.7797 | 2.6575 | −1.2957 |
| 0.9660 | KIAA0010/SETBP1 | −0.64252 | −1.1506 | −3.5385 | 1.6628 | −2.1683 |
| 0.9660 | LAMCA/PBEF1 | −18.312 | 2.023 | 5.954 | −0.29688 | 2.2115 |
| 0.9656 | HDGF/PF4 | 24.691 | 1.7387 | 2.2619 | 2.5986 | −2.3179 |
| 0.9656 | IL13RA1/SETBP1 | −3.2892 | −1.5424 | 1.4252 | −3.4094 | 2.9185 |
| 0.9656 | ILF1/TNFSF10S | 1.569 | −2.4172 | −1.4707 | 5.458 | −5.1279 |
| 0.9656 | CPTIALAMCA | −13.969 | −3.8708 | 1.3911 | 2.768 | −1.9937 |
| 0.9652 | HDGF/PF4 | 7.2972 | −3.1978 | 3.1344 | −0.31809 | −1.7931 |
| 0.9648 | CKLFSF3/PDK4 | 2.4464 | −3.0586 | 1.4994 | 1.2046 | 0.77339 |
| 0.9644 | CYBRD1/RPS6KA2 | 5.9149 | −2.0276 | 4.4205 | 1.2494 | −1.0971 |

Example 10

Use of Classifiers to Determine Presence or Absence of Mild Osteoarthritis in a Test Individual Classifiers such as those identified in Example 9 can be used to diagnose a test individual. For example, measurement of values for RNA species corresponding to biomarkers of any one equation noted in Table A can be determined for a test individual. Thus for example where the classifier noted below using the two biomarkers CPTIA and IL13RA1 are used, measurement of RNA product corresponding to CPT1A and IL13RA1 are determined using quantitative real time RT PCR. Primers specific for CPT1A and IL13RA1 are noted in Tables 5 as well as in Table 8. Ct's are measured using quantitative real time RT-PCR can be obtained using primers as discussed in conjunction with an intercolating dye such as Sybr® Green, or may be used in conjunction with TaqMan® probes. Exemplary TaqMan® probes for the two biomarkers are noted in Table 8.

| AUC | Sens @ 50% Spec | Spec @ 50% Sens | Two Gene Combination | Constant B0) | Coeff (B1) |
|---|---|---|---|---|---|
| 0.892 | 96.08 | 93.88 | CPT1A/IL13RA1 | −9.44E−02 | −2.1336 |
| 0.892 | 96.08 | 93.88 | CPT1A/IL13RA1 | −9.44E−02 | −2.1336 |

Raw Ct values are converted to Delta Ct using a housekeeping gene such as Beta Actin which has been determined not to be differentially expressed as between individuals having mild OA and individuals not having OA. Delta Ct values for CPT1A (Ct1) and IL13RA1 (Ct2) are substituted into the equation listed below $$X = \text{Logit}(P) = \ln(P/(1-P)) = b_0 + b_1(\Delta Ct_1 - \Delta Ct_2) \quad \text{(Eq 2)}$$

$$X = \text{Logit}(P) = \ln(P/1-P) = -9.44 \times 10 - 2 - 2.1336(\Delta Ct_1 - \Delta Ct_2)$$

Where X is indicative of the likelihood that individual has mild OA. In some embodiments the cutoff chosen to indicate mild OA are non OA is 0 so that an X of greater than 0 indicates the individual has mild OA whereas an X of less than 0 indicates the individual does not have OA. In some cases the cutoff is not zero but is chosen on the basis of the training set or scoring population so as to ensure that the greatest population of individuals is called correctly, or so as to ensure an increase in sensitivity or specificity depending upon the criteria chosen.

Example 11

Use of the Combination Identified to Determine Presence or Absence of Mild Osteoarthritis in a Test Individual by Measuring RNA or Protein Products of the Biomarker Combinations Biomarker Combinations Identified by Classifiers such as those identified in Example 9 can also be used independently of the Classifier to diagnose a test individual. Measurement of values for RNA or Protein Products of the biomarkers of any one equation noted in Table A can be determined for a test individual. Thus for example where the classifier noted below using the two biomarkers CPT1A and IL13RA1 are used, measurement of RNA product corresponding to CPT1A and IL13RA1 are determined using quantitative real time RT PCR. Primers specific for CPT1A and IL13RA1 are noted in Tables 5 as well as in Table 8. Ct's are measured using quantitative real time RT-PCR can be obtained using primers as discussed in conjunction with an intercalating dye such as Sybr® Green, or may be used in conjunction with TaqMan® probes. Exemplary TaqMan® probes for the two biomarkers are noted in Table 8. Alternatively, antibodies corresponding to the protein products of CPT1A and IL13RA1 can be utilized. Antibodies which are commercially available corresponding to the biomarkers in Table 4 are found in Table 8. Additional Antibodies corresponding to the other biomarkers of the invention can be made using standard molecular biology techniques as further described herein. Without using the classifier, one can diagnose a test individual by comparing the amount of protein or RNA product corresponding to CPT1A and IL13RA1 in the test individual as compared with the amount of product corresponding to CPT1A and IL13RA1 in control individuals including positive control individuals having mild OA and negative control individuals not having OA. The test individual is then diagnosed as having mild OA if the gene expression pattern of the test individual is more similar to the positive control individuals as compared with the negative control individuals.

$$X = \text{Logit}(P) = \ln(P/(1-P)) = b_0 + b_1(\Delta Ct_1 - \Delta Ct_2) \quad \text{Eq 2}$$

$$X = \text{Logit}(P) = \ln(P/1-P) = -9.44 \times 10 - 2 - 2.1336(\Delta Ct_1 - \Delta Ct_2)$$

Where X is indicative of the likelihood that individual has mild OA. In some embodiments the cutoff chosen to indicate mild OA are non OA is 0 so that an X of greater than 0 indicates the individual has mild OA whereas an X of less than 0 indicates the individual does not have OA. In some cases the cutoff is not zero but is chosen on the basis of the training set or scoring population so as to ensure that the greatest population of individuals is called correctly, or so as to ensure an increase in sensitivity or specificity depending upon the criteria chosen.

Tables

TABLE 1

| LocusID | GeneSymbol | DefaultGeneName |
|---|---|---|
| 196294 | FLJ25059 | hypothetical protein FLJ25059 |
| 53635 | PTOV1 | prostate tumor overexpressed gene 1 |
| 84937 | ZNRF1 | zinc and ring finger protein 1 |
| 152100 | MGC61571 | hypothetical protein MGC61571 |
| 111 | ADCY5 | adenylate cyclase 5 |
| 51602 | NOP5/NOP58 | nucleolar protein NOP5/NOP58 |
| 54583 | EGLN1 | egl nine homolog 1 (*C. elegans*) |
| 1652 | DDT | D-dopachrome tautomerase |
| 10963 | STIP1 | stress-induced-phosphoprotein 1 (Hsp70/Hsp90-organizing protein) |
| 64223 | GBL | G protein beta subunit-like |
| 10245 | TIMM17B | translocase of inner mitochondrial membrane 17 homolog B (yeast) |
| 53827 | FXYD5 | FXYD domain containing ion transport regulator 5 |
| 9524 | GPSN2 | glycoprotein, synaptic 2 |
| 56929 | FEM1C | fem-1 homolog c (*C. elegans*) |
| 5433 | POLR2D | polymerase (RNA) II (DNA directed) polypeptide D |
| 114609 | TIRAP | toll-interleukin 1 receptor (TIR) domain containing adaptor protein |
| 891 | CCNB1 | cyclin B1 |
| 5216 | PFN1 | profilin 1 |
| 51594 | NAG | neuroblastoma-amplified protein |
| 4192 | MDK | midkine (neurite growth-promoting factor 2) |
| 10082 | GPC6 | glypican 6 |
| 54986 | FLJ20574 | hypothetical protein FLJ20574 |
| 23558 | WBP2 | WW domain binding protein 2 |
| 283588 | LOC283588 | hypothetical protein LOC283588 |
| 9787 | DLG7 | discs, large homolog 7 (*Drosophila*) |
| 150094 | SNF1LK | SNF1-like kinase |
| 25804 | LSM4 | LSM4 homolog, U6 small nuclear RNA associated (*S. cerevisiae*) |
| 5714 | PSMD8 | proteasome (prosome, macropain) 26S subunit, non-ATPase, 8 |
| 57017 | DKFZP434K046 | hypothetical protein DKFZp434K046 |
| 841 | CASP8 | caspase 8, apoptosis-related cysteine protease |
| 25894 | DKFZP434I216 | DKFZP434I216 protein |
| 1376 | CPT2 | carnitine palmitoyltransferase II |
| 1196 | CLK2 | CDC-like kinase 2 |
| 55920 | TD-60 | RCC1-like |
| 2244 | FGB | fibrinogen, B beta polypeptide |
| 51042 | ZNF593 | zinc finger protein 593 |
| 23240 | KIAA0922 | KIAA0922 protein |
| 533 | ATP6V0B | ATPase, H+ transporting, lysosomal 21 kDa, V0 subunit c" |
| 2628 | GATM | glycine amidinotransferase (L-arginine: glycine amidinotransferase) |
| 344978 | LOC344978 | similar to actinin, alpha 4 |
| 2104 | ESRRG | estrogen-related receptor gamma |
| 55030 | FBXO34 | F-box protein 34 |

TABLE 1-continued

| LocusID | GeneSymbol | DefaultGeneName |
|---|---|---|
| 5998 | RGS3 | regulator of G-protein signalling 3 |
| 3476 | IGBP1 | immunoglobulin (CD79A) binding protein 1 |
| 10365 | KLF2 | Kruppel-like factor 2 (lung) |
| 29763 | PACSIN3 | protein kinase C and casein kinase substrate in neurons 3 |
| 3727 | JUND | jun D proto-oncogene |
| 10381 | TUBB4 | tubulin, beta, 4 |
| 890 | CCNA2 | cyclin A2 |
| 10519 | CIB1 | calcium and integrin binding 1 (calmyrin) |
| 285196 | FLJ25863 | hypothetical protein FLJ25863 |
| 378938 | MALAT1 | metastasis associated lung adenocarcinoma transcript 1 (non-coding RNA) |
| 359844 | PRDX2P1 | peroxiredoxin 2 pseudogene 1 |
| 23506 | KIAA0240 | KIAA0240 |
| 283658 | LOC283658 | hypothetical protein LOC283658 |
| 4594 | MUT | methylmalonyl Coenzyme A mutase |
| 9204 | ZNF258 | zinc finger protein 258 |
| 10000 | AKT3 | v-akt murine thymoma viral oncogene homolog 3 (protein kinase B, gamma) |
| 84641 | FLJ14753 | hypothetical protein FLJ14753 |
| 51605 | CGI-09 | CGI-09 protein |
| 254013 | MGC50559 | hypothetical protein MGC50559 |
| 401459 | FLJ46365 | FLJ46365 protein |
| 158947 | MGC40053 | hypothetical protein MGC40053 |
| 9343 | U5-116 KD | U5 snRNP-specific protein, 116 kD |
| 1880 | EBI2 | Epstein-Barr virus induced gene 2 (lymphocyte-specific G protein-coupled receptor) |
| 604 | BCL6 | B-cell CLL/lymphoma 6 (zinc finger protein 51) |
| 54583 | EGLN1 | egl nine homolog 1 (C. elegans) |
| 170687 | NUDT4P1 | nudix (nucleoside diphosphate linked moiety X)-type motif 4 pseudogene 1 |
| 10269 | ZMPSTE24 | zinc metalloproteinase (STE24 homolog, yeast) |
| 54433 | NOLA1 | nucleolar protein family A, member 1 (H/ACA small nucleolar RNPs) |
| 285813 | LOC285813 | hypothetical protein LOC285813 |
| 57219 | KIAA1327 | KIAA1327 protein |
| 55827 | PC326 | PC326 protein |
| 22877 | MONDOA | Mlx interactor |
| 378938 | MALAT1 | metastasis associated lung adenocarcinoma transcript 1 (non-coding RNA) |
| 92822 | ZFP276 | zinc finger protein 276 homolog (mouse) |
| 23408 | SIRT5 | sirtuin (silent mating type information regulation 2 homolog) 5 (S. cerevisiae) |
| 8544 | PIR | pirin (iron-binding nuclear protein) |
| 10806 | SDCCAG8 | serologically defined colon cancer antigen 8 |
| 338755 | OR2AG2 | olfactory receptor, family 2, subfamily AG, member 2 |
| 55352 | HSA272196 | hypothetical protein, clone 2746033 |
| 122552 | PPIAP4 | peptidylprolyl isomerase A (cyclophilin A) pseudogene 4 |
| 10785 | WDR4 | WD repeat domain 4 |
| 140890 | SFRS12 | splicing factor, arginine/serine-rich 12 |
| 195 | AHNAK | AHNAK nucleoprotein (desmoyokin) |
| 140688 | C20orf112 | chromosome 20 open reading frame 112 |
| 8815 | BANF1 | barrier to autointegration factor 1 |
| 378938 | MALAT1 | metastasis associated lung adenocarcinoma transcript 1 (non-coding RNA) |
| 160335 | DKFZp762A217 | hypothetical protein DKFZp762A217 |
| 10367 | CBARA1 | calcium binding atopy-related autoantigen 1 |
| 378938 | MALAT1 | metastasis associated lung adenocarcinoma transcript 1 (non-coding RNA) |
| 55500 | EKI1 | ethanolamine kinase |
| 7453 | WARS | tryptophanyl-tRNA synthetase |
| 5527 | PPP2R5C | protein phosphatase 2, regulatory subunit B (B56), gamma isoform |
| 6722 | SRF | serum response factor (c-fos serum response element-binding transcription factor) |
| 29005 | PRO1073 | PRO1073 protein |
| 7786 | MAP3K12 | mitogen-activated protein kinase kinase kinase 12 |
| 282991 | BLOC1S2 | biogenesis of lysosome-related organelles complex-1, subunit 2 |
| 4065 | LY75 | lymphocyte antigen 75 |
| 378938 | MALAT1 | metastasis associated lung adenocarcinoma transcript 1 (non-coding RNA) |
| 50618 | ITSN2 | intersectin 2 |
| 170954 | KIAA1949 | KIAA1949 |
| 29005 | PRO1073 | PRO1073 protein |
| 378938 | MALAT1 | metastasis associated lung adenocarcinoma transcript 1 (non-coding RNA) |
| 11083 | DATF1 | death associated transcription factor 1 |
| 25937 | TAZ | transcriptional co-activator with PDZ-binding motif (TAZ) |
| 7571 | ZNF23 | zinc finger protein 23 (KOX 16) |
| 23035 | KIAA0931 | KIAA0931 protein |
| 4739 | NEDD9 | neural precursor cell expressed, developmentally down-regulated 9 |
| 51780 | JMJD1B | jumonji domain containing 1B |
| 3652 | IPP | intracisternal A particle-promoted polypeptide |
| 1793 | DOCK1 | dedicator of cytokinesis 1 |
| 29005 | PRO1073 | PRO1073 protein |
| 23404 | EXOSC2 | exosome component 2 |
| 170371 | C10orf128 | chromosome 10 open reading frame 128 |
| 246135 | LOC246135 | TBP-associated factor 9-like pseudogene |
| 27173 | SLC39A1 | solute carrier family 39 (zinc transporter), member 1 |
| 50809 | HP1-BP74 | HP1-BP74 |
| 5869 | RAB5B | RAB5B, member RAS oncogene family |
| 27236 | ARFIP1 | ADP-ribosylation factor interacting protein 1 (arfaptin 1) |
| 51077 | C14orf111 | chromosome 14 open reading frame 111 |

TABLE 1-continued

| LocusID | GeneSymbol | DefaultGeneName |
|---|---|---|
| 399511 | LOC399511 | transcription elongation factor A (SII), 1 pseudogene |
| 10771 | ZMYND11 | zinc finger, MYND domain containing 11 |
| 55250 | STATIP1 | signal transducer and activator of transcription 3 interacting protein 1 |
| 29005 | PRO1073 | PRO1073 protein |
| 8578 | SCARF1 | scavenger receptor class F, member 1 |
| 4092 | SMAD7 | SMAD, mothers against DPP homolog 7 (Drosophila) |
| 3778 | KCNMA1 | potassium large conductance calcium-activated channel, subfamily M, alpha member 1 |
| 27125 | AF5Q31 | ALL1 fused gene from 5q31 |
| 5179 | PENK | proenkephalin |
| 828 | CAPS | calcyphosine |
| 26520 | TIMM9 | translocase of inner mitochondrial membrane 9 homolog (yeast) |
| 220359 | TIGD3 | tigger transposable element derived 3 |
| 9874 | TLK1 | tousled-like kinase 1 |
| 57213 | C13orf1 | chromosome 13 open reading frame 1 |
| 7372 | UMPS | uridine monophosphate synthetase (orotate phosphoribosyl transferase and orotidine-5'-decarboxylase) |
| 65983 | NS3TP2 | HCV NS3-transactivated protein 2 |
| 128637 | C20orf140 | chromosome 20 open reading frame 140 |
| 5594 | MAPK1 | mitogen-activated protein kinase 1 |
| 25923 | DKFZP564J0863 | DKFZP564J0863 protein |
| 7249 | TSC2 | tuberous sclerosis 2 |
| 8621 | CDC2L5 | cell division cycle 2-like 5 (cholinesterase-related cell division controller) |
| 23032 | USP33 | ubiquitin specific protease 33 |
| 80790 | CMIP | c-Maf-inducing protein |
| 246784 | LOC246784 | homolog of C. elegans smu-1 pseudogene |
| 2013 | EMP2 | epithelial membrane protein 2 |
| 113386 | LOC113386 | similar to envelope protein |
| 51692 | CPSF3 | cleavage and polyadenylation specific factor 3, 73 kDa |
| 11238 | CA5B | carbonic anhydrase VB, mitochondrial |
| 23389 | THRAP2 | thyroid hormone receptor associated protein 2 |
| 10747 | MASP2 | mannan-binding lectin serine protease 2 |
| 84641 | FLJ14753 | hypothetical protein FLJ14753 |
| 7024 | TFCP2 | transcription factor CP2 |
| 10489 | MUF1 | MUF1 protein |
| 8543 | LMO4 | LIM domain only 4 |
| 9847 | KIAA0528 | KIAA0528 gene product |
| 267 | AMFR | autocrine motility factor receptor |
| 1387 | CREBBP | CREB binding protein (Rubinstein-Taybi syndrome) |
| 3608 | ILF2 | interleukin enhancer binding factor 2, 45 kDa |
| 3328 | HSPCP2 | heat shock 90 kDa protein 1, beta pseudogene 2 |
| 25852 | HSPC056 | HSPC056 protein |
| 10046 | CXorf6 | chromosome X open reading frame 6 |
| 317786 | C14orf62 | chromosome 14 open reading frame 62 |
| 200765 | TIGD1 | tigger transposable element derived 1 |
| 10569 | SLU7 | step II splicing factor SLU7 |
| 83 | ACTGP10 | actin, gamma pseudogene 10 |
| 57489 | KIAA1229 | KIAA1229 protein |
| 29005 | PRO1073 | PRO1073 protein |
| 10124 | ARL4A | ADP-ribosylation factor-like 4A |
| 10124 | ARL4A | ADP-ribosylation factor-like 4A |
| 83478 | ARHGAP24 | Rho GTPase activating protein 24 |
| 167153 | PAPD4 | PAP associated domain containing 4 |
| 51710 | ZNF44 | zinc finger protein 44 (KOX 7) |
| 84864 | MINA | MYC induced nuclear antigen |

TABLE 2

| Alternative Gene Symbols | HGNC_Symbol | Locus Link ID |
|---|---|---|
| ABCA1 | ABCA1 | 19 |
| ABCG1 | ABCG1 | 9619 |
| ACP1 | ACP1 | 52 |
| ADPRT | ADPRT | 142 |
| ANGPTL2 | ANGPTL2 | 23452 |
| B2M | B2M | 567 |
| BCL6 | BCL6 | 604 |
| BMPR2 | BMPR2 | 659 |
| C19orf13 | C19orf13 | 26065 |
| C1QR1 | C1QR1 | 22918 |
| CCNC | CCNC | 892 |
| CLECSF6 | CLECSF6 | 50856 |
| CLIC4 | CLIC4 | 25932 |
| CLN3 | CLN3 | 1201 |
| DNAPTP6 | DNAPTP6 | 26010 |
| EBNA1BP2 | EBNA1BP2 | 10969 |
| EGR1 | EGR1 | 1958 |
| F2RL1 | F2RL1 | 2150 |
| FLJ11000 | FLJ11000 | 55281 |
| FLJ11142 | FLJ11142 | 55779 |
| FLJ13612 | EFHD1 | 80303 |
| FLJ32234 | C6orf151 | 154007 |
| G2AN | GANAB | 23193 |
| HSPCA | HSPCAL3 | 3320 |
| HSPCB | HSPCB | 3326 |
| IKBKAP | IKBKAP | 8518 |
| IL13RA1 | IL13RA1 | 3597 |
| ILF1 | FOXK2 | 3607 |
| IRF1 | IRF1 | 3659 |
| LAMC1 | LAMC1 | 3915 |
| LCMT2 | LCMT2 | 9836 |
| MAFB | MAFB | 9935 |
| NCOA1 | NCOA1 | 8648 |
| NXN | NXN | 64359 |
| PAIP2 | PAIP2 | 51247 |
| PDCD5 | PDCD5 | 9141 |
| PDK4 | PDK4 | 5166 |
| PER1 | PER1 | 5187 |
| PF4 | PF4V1 | 5196 |
| PF4 | PF4 | 5197 |
| PMSCL2 | EXOSC10 | 5394 |
| PPIF | PPIF | 10105 |
| SETBP1 | SETBP1 | 26040 |

TABLE 2-continued

| Alternative Gene Symbols | HGNC_Symbol | Locus Link ID |
|---|---|---|
| SFRS6 | SFRS6 | 6431 |
| SLC5A6 | SLC5A6 | 8884 |
| TNFAIP6 | TNFAIP6 | 7130 |
| TSPAN2 | TSPAN-2 | 64521 |
| WDR9 | C21orf107 | 54014 |

TABLE 2-continued

| Alternative Gene Symbols | HGNC_Symbol | Locus Link ID |
|---|---|---|
| YES1 | YES1 | 7525 |
| ZFR | ZFR | 51663 |
| ZNF397 | ZNF397 | 84307 |
| WWP2 | WWP2 | 11060 |

TABLE 3

| Gene Symbol | Locus LinkID | Accession | RefSeq Accession | Protein Accession | Gene Name |
|---|---|---|---|---|---|
| ACTGP10 | 83 | AL139396 | NG_003039 | | |
| ADCY5 | 111 | AF497517 | NM_183357 | NP_899200 | *Homo sapiens* adenylate cyclase 5 (ADCY5), mRNA |
| ADCY5 | 111 | AF497517 | XM_351567 | XP_351568 | |
| AF5Q31 | 27125 | NM_014423 | NM_014423 | NP_055238 | *Homo sapiens* ALL1 fused gene from 5q31 (AF5Q31), mRNA |
| AHNAK | 195 | M80902 | | | |
| AKT3 | 10000 | AK055109 | NM_005465 | NP_005456 | *Homo sapiens* v-akt murine thymoma viral oncogene homolog 3 (protein kinase B, gamma) (AKT3), transcript variant 1, mRNA |
| AKT3 | 10000 | AK055109 | NM_181690 | NP_859029 | *Homo sapiens* v-akt murine thymoma viral oncogene homolog 3 (protein kinase B, gamma) (AKT3), transcript variant 2, mRNA |
| AMFR | 267 | NM_001144 | NM_001144 | NP_001135 | *Homo sapiens* autocrine motility factor receptor (AMFR), transcript variant 1, mRNA |
| AMFR | 267 | NM_001144 | NM_138958 | NP_620408 | *Homo sapiens* autocrine motility factor receptor (AMFR), transcript variant 2, mRNA |
| ARFIP1 | 27236 | AK096509 | NM_014447 | NP_055262 | *Homo sapiens* ADP-ribosylation factor interacting protein 1 (arfaptin 1) (ARFIP1), mRNA |
| ARHGAP24 | 83478 | NM_031305 | NM_031305 | NP_112595 | *Homo sapiens* Rho GTPase activating protein 24 (ARHGAP24), mRNA |
| ARL4A | 10124 | NM_005738 | NM_005738 | NP_005729 | *Homo sapiens* ADP-ribosylation factor-like 4A (ARL4A), transcript variant 1, mRNA |
| ARL4A | 10124 | NM_005738 | NM_212460 | NP_997625 | *Homo sapiens* ADP-ribosylation factor-like 4A (ARL4A), transcript variant 2, mRNA |

TABLE 3-continued

| Gene Symbol | Locus LinkID | Accession | RefSeq Accession | Protein Accession | Gene Name |
|---|---|---|---|---|---|
| ATP6V0B | 533 | NM_004047 | NM_004047 | NP_004038 | *Homo sapiens* ATPase, H+ transporting, lysosomal 21 kDa, V0 subunit c" (ATP6V0B), mRNA |
| BANF1 | 8815 | NM_003860 | NM_003860 | NP_003851 | *Homo sapiens* barrier to autointegration factor 1 (BANF1), mRNA |
| BCL6 | 604 | NM_138931 | NM_001706 | NP_001697 | *Homo sapiens* B-cell CLL/lymphoma 6 (zinc finger protein 51) (BCL6), transcript variant 1, mRNA |
| BCL6 | 604 | NM_138931 | NM_138931 | NP_620309 | *Homo sapiens* B-cell CLL/lymphoma 6 (zinc finger protein 51) (BCL6), transcript variant 2, mRNA |
| BLOC1S2 | 282991 | AK054697 | NM_001001342 | NP_001001342 | *Homo sapiens* biogenesis of lysosome-related organelles complex-1, subunit 2 (BLOC1S2), transcript variant 2, mRNA |
| BLOC1S2 | 282991 | AK054697 | NM_173809 | NP_776170 | *Homo sapiens* biogenesis of lysosome-related organelles complex-1, subunit 2 (BLOC1S2), transcript variant 1, mRNA |
| C10orf128 | 170371 | BC031641 | XM_498485 | XP_498485 | PREDICTED: *Homo sapiens* chromosome 10 open reading frame 128 (C10orf128), mRNA |
| C13orf1 | 57213 | NM_020456 | NM_020456 | NP_065189 | *Homo sapiens* chromosome 13 open reading frame 1 (C13orf1), mRNA |
| C14orf111 | 51077 | NM_015962 | NM_015962 | NP_057046 | *Homo sapiens* chromosome 14 open reading frame 111 (C14orf111), mRNA |
| C14orf62 | 317786 | AL133467 | NR_001459 | | *Homo sapiens* chromosome 14 open reading frame 62 (C14orf62) on chromosome 14 |
| C20orf112 | 140688 | AL122043 | NM_080616 | NP_542183 | *Homo sapiens* chromosome 20 open reading frame 112 (C20orf112), mRNA |

TABLE 3-continued

| Gene Symbol | Locus LinkID | Accession | RefSeq Accession | Protein Accession | Gene Name |
|---|---|---|---|---|---|
| C20orf140 | 128637 | AK095110 | NM_144628 | NP_653229 | *Homo sapiens* TBC1 domain family, member 20 (TBC1D20), mRNA |
| CA5B | 11238 | AK057568 | NM_007220 | NP_009151 | *Homo sapiens* carbonic anhydrase VB, mitochondrial (CA5B), nuclear gene encoding mitochondrial protein, mRNA |
| CAPS | 828 | NM_004058 | NM_004058 | NP_004049 | *Homo sapiens* calcyphosine (CAPS), transcript variant 1, mRNA |
| CAPS | 828 | NM_004058 | NM_080590 | NP_542157 | *Homo sapiens* calcyphosine (CAPS), transcript variant 2, mRNA |
| CASP8 | 841 | NM_033357 | NM_001228 | NP_001219 | *Homo sapiens* caspase 8, apoptosis-related cysteine protease (CASP8), transcript variant A, mRNA |
| CASP8 | 841 | NM_033357 | NM_033355 | NP_203519 | *Homo sapiens* caspase 8, apoptosis-related cysteine protease (CASP8), transcript variant B, mRNA |
| CASP8 | 841 | NM_033357 | NM_033356 | NP_203520 | *Homo sapiens* caspase 8, apoptosis-related cysteine protease (CASP8), transcript variant C, mRNA |
| CASP8 | 841 | NM_033357 | NM_033357 | NP_203521 | *Homo sapiens* caspase 8, apoptosis-related cysteine protease (CASP8), transcript variant D, mRNA |
| CASP8 | 841 | NM_033357 | NM_033358 | NP_203522 | *Homo sapiens* caspase 8, apoptosis-related cysteine protease (CASP8), transcript variant E, mRNA |
| CBARA1 | 10367 | NM_006077 | NM_006077 | NP_006068 | *Homo sapiens* calcium binding atopy-related autoantigen 1 (CBARA1), mRNA |
| CCNA2 | 890 | AF518006 | NM_001237 | NP_001228 | *Homo sapiens* cyclin A2 (CCNA2), mRNA |
| CCNB1 | 891 | NM_031966 | NM_031966 | NP_114172 | *Homo sapiens* cyclin B1 (CCNB1), mRNA |
| CDC2L5 | 8621 | NM_003718 | NM_003718 | NP_003709 | *Homo sapiens* cell division cycle 2-like 5 |

TABLE 3-continued

| Gene Symbol | Locus LinkID | Accession | RefSeq Accession | Protein Accession | Gene Name |
|---|---|---|---|---|---|
| CDC2L5 | 8621 | NM_003718 | NM_031267 | NP_112557 | (cholinesterase-related cell division controller) (CDC2L5), transcript variant 1, mRNA<br>*Homo sapiens* cell division cycle 2-like 5 (cholinesterase-related cell division controller) (CDC2L5), transcript variant 2, mRNA |
| CGI-09 | 51605 | NM_015939 | NM_015939 | NP_057023 | *Homo sapiens* CGI-09 protein (CGI-09), mRNA |
| CIB1 | 10519 | AB021866 | NM_006384 | NP_006375 | *Homo sapiens* calcium and integrin binding 1 (calmyrin) (CIB1), mRNA |
| CLK2 | 1196 | NM_003993 | NM_001291 | NP_001282 | *Homo sapiens* CDC-like kinase 2 (CLK2), transcript variant 2, mRNA |
| CLK2 | 1196 | NM_003993 | NM_003993 | NP_003984 | *Homo sapiens* CDC-like kinase 2 (CLK2), transcript variant 1, mRNA |
| CMIP | 80790 | AB051481 | NM_030629 | NP_085132 | *Homo sapiens* c-Maf-inducing protein (CMIP), transcript variant Tc-mip, mRNA |
| CMIP | 80790 | AB051481 | NM_198390 | NP_938204 | *Homo sapiens* c-Maf-inducing protein (CMIP), transcript variant C-mip, mRNA |
| CPSF3 | 51692 | NM_016207 | NM_016207 | NP_057291 | *Homo sapiens* cleavage and polyadenylation specific factor 3, 73 kDa (CPSF3), mRNA |
| CPT2 | 1376 | NM_000098 | NM_000098 | NP_000089 | *Homo sapiens* carnitine palmitoyltransferase II (CPT2), nuclear gene encoding mitochondrial protein, mRNA |
| CREBBP | 1387 | NM_004380 | NM_004380 | NP_004371 | *Homo sapiens* CREB binding protein (Rubinstein-Taybi syndrome) (CREBBP), mRNA |
| CXorf6 | 10046 | NM_005491 | NM_005491 | NP_005482 | *Homo sapiens* chromosome X open reading frame 6 (CXorf6), mRNA |
| DATF1 | 11083 | NM_022105 | NM_022105 | NP_071388 | *Homo sapiens* death associated transcription factor 1 (DATF1), transcript variant 1, mRNA |
| DATF1 | 11083 | NM_022105 | NM_080796 | NP_542986 | *Homo sapiens* death associated |

TABLE 3-continued

| Gene Symbol | Locus LinkID | Accession | RefSeq Accession | Protein Accession | Gene Name |
|---|---|---|---|---|---|
| | | | | | transcription factor 1 (DATF1), transcript variant 2, mRNA |
| DATF1 | 11083 | NM_022105 | NM_080797 | NP_542987 | Homo sapiens death associated transcription factor 1 (DATF1), transcript variant 3, mRNA |
| DDT | 1652 | AF058293 | NM_001355 | NP_001346 | Homo sapiens D-dopachrome tautomerase (DDT), mRNA |
| DKFZP434I216 | 25894 | AK024475 | NM_015432 | NP_056247 | Homo sapiens DKFZP434I216 protein (DKFZP434I216), mRNA |
| DKFZP434I216 | 25894 | AK024475 | XM_290684 | XP_290684 | |
| DKFZP434K046 | 57017 | BC029341 | NM_020312 | NP_064708 | Homo sapiens hypothetical protein DKFZp434K046 (DKFZP434K046), mRNA |
| DKFZP434K046 | 57017 | BC029341 | XM_166276 | XP_166276 | |
| DKFZP564J0863 | 25923 | AK090822 | NM_015459 | NP_056274 | Homo sapiens DKFZP564J0863 protein (DKFZP564J0863), mRNA |
| DKFZP564J0863 | 25923 | AK090822 | NM_175893 | NP_787089 | |
| DKFZp762A217 | 160335 | NM_152588 | NM_152588 | NP_689801 | Homo sapiens hypothetical protein DKFZp762A217 (DKFZp762A217), mRNA |
| DLG7 | 9787 | NM_014750 | NM_014750 | NP_055565 | Homo sapiens discs, large homolog 7 (Drosophila) (DLG7), mRNA |
| DOCK1 | 1793 | NM_001380 | NM_001380 | NP_001371 | Homo sapiens dedicator of cytokinesis 1 (DOCK1), mRNA |
| EBI2 | 1880 | NM_004951 | NM_004951 | NP_004942 | Homo sapiens Epstein-Barr virus induced gene 2 (lymphocyte-specific G protein-coupled receptor) (EBI2), mRNA |
| EGLN1 | 54583 | AJ310543 | NM_022051 | NP_071334 | Homo sapiens egl nine homolog 1 (C. elegans) (EGLN1), mRNA |
| EGLN1 | 54583 | AF246631 | NM_022051 | NP_071334 | Homo sapiens egl nine homolog 1 (C. elegans) (EGLN1), mRNA |
| EKI1 | 55500 | NM_018638 | NM_018638 | NP_061108 | Homo sapiens ethanolamine kinase 1 (ETNK1), mRNA |
| EMP2 | 2013 | NM_001424 | NM_001424 | NP_001415 | Homo sapiens epithelial membrane protein 2 (EMP2), mRNA |
| ESRRG | 2104 | NM_001438 | NM_001438 | NP_001429 | Homo sapiens estrogen-related receptor gamma (ESRRG), transcript variant 1, mRNA |

TABLE 3-continued

| Gene Symbol | Locus LinkID | Accession | RefSeq Accession | Protein Accession | Gene Name |
|---|---|---|---|---|---|
| ESRRG | 2104 | NM_001438 | NM_206594 | NP_996317 | *Homo sapiens* estrogen-related receptor gamma (ESRRG), transcript variant 2, mRNA |
| ESRRG | 2104 | NM_001438 | NM_206595 | NP_996318 | *Homo sapiens* estrogen-related receptor gamma (ESRRG), transcript variant 3, mRNA |
| EXOSC2 | 23404 | NM_014285 | NM_014285 | NP_055100 | *Homo sapiens* exosome component 2 (EXOSC2), mRNA |
| FBXO34 | 55030 | NM_017943 | NM_017943 | NP_060413 | *Homo sapiens* F-box protein 34 (FBXO34), mRNA |
| FEM1C | 56929 | BC028369 | NM_020177 | NP_064562 | *Homo sapiens* fem-1 homolog c (*C. elegans*) (FEM1C), mRNA |
| FGB | 2244 | NM_005141 | NM_005141 | NP_005132 | *Homo sapiens* fibrinogen, B beta polypeptide (FGB), mRNA |
| FLJ10094 | 55068 | NM_017993 | NM_017993 | NP_060463 | *Homo sapiens* hypothetical protein FLJ10094 (FLJ10094), mRNA |
| FLJ14753 | 84641 | NM_032558 | NM_032558 | NP_115947 | *Homo sapiens* hypothetical protein FLJ14753 (FLJ14753), mRNA |
| FLJ14753 | 84641 | NM_032558 | NM_032558 | NP_115947 | *Homo sapiens* hypothetical protein FLJ14753 (FLJ14753), mRNA |
| FLJ20574 | 54986 | NM_017886 | | | |
| FLJ25059 | 196294 | NM_144981 | NM_144981 | NP_659418 | *Homo sapiens* hypothetical protein FLJ25059 (FLJ25059), mRNA |
| FLJ25863 | 285196 | BC043583 | | | |
| FLJ46365 | 401459 | AK128232 | NM_207504 | NP_997387 | *Homo sapiens* FLJ46365 protein (FLJ46365), mRNA |
| FXYD5 | 53827 | NM_014164 | NM_014164 | NP_054883 | *Homo sapiens* FXYD domain containing ion transport regulator 5 (FXYD5), transcript variant 2, mRNA |
| FXYD5 | 53827 | NM_014164 | NM_144779 | NP_659003 | *Homo sapiens* FXYD domain containing ion transport regulator 5 (FXYD5), transcript variant 1, mRNA |
| GATM | 2628 | NM_001482 | NM_001482 | NP_001473 | *Homo sapiens* glycine amidinotransferase (L-arginine:glycine amidinotransferase) (GATM), mRNA |

TABLE 3-continued

| Gene Symbol | Locus LinkID | Accession | RefSeq Accession | Protein Accession | Gene Name |
|---|---|---|---|---|---|
| GBL | 64223 | NM_022372 | NM_022372 | NP_071767 | *Homo sapiens* G protein beta subunit-like (GBL), mRNA |
| GPC6 | 10082 | NM_005708 | NM_005708 | NP_005699 | *Homo sapiens* glypican 6 (GPC6), mRNA |
| GPSN2 | 9524 | NM_138501 | NM_004868 | NP_004859 | *Homo sapiens* glycoprotein, synaptic 2 (GPSN2), mRNA |
| GPSN2 | 9524 | NM_138501 | NM_138501 | NP_612510 | *Homo sapiens* glycoprotein, synaptic 2 (GPSN2), mRNA |
| HP1-BP74 | 50809 | AK023129 | NM_016287 | NP_057371 | *Homo sapiens* HP1-BP74 (HP1-BP74), mRNA |
| HSA272196 | 55352 | AJ272196 | NM_018405 | NP_060875 | *Homo sapiens* hypothetical protein, clone 2746033 (HSA272196), mRNA |
| HSPC056 | 25852 | NM_015396 | NM_014154 | NP_054873 | *Homo sapiens* armadillo repeat containing 8 (ARMC8), mRNA |
| HSPC056 | 25852 | NM_015396 | NM_015396 | NP_056211 | *Homo sapiens* armadillo repeat containing 8 (ARMC8), mRNA |
| HSPC056 | 25852 | NM_015396 | NM_213654 | NP_998819 | *Homo sapiens* armadillo repeat containing 8 (ARMC8), mRNA |
| HSPCP2 | 3328 | AC091046 | | | |
| IGBP1 | 3476 | BT006736 | NM_001551 | NP_001542 | *Homo sapiens* immunoglobulin (CD79A) binding protein 1 (IGBP1), mRNA |
| ILF2 | 3608 | NM_004515 | NM_004515 | NP_004506 | *Homo sapiens* interleukin enhancer binding factor 2, 45 kDa (ILF2), mRNA |
| IPP | 3652 | NM_005897 | NM_005897 | NP_005888 | *Homo sapiens* intracisternal A particle-promoted polypeptide (IPP), mRNA |
| ITSN2 | 50618 | NM_006277 | NM_006277 | NP_006268 | *Homo sapiens* intersectin 2 (ITSN2), transcript variant 1, mRNA |
| ITSN2 | 50618 | NM_006277 | NM_019595 | NP_062541 | *Homo sapiens* intersectin 2 (ITSN2), transcript variant 3, mRNA |
| ITSN2 | 50618 | NM_006277 | NM_147152 | NP_671494 | *Homo sapiens* intersectin 2 (ITSN2), transcript variant 2, mRNA |
| JMJD1B | 51780 | NM_016604 | NM_016604 | NP_057688 | *Homo sapiens* jumonji domain containing 1B (JMJD1B), mRNA |
| JUND | 3727 | NM_005354 | NM_005354 | NP_005345 | *Homo sapiens* jun D proto-oncogene (JUND), mRNA |
| KCNMA1 | 3778 | NM_002247 | NM_002247 | NP_002238 | *Homo sapiens* potassium large conductance calcium-activated channel, subfamily M, alpha member |

TABLE 3-continued

| Gene Symbol | Locus LinkID | Accession | RefSeq Accession | Protein Accession | Gene Name |
|---|---|---|---|---|---|
| | | | | | 1 (KCNMA1), mRNA |
| KIAA0240 | 23506 | AL833540 | NM_015349 | NP_056164 | *Homo sapiens* KIAA0240 (KIAA0240), mRNA |
| KIAA0240 | 23506 | AL833540 | XM_166479 | XP_166479 | |
| KIAA0528 | 9847 | AB011100 | NM_014802 | NP_055617 | *Homo sapiens* KIAA0528 gene product (KIAA0528), mRNA |
| KIAA0922 | 23240 | NM_015196 | NM_015196 | NP_056011 | *Homo sapiens* KIAA0922 protein (KIAA0922), mRNA |
| KIAA0931 | 23035 | AB023148 | NM_015020 | NP_055835 | *Homo sapiens* KIAA0931 protein (KIAA0931), mRNA |
| KIAA0931 | 23035 | AB023148 | XM_041191 | XP_041191 | |
| KIAA1229 | 57489 | AB033055 | NM_001007022 | NP_001007023 | *Homo sapiens* KIAA1229 protein (KIAA1229), transcript variant 2, mRNA |
| KIAA1229 | 57489 | AB033055 | NM_020729 | NP_065780 | *Homo sapiens* KIAA1229 protein (KIAA1229), transcript variant 1, mRNA |
| KIAA1229 | 57489 | AB033055 | XM_030665 | XP_030665 | |
| KIAA1327 | 57219 | AB037748 | | | |
| KIAA1596 | 57697 | AL833656 | XM_048128 | XP_048128 | PREDICTED: *Homo sapiens* KIAA1596 (KIAA1596), mRNA |
| KIAA1949 | 170954 | AB075829 | | | |
| KLF2 | 10365 | NM_016270 | NM_016270 | NP_057354 | *Homo sapiens* Kruppel-like factor 2 (lung) (KLF2), mRNA |
| LMO4 | 8543 | NM_006769 | NM_006769 | NP_006760 | *Homo sapiens* LIM domain only 4 (LMO4), mRNA |
| LOC113386 | 113386 | NM_138781 | NM_138781 | NP_620136 | *Homo sapiens* similar to envelope protein (LOC113386), mRNA |
| LOC246135 | 246135 | AC092798 | NG_001574 | | |
| LOC246784 | 246784 | AL157713 | NG_001588 | | |
| LOC283588 | 283588 | AK095276 | | | |
| LOC283658 | 283658 | AL833463 | | | |
| LOC285813 | 285813 | AK094269 | | | |
| LOC344978 | 344978 | XM_293669 | | | |
| LOC399511 | 399511 | AC097359 | NG_003186 | | |
| LSM4 | 25804 | NM_012321 | NM_012321 | NP_036453 | *Homo sapiens* LSM4 homolog, U6 small nuclear RNA associated (*S. cerevisiae*) (LSM4), mRNA |
| LY75 | 4065 | NM_002349 | NM_002349 | NP_002340 | *Homo sapiens* lymphocyte antigen 75 (LY75), mRNA |
| MALAT1 | 378938 | AF001540 | | | |
| MALAT1 | 378938 | AF203815 | | | |
| MALAT1 | 378938 | AF203815 | | | |
| MALAT1 | 378938 | AF203815 | | | |
| MALAT1 | 378938 | AF203815 | | | |
| MALAT1 | 378938 | AF203815 | | | |
| MALAT1 | 378938 | AF203815 | | | |

TABLE 3-continued

| Gene Symbol | Locus LinkID | Accession | RefSeq Accession | Protein Accession | Gene Name |
|---|---|---|---|---|---|
| MAP3K12 | 7786 | NM_006301 | NM_006301 | NP_006292 | *Homo sapiens* mitogen-activated protein kinase kinase kinase 12 (MAP3K12), mRNA |
| MAPK1 | 5594 | NM_002745 | NM_002745 | NP_002736 | *Homo sapiens* mitogen-activated protein kinase 1 (MAPK1), transcript variant 1, mRNA |
| MAPK1 | 5594 | NM_002745 | NM_138957 | NP_620407 | *Homo sapiens* mitogen-activated protein kinase 1 (MAPK1), transcript variant 2, mRNA |
| MASP2 | 10747 | NM_006610 | NM_006610 | NP_006601 | *Homo sapiens* mannan-binding lectin serine protease 2 (MASP2), transcript variant 1, mRNA |
| MASP2 | 10747 | NM_006610 | NM_139208 | NP_631947 | *Homo sapiens* mannan-binding lectin serine protease 2 (MASP2), transcript variant 2, mRNA |
| MDK | 4192 | NM_002391 | NM_002391 | NP_002382 | *Homo sapiens* midkine (neurite growth-promoting factor 2) (MDK), mRNA |
| MGC40053 | 158947 | NM_152583 | NM_152583 | NP_689796 | *Homo sapiens* armadillo repeat containing, X-linked 4 (ARMCX4), mRNA |
| MGC50559 | 254013 | BC039417 | NM_173802 | NP_776163 | *Homo sapiens* hypothetical protein MGC50559 (MGC50559), mRNA |
| MGC61571 | 152100 | BX648671 | NM_182523 | NP_872329 | *Homo sapiens* hypothetical protein MGC61571 (MGC61571), mRNA |
| MINA | 84864 | NM_032778 | NM_032778 | NP_116167 | *Homo sapiens* MYC induced nuclear antigen (MINA), transcript variant 2, mRNA |
| MINA | 84864 | NM_032778 | NM_153182 | NP_694822 | *Homo sapiens* MYC induced nuclear antigen (MINA), transcript variant 3, mRNA |
| MONDOA | 22877 | NM_014938 | NM_014938 | NP_055753 | *Homo sapiens* Mlx interactor (MONDOA), mRNA |
| MUF1 | 10489 | NM_006369 | NM_006369 | NP_006360 | *Homo sapiens* MUF1 protein (MUF1), mRNA |
| MUT | 4594 | NM_000255 | NM_000255 | NP_000246 | *Homo sapiens* methylmalonyl Coenzyme A mutase (MUT), nuclear gene |

TABLE 3-continued

| Gene Symbol | Locus LinkID | Accession | RefSeq Accession | Protein Accession | Gene Name |
|---|---|---|---|---|---|
| | | | | | encoding mitochondrial protein, mRNA |
| NAG | 51594 | NM_015909 | NM_015909 | NP_056993 | *Homo sapiens* neuroblastoma-amplified protein (NAG), mRNA |
| NEDD9 | 4739 | NM_006403 | NM_006403 | NP_006394 | *Homo sapiens* neural precursor cell expressed, developmentally down-regulated 9 (NEDD9), mRNA |
| NEDD9 | 4739 | NM_006403 | NM_182966 | NP_892011 | *Homo sapiens* neural precursor cell expressed, developmentally down-regulated 9 (NEDD9), mRNA |
| NOLA1 | 54433 | NM_018983 | NM_018983 | NP_061856 | *Homo sapiens* nucleolar protein family A, member 1 (H/ACA small nucleolar RNPs) (NOLA1), transcript variant 1, mRNA |
| NOLA1 | 54433 | NM_018983 | NM_032993 | NP_127460 | *Homo sapiens* nucleolar protein family A, member 1 (H/ACA small nucleolar RNPs) (NOLA1), transcript variant 2, mRNA |
| NOP5/NOP58 | 51602 | NM_015934 | NM_015934 | NP_057018 | *Homo sapiens* nucleolar protein NOP5/NOP58 (NOP5/NOP58), mRNA |
| NS3TP2 | 65983 | NM_023927 | NM_023927 | NP_076416 | *Homo sapiens* HCV NS3-transactivated protein 2 (NS3TP2), mRNA |
| NUDT4P1 | 170687 | AL359758 | | | |
| OR2AG2 | 338755 | AC091564 | NM_001004490 | NP_001004490 | *Homo sapiens* olfactory receptor, family 2, subfamily AG, member 2 (OR2AG2), mRNA |
| OR2AG2 | 338755 | AC091564 | XM_291980 | XP_291980 | |
| PACSIN3 | 29763 | NM_016223 | NM_016223 | NP_057307 | *Homo sapiens* protein kinase C and casein kinase substrate in neurons 3 (PACSIN3), mRNA |
| PAPD4 | 167153 | BC047581 | NM_173797 | NP_776158 | *Homo sapiens* PAP associated domain containing 4 (PAPD4), mRNA |
| PC326 | 55827 | NM_018442 | NM_018442 | NP_060912 | *Homo sapiens* IQ motif and WD repeats 1 (IQWD1), mRNA |
| PENK | 5179 | J00123 | NM_006211 | NP_006202 | *Homo sapiens* proenkephalin (PENK), mRNA |
| PFN1 | 5216 | NM_005022 | NM_005022 | NP_005013 | *Homo sapiens* profilin 1 (PFN1), mRNA |

TABLE 3-continued

| Gene Symbol | Locus LinkID | Accession | RefSeq Accession | Protein Accession | Gene Name |
|---|---|---|---|---|---|
| PIR | 8544 | NM_003662 | NM_003662 | NP_003653 | *Homo sapiens* pirin (iron-binding nuclear protein) (PIR), mRNA |
| POLR2D | 5433 | NM_004805 | NM_004805 | NP_004796 | *Homo sapiens* polymerase (RNA) II (DNA directed) polypeptide D (POLR2D), mRNA |
| PPIAP4 | 122552 | AL109628 | NG_002483 | | |
| PPP2R5C | 5527 | AY052369 | NM_002719 | NP_002710 | *Homo sapiens* protein phosphatase 2, regulatory subunit B (B56), gamma isoform (PPP2R5C), transcript variant 1, mRNA |
| PPP2R5C | 5527 | AY052369 | NM_178586 | NP_848701 | *Homo sapiens* protein phosphatase 2, regulatory subunit B (B56), gamma isoform (PPP2R5C), transcript variant 2, mRNA |
| PPP2R5C | 5527 | AY052369 | NM_178587 | NP_848702 | *Homo sapiens* protein phosphatase 2, regulatory subunit B (B56), gamma isoform (PPP2R5C), transcript variant 3, mRNA |
| PPP2R5C | 5527 | AY052369 | NM_178588 | NP_848703 | *Homo sapiens* protein phosphatase 2, regulatory subunit B (B56), gamma isoform (PPP2R5C), transcript variant 4, mRNA |
| PRDX2P1 | 359844 | AL356750 | NG_002915 | | |
| PRO1073 | 29005 | AF001542 | | | |
| PRO1073 | 29005 | AF001542 | | | |
| PRO1073 | 29005 | AF001542 | | | |
| PRO1073 | 29005 | AF001542 | | | |
| PRO1073 | 29005 | AF001542 | | | |
| PSMD8 | 5714 | NM_002812 | NM_002812 | NP_002803 | *Homo sapiens* proteasome (prosome, macropain) 26S subunit, non-ATPase, 8 (PSMD8), mRNA |
| PTOV1 | 53635 | NM_017432 | NM_017432 | NP_059128 | *Homo sapiens* prostate tumor overexpressed gene 1 (PTOV1), mRNA |
| RAB5B | 5869 | BC050558 | NM_002868 | NP_002859 | *Homo sapiens* RAB5B, member RAS oncogene family (RAB5B), mRNA |
| RGS3 | 5998 | NM_144488 | NM_017790 | NP_060260 | *Homo sapiens* regulator of G-protein signalling 3 (RGS3), transcript variant 3, mRNA |

TABLE 3-continued

| Gene Symbol | Locus LinkID | Accession | RefSeq Accession | Protein Accession | Gene Name |
|---|---|---|---|---|---|
| RGS3 | 5998 | NM_144488 | NM_021106 | NP_066929 | *Homo sapiens* regulator of G-protein signalling 3 (RGS3), transcript variant 2, mRNA |
| RGS3 | 5998 | NM_144488 | NM_130795 | NP_570613 | *Homo sapiens* regulator of G-protein signalling 3 (RGS3), transcript variant 1, mRNA |
| RGS3 | 5998 | NM_144488 | NM_134427 | NP_602299 | *Homo sapiens* regulator of G-protein signalling 3 (RGS3), transcript variant 4, mRNA |
| RGS3 | 5998 | NM_144488 | NM_144488 | NP_652759 | *Homo sapiens* regulator of G-protein signalling 3 (RGS3), transcript variant 6, mRNA |
| RGS3 | 5998 | NM_144488 | NM_144489 | NP_652760 | *Homo sapiens* regulator of G-protein signalling 3 (RGS3), transcript variant 5, mRNA |
| SCARF1 | 8578 | NM_003693 | NM_003693 | NP_003684 | *Homo sapiens* scavenger receptor class F, member 1 (SCARF1), transcript variant 1, mRNA |
| SCARF1 | 8578 | NM_003693 | NM_145349 | NP_663324 | *Homo sapiens* scavenger receptor class F, member 1 (SCARF1), transcript variant 2, mRNA |
| SCARF1 | 8578 | NM_003693 | NM_145350 | NP_663325 | *Homo sapiens* scavenger receptor class F, member 1 (SCARF1), transcript variant 3, mRNA |
| SCARF1 | 8578 | NM_003693 | NM_145351 | NP_663326 | *Homo sapiens* scavenger receptor class F, member 1 (SCARF1), transcript variant 4, mRNA |
| SCARF1 | 8578 | NM_003693 | NM_145352 | NP_663327 | *Homo sapiens* scavenger receptor class F, member 1 (SCARF1), transcript variant 5, mRNA |
| SDCCAG8 | 10806 | NM_006642 | NM_006642 | NP_006633 | *Homo sapiens* serologically defined colon cancer antigen 8 (SDCCAG8), mRNA |
| SFRS12 | 140890 | NM_139168 | NM_139168 | NP_631907 | *Homo sapiens* splicing factor, arginine/serine-rich 12 (SFRS12), mRNA |
| SIRT5 | 23408 | AL441883 | NM_012241 | NP_036373 | *Homo sapiens* sirtuin (silent mating type information regulation 2 homolog) 5 (*S. cerevisiae*) |

TABLE 3-continued

| Gene Symbol | Locus LinkID | Accession | RefSeq Accession | Protein Accession | Gene Name |
|---|---|---|---|---|---|
| SIRT5 | 23408 | AL441883 | NM_031244 | NP_112534 | (SIRT5), transcript variant 1, mRNA *Homo sapiens* sirtuin (silent mating type information regulation 2 homolog) 5 (*S. cerevisiae*) (SIRT5), transcript variant 2, mRNA |
| SLC39A1 | 27173 | NM_014437 | NM_014437 | NP_055252 | *Homo sapiens* solute carrier family 39 (zinc transporter), member 1 (SLC39A1), mRNA |
| SLU7 | 10569 | NM_006425 | NM_006425 | NP_006416 | *Homo sapiens* step II splicing factor SLU7 (SLU7), mRNA |
| SMAD7 | 4092 | NM_005904 | NM_005904 | NP_005895 | *Homo sapiens* SMAD, mothers against DPP homolog 7 (*Drosophila*) (SMAD7), mRNA |
| SNF1LK | 150094 | NM_173354 | NM_173354 | NP_775490 | *Homo sapiens* SNF1-like kinase (SNF1LK), mRNA |
| SRF | 6722 | NM_003131 | NM_003131 | NP_003122 | *Homo sapiens* serum response factor (c-fos serum response element-binding transcription factor) (SRF), mRNA |
| STATIP1 | 55250 | NM_018255 | NM_018255 | NP_060725 | *Homo sapiens* signal transducer and activator of transcription 3 interacting protein 1 (STATIP1), mRNA |
| STIP1 | 10963 | NM_006819 | NM_006819 | NP_006810 | *Homo sapiens* stress-induced-phosphoprotein 1 (Hsp70/Hsp90-organizing protein) (STIP1), mRNA |
| TAZ | 25937 | AL833852 | NM_015472 | NP_056287 | *Homo sapiens* WW domain containing transcription regulator 1 (WWTR1), mRNA |
| TD-60 | 55920 | AJ421269 | NM_018715 | NP_061185 | *Homo sapiens* RCC1-like (TD-60), mRNA |
| TFCP2 | 7024 | NM_005653 | NM_005653 | NP_005644 | *Homo sapiens* transcription factor CP2 (TFCP2), mRNA |
| THRAP2 | 23389 | AB028948 | NM_015335 | NP_056150 | *Homo sapiens* thyroid hormone receptor associated protein 2 (THRAP2), mRNA |
| THRAP2 | 23389 | AB028948 | XM_034056 | XP_034056 | |

TABLE 3-continued

| Gene Symbol | Locus LinkID | Accession | RefSeq Accession | Protein Accession | Gene Name |
|---|---|---|---|---|---|
| TIGD1 | 200765 | NM_145702 | NM_145702 | NP_663748 | *Homo sapiens* tigger transposable element derived 1 (TIGD1), mRNA |
| TIGD3 | 220359 | AC000353 | NM_145719 | NP_663771 | *Homo sapiens* tigger transposable element derived 3 (TIGD3), mRNA |
| TIMM17B | 10245 | NM_005834 | NM_005834 | NP_005825 | *Homo sapiens* translocase of inner mitochondrial membrane 17 homolog B (yeast) (TIMM17B), mRNA |
| TIMM9 | 26520 | AF150100 | NM_012460 | NP_036592 | *Homo sapiens* translocase of inner mitochondrial membrane 9 homolog (yeast) (TIMM9), mRNA |
| TIRAP | 114609 | NM_052887 | NM_052887 | NP_443119 | *Homo sapiens* toll-interleukin 1 receptor (TIR) domain containing adaptor protein (TIRAP), transcript variant 1, mRNA |
| TIRAP | 114609 | NM_052887 | NM_148910 | NP_683708 | *Homo sapiens* toll-interleukin 1 receptor (TIR) domain containing adaptor protein (TIRAP), transcript variant 2, mRNA |
| TLK1 | 9874 | BC032657 | NM_012290 | NP_036422 | *Homo sapiens* tousled-like kinase 1 (TLK1), mRNA |
| TSC2 | 7249 | NM_000548 | NM_000548 | NP_000539 | *Homo sapiens* tuberous sclerosis 2 (TSC2), transcript variant 1, mRNA |
| TSC2 | 7249 | NM_000548 | NM_021055 | NP_066399 | *Homo sapiens* tuberous sclerosis 2 (TSC2), transcript variant 2, mRNA |
| TSC2 | 7249 | NM_000548 | NM_021056 | NP_066400 | *Homo sapiens* tuberous sclerosis 2 (TSC2), transcript variant 3, mRNA |
| TUBB4 | 10381 | NM_006086 | NM_006086 | NP_006077 | *Homo sapiens* tubulin, beta 3 (TUBB3), mRNA |
| U5-116 KD | 9343 | NM_004247 | NM_004247 | NP_004238 | *Homo sapiens* U5 snRNP-specific protein, 116 kD (U5-116 KD), mRNA |
| UMPS | 7372 | NM_000373 | NM_000373 | NP_000364 | *Homo sapiens* uridine monophosphate synthetase (orotate phosphoribosyl transferase and orotidine-5'-decarboxylase) (UMPS), mRNA |
| USP33 | 23032 | NM_015017 | NM_015017 | NP_055832 | *Homo sapiens* ubiquitin specific protease 33 |

TABLE 3-continued

| Gene Symbol | Locus LinkID | Accession | RefSeq Accession | Protein Accession | Gene Name |
|---|---|---|---|---|---|
| USP33 | 23032 | NM_015017 | NM_201624 | NP_963918 | (USP33), transcript variant 1, mRNA<br>*Homo sapiens* ubiquitin specific protease 33 (USP33), transcript variant 2, mRNA |
| USP33 | 23032 | NM_015017 | NM_201626 | NP_963920 | *Homo sapiens* ubiquitin specific protease 33 (USP33), transcript variant 3, mRNA |
| WARS | 7453 | NM_004184 | NM_004184 | NP_004175 | *Homo sapiens* tryptophanyl-tRNA synthetase (WARS), transcript variant 1, mRNA |
| WARS | 7453 | NM_004184 | NM_173701 | NP_776049 | *Homo sapiens* tryptophanyl-tRNA synthetase (WARS), transcript variant 2, mRNA |
| WARS | 7453 | NM_004184 | NM_213645 | NP_998810 | *Homo sapiens* tryptophanyl-tRNA synthetase (WARS), transcript variant 3, mRNA |
| WARS | 7453 | NM_004184 | NM_213646 | NP_998811 | *Homo sapiens* tryptophanyl-tRNA synthetase (WARS), transcript variant 4, mRNA |
| WBP2 | 23558 | NM_012478 | NM_012478 | NP_036610 | *Homo sapiens* WW domain binding protein 2 (WBP2), mRNA |
| WDR4 | 10785 | AB039887 | NM_018669 | NP_061139 | *Homo sapiens* WD repeat domain 4 (WDR4), transcript variant 1, mRNA |
| WDR4 | 10785 | AB039887 | NM_033661 | NP_387510 | *Homo sapiens* WD repeat domain 4 (WDR4), transcript variant 2, mRNA |
| WDR4 | 10785 | AB039887 | NM_033662 | NP_387511 | |
| ZFP276 | 92822 | BC038839 | NM_152287 | NP_689500 | *Homo sapiens* zinc finger protein 276 homolog (mouse) (ZFP276), mRNA |
| ZMPSTE24 | 10269 | NM_005857 | NM_005857 | NP_005848 | *Homo sapiens* zinc metallopeptidase (STE24 homolog, yeast) (ZMPSTE24), mRNA |
| ZMYND11 | 10771 | NM_006624 | NM_006624 | NP_006615 | *Homo sapiens* zinc finger, MYND domain containing 11 (ZMYND11), transcript variant 1, mRNA |
| ZMYND11 | 10771 | NM_006624 | NM_212479 | NP_997644 | *Homo sapiens* zinc finger, MYND domain containing 11 (ZMYND11), transcript variant 2, mRNA |

TABLE 3-continued

| Gene Symbol | Locus LinkID | Accession | RefSeq Accession | Protein Accession | Gene Name |
|---|---|---|---|---|---|
| ZNF23 | 7571 | NM_145911 | NM_145911 | NP_666016 | *Homo sapiens* zinc finger protein 23 (KOX 16) (ZNF23), mRNA |
| ZNF258 | 9204 | NM_007167 | NM_007167 | NP_009098 | *Homo sapiens* zinc finger protein 258 (ZNF258), mRNA |
| ZNF258 | 9204 | NM_007167 | NM_145310 | NP_660353 | *Homo sapiens* zinc finger protein 258 (ZNF258), mRNA |
| ZNF44 | 51710 | NM_016264 | NM_016264 | NP_057348 | *Homo sapiens* zinc finger protein 44 (KOX 7) (ZNF44), mRNA |
| ZNF593 | 51042 | NM_015871 | NM_015871 | NP_056955 | *Homo sapiens* zinc finger protein 593 (ZNF593), mRNA |
| ZNRF1 | 84937 | NM_032268 | NM_032268 | NP_115644 | *Homo sapiens* zinc and ring finger 1 (ZNRF1), mRNA |
| ZNRF1 | 84937 | NM_032268 | NM_032851 | NP_116240 | |

TABLE 4

| Gene symbol | Default GeneSymbol | Gene ID | p value | MildOA/Ctrl | direction | Default Gene Description |
|---|---|---|---|---|---|---|
| ASAHL | ASAHL | 27163 | 0.009 | 1.274891308 | up-regulated | N-acylsphingosine amidohydrolase (acid ceramidase)-like |
| ASGR1 | ASGR1 | 432 | 0.077 | 0.861159722 | down-regulated | asialoglycoprotein receptor 1 |
| ATP1B1 | ATP1B1 | 481 | 0.005 | 1.316358494 | up-regulated | ATPase, Na+/K+ transporting, beta 1 polypeptide |
| BMP6 | BMP6 | 654 | 0.003 | 0.796341318 | down-regulated | bone morphogenetic protein 6 |
| C4BPA | C4BPA | 722 | 0.037 | 0.737432267 | down-regulated | complement component 4 binding protein, alpha |
| CKLF | CKLF | 51192 | 0.177 | 0.956880843 | down-regulated | chemokine-like factor |
| CKLFSF3 | CMTM3 | 123920 | 0.17 | 0.881792622 | down-regulated | CKLF-like MARVEL transmembrane domain containing 3 |
| CKLFSF7 | CMTM7 | 112616 | 0.007 | 0.830860996 | down-regulated | CKLF-like MARVEL transmembrane domain containing 7 |
| CLECSF6 | CLEC4A | 50856 | <0.001 | 0.882012865 | down-regulated | C-type lectin domain family 4, member A |
| CLIC5 | CLIC5 | 53405 | 0.007 | 1.361931949 | up-regulated | chloride intracellular channel 5 |
| CPT1A | CPT1A | 1374 | 0.000 | 1.515183811 | up-regulated | carnitine palmitoyltransferase 1A (liver) |
| F2RL1 | F2RL1 | 2150 | 0.03 | 0.748628617 | down-regulated | coagulation factor II (thrombin) receptor-like 1 |
| FLJ11142 | WDR52 | 55779 | 0.097 | 1.033432697 | | WD repeat domain 52 |
| HDGF | HDGF | 3068 | 0.015 | 1.172846981 | up-regulated | hepatoma-derived growth factor (high-mobility group protein 1-like) |
| HSPCA | HSPCA | 3320 | 0.092 | 0.908589998 | down-regulated | heat shock 90 kDa protein 1, alpha |
| IL13RA1 | IL13RA1 | 3597 | 2.4586674377e−009 | 0.601129904 | down-regulated | interleukin 13 receptor, alpha 1 |
| ILF1 | FOXK2 | 3607 | 0.096 | 1.129335679 | up-regulated | forkhead box K2 |
| KIAA0010 | UBE3C | 9690 | 0.039 | 1.147791932 | up-regulated | ubiquitin protein ligase E3C |
| LOC283337 | LOC283337 | 283337 | 0.071 | 1.201988295 | up-regulated | hypothetical protein LOC283337 |
| LOC286286 | FLJ30435 | 387628 | 0.003 | 1.299053205 | up-regulated | hypothetical protein FLJ30435 |

TABLE 4-continued

| Gene symbol | Default GeneSymbol | Gene ID | p value | MildOA/Ctrl | direction | Default Gene Description |
|---|---|---|---|---|---|---|
| LRMP | LRMP | 4033 | 0.199 | 0.91529472 | down-regulated | lymphoid-restricted membrane protein |
| LRPPRC | LRPPRC | 10128 | 0.067 | 1.159461432 | up-regulated | leucine-rich PPR-motif containing |
| NOV | NOV | 4856 | 0.052 | 1.334728983 | up-regulated | nephroblastoma overexpressed gene |
| PDK4 | PDK4 | 5166 | 0.0001 | 1.414873975 | up-regulated | pyruvate dehydrogenase kinase, isozyme 4 |
| PF4 | PF4 | 5196 | 3.1409597922e−005 | 0.584997455 | down-regulated | platelet factor 4 (chemokine (C—X—C motif) ligand 4) |
| RPS6KA2 | RPS6KA2 | 6196 | 0.173 | 0.898669396 | down-regulated | ribosomal protein S6 kinase, 90 kDa, polypeptide 2 |
| SERPINE1 | SERPINE1 | 5054 | 0.014 | 0.661094627 | down-regulated | serpin peptidase inhibitor, clade E (nexin, plasminogen activator inhibitor type 1), member 1 |
| SERPING1 | SERPING1 | 710 | 0.045 | 0.750552389 | down-regulated | serpin peptidase inhibitor, clade G (C1 inhibitor), member 1, (angioedema, hereditary) |
| SETBP1 | SETBP1 | 26040 | 0.122 | 0.97735996 | | SET binding protein 1 |
| TNF | TNF | 7124 | 0.060 | 0.882124093 | down-regulated | tumor necrosis factor (TNF superfamily, member 2) |
| TNFAIP6 | TNFAIP6 | 7130 | 0.017 | 0.732318557 | down-regulated | tumor necrosis factor, alpha-induced protein 6 |
| TNFSF6 | FASLG | 356 | 0.005 | 1.329513627 | up-regulated | Fas ligand (TNF superfamily, member 6) |
| WASF2 | WASF2 | 10163 | 0.09 | 0.74783735 | down-regulated | WAS protein family, member 2 |

TABLE 5

| Gene symbol | Default GeneSymbol | GeneID | Rna Accession | Protein Access'n |
|---|---|---|---|---|
| ASAHL | ASAHL | 27163 | NM_014435 | NP_055250 |
| ASGR1 | ASGR1 | 432 | NM_001671 | NP_001662 |
| ATP1B1 | ATP1B1 | 481 | NM_001001787 | NP_001001787 |
| ATP1B1 | ATP1B1 | 481 | NM_001677 | NP_001668 |
| BMP6 | BMP6 | 654 | NM_001718 | NP_001709 |
| C4BPA | C4BPA | 722 | NM_000715 | NP_000706 |
| CKLF | CKLF | 51192 | NM_016326 | NP_057410 |
| CKLF | CKLF | 51192 | NM_016951 | NP_058647 |
| CKLF | CKLF | 51192 | NM_181640 | NP_857591 |
| CKLF | CKLF | 51192 | NM_181641 | NP_857592 |
| CKLFSF3 | CMTM3 | 123920 | NM_144601 | NP_653202 |
| CKLFSF3 | CMTM3 | 123920 | NM_181553 | NP_853531 |
| CKLFSF3 | CMTM3 | 123920 | NM_181554 | NP_853532 |
| CKLFSF3 | CMTM3 | 123920 | NM_181555 | NP_853533 |
| CKLFSF7 | CMTM7 | 112616 | NM_138410 | NP_612419 |
| CKLFSF7 | CMTM7 | 112616 | NM_181472 | NP_852137 |
| CLECSF6 | CLEC4A | 50856 | NM_016184 | NP_057268 |
| CLECSF6 | CLEC4A | 50856 | NM_194447 | NP_919429 |
| CLECSF6 | CLEC4A | 50856 | NM_194448 | NP_919430 |
| CLECSF6 | CLEC4A | 50856 | NM_194450 | NP_919432 |
| CLIC5 | CLIC5 | 53405 | NM_016929 | NP_058625 |
| CPT1A | CPT1A | 1374 | NM_001876 | NP_001867 |
| F2RL1 | F2RL1 | 2150 | NM_005242 | NP_005233 |
| FLJ11142 | WDR52 | 55779 | NM_018338 | NP_060808 |
| HDGF | HDGF | 3068 | NM_004494 | NP_004485 |
| HSPCA | HSPCA | 3320 | NM_005348 | NP_005339 |
| IL13RA1 | IL13RA1 | 3597 | NM_001560 | NP_001551 |
| ILF1 | FOXK2 | 3607 | NM_004514 | NP_004505 |
| ILF1 | FOXK2 | 3607 | NM_181430 | NP_852095 |
| ILF1 | FOXK2 | 3607 | NM_181431 | NP_852096 |
| KIAA0010 | UBE3C | 9690 | NM_014671 | NP_055486 |
| LOC283337 | LOC283337 | 283337 | NM_001004304 | NP_001004304 |
| LOC286286 | FLJ30435 | 387628 | NM_174950 | NP_777610 |
| LRMP | LRMP | 4033 | NM_006152 | NP_006143 |
| LRPPRC | LRPPRC | 10128 | NM_133259 | NP_573566 |

TABLE 5-continued

| Gene symbol | Default GeneSymbol | GeneID | Rna Accession | Protein Access'n |
|---|---|---|---|---|
| NOV | NOV | 4856 | NM_002514 | NP_002505 |
| PDK4 | PDK4 | 5166 | NM_002612 | NP_002603 |
| PF4 | PF4 | 5196 | NM_002619 | NP_002610 |
| RPS6KA2 | RPS6KA2 | 6196 | NM_001006932 | NP_001006933 |
| RPS6KA2 | RPS6KA2 | 6196 | NM_021135 | NP_066958 |
| SERPINE1 | SERPINE1 | 5054 | NM_000602 | NP_000593 |
| SERPING1 | SERPING1 | 710 | NM_000062 | NP_000053 |
| SETBP1 | SETBP1 | 26040 | NM_015559 | NP_056374 |
| TNF | TNF | 7124 | NM_000594 | NP_000585 |
| TNFAIP6 | TNFAIP6 | 7130 | NM_007115 | NP_009046 |
| TNFSF6 | FASLG | 356 | NM_000639 | NP_000630 |
| WASF2 | WASF2 | 10163 | NM_006990 | NP_008921 |

TABLE 6

| | | 5' Primer | | | 3' Primer | | | |
|---|---|---|---|---|---|---|---|---|
| Symbol | Ref. ID | Primer Sequence | Position | SEQ ID NO: | Primer Sequence | Position | SEQ ID NO: | Product Length |
| ASAHL | NM_014435 | CTACGAGTCCTCCG TGTTC | 410 | 1 | AGAATTGCACAT CCACTGTC | 537 | 2 | 128 |
| ASGR1 | NM_001671 | GGAGCAGAAATTT GTCCAGCAC | 767 | 3 | TTCTTGAAGCCCG TCTCGTAGT | 883 | 4 | 117 |
| ATP1B1 | NM_001677 | CTAAGCCTCCCAAG AATGAG | 649 | 5 | CTTATCTTCATCT CGCTTGC | 749 | 6 | 101 |
| BMP6 | NM_001718 | ATGGCAGGACTGG ATCATTGC | 1454 | 7 | AATCGCGTGGTTG GTTGCAT | 1559 | 8 | 106 |
| C4BPA | NM_000715 | CCTGCAGTTATTCA CACTGG | 1594 | 9 | CACCATAGCCAG AATCACAT | 1743 | 10 | 150 |
| CKLF | NM_016951 | TTCTGCTTCAGTGT GAAAGG | 184 | 11 | ATAACGGTGACTT CAAATCCA | 314 | 12 | 131 |
| CKLFSF3 | NM_181553 | AGTCGGGTCTCTCA TTCATC | 285 | 13 | GCATCAGCAAAG AGGAAGTA | 399 | 14 | 115 |
| CKLFSF7 | NM_138410 | TTTACCTGGTCCAC CTCTTC | 508 | 15 | CGCTCTGGTTGTA ACTCTTG | 651 | 16 | 144 |
| CLECSF6 | NM_016184 | ATATGCCCGTGGA AGAGACA | 531 | 17 | TGAGCCTCCATTC TAGCACAGT | 666 | 18 | 136 |
| CLIC5 | NM_016929 | TCCATGTGGTCAAG ATTGTGGC | 890 | 19 | TAGGCCAACTCG ATCTCACTGT | 1037 | 20 | 148 |
| CPT1A | NM_001876 | CTGAGCCTTGGAG ATTATCA | 2112 | 21 | ATGTACGACACA CCATAGCC | 2250 | 22 | 139 |
| F2RL1 | NM_005242 | TGGCACCATCCAA GGAACCAAT | 223 | 23 | TTCCAGTGAGGA CAGATGCAGA | 368 | 24 | 146 |
| FLJ11142 | NM_018338 | TCGTTTCTTGGTGA CTGCTGGA | 2656 | 25 | TCCAAACCTGGG AGATGGAACT | 2767 | 26 | 112 |
| HDGF | NM_00494 | CAAAGACCTCTTCC CTTACG | 495 | 27 | TTTCTGGGAGGAC TGATAGC | 630 | 28 | 136 |
| HSPCA | NM_005348 | ATGATTGGCCAGTT CGGTGTTG | | 29 | TTCACCTGTGTCT GTCCTCACT | | 30 | 147 |
| IL13RA1 | NM_001560 | CATTGTTCCAGTCA TCGTCGCA | | 31 | TCTTGCCAGGATC AGGAATTGG | | 32 | 101 |
| ILF1 | NM_181431 | AGACAGCCCGAAG GATGATT | 921 | 33 | TTGTCCGCAGTCC TGTAGTA | 1070 | 34 | 150 |
| KIAA0010 | BC014029 | TGATGGTACCCAA AGTCAGGCT | 1385 | 35 | AACGGTACCATA GACCCTGTGA | 1505 | 36 | 121 |

TABLE 6-continued

| | | 5' Primer | | | 3' Primer | | | |
|---|---|---|---|---|---|---|---|---|
| Symbol | Ref. ID | Primer Sequence | Position | SEQ ID NO: | Primer Sequence | Position | SEQ ID NO: | Product Length |
| LOC283337 | BM786513 | AACAGGACTGATGGGACACGAA | 268 | 37 | ACTTGCCTGAGCCATGCTGAT | 412 | 38 | 145 |
| LOC286286 | NM_174950 | CACCAGGAGCACACTTATATCATGGA | 638 | 39 | CCTCGTTCATTGCAAGATAGAATTCAC | 737 | 40 | 100 |
| LRMP | NM_006152 | GAGCACGCTGAATTAGAAGA | 1848 | 41 | GAGAAGATGGCTTGGAGTTT | 1977 | 42 | 130 |
| LRPPRC | NM_133259 | CGTTTGACGTACCTGAGTTGTGG | | 43 | TTGGTTCAATCGGCAGGCAA | | 44 | 119 |
| NOV | NM_002514 | CAGAGCAGCCAACAGATAAG | 830 | 45 | AGAACCTGGGCTTGTAGGT | 946 | 46 | 117 |
| PDK4 | NM_002612 | ACTCGGATGCTGATGAACCA | 705 | 47 | AAGGCATCTTGGACCACTGCTA | 823 | 48 | 119 |
| PF4 | NM_002619 | GTTGCTGCTCCTGCCACTT | | 49 | GTGGCTATCAGTTGGGCAGT | | 50 | |
| RPS6KA2 | NM_021135 | ACCCAATCGTGCAGCAGTTACA | 1411 | 51 | ATGCACACATCGCTTGCACA | 1520 | 52 | 110 |
| SERPINE1 | NM_000602 | ATCAGCCACTGGAAAGGCAACA | 919 | 53 | AACATGTCGGTCATTCCCAGGT | 1040 | 54 | 122 |
| SERPING1 | NM_000062 | CCCATGATGAATAGCAAGAA | 1027 | 55 | AGACGATGTTTCAGGTTCTG | 1160 | 56 | 134 |
| SETBP1 | NM_015559 | TGAAGGCTTTGGAACGTACAGG | 3752 | 57 | GGGACTTGGCATCCCTGGAG | 3857 | 58 | 106 |
| TNF | NM_000594 | ATGTTGTAGCAAACCCTCAA | 441 | 59 | GAAGAGGACCTGGGAGTAGA | 589 | 60 | 149 |
| TNFAIP6 | NM_007115 | ATATGGCTTGAACGAGCAGC | 161 | 61 | TGGCCGCCTTCAAATTCACA | 267 | 62 | 107 |
| TNFSF6 | NM_000639 | CATTTAACAGGCAAGTCCAA | 599 | 63 | CAAGGCCACCCTTCTTATAC | 701 | 64 | 103 |
| WASF2 | NM_006990 | GTTCAGCAACTTCACAGCGA | 407 | 65 | CACTCAGGTCCTTCTGCTGTTT | 531 | 66 | 125 |

TABLE 7

| Gene Symbol | Description | Commercially Available Antibody Reference | Scientific Reference |
|---|---|---|---|
| ASAHL | N-acylsphingosine amidohydrolase (acid ceramidase)-like | | |
| ASGR1 | asialoglycoprotein receptor 1 | | |
| ATP1B1 | ATPase, Na+/K+ transporting, beta 1 polypeptide | | |
| BMP6 | bone morphogenetic protein 6 | ab15640 and ab10859 AbCam AntiHuman Rat Monoclonal | Schluesener HJ & Meyermann R Immunolocalization of BMP-6, a novel TGF-beta-related cytokine, in normal and atherosclerotic smooth muscle cells. Atherosclerosis 113: 153-6 (1995) |
| C4BPA | complement component 4 | | |

TABLE 7-continued

| Gene Symbol | Description | Commercially Available Antibody Reference | Scientific Reference |
|---|---|---|---|
| CKLF | binding protein, alpha chemokine-like factor | | |
| CKLFSF3 | CKLF-like MARVEL transmembrane domain containing 3 | | |
| CKLFSF7 | CKLF-like MARVEL transmembrane domain containing 7 | | |
| CLECSF6 | C-type lectin domain family 4, member A | ab15854 AbCam AntiHuman Chicken Polyclonal | Bates EE et al. APCs express DCIR, a novel C-type lectin surface receptor containing an immunoreceptor tyrosine-based inhibitory motif. J Immunol 163: 1973-83 (1999). |
| CLIC5 | chloride intracellular channel 5 | | |
| CPT1A | carnitine palmitoyltransferase 1A (liver) | | |
| F2RL1 | coagulation factor II (thrombin) receptor-like 1 | AbCam Ab13097 or Ab13388 PAR2 AntiHuman Rabbit Polyclonal Antibody | |
| FLJ11142 | WD repeat domain 52 | | |
| HDGF | hepatoma-derived growth factor (high-mobility group protein 1-like) | | |
| HSPCA | heat shock 90 kDa protein 1, alpha | AbCam Ab1429 AntiHuman Mouse Monoclonal Antibody | Riehl RM et al. Immunological evidence that the nonhormone binding component of avian steroid receptors exists in a wide range of tissues and species. Biochemistry 24: 6586-91 (1985). |
| IL13RA1 | interleukin 13 receptor, alpha 1 | | |
| ILF1 | forkhead box K2 | AbCam Ab5298 AntiHuman Goat Polyclonal Antibody | Li C et al. Cloning of a cellular factor, interleukin binding factor, that binds to NFAT-like motifs in the human immunodeficiency virus long terminal repeat. Proc Natl Acad Sci USA 88: 7739-43 (1991). |
| KIAA0010 | ubiquitin protein ligase E3C | | |
| LOC283337 | hypothetical protein LOC283337 | | |
| LOC286286 | hypothetical protein FLJ30435 | | |
| LRMP | lymphoid-restricted membrane protein | AbCam Ab9931 AntiHuman Goat Polyclonal Antibody | Behrens TW et al. Carboxyl-terminal targeting and novel post-translational processing of JAW1, a lymphoid protein of the endoplasmic reticulum. J Biol Chem 271: 23528-34 (1996). |
| LRPPRC | leucine-rich PPR-motif containing | | |

TABLE 7-continued

| Gene Symbol | Description | Commercially Available Antibody Reference | Scientific Reference |
|---|---|---|---|
| NOV | nephroblastoma overexpressed gene | Abcam Ab 10888 CCN3 Antibody Rabbit Polyclonal Predicted to react against Human | Lin CG et al. Integrin-dependent functions of the angiogenic inducer NOV (CCN3): implication in wound healing. J Biol Chem 280: 8229-37 (2005). |
| PDK4 | pyruvate dehydrogenase kinase, isozyme 4 | | |
| PF4 | platelet factor 4 (chemokine (C—X—C motif) ligand 4) | Abcam Ab9561 AntiHuman Rabbit Polyclonal | |
| RPS6KA2 | ribosomal protein S6 kinase, 90 kDa, polypeptide 2 | | |
| SERPINE1 | serpin peptidase inhibitor, clade E (nexin, plasminogen activator inhibitor type 1), member 1 | AbCam Ab12499 PAI1 AntiHuman Mouse Monoclonal | |
| SERPING1 | serpin peptidase inhibitor, clade G (C1 inhibitor), member 1, (angioedema, hereditary) | AbCam Ab8778 C1 AntiHuman Sheep Polyclonal Ab17193 AntiHuman Mouse Monoclonal | |
| SETBP1 | SET binding protein 1 | | |
| TNF | tumor necrosis factor (TNF superfamily, member 2) | AbCam Ab6671 AntiHuman Rabbit Polyclonal | Baarsch MJ et al. Detection of tumor necrosis factor alpha from porcine alveolar macrophages using an L929 fibroblast bioassay. J Immunol Methods 140: 15-22 (1991). |
| TNFAIP6 | tumor necrosis factor, alpha-induced protein 6 | | |
| TNFSF6 | Fas ligand (TNF superfamily, member 6) | | |
| WASF2 | WAS protein family, member 2 | | |

TABLE 8

| Gene Symbol | Acc'n Number | SensePrimer | SEQ ID NO: | AntisensePrimer | SEQ ID NO: | TaqManProbe | SEQ ID NO: |
|---|---|---|---|---|---|---|---|
| ASAHL | NM_014435 | TAATGCTACAGGACAAGCAAA | 67 | GGTCTTGAACTCCTGACCTC | 68 | CACCGCACCTGGCCTGCTTT | 69 |
| ASAHL | NM_014435 | CTACGAGTCCTCCGTGTTC | 70 | AGAATTGCACATCCACTGTC | 71 | TGGCTCAAGACTCCAGAGGCCA | 72 |
| ASAHL | NM_014435 | TTGGCCTCTAGATCCTTTGA | 73 | TTTGCTTGTCCTGTAGCATT | 74 | CCACTGGAAGCCAGCACCCA | 75 |

TABLE 8-continued

| Gene Symbol | Acc'n Number | SensePrimer | SEQ ID NO: | AntisensePrimer | SEQ ID NO: | TaqManProbe | SEQ ID NO: |
|---|---|---|---|---|---|---|---|
| ASGR1 | NM_001671 | AGAGACGTTCAGCAACTTCA | 76 | AGGTCCTTCTGCTGTTTCTC | 77 | CCCTTGACCTGGGCCTCCGT | 78 |
| ASGR1 | NM_001671 | TGAGAGAGACGTTCAGCAAC | 79 | AGGTCCTTCTGCTGTTTCTC | 80 | CCCTTGACCTGGGCCTCCGT | 81 |
| ASGR1 | NM_001671 | AGAGACGTTCAGCAACTTCA | 82 | ACTCAGGTCCTTCTGCTGTT | 83 | CCCTTGACCTGGGCCTCCGT | 84 |
| ATP1B1 | NM_001677 | CCTCCGGTATGTTCTAAAGC | 85 | ATGTGATGCCTCCAGAAAG | 86 | TGGATCTGCCCATCACTTTGGC | 87 |
| ATP1B1 | NM_001677 | GTACAAAGATTCAGCCCAGA | 88 | GCTCCTCGTTCATGATTA | 89 | TCACTGGGCACATCGCCACA | 90 |
| ATP1B1 | NM_001677 | GGACACTGAAATTCGCATAG | 91 | AAATGGCTAGTGGGAAAGAT | 92 | CCCAATGTTCTCACCGTACGCCT | 93 |
| BMP6 | NM_001718 | GTGCCTTATTACCCAGGAAG | 94 | GCAGTTACCAGACCTTATGCT | 95 | CATCCAAACTCAGCTTGCTACAGACCA | 96 |
| BMP6 | NM_001718 | AGTGCCTTATTACCCAGGAA | 97 | GCAGTTACCAGACCTTATGCT | 98 | CATCCAAACTCAGCTTGCTACAGACCA | 99 |
| BMP6 | NM_001718 | TCATGCCAGTGCCTTATTAC | 100 | TTTCTGCAGTTACCAGACCT | 101 | TGCTACAGACATCCAAACTCAGCTTGC | 102 |
| C4BPA | NM_000715 | AATGGAATCCTTCTCCTCCT | 103 | CCTTAACACAGTCCCAACAA | 104 | CAGACATTCCACATGCTTCCTGGG | 105 |
| C4BPA | NM_000715 | TCCACCCACTTTATCATTTG | 106 | CTGAGTTGAATGGGATCTGA | 107 | TGAAATACACCTGCCTCCCTGGC | 108 |
| C4BPA | NM_000715 | TCCACCCACTTTATCATTTG | 109 | TCTGAGTTGAATGGGATCTG | 110 | ACACCTGCCTCCCTGGCTACGT | 111 |
| CKLF | NM_181641 | TCACTGGATTTGAAGTCACC | 112 | GTCGGCAAGACAGCATAC | 113 | TGCAAACACAAGCAAAGGCCAAA | 114 |
| CKLF | NM_181641 | CAGCCAGCTGAGAAGAGTT | 115 | GCCTTTCACACTGAAGCAG | 116 | CGCGTCTGCAGACCCAGCAG | 117 |
| CKLF | NM_181641 | CCCTTCTGCTTCAGTGTG | 118 | GGTGACTTCAAATCCAGTGA | 119 | CCAGCCGCAGCATCTTCACG | 120 |
| CLIC5 | NM_016929 | TGGATGACTACCTGAACACC | 121 | ATCTTGACCACATGGAGCTT | 122 | CCATCCAGGAACTTGCGCCG | 123 |
| CLIC5 | NM_016929 | GAGTACCGAGCTGGCTATG | 124 | TGCAACAAACTGAGAATGTG | 125 | CCAGTCTGGCCCTTAGTGCCCA | 126 |
| CLIC5 | NM_016929 | AGCCTCATCTTGCTGGTATC | 127 | CGAAAGGTGGACTGTGTCTA | 128 | CAGCACCATCCCTGGCCTCC | 129 |
| CPT1A | NM_001876 | AAGACTTCAAACGGATGACA | 130 | AGATGTACTCCTCCCACCAG | 131 | TCTTGGTCCAAGACCGACAGCAA | 132 |
| CPT1A | NM_001876 | AAGACTTCAAACGGATGACA | 133 | TAGATGTACTCCTCCCACCA | 134 | TCTTGGTCCAAGACCGACAGCAA | 135 |
| CPT1A | NM_001876 | GACAGCACTTGCTCAAGATT | 136 | ATGTACTCCTCCCACCAGTC | 137 | TCTTGGTCCAAGACCGACAGCAA | 138 |
| F2RL1 | NM_005242 | GCCTCTCTACCCTTAACAGC | 139 | CTTTACAGTGCGGACACTTC | 140 | TGCAAAGAACGCTCTCCTTTGCC | 141 |
| F2RL1 | NM_005242 | CCTCTGCCTCTCTACCCTTA | 142 | CTTTACAGTGCGGACACTTC | 143 | TGCAAAGAACGCTCTCCTTTGCC | 144 |
| F2RL1 | NM_005242 | GTAACCTTCTGCTTGTGGTG | 145 | TGCAGCTGTTAAGGGTAGAG | 146 | CATGGCTCTGGCCCTGGCTC | 147 |
| HDGF | NM_004494 | CAGCCAACAAATACCAAGTC | 148 | CTGAACCCTTTCCTCTTGTT | 149 | CCGTCTCGTGGGTCCCGAAA | 150 |
| HDGF | NM_004494 | GTAGGAATGGAAGGATGGAG | 151 | TAGGCAGCTGGGATAATAGG | 152 | CACAGGAGGGCGGCCTCCTT | 153 |

TABLE 8-continued

| Gene Symbol | Acc'n Number | SensePrimer | SEQ ID NO: | AntisensePrimer | SEQ ID NO: | TaqManProbe | SEQ ID NO: |
|---|---|---|---|---|---|---|---|
| HDGF | NM_004494 | GAGACCTGAAGGGTTGACTT | 154 | TGACTATAAGCTGGCCTTGA | 155 | TCAACACTCCCACCCAAATGGG | 156 |
| HSPCA | BX247955 | TACACATCTGCCTCTGGTG | 157 | GTTAGCTACCTGGTCCTTGG | 158 | TCTGGTTCTCCTTCATTCTGGTGCA | 159 |
| HSPCA | BX247955 | AAATCGGAAGAAGCTTTCAG | 160 | CTGGTTCTCCTTCATTCTGG | 161 | CCATCTCATCACCAGAGGCAGATGTG | 162 |
| HSPCA | BX247955 | TGGTGATGAGATGGTTTCTC | 163 | CTAAGCCATGTTTCCGAAG | 164 | CCTGGTCCTTGGTCTCACCTGTGA | 165 |
| IL13RA1 | NM_001560 | CTCATTGTTCCAGTCATCGT | 166 | TCATTCTGGTCTCCAAACAT | 167 | CCCTCCAATTCCTGATCCTGGCA | 168 |
| IL13RA1 | NM_001560 | GTCAAGGATAATGCAGGAAA | 169 | GTCATCATTGTGGAAGGAGA | 170 | CCCGTGTGAAACCTGATCCTCCA | 171 |
| IL13RA1 | NM_001560 | ACCTAAGCAAACCCAGTGTC | 172 | AACAATCCCTGGTTGAAGAC | 173 | CCCTTCATCTGGGCACTGAAGGG | 174 |
| LRMP | NM_006152 | GAGCACGCTGAATTAGAAGA | 175 | GGCTTGGAGTTTAGAGAAGC | 176 | TCCTCTTGAAGATGATGATGACTGCCA | 177 |
| LRMP | NM_006152 | GAGCACGCTGAATTAGAAGA | 178 | TTCGTAGAGAAGATGGCTTG | 179 | TCCTCTTGAAGATGATGATGACTGCCA | 180 |
| LRMP | NM_006152 | AGGAAGCCAAGTCTTTCTGA | 181 | GGCCTTATTAGCCTTTCTGA | 182 | TGGGCAACAAATCTCAAGTCCTCCA | 183 |
| LRPPRC | NM_133259 | CCTGTTACTTGTGCTTGGTC | 184 | CCGAGACTCAATTTCAGAGA | 185 | TGCCGAAGAGCCTCCAGGCA | 186 |
| LRPPRC | NM_133259 | TTGATTGACAGCATGAGTGA | 187 | TGGTAGCTTTCCAGGAGATT | 188 | TCTCAAATGCTCCTCCTTGGCCTG | 189 |
| LRPPRC | NM_133259 | CAGCTGGAGAAGATGAATGT | 190 | CTCTCAACCAACAAGTGAGC | 191 | TCCTGGAAAGCTACCATGTTCCTGA | 192 |
| NOV | NM_002514 | TACCGCAGTGGAGAGAAAAT | 193 | AGTTAGGCTCAGGCAGTAGC | 194 | TGCCCATCTCTGCAGGTGCA | 195 |
| NOV | NM_002514 | CAGATGAGGAGGATTCACTG | 196 | TCTGTGGTCTGTTCAATGC | 197 | CAGGCCAGAAGCCACCCTAGGA | 198 |
| NOV | NM_002514 | ATTGAGGTTCATTGGGAAGA | 199 | GTCATGTTGAAGAGCTGCAT | 200 | CCAGCTCTGAACTTCCAAGCTCCA | 201 |
| PDK4 | NM_002612 | CCTTTGAGTGTTCAAGGATG | 202 | AGAGCATATGATGGAGGTGA | 203 | TCCAGACCAACCAATTCACATCGTG | 204 |
| PDK4 | NM_002612 | CCTTTGAGTGTTCAAGGATG | 205 | GAGCATATGATGGAGGTGAG | 206 | TCCAGACCAACCAATTCACATCGTG | 207 |
| PDK4 | NM_002612 | CCTTTGAGTGTTCAAGGATG | 208 | AGCATATGATGGAGGTGAGA | 209 | TCCAGACCAACCAATTCACATCGTG | 210 |
| PF4 | NM_002619 | ACTGATAGCCACGCTGAA | 211 | ATAGCAAATGCACACACGTA | 212 | TTTGCTTGGACCTGCAAGCCC | 213 |
| PF4 | NM_002619 | CTGTGTGTGAAGACCACCTC | 214 | CTTCAGCGTGGCTATCAG | 215 | CCGTCCCAGGCACATCACCA | 216 |
| PF4 | NM_002619 | AACTGATAGCCACGCTGAA | 217 | ATAGCAAATGCACACACGTAG | 218 | TTTGCTTGGACCTGCAAGCCC | 219 |
| RPS6KA2 | NM_021135 | GACCGAGTGAGATCGAAGAT | 220 | GGAAGTCCAGGATCAGGTAG | 221 | AGCTTTCCTTCCGTCTGAAAGGCA | 222 |
| RPS6KA2 | NM_021135 | GCTTCATTATGCCTTTCAGA | 223 | TGAACATGACCTCTTTGGAG | 224 | CCCGCAGGAAGTCCAGGATCA | 225 |
| RPS6KA2 | NM_021135 | TGAGATCGAAGATGGAGAGA | 226 | AGTCCAGGATCAGGTAGAGC | 227 | CCTTCCGTCTGAAAGGCATAATGAAGC | 228 |

TABLE 8-continued

| Gene Symbol | Acc'n Number | SensePrimer | SEQ ID NO: | AntisensePrimer | SEQ ID NO: | TaqManProbe | SEQ ID NO: |
|---|---|---|---|---|---|---|---|
| SERPINE1 | NM_000602 | ATGAGATCAGCACCACAGAC | 229 | TTGATGATGAATCTGGCTCT | 230 | TGGTCCAGGGCTTCATGCCC | 231 |
| SERPINE1 | NM_000602 | AATGACTGGGTGAAGACACA | 232 | TTGAAGTAGAGGGCATTCAC | 233 | CCAGCTGACACGGCTGGTGC | 234 |
| SERPINE1 | NM_000602 | GCAGCTATGGGATTCAAGAT | 235 | GTGCTGATCTCATCCTTGTT | 236 | CCGCCCTCCGGCATCTGTAC | 237 |
| SERPING1 | NM_000062 | CATAAGGGACACCTTTGTGA | 238 | GCTGATCTTGTTGTTGGTGT | 239 | TCATCAACACCTGGGTGGCCA | 240 |
| SERPING1 | NM_000062 | CTCTGCTCTGACTTGGAGAG | 241 | ATGTTGGTCTCCACCTTCTT | 242 | CCCAACACGGCCTCTGTTGAATG | 243 |
| SERPING1 | NM_000062 | CTCTCTGCTCTGACTTGGAG | 244 | ATGTTGGTCTCCACCTTCTT | 245 | CCCAACACGGCCTCTGTTGAATG | 246 |
| SE1BP1 | NM_015559 | CAGATCTTGTCCTGTTCCAG | 247 | TCTTGCCAATGTAGATGGTT | 248 | TGCTTTCAATGGCTGCTGCCC | 249 |
| SETBP1 | NM_015559 | TCAAGATGGAGGAGGTACAA | 250 | GGGTTTGGTATGGTCTGACT | 251 | CCACCTACGGTGGGCAGCAA | 252 |
| SETBP1 | NM_015559 | TCAAGATGGAGGAGGTACAA | 253 | GTCTGGGTTTGGTATGGTCT | 254 | CCACCTACGGTGGGCAGCAA | 255 |
| TNF | NM_000594 | ATCCCTGACATCTGGAATCT | 256 | GGAAACATCTGGAGAGAGGA | 257 | TGGCCAGAACCAAAGGCTCC | 258 |
| TNF | NM_000594 | ATCCCTGACATCTGGAATCT | 259 | AACATCTGGAGAGAGGAAGG | 260 | TGGCCAGAACCAAAGGCTCC | 261 |
| TNF | NM_000594 | ACATCTGGAATCTGGAGACC | 262 | GAGAGAGGAAGGCCTAAGGT | 263 | TGGCCAGAACCAAAGGCTCC | 264 |
| TNFAIP6 | NM_007115 | GGTGTGTACCACAGAGAAGC | 265 | AGCACAGACATGAAATCCAA | 266 | TTTGAAGGCGGCCATCTCGC | 267 |
| TNFAIP6 | NM_007115 | TATGGTCAGCGTATTCACCT | 268 | TCCACAGTATCTTCCCACAA | 269 | TCAGCCAAGCAACCTGGGTCA | 270 |
| TNFAIP6 | NM_007115 | TACTGTGGAGATGAGCTTCC | 271 | ACAGGATCCATTGCAACATA | 272 | CCTCCAGCTGTCACTGAAGCATCA | 273 |
| WASF2 | NM_006990 | ATCCCTTTGGTGAGTATGGT | 274 | TGTCAGGGATAGTTTGGTCA | 275 | TCAGGATGCACCACCACCACC | 276 |
| WASF2 | NM_006990 | CTGCGGAAGGTAGGATTAGA | 277 | GGACTTGCAGATCATTACCA | 278 | AGCACATCGAAACCCTAGGAGGTCA | 279 |
| WASF2 | NM_006990 | CTTTCTGTAGGCTGGTGTTG | 280 | AGGGATAGTTTGGTCATGGA | 281 | TGCCTCCCTCCCAGGATCCC | 282 |

REFERENCES

Zaleske D J. Cartilage and Bone Development. Instr Course Lect 1998; 47:461

Buckwalter J A, Mankin H J. Articular Cartilage: Tissue Design and Chondrocyte-Matrix Interactions. Instr Course Lect 1998; 47:477-86.

Westacott C I, Sharif M. Cytokines in Osteoarthritis: Mediators or Markers of Joint Destruction? Semin Arthritis Rheum 1996; 25:254-72

Adams M D, Kerlavage A R, Fleischmann R D, Fuldner R A, Bult C J, Lee N H, et al. Initial assessment of human gene diversity and expression patterns based upon 83 million nucleotides of cDNA sequence. Nature 1995; 377 Suppl: 3-174.

Hwang D M, Dempsey A A, Wang R X, Rezvani M, Barrans J D, Dai K S, et al. A Genome-Based Resource for Molecular Cardiovascular Medicine: Toward a Compendium of Cardiovascular Genes. Circulation 1997; 96:4146-203.

Mao M, Fu G, Wu J S, Zhang Q H, Zhou J, Kan L X, et al. Identification of genes expressed in human CD34+ hematopoietic stem/progenitor cells by expressed sequence tags and efficient full-length cDNA cloning. Proc Natl Acad Sci 1998; 95:8175-80.

Hillier L D, Lennon G, Becker M, Bonaldo M F, Chiapelli B, Chissoe S, et al. Generation and analysis of 280,000 human expressed sequence tags. Genome Res. 1996; 6:807-28.

Altschul S F, Gish W, Miller W, Myers E W, Lipman D J. Basic local alignment search tool. J Mol Biol 1990; 215: 403-10.

Mundlos S, Zabel B. Developmental Expression of Human Cartilage Matrix Protein. Dev Dyn 1994; 199:241-52.

Nakamura S, Kamihagi K, Satakeda H, Katayama M, Pan H, Okamoto H, et al. Enhancement of SPARC (osteonectin) synthesis in arthritic cartilage. Increased levels in synovial fluids from patients with rheumatoid arthritis and regulation by growth factors and cytokines in chondrocyte cultures. Arthritis Rheum 1996; 39:539-51.

Eyre D R, The Collagens of Articular Cartilage. Semin Arthritis Rheum 1991; 21 (3 Suppl 2):2-11.

Okihana H, Yamada K. Preparation of a cDNA Library and Preliminary Assessment of 1400 Genes from Mouse Growth Cartilage. J Bone Miner Res 1999; 14:304-10.

Morrison E H, Ferguson M W J, Bayliss M T, Archer C W. The developmental of articular cartilage: I. The spatial and temporal patterns of collagen types. J Anat 1996; 189:9-22.

Treilleux I, Mallein-Gerin F, le Guellec D, Herbage D. Localization of the Expression of Type I, II, III Collagens, and Aggrecan Core Protein Genes in Developing Human Articular Cartilage. Matrix 1992; 12:221-32.

Eyre D R, Wu J J, Niyibizi C. The collagens of bone and cartilage: Molecular diversity and supramolecular assembly. In Cohn D V, Glorieux F H, Martin T J, editors. Calcium Regulation and Bone Metabolism. Amsterdam. The Netherlands: Elsevier; 1990. p. 188-94.

Birnbacher R. Amann G, Breitschopf H, Lassmann H, Suchanek G, Heinz-Erian P. Cellular localization of insulin-like growth factor II mRNA in the human fetus and the placenta: detection with a digoxigenin-labeled cRNA probe and immunocytochemistry. Pediatr Res 1998; 43:614-20.

Wang E, Wang J, Chin E, Zhou J, Bondy C A. Cellular patterns of insulin-like growth factor system gene expression in murine chondrogenesis and osteogenesis. Endocrinology 1995; 136:2741-51.

van Kleffens M, Groffen C, Rosato R R, van den Eijnde S M, van Neck J W, Lindenbergh-Kortleve D J, et al. mRNA expression patterns of the IGF system during mouse limb bud development, determined by whole mount in situ hybridization. Mol Cell Endocrinol 1998; 138:151-61.

Braulke T, Gotz W, Claussen M. Immunohistochemical localization of insulin-like growth factor binding protein-1, -3, and -4 in human fetal tissues and their analysis in media from fetal tissue explants. Growth Regul 1996; 6:55-65.

Kessler E, Takahara K, Biniaminov L, Brusel M, Greenspan D S. Bone Morphogenetic Protein-1: The Type I Procollagen C-Proteinase. Science 1996; 271:360-2.

Ausubel et al., John Weley & Sons, Inc., 1997, Current Protocols in Molecular Biology Marshall, K. et al., 2000, 46$^{th}$ Annual Meeting, ORS, paper No. 919.

Kumar, S., et al., 2000, 46$^{th}$ Annual Meeting, ORS, paper No. 1031.

Marshall K., et al., 2002, 48$^{th}$ Annual meeting, ORS (submitted).

Migita K., et al., Biochem Biophys Res Commun 1997, 239: 621-625.

Migita K., et al., Kidney Int 1999, 55:572-578.

The contents of all references, patents and patent applications (including, published patent applications) cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of diagnosing a human test subject as more likely to either have mild osteoarthritis or not have osteoarthritis, said method comprising,
   (a) for each gene of a set of genes consisting of CKLFSF3, CPT1A, IL13RA1, ILF1, KIAA0010, PF4, PDK4 and SERPINE1, detecting the level of RNA encoded by said gene in a blood sample from said test subject using at least one oligonucleotide of predetermined sequence which is specific for RNA encoded by said gene and/or for DNA complementary to RNA encoded by said gene, thereby obtaining test levels of RNA encoded by said genes; and
   (b) applying logistic regression analysis to said test levels to classify the test subject as more likely to either have mild osteoarthritis or not have osteoarthritis, wherein said logistic regression analysis is performed using a logistic regression model fitted to levels of RNA encoded by said genes in blood of subjects having mild osteoarthritis, and levels of RNA encoded by said genes in blood of subjects not having osteoarthritis,
   thereby diagnosing said human test subject as more likely to either have mild osteoarthritis or not have osteoarthritis.

2. The method of claim 1, wherein said detecting is effected using nucleic acid amplification.

3. The method of claim 2, wherein, for each gene of said set of genes, said nucleic acid amplification is effected using primers which can hybridize specifically to RNA encoded by said gene and/or to DNA complementary to RNA encoded by said gene.

4. The method of claim 2, wherein said nucleic acid amplification is effected using primers having the nucleic acid sequences identified as SEQ ID NO: 11, SEQ ID NO: 12, SEQ ID NO: 21, SEQ ID NO: 22, SEQ ID NO: 31, SEQ ID NO: 32, SEQ ID NO: 33, SEQ ID NO: 34, SEQ ID NO: 35, SEQ ID NO: 36, SEQ ID NO: 47, SEQ ID NO: 48, SEQ ID NO: 49, SEQ ID NO: 50, SEQ ID NO: 53 and SEQ ID NO: 54.

5. The method of claim 1, wherein, for each gene of said set of genes, said detecting is effected using an immobilized nucleic acid probe which can hybridize specifically to RNA encoded by said gene and/or to DNA complementary to RNA encoded by said gene.

6. The method of claim 1, wherein said detecting comprises:
   (i) isolating RNA from said blood sample, thereby obtaining a sample of isolated RNA, and
   (ii) for each gene of said set of genes, quantifying a level of RNA encoded by said gene in said sample of isolated RNA.

7. The method of claim 1, wherein said test subject is suspected of having osteoarthritis.

8. The method of claim 1, further comprising, for each gene of said set of genes quantifying the levels of RNA encoded by said gene in blood samples of subjects diagnosed as having mild osteoarthritis and in blood samples of subjects diagnosed as not having osteoarthritis, thereby providing said reference dataset.

9. The method of claim 1, wherein said logistic regression model has the form:

$$X = \ln[(B0) + (B1)(\text{level}_{CKLFSF3}/\text{level}_{CPT1A}) + (B2)(\text{level}_{IL13RA1}/\text{level}_{ILF1}) + (B3)(\text{level}_{KIAA0010}/\text{level}_{PF4}) + (B4)(\text{level}_{PDK4}/\text{level}_{SERPINE1})],$$

where "ln" is the natural logarithm; "$\text{level}_{CKLFSF3}$", "$\text{level}_{CPT1A}$", "$\text{level}_{IL13RA1}$", "$\text{level}_{ILF1}$", "$\text{level}_{KIAA0010}$", "$\text{level}_{PF4}$", "$\text{level}_{PDK4}$" and "$\text{level}_{SERPINE1}$" are the levels of RNA encoded by CKLFSF3, CPT1A, IL13RA1, ILF1, KIAA0010, PF4, PDK4 and SERPINE1, respectively, detected in said sample from said test subject; (B0) is a constant having the value 10.631; and (B1), (B2), (B3) and (B4) are coefficients having the values 2.1326, 4.5517, −1.4928 and −0.86575, respectively, wherein a value of X greater than or equal to zero indicates that the test subject is more likely to have mild osteoarthritis than to not have osteoarthritis, and wherein a value of X of less than zero indicates that the test subject is more likely to not have osteoarthritis than to have mild osteoarthritis.

10. A method of determining the likelihood that a human test subject has mild osteoarthritis as opposed to not having osteoarthritis, said method comprising,
   (a) for each gene of a set of genes consisting of CKLFSF3, CPT1A, IL13RA1, ILF1, KIAA0010, PF4, PDK4 and SERPINE1, detecting the level of RNA encoded by said gene in a blood sample from said test subject using at least one oligonucleotide of predetermined sequence which is specific for RNA encoded by said gene and/or for DNA complementary to RNA encoded by said gene, thereby obtaining test levels of RNA encoded by said genes; and
   (b) applying logistic regression analysis to said test levels to determine the likelihood that the subject has mild osteoarthritis as opposed to not having osteoarthritis, wherein said logistic regression analysis is performed using a logistic regression model fitted to levels of RNA encoded by said genes in blood of subjects having mild osteoarthritis, and levels of RNA encoded by said genes in blood of subjects not having osteoarthritis;
   thereby determining the likelihood that said human test subject has mild osteoarthritis as opposed to not having osteoarthritis.

11. The method of claim 10, wherein said detecting is effected using nucleic acid amplification.

12. The method of claim 11, wherein, for each gene of said set of genes, said nucleic acid amplification is effected using primers which can hybridize specifically to RNA encoded by said gene and/or to DNA complementary to RNA encoded by said gene.

13. The method of claim 11, wherein said nucleic acid amplification is effected using primers having the nucleic acid sequences identified as SEQ ID NO: 11, SEQ ID NO: 12, SEQ ID NO: 21, SEQ ID NO: 22, SEQ ID NO: 31, SEQ ID NO: 32, SEQ ID NO: 33, SEQ ID NO: 34 SEQ ID NO: 35, SEQ ID NO: 36, SEQ ID NO: 47, SEQ ID NO: 48, SEQ ID NO: 49, SEQ ID NO: 50, SEQ ID NO: 53 and SEQ ID NO: 54.

14. The method of claim 10, wherein, for each gene of said set of genes, said detecting is effected using an immobilized nucleic acid probe which can hybridize specifically to RNA encoded by said gene and/or to DNA complementary to RNA encoded by said gene.

15. The method of claim 10, further comprising, for each gene of said set of genes quantifying the levels of RNA encoded by said gene in blood samples of subjects diagnosed as having mild osteoarthritis and in blood samples of subjects diagnosed as not having osteoarthritis, thereby providing said reference dataset.

16. The method of claim 10, wherein said logistic regression model has the form:

$$[P/(1-P)] = e^{[(B0)+(B1)(\text{level}_{CKLFSF3}/\text{level}_{CPT1A})+(B2)(\text{level}_{IL13RA1}/\text{level}_{ILF1})+(B3)(\text{level}_{KIAA0010}/\text{level}_{PF4})+(B4)(\text{level}_{PDK4}/\text{level}_{SERPINE1})]},$$

where "[P/(1−P)]" is the likelihood that said test subject has mild osteoarthritis as opposed to not having osteoarthritis; "e" is the mathematical constant e; "level$_{CKLFSF3}$", "level$_{CPT1A}$", "level$_{IL13RA1}$", "level$_{ILF1}$", "level$_{KIAA0010}$", "level$_{PF4}$", "level$_{PDK4}$" and "level$_{SERPINE1}$" are the levels of RNA encoded by CKLFSF3, CPT1A, IL13RA1, ILF1, KIAA0010, PF4, PDK4 and SERPINE1, respectively, detected in said sample from said test subject; (B0) is a constant having the value 10.631; and (B1), (B2), (B3) and (B4) are coefficients having the values 2.1326, 4.5517, −1.4928 and -0.86575, respectively.

* * * * *

SEQUENCE LISTING

<160> NUMBER OF SEQ ID NOS: 282

<210> SEQ ID NO 1
<211> LENGTH: 19
<212> TYPE: DNA
<213> ORGANISM: Artificial
<220> FEATURE:
<223> OTHER INFORMATION: ASAHL 5' Primer

<400> SEQUENCE: 1
ctacgagtcc tccgtgttc                                              19

<210> SEQ ID NO 2
<211> LENGTH: 20
<212> TYPE: DNA
<213> ORGANISM: Artificial
<220> FEATURE:
<223> OTHER INFORMATION: ASAHL 3' Primer

<400> SEQUENCE: 2
agaattgcac atccactgtc                                             20

<210> SEQ ID NO 3
<211> LENGTH: 22
<212> TYPE: DNA
<213> ORGANISM: Artificial
<220> FEATURE:
<223> OTHER INFORMATION: ASGR1 5' Primer

<400> SEQUENCE: 3
ggagcagaaa tttgtccagc ac                                          22

<210> SEQ ID NO 4
<211> LENGTH: 22
<212> TYPE: DNA
<213> ORGANISM: Artificial
<220> FEATURE:
<223> OTHER INFORMATION: ASGR1 3' Primer

<400> SEQUENCE: 4
ttcttgaagc ccgtctcgta gt                                           22

<210> SEQ ID NO 5
<211> LENGTH: 20
<212> TYPE: DNA
<213> ORGANISM: Artificial
<220> FEATURE:
<223> OTHER INFORMATION: ATP1B1 5' Primer

<400> SEQUENCE: 5
ctaagcctcc caagaatgag                                              20

<210> SEQ ID NO 6
<211> LENGTH: 20
<212> TYPE: DNA
<213> ORGANISM: Artificial
<220> FEATURE:
<223> OTHER INFORMATION: ATP1B1 3' Primer

<400> SEQUENCE: 6
cttatcttca tctcgcttgc                                              20

<210> SEQ ID NO 7
<211> LENGTH: 21
<212> TYPE: DNA
<213> ORGANISM: Artificial
<220> FEATURE:
<223> OTHER INFORMATION: BMP6 5' Primer

<400> SEQUENCE: 7
atggcaggac tggatcattg c                                            21

<210> SEQ ID NO 8
<211> LENGTH: 20
<212> TYPE: DNA
<213> ORGANISM: Artificial
<220> FEATURE:
<223> OTHER INFORMATION: BMP6 3' Primer

<400> SEQUENCE: 8
aatcgcgtgg ttggttgcat                                              20

<210> SEQ ID NO 9
<211> LENGTH: 20
<212> TYPE: DNA
<213> ORGANISM: Artificial
<220> FEATURE:
<223> OTHER INFORMATION: C4BPA 5' Primer

<400> SEQUENCE: 9
cctgcagtta ttcacactgg                                              20

<210> SEQ ID NO 10
<211> LENGTH: 20
<212> TYPE: DNA
<213> ORGANISM: Artificial
<220> FEATURE:
<223> OTHER INFORMATION: C4BPA 3' Primer

```
<400> SEQUENCE: 10
caccatagcc agaatcacat                                              20

<210> SEQ ID NO 11
<211> LENGTH: 20
<212> TYPE: DNA
<213> ORGANISM: Artificial
<220> FEATURE:
<223> OTHER INFORMATION: CKLF 5' Primer

<400> SEQUENCE: 11
ttctgcttca gtgtgaaagg                                              20

<210> SEQ ID NO 12
<211> LENGTH: 21
<212> TYPE: DNA
<213> ORGANISM: Artificial
<220> FEATURE:
<223> OTHER INFORMATION: CKLF 3' Primer

<400> SEQUENCE: 12
ataacggtga cttcaaatcc a                                            21

<210> SEQ ID NO 13
<211> LENGTH: 20
<212> TYPE: DNA
<213> ORGANISM: Artificial
<220> FEATURE:
<223> OTHER INFORMATION: CKLFSF3 5' Primer

<400> SEQUENCE: 13
agtcgggtct ctcattcatc                                              20

<210> SEQ ID NO 14
<211> LENGTH: 20
<212> TYPE: DNA
<213> ORGANISM: Artificial
<220> FEATURE:
<223> OTHER INFORMATION: CKLFSF3 3' Primer

<400> SEQUENCE: 14
gcatcagcaa agaggaagta                                              20

<210> SEQ ID NO 15
<211> LENGTH: 20
<212> TYPE: DNA
<213> ORGANISM: Artificial
<220> FEATURE:
<223> OTHER INFORMATION: CKLFSF7 5' Primer

<400> SEQUENCE: 15
tttacctggt ccacctcttc                                              20

<210> SEQ ID NO 16
<211> LENGTH: 20
<212> TYPE: DNA
<213> ORGANISM: Artificial
<220> FEATURE:
<223> OTHER INFORMATION: CKLFSF7 3' Primer

<400> SEQUENCE: 16
cgctctggtt gtaactcttg                                              20

<210> SEQ ID NO 17
<211> LENGTH: 20
```

```
<212> TYPE: DNA
<213> ORGANISM: Artificial
<220> FEATURE:
<223> OTHER INFORMATION: CLECSF6 5' Primer

<400> SEQUENCE: 17
atatgcccgt ggaagagaca                                              20

<210> SEQ ID NO 18
<211> LENGTH: 22
<212> TYPE: DNA
<213> ORGANISM: Artificial
<220> FEATURE:
<223> OTHER INFORMATION: CLECSF6 3' Primer

<400> SEQUENCE: 18
tgagcctcca ttctagcaca gt                                           22

<210> SEQ ID NO 19
<211> LENGTH: 22
<212> TYPE: DNA
<213> ORGANISM: Artificial
<220> FEATURE:
<223> OTHER INFORMATION: CLIC5 5' Primer

<400> SEQUENCE: 19
tccatgtggt caagattgtg gc                                           22

<210> SEQ ID NO 20
<211> LENGTH: 22
<212> TYPE: DNA
<213> ORGANISM: Artificial
<220> FEATURE:
<223> OTHER INFORMATION: CLIC5 3' Primer

<400> SEQUENCE: 20
taggccaact cgatctcact gt                                           22

<210> SEQ ID NO 21
<211> LENGTH: 20
<212> TYPE: DNA
<213> ORGANISM: Artificial
<220> FEATURE:
<223> OTHER INFORMATION: CPT1A 5' Primer

<400> SEQUENCE: 21
ctgagccttg gagattatca                                              20

<210> SEQ ID NO 22
<211> LENGTH: 20
<212> TYPE: DNA
<213> ORGANISM: Artificial
<220> FEATURE:
<223> OTHER INFORMATION: CPT1A 3' Primer

<400> SEQUENCE: 22
atgtacgaca caccatagcc                                              20

<210> SEQ ID NO 23
<211> LENGTH: 22
<212> TYPE: DNA
<213> ORGANISM: Artificial
<220> FEATURE:
<223> OTHER INFORMATION: F2RL1 5' Primer

<400> SEQUENCE: 23
tggcaccatc caaggaacca at                                           22
```

<210> SEQ ID NO 24
<211> LENGTH: 22
<212> TYPE: DNA
<213> ORGANISM: Artificial
<220> FEATURE:
<223> OTHER INFORMATION: F2RL1 3' Primer

<400> SEQUENCE: 24
ttccagtgag gacagatgca ga                                          22

<210> SEQ ID NO 25
<211> LENGTH: 22
<212> TYPE: DNA
<213> ORGANISM: Artificial
<220> FEATURE:
<223> OTHER INFORMATION: FLJ11142 5' Primer

<400> SEQUENCE: 25
tcgtttcttg gtgactgctg ga                                          22

<210> SEQ ID NO 26
<211> LENGTH: 22
<212> TYPE: DNA
<213> ORGANISM: Artificial
<220> FEATURE:
<223> OTHER INFORMATION: FLJ11142 3' Primer

<400> SEQUENCE: 26
tccaaacctg ggagatggaa ct                                          22

<210> SEQ ID NO 27
<211> LENGTH: 20
<212> TYPE: DNA
<213> ORGANISM: Artificial
<220> FEATURE:
<223> OTHER INFORMATION: HDGF 5' Primer

<400> SEQUENCE: 27
caaagacctc ttcccttacg                                             20

<210> SEQ ID NO 28
<211> LENGTH: 20
<212> TYPE: DNA
<213> ORGANISM: Artificial
<220> FEATURE:
<223> OTHER INFORMATION: HDGF 3' Primer

<400> SEQUENCE: 28
tttctgggag gactgatagc                                             20

<210> SEQ ID NO 29
<211> LENGTH: 22
<212> TYPE: DNA
<213> ORGANISM: Artificial
<220> FEATURE:
<223> OTHER INFORMATION: HSPCA 5' Primer

<400> SEQUENCE: 29
atgattggcc agttcggtgt tg                                          22

<210> SEQ ID NO 30
<211> LENGTH: 22
<212> TYPE: DNA
<213> ORGANISM: Artificial
<220> FEATURE:
<223> OTHER INFORMATION: HSPCA 3' Primer

```
<400> SEQUENCE: 30
ttcacctgtg tctgtcctca ct                                          22

<210> SEQ ID NO 31
<211> LENGTH: 22
<212> TYPE: DNA
<213> ORGANISM: Artificial
<220> FEATURE:
<223> OTHER INFORMATION: IL13RA1 5' Primer

<400> SEQUENCE: 31
cattgttcca gtcatcgtcg ca                                          22

<210> SEQ ID NO 32
<211> LENGTH: 22
<212> TYPE: DNA
<213> ORGANISM: Artificial
<220> FEATURE:
<223> OTHER INFORMATION: IL13RA1 3' Primer

<400> SEQUENCE: 32
tcttgccagg atcaggaatt gg                                          22

<210> SEQ ID NO 33
<211> LENGTH: 20
<212> TYPE: DNA
<213> ORGANISM: Artificial
<220> FEATURE:
<223> OTHER INFORMATION: ILF1 5' Primer

<400> SEQUENCE: 33
agacagcccg aaggatgatt                                             20

<210> SEQ ID NO 34
<211> LENGTH: 20
<212> TYPE: DNA
<213> ORGANISM: Artificial
<220> FEATURE:
<223> OTHER INFORMATION: ILF1 3' Primer

<400> SEQUENCE: 34
ttgtccgcag tcctgtagta                                             20

<210> SEQ ID NO 35
<211> LENGTH: 22
<212> TYPE: DNA
<213> ORGANISM: Artificial
<220> FEATURE:
<223> OTHER INFORMATION: KIAA0010 5' Primer

<400> SEQUENCE: 35
tgatggtacc caaagtcagg ct                                          22

<210> SEQ ID NO 36
<211> LENGTH: 22
<212> TYPE: DNA
<213> ORGANISM: Artificial
<220> FEATURE:
<223> OTHER INFORMATION: KIAA0010 3' Primer

<400> SEQUENCE: 36
aacggtacca tagaccctgt ga                                          22

<210> SEQ ID NO 37
<211> LENGTH: 22
```

```
<212> TYPE: DNA
<213> ORGANISM: Artificial
<220> FEATURE:
<223> OTHER INFORMATION: LOC283337 5' Primer

<400> SEQUENCE: 37
aacaggactg atgggacacg aa                                              22

<210> SEQ ID NO 38
<211> LENGTH: 21
<212> TYPE: DNA
<213> ORGANISM: Artificial
<220> FEATURE:
<223> OTHER INFORMATION: LOC283337 3' Primer

<400> SEQUENCE: 38
acttgcctga gccatgctga t                                               21

<210> SEQ ID NO 39
<211> LENGTH: 26
<212> TYPE: DNA
<213> ORGANISM: Artificial
<220> FEATURE:
<223> OTHER INFORMATION: LOC286286 5' Primer

<400> SEQUENCE: 39
caccaggagc acacttatat catgga                                          26

<210> SEQ ID NO 40
<211> LENGTH: 27
<212> TYPE: DNA
<213> ORGANISM: Artificial
<220> FEATURE:
<223> OTHER INFORMATION: LOC286286 3' Primer

<400> SEQUENCE: 40
cctcgttcat tgcaagatag aattcac                                         27

<210> SEQ ID NO 41
<211> LENGTH: 20
<212> TYPE: DNA
<213> ORGANISM: Artificial
<220> FEATURE:
<223> OTHER INFORMATION: LRMP 5' Primer

<400> SEQUENCE: 41
gagcacgctg aattagaaga                                                 20

<210> SEQ ID NO 42
<211> LENGTH: 20
<212> TYPE: DNA
<213> ORGANISM: Artificial
<220> FEATURE:
<223> OTHER INFORMATION: LRMP 3' Primer

<400> SEQUENCE: 42
gagaagatgg cttggagttt                                                 20

<210> SEQ ID NO 43
<211> LENGTH: 23
<212> TYPE: DNA
<213> ORGANISM: Artificial
<220> FEATURE:
<223> OTHER INFORMATION: LRPPRC 5' Primer

<400> SEQUENCE: 43
cgtttgacgt acctgagttg tgg                                             23
```

<210> SEQ ID NO 44
<211> LENGTH: 20
<212> TYPE: DNA
<213> ORGANISM: Artificial
<220> FEATURE:
<223> OTHER INFORMATION: LRPPRC 3' Primer

<400> SEQUENCE: 44
ttggttcaat cggcaggcaa                                              20

<210> SEQ ID NO 45
<211> LENGTH: 20
<212> TYPE: DNA
<213> ORGANISM: Artificial
<220> FEATURE:
<223> OTHER INFORMATION: NOV 5' Primer

<400> SEQUENCE: 45
cagagcagcc aacagataag                                              20

<210> SEQ ID NO 46
<211> LENGTH: 19
<212> TYPE: DNA
<213> ORGANISM: Artificial
<220> FEATURE:
<223> OTHER INFORMATION: NOV 3' Primer

<400> SEQUENCE: 46
agaacctggg cttgtaggt                                               19

<210> SEQ ID NO 47
<211> LENGTH: 20
<212> TYPE: DNA
<213> ORGANISM: Artificial
<220> FEATURE:
<223> OTHER INFORMATION: PDK4 5' Primer

<400> SEQUENCE: 47
actcggatgc tgatgaacca                                              20

<210> SEQ ID NO 48
<211> LENGTH: 22
<212> TYPE: DNA
<213> ORGANISM: Artificial
<220> FEATURE:
<223> OTHER INFORMATION: PDK4 3' Primer

<400> SEQUENCE: 48
aaggcatctt ggaccactgc ta                                           22

<210> SEQ ID NO 49
<211> LENGTH: 19
<212> TYPE: DNA
<213> ORGANISM: Artificial
<220> FEATURE:
<223> OTHER INFORMATION: PF4 5' Primer

<400> SEQUENCE: 49
gttgctgctc ctgccactt                                               19

<210> SEQ ID NO 50
<211> LENGTH: 20
<212> TYPE: DNA
<213> ORGANISM: Artificial
<220> FEATURE:
<223> OTHER INFORMATION: PF4 3' Primer

```
<400> SEQUENCE: 50
gtggctatca gttgggcagt                                              20

<210> SEQ ID NO 51
<211> LENGTH: 22
<212> TYPE: DNA
<213> ORGANISM: Artificial
<220> FEATURE:
<223> OTHER INFORMATION: RPS6KA2 5' Primer

<400> SEQUENCE: 51
acccaatcgt gcagcagtta ca                                           22

<210> SEQ ID NO 52
<211> LENGTH: 20
<212> TYPE: DNA
<213> ORGANISM: Artificial
<220> FEATURE:
<223> OTHER INFORMATION: RPS6KA2 3' Primer

<400> SEQUENCE: 52
atgcacacat cgcttgcaca                                              20

<210> SEQ ID NO 53
<211> LENGTH: 22
<212> TYPE: DNA
<213> ORGANISM: Artificial
<220> FEATURE:
<223> OTHER INFORMATION: SERPINE1 5' Primer

<400> SEQUENCE: 53
atcagccact ggaaaggcaa ca                                           22

<210> SEQ ID NO 54
<211> LENGTH: 22
<212> TYPE: DNA
<213> ORGANISM: Artificial
<220> FEATURE:
<223> OTHER INFORMATION: SERPINE1 3' Primer

<400> SEQUENCE: 54
aacatgtcgg tcattcccag gt                                           22

<210> SEQ ID NO 55
<211> LENGTH: 20
<212> TYPE: DNA
<213> ORGANISM: Artificial
<220> FEATURE:
<223> OTHER INFORMATION: SERPING1 5' Primer

<400> SEQUENCE: 55
cccatgatga atagcaagaa                                              20

<210> SEQ ID NO 56
<211> LENGTH: 20
<212> TYPE: DNA
<213> ORGANISM: Artificial
<220> FEATURE:
<223> OTHER INFORMATION: SERPING1 3' Primer

<400> SEQUENCE: 56
agacgatgtt tcaggttctg                                              20

<210> SEQ ID NO 57
<211> LENGTH: 22
```

```
<212> TYPE: DNA
<213> ORGANISM: Artificial
<220> FEATURE:
<223> OTHER INFORMATION: SETBP1 5' Primer

<400> SEQUENCE: 57
tgaaggcttt ggaacgtaca gg                                              22

<210> SEQ ID NO 58
<211> LENGTH: 20
<212> TYPE: DNA
<213> ORGANISM: Artificial
<220> FEATURE:
<223> OTHER INFORMATION: SETBP1 3' Primer

<400> SEQUENCE: 58
gggacttggc atccctggag                                                 20

<210> SEQ ID NO 59
<211> LENGTH: 20
<212> TYPE: DNA
<213> ORGANISM: Artificial
<220> FEATURE:
<223> OTHER INFORMATION: TNF 5' Primer

<400> SEQUENCE: 59
atgttgtagc aaaccctcaa                                                 20

<210> SEQ ID NO 60
<211> LENGTH: 20
<212> TYPE: DNA
<213> ORGANISM: Artificial
<220> FEATURE:
<223> OTHER INFORMATION: TNF 3' Primer

<400> SEQUENCE: 60
gaagaggacc tgggagtaga                                                 20

<210> SEQ ID NO 61
<211> LENGTH: 20
<212> TYPE: DNA
<213> ORGANISM: Artificial
<220> FEATURE:
<223> OTHER INFORMATION: TNFAIP6 5' Primer

<400> SEQUENCE: 61
atatggcttg aacgagcagc                                                 20

<210> SEQ ID NO 62
<211> LENGTH: 20
<212> TYPE: DNA
<213> ORGANISM: Artificial
<220> FEATURE:
<223> OTHER INFORMATION: TNFAIP6 3' Primer

<400> SEQUENCE: 62
tggccgcctt caaattcaca                                                 20

<210> SEQ ID NO 63
<211> LENGTH: 20
<212> TYPE: DNA
<213> ORGANISM: Artificial
<220> FEATURE:
<223> OTHER INFORMATION: TNFSF6 5' Primer

<400> SEQUENCE: 63
catttaacag gcaagtccaa                                                 20
```

<210> SEQ ID NO 64
<211> LENGTH: 20
<212> TYPE: DNA
<213> ORGANISM: Artificial
<220> FEATURE:
<223> OTHER INFORMATION: TNFSF6 3' Primer

<400> SEQUENCE: 64
caaggccacc cttcttatac                                            20

<210> SEQ ID NO 65
<211> LENGTH: 20
<212> TYPE: DNA
<213> ORGANISM: Artificial
<220> FEATURE:
<223> OTHER INFORMATION: WASF2 5' Primer

<400> SEQUENCE: 65
gttcagcaac ttcacagcga                                            20

<210> SEQ ID NO 66
<211> LENGTH: 22
<212> TYPE: DNA
<213> ORGANISM: Artificial
<220> FEATURE:
<223> OTHER INFORMATION: WASF2 3' Primer

<400> SEQUENCE: 66
cactcaggtc cttctgctgt tt                                         22

<210> SEQ ID NO 67
<211> LENGTH: 21
<212> TYPE: DNA
<213> ORGANISM: Artificial
<220> FEATURE:
<223> OTHER INFORMATION: ASAHL SensePrimer

<400> SEQUENCE: 67
taatgctaca ggacaagcaa a                                          21

<210> SEQ ID NO 68
<211> LENGTH: 20
<212> TYPE: DNA
<213> ORGANISM: Artificial
<220> FEATURE:
<223> OTHER INFORMATION: ASAHL AntisensePrimer

<400> SEQUENCE: 68
ggtcttgaac tcctgacctc                                            20

<210> SEQ ID NO 69
<211> LENGTH: 20
<212> TYPE: DNA
<213> ORGANISM: Artificial
<220> FEATURE:
<223> OTHER INFORMATION: ASAHL TaqManProbe

<400> SEQUENCE: 69
caccgcacct ggcctgcttt                                            20

<210> SEQ ID NO 70
<211> LENGTH: 19
<212> TYPE: DNA
<213> ORGANISM: Artificial
<220> FEATURE:
<223> OTHER INFORMATION: ASAHL SensePrimer

<400> SEQUENCE: 70
ctacgagtcc tccgtgttc                                                19

<210> SEQ ID NO 71
<211> LENGTH: 20
<212> TYPE: DNA
<213> ORGANISM: Artificial
<220> FEATURE:
<223> OTHER INFORMATION: ASAHL AntisensePrimer

<400> SEQUENCE: 71
agaattgcac atccactgtc                                               20

<210> SEQ ID NO 72
<211> LENGTH: 22
<212> TYPE: DNA
<213> ORGANISM: Artificial
<220> FEATURE:
<223> OTHER INFORMATION: ASAHL TaqManProbe

<400> SEQUENCE: 72
tggctcaaga ctccagaggc ca                                            22

<210> SEQ ID NO 73
<211> LENGTH: 20
<212> TYPE: DNA
<213> ORGANISM: Artificial
<220> FEATURE:
<223> OTHER INFORMATION: ASAHL SensePrimer

<400> SEQUENCE: 73
ttggcctcta gatcctttga                                               20

<210> SEQ ID NO 74
<211> LENGTH: 20
<212> TYPE: DNA
<213> ORGANISM: Artificial
<220> FEATURE:
<223> OTHER INFORMATION: ASAHL AntisensePrimer

<400> SEQUENCE: 74
tttgcttgtc ctgtagcatt                                               20

<210> SEQ ID NO 75
<211> LENGTH: 20
<212> TYPE: DNA
<213> ORGANISM: Artificial
<220> FEATURE:
<223> OTHER INFORMATION: ASAHL TaqManProbe

<400> SEQUENCE: 75
ccactggaag ccagcaccca                                               20

<210> SEQ ID NO 76
<211> LENGTH: 20
<212> TYPE: DNA
<213> ORGANISM: Artificial
<220> FEATURE:
<223> OTHER INFORMATION: ASGR1 SensePrimer

<400> SEQUENCE: 76
agagacgttc agcaacttca                                               20

<210> SEQ ID NO 77
<211> LENGTH: 20

```
<212> TYPE: DNA
<213> ORGANISM: Artificial
<220> FEATURE:
<223> OTHER INFORMATION: ASGR1 AntisensePrimer

<400> SEQUENCE: 77
aggtccttct gctgtttctc                                           20

<210> SEQ ID NO 78
<211> LENGTH: 20
<212> TYPE: DNA
<213> ORGANISM: Artificial
<220> FEATURE:
<223> OTHER INFORMATION: ASGR1 TaqManProbe

<400> SEQUENCE: 78
cccttgacct gggcctccgt                                           20

<210> SEQ ID NO 79
<211> LENGTH: 20
<212> TYPE: DNA
<213> ORGANISM: Artificial
<220> FEATURE:
<223> OTHER INFORMATION: ASGR1 SensePrimer

<400> SEQUENCE: 79
tgagagagac gttcagcaac                                           20

<210> SEQ ID NO 80
<211> LENGTH: 20
<212> TYPE: DNA
<213> ORGANISM: Artificial
<220> FEATURE:
<223> OTHER INFORMATION: ASGR1 AntisensePrimer

<400> SEQUENCE: 80
aggtccttct gctgtttctc                                           20

<210> SEQ ID NO 81
<211> LENGTH: 20
<212> TYPE: DNA
<213> ORGANISM: Artificial
<220> FEATURE:
<223> OTHER INFORMATION: ASGR1 TaqManProbe

<400> SEQUENCE: 81
cccttgacct gggcctccgt                                           20

<210> SEQ ID NO 82
<211> LENGTH: 20
<212> TYPE: DNA
<213> ORGANISM: Artificial
<220> FEATURE:
<223> OTHER INFORMATION: ASGR1 SensePrimer

<400> SEQUENCE: 82
agagacgttc agcaacttca                                           20

<210> SEQ ID NO 83
<211> LENGTH: 20
<212> TYPE: DNA
<213> ORGANISM: Artificial
<220> FEATURE:
<223> OTHER INFORMATION: ASGR1 AntisensePrimer

<400> SEQUENCE: 83
actcaggtcc ttctgctgtt                                           20
```

```
<210> SEQ ID NO 84
<211> LENGTH: 20
<212> TYPE: DNA
<213> ORGANISM: Artificial
<220> FEATURE:
<223> OTHER INFORMATION: ASGR1 TaqManProbe

<400> SEQUENCE: 84
cccttgacct gggcctccgt                                               20

<210> SEQ ID NO 85
<211> LENGTH: 20
<212> TYPE: DNA
<213> ORGANISM: Artificial
<220> FEATURE:
<223> OTHER INFORMATION: ATP1B1 SensePrimer

<400> SEQUENCE: 85
cctccggtat gttctaaagc                                               20

<210> SEQ ID NO 86
<211> LENGTH: 19
<212> TYPE: DNA
<213> ORGANISM: Artificial
<220> FEATURE:
<223> OTHER INFORMATION: ATP1B1 AntisensePrimer

<400> SEQUENCE: 86
atgtgatgcc tccagaaag                                                19

<210> SEQ ID NO 87
<211> LENGTH: 22
<212> TYPE: DNA
<213> ORGANISM: Artificial
<220> FEATURE:
<223> OTHER INFORMATION: ATP1B1 TaqManProbe

<400> SEQUENCE: 87
tggatctgcc catcactttg gc                                            22

<210> SEQ ID NO 88
<211> LENGTH: 20
<212> TYPE: DNA
<213> ORGANISM: Artificial
<220> FEATURE:
<223> OTHER INFORMATION: ATP1B1 SensePrimer

<400> SEQUENCE: 88
gtacaaagat tcagcccaga                                               20

<210> SEQ ID NO 89
<211> LENGTH: 20
<212> TYPE: DNA
<213> ORGANISM: Artificial
<220> FEATURE:
<223> OTHER INFORMATION: ATP1B1 AntisensePrimer

<400> SEQUENCE: 89
gctctcctcg ttcatgatta                                               20

<210> SEQ ID NO 90
<211> LENGTH: 20
<212> TYPE: DNA
<213> ORGANISM: Artificial
<220> FEATURE:
<223> OTHER INFORMATION: ATP1B1 TaqManProbe
```

<400> SEQUENCE: 90
tcactgggca catcgccaca                                              20

<210> SEQ ID NO 91
<211> LENGTH: 20
<212> TYPE: DNA
<213> ORGANISM: Artificial
<220> FEATURE:
<223> OTHER INFORMATION: ATP1B1 SensePrimer

<400> SEQUENCE: 91
gtgccttatt acccaggaag                                              20

<210> SEQ ID NO 92
<211> LENGTH: 21
<212> TYPE: DNA
<213> ORGANISM: Artificial
<220> FEATURE:
<223> OTHER INFORMATION: ATP1B1 AntisensePrimer

<400> SEQUENCE: 92
gcagttacca gaccttatgc t                                            21

<210> SEQ ID NO 93
<211> LENGTH: 27
<212> TYPE: DNA
<213> ORGANISM: Artificial
<220> FEATURE:
<223> OTHER INFORMATION: ATP1B1 TaqManProbe

<400> SEQUENCE: 93
catccaaact cagcttgcta cagacca                                      27

<210> SEQ ID NO 94
<211> LENGTH: 20
<212> TYPE: DNA
<213> ORGANISM: Artificial
<220> FEATURE:
<223> OTHER INFORMATION: BMP6 SensePrimer

<400> SEQUENCE: 94
tcatgccagt gccttattac                                              20

<210> SEQ ID NO 95
<211> LENGTH: 20
<212> TYPE: DNA
<213> ORGANISM: Artificial
<220> FEATURE:
<223> OTHER INFORMATION: BMP6 AntisensePrimer

<400> SEQUENCE: 95
tttctgcagt taccagacct                                              20

<210> SEQ ID NO 96
<211> LENGTH: 27
<212> TYPE: DNA
<213> ORGANISM: Artificial
<220> FEATURE:
<223> OTHER INFORMATION: BMP6 TaqManProbe

<400> SEQUENCE: 96
tgctacagac atccaaactc agcttgc                                      27

<210> SEQ ID NO 97
<211> LENGTH: 20

```
<212> TYPE: DNA
<213> ORGANISM: Artificial
<220> FEATURE:
<223> OTHER INFORMATION: BMP6 SensePrimer

<400> SEQUENCE: 97
agtgccttat tacccaggaa                                                     20

<210> SEQ ID NO 98
<211> LENGTH: 21
<212> TYPE: DNA
<213> ORGANISM: Artificial
<220> FEATURE:
<223> OTHER INFORMATION: BMP6 AntisensePrimer

<400> SEQUENCE: 98
gcagttacca gaccttatgc t                                                   21

<210> SEQ ID NO 99
<211> LENGTH: 27
<212> TYPE: DNA
<213> ORGANISM: Artificial
<220> FEATURE:
<223> OTHER INFORMATION: BMP6 TaqManProbe

<400> SEQUENCE: 99
catccaaact cagcttgcta cagacca                                             27

<210> SEQ ID NO 100
<211> LENGTH: 20
<212> TYPE: DNA
<213> ORGANISM: Artificial
<220> FEATURE:
<223> OTHER INFORMATION: BMP6 SensePrimer

<400> SEQUENCE: 100
tcatgccagt gccttattac                                                     20

<210> SEQ ID NO 101
<211> LENGTH: 20
<212> TYPE: DNA
<213> ORGANISM: Artificial
<220> FEATURE:
<223> OTHER INFORMATION: BMP6 AntisensePrimer

<400> SEQUENCE: 101
tttctgcagt taccagacct                                                     20

<210> SEQ ID NO 102
<211> LENGTH: 27
<212> TYPE: DNA
<213> ORGANISM: Artificial
<220> FEATURE:
<223> OTHER INFORMATION: BMP6 TaqManProbe

<400> SEQUENCE: 102
tgctacagac atccaaactc agcttgc                                             27

<210> SEQ ID NO 103
<211> LENGTH: 20
<212> TYPE: DNA
<213> ORGANISM: Artificial
<220> FEATURE:
<223> OTHER INFORMATION: C4BPA SensePrimer

<400> SEQUENCE: 103
aatggaatcc ttctcctcct                                                     20
```

<210> SEQ ID NO 104
<211> LENGTH: 20
<212> TYPE: DNA
<213> ORGANISM: Artificial
<220> FEATURE:
<223> OTHER INFORMATION: C4BPA AntisensePrimer

<400> SEQUENCE: 104
ccttaacaca gtcccaacaa                                                  20

<210> SEQ ID NO 105
<211> LENGTH: 23
<212> TYPE: DNA
<213> ORGANISM: Artificial
<220> FEATURE:
<223> OTHER INFORMATION: C4BPA TaqManProbe

<400> SEQUENCE: 105
cagacattcc acatgcttcc tgg                                              23

<210> SEQ ID NO 106
<211> LENGTH: 20
<212> TYPE: DNA
<213> ORGANISM: Artificial
<220> FEATURE:
<223> OTHER INFORMATION: C4BPA SensePrimer

<400> SEQUENCE: 106
tccacccact ttatcatttg                                                  20

<210> SEQ ID NO 107
<211> LENGTH: 20
<212> TYPE: DNA
<213> ORGANISM: Artificial
<220> FEATURE:
<223> OTHER INFORMATION: C4BPA AntisensePrimer

<400> SEQUENCE: 107
ctgagttgaa tgggatctga                                                  20

<210> SEQ ID NO 108
<211> LENGTH: 23
<212> TYPE: DNA
<213> ORGANISM: Artificial
<220> FEATURE:
<223> OTHER INFORMATION: C4BPA TaqManProbe

<400> SEQUENCE: 108
tgaaatacac ctgcctccct ggc                                              23

<210> SEQ ID NO 109
<211> LENGTH: 20
<212> TYPE: DNA
<213> ORGANISM: Artificial
<220> FEATURE:
<223> OTHER INFORMATION: C4BPA SensePrimer

<400> SEQUENCE: 109
tccacccact ttatcatttg                                                  20

<210> SEQ ID NO 110
<211> LENGTH: 20
<212> TYPE: DNA
<213> ORGANISM: Artificial
<220> FEATURE:
<223> OTHER INFORMATION: C4BPA AntisensePrimer

<400> SEQUENCE: 110
tctgagttga atgggatctg                  20

<210> SEQ ID NO 111
<211> LENGTH: 22
<212> TYPE: DNA
<213> ORGANISM: Artificial
<220> FEATURE:
<223> OTHER INFORMATION: C4BPA TaqManProbe

<400> SEQUENCE: 111
acacctgcct ccctggctac gt               22

<210> SEQ ID NO 112
<211> LENGTH: 20
<212> TYPE: DNA
<213> ORGANISM: Artificial
<220> FEATURE:
<223> OTHER INFORMATION: CKLF SensePrimer

<400> SEQUENCE: 112
tcactggatt tgaagtcacc                  20

<210> SEQ ID NO 113
<211> LENGTH: 18
<212> TYPE: DNA
<213> ORGANISM: Artificial
<220> FEATURE:
<223> OTHER INFORMATION: CKLF AntisensePrimer

<400> SEQUENCE: 113
gtcggcaaga cagcatac                    18

<210> SEQ ID NO 114
<211> LENGTH: 23
<212> TYPE: DNA
<213> ORGANISM: Artificial
<220> FEATURE:
<223> OTHER INFORMATION: CKLF TaqManProbe

<400> SEQUENCE: 114
tgcaaacaca agcaaaggcc aaa              23

<210> SEQ ID NO 115
<211> LENGTH: 19
<212> TYPE: DNA
<213> ORGANISM: Artificial
<220> FEATURE:
<223> OTHER INFORMATION: CKLF SensePrimer

<400> SEQUENCE: 115
cagccagctg agaagagtt                   19

<210> SEQ ID NO 116
<211> LENGTH: 19
<212> TYPE: DNA
<213> ORGANISM: Artificial
<220> FEATURE:
<223> OTHER INFORMATION: CKLF AntisensePrimer

<400> SEQUENCE: 116
gcctttcaca ctgaagcag                   19

<210> SEQ ID NO 117
<211> LENGTH: 20

```
<212> TYPE: DNA
<213> ORGANISM: Artificial
<220> FEATURE:
<223> OTHER INFORMATION: CKLF TaqManProbe

<400> SEQUENCE: 117
cgcgtctgca gacccagcag                                              20

<210> SEQ ID NO 118
<211> LENGTH: 18
<212> TYPE: DNA
<213> ORGANISM: Artificial
<220> FEATURE:
<223> OTHER INFORMATION: CKLF SensePrimer

<400> SEQUENCE: 118
cccttctgct tcagtgtg                                                18

<210> SEQ ID NO 119
<211> LENGTH: 20
<212> TYPE: DNA
<213> ORGANISM: Artificial
<220> FEATURE:
<223> OTHER INFORMATION: CKLF AntisensePrimer

<400> SEQUENCE: 119
ggtgacttca aatccagtga                                              20

<210> SEQ ID NO 120
<211> LENGTH: 20
<212> TYPE: DNA
<213> ORGANISM: Artificial
<220> FEATURE:
<223> OTHER INFORMATION: CKLF TaqManProbe

<400> SEQUENCE: 120
ccagccgcag catcttcacg                                              20

<210> SEQ ID NO 121
<211> LENGTH: 20
<212> TYPE: DNA
<213> ORGANISM: Artificial
<220> FEATURE:
<223> OTHER INFORMATION: CLIC5 SensePrimer

<400> SEQUENCE: 121
tggatgacta cctgaacacc                                              20

<210> SEQ ID NO 122
<211> LENGTH: 20
<212> TYPE: DNA
<213> ORGANISM: Artificial
<220> FEATURE:
<223> OTHER INFORMATION: CLIC5 AntisensePrimer

<400> SEQUENCE: 122
atcttgacca catggagctt                                              20

<210> SEQ ID NO 123
<211> LENGTH: 20
<212> TYPE: DNA
<213> ORGANISM: Artificial
<220> FEATURE:
<223> OTHER INFORMATION: CLIC5 TaqManProbe

<400> SEQUENCE: 123
ccatccagga acttgcgccg                                              20
```

<210> SEQ ID NO 124
<211> LENGTH: 19
<212> TYPE: DNA
<213> ORGANISM: Artificial
<220> FEATURE:
<223> OTHER INFORMATION: CLIC5 SensePrimer

<400> SEQUENCE: 124
gagtaccgag ctggctatg                                                  19

<210> SEQ ID NO 125
<211> LENGTH: 20
<212> TYPE: DNA
<213> ORGANISM: Artificial
<220> FEATURE:
<223> OTHER INFORMATION: CLIC5 AntisensePrimer

<400> SEQUENCE: 125
tgcaacaaac tgagaatgtg                                                 20

<210> SEQ ID NO 126
<211> LENGTH: 22
<212> TYPE: DNA
<213> ORGANISM: Artificial
<220> FEATURE:
<223> OTHER INFORMATION: CLIC5 TaqManProbe

<400> SEQUENCE: 126
ccagtctggc ccttagtgcc ca                                              22

<210> SEQ ID NO 127
<211> LENGTH: 20
<212> TYPE: DNA
<213> ORGANISM: Artificial
<220> FEATURE:
<223> OTHER INFORMATION: CLIC5 SensePrimer

<400> SEQUENCE: 127
agcctcatct tgctggtatc                                                 20

<210> SEQ ID NO 128
<211> LENGTH: 20
<212> TYPE: DNA
<213> ORGANISM: Artificial
<220> FEATURE:
<223> OTHER INFORMATION: CLIC5 AntisensePrimer

<400> SEQUENCE: 128
cgaaaggtgg actgtgtcta                                                 20

<210> SEQ ID NO 129
<211> LENGTH: 20
<212> TYPE: DNA
<213> ORGANISM: Artificial
<220> FEATURE:
<223> OTHER INFORMATION: CLIC5 TaqManProbe

<400> SEQUENCE: 129
cagcaccatc cctggcctcc                                                 20

<210> SEQ ID NO 130
<211> LENGTH: 20
<212> TYPE: DNA
<213> ORGANISM: Artificial
<220> FEATURE:
<223> OTHER INFORMATION: CPT1A SensePrimer

```
<400> SEQUENCE: 130
aagacttcaa acggatgaca                                              20

<210> SEQ ID NO 131
<211> LENGTH: 20
<212> TYPE: DNA
<213> ORGANISM: Artificial
<220> FEATURE:
<223> OTHER INFORMATION: CPT1A Antisense Primer

<400> SEQUENCE: 131
agatgtactc ctcccaccag                                              20

<210> SEQ ID NO 132
<211> LENGTH: 23
<212> TYPE: DNA
<213> ORGANISM: Artificial
<220> FEATURE:
<223> OTHER INFORMATION: CPT1A TaqManProbe

<400> SEQUENCE: 132
tcttggtcca agaccgacag caa                                          23

<210> SEQ ID NO 133
<211> LENGTH: 20
<212> TYPE: DNA
<213> ORGANISM: Artificial
<220> FEATURE:
<223> OTHER INFORMATION: CPT1A SensePrimer

<400> SEQUENCE: 133
aagacttcaa acggatgaca                                              20

<210> SEQ ID NO 134
<211> LENGTH: 20
<212> TYPE: DNA
<213> ORGANISM: Artificial
<220> FEATURE:
<223> OTHER INFORMATION: CPT1A AntisenseProbe

<400> SEQUENCE: 134
tagatgtact cctcccacca                                              20

<210> SEQ ID NO 135
<211> LENGTH: 23
<212> TYPE: DNA
<213> ORGANISM: Artificial
<220> FEATURE:
<223> OTHER INFORMATION: CPT1A TaqManProbe

<400> SEQUENCE: 135
tcttggtcca agaccgacag caa                                          23

<210> SEQ ID NO 136
<211> LENGTH: 20
<212> TYPE: DNA
<213> ORGANISM: Artificial
<220> FEATURE:
<223> OTHER INFORMATION: CPT1A SensePrimer

<400> SEQUENCE: 136
gacagcactt gctcaagatt                                              20

<210> SEQ ID NO 137
<211> LENGTH: 20
```

-continued

```
<212> TYPE: DNA
<213> ORGANISM: Artificial
<220> FEATURE:
<223> OTHER INFORMATION: CPT1A AntisensePrimer

<400> SEQUENCE: 137
atgtactcct cccaccagtc                                                  20

<210> SEQ ID NO 138
<211> LENGTH: 23
<212> TYPE: DNA
<213> ORGANISM: Artificial
<220> FEATURE:
<223> OTHER INFORMATION: CPT1A TaqManProbe

<400> SEQUENCE: 138
tcttggtcca agaccgacag caa                                              23

<210> SEQ ID NO 139
<211> LENGTH: 20
<212> TYPE: DNA
<213> ORGANISM: Artificial
<220> FEATURE:
<223> OTHER INFORMATION: F2RL1 SensePrimer

<400> SEQUENCE: 139
gcctctctac ccttaacagc                                                  20

<210> SEQ ID NO 140
<211> LENGTH: 20
<212> TYPE: DNA
<213> ORGANISM: Artificial
<220> FEATURE:
<223> OTHER INFORMATION: F2RL1 AntisensePrimer

<400> SEQUENCE: 140
ctttacagtg cggacacttc                                                  20

<210> SEQ ID NO 141
<211> LENGTH: 23
<212> TYPE: DNA
<213> ORGANISM: Artificial
<220> FEATURE:
<223> OTHER INFORMATION: F2RL1 TaqManProbe

<400> SEQUENCE: 141
tgcaaagaac gctctccttt gcc                                              23

<210> SEQ ID NO 142
<211> LENGTH: 20
<212> TYPE: DNA
<213> ORGANISM: Artificial
<220> FEATURE:
<223> OTHER INFORMATION: F2RL1 SensePrimer

<400> SEQUENCE: 142
cctctgcctc tctaccctta                                                  20

<210> SEQ ID NO 143
<211> LENGTH: 20
<212> TYPE: DNA
<213> ORGANISM: Artificial
<220> FEATURE:
<223> OTHER INFORMATION: F2RL1 AntisensePrimer

<400> SEQUENCE: 143
ctttacagtg cggacacttc                                                  20
```

<210> SEQ ID NO 144
<211> LENGTH: 23
<212> TYPE: DNA
<213> ORGANISM: Artificial
<220> FEATURE:
<223> OTHER INFORMATION: T2RL1 TaqManProbe

<400> SEQUENCE: 144
tgcaaagaac gctctccttt gcc                                              23

<210> SEQ ID NO 145
<211> LENGTH: 20
<212> TYPE: DNA
<213> ORGANISM: Artificial
<220> FEATURE:
<223> OTHER INFORMATION: F2RL1 SensePrimer

<400> SEQUENCE: 145
gtaaccttct gcttgtggtg                                                  20

<210> SEQ ID NO 146
<211> LENGTH: 20
<212> TYPE: DNA
<213> ORGANISM: Artificial
<220> FEATURE:
<223> OTHER INFORMATION: F2RL1 AntisensePrimer

<400> SEQUENCE: 146
tgcagctgtt aagggtagag                                                  20

<210> SEQ ID NO 147
<211> LENGTH: 20
<212> TYPE: DNA
<213> ORGANISM: Artificial
<220> FEATURE:
<223> OTHER INFORMATION: F2RL1 TaqManProbe

<400> SEQUENCE: 147
catggctctg gccctggctc                                                  20

<210> SEQ ID NO 148
<211> LENGTH: 20
<212> TYPE: DNA
<213> ORGANISM: Artificial
<220> FEATURE:
<223> OTHER INFORMATION: HDGF SensePrimer

<400> SEQUENCE: 148
cagccaacaa ataccaagtc                                                  20

<210> SEQ ID NO 149
<211> LENGTH: 20
<212> TYPE: DNA
<213> ORGANISM: Artificial
<220> FEATURE:
<223> OTHER INFORMATION: HDGF AntisensePrimer

<400> SEQUENCE: 149
ctgaaccctt tcctcttgtt                                                  20

<210> SEQ ID NO 150
<211> LENGTH: 20
<212> TYPE: DNA
<213> ORGANISM: Artificial
<220> FEATURE:
<223> OTHER INFORMATION: HDGF TaqManProbe

```
<400> SEQUENCE: 150
ccgtctcgtg ggtcccgaaa                                               20

<210> SEQ ID NO 151
<211> LENGTH: 20
<212> TYPE: DNA
<213> ORGANISM: Artificial
<220> FEATURE:
<223> OTHER INFORMATION: HDGF SensePrimer

<400> SEQUENCE: 151
gtaggaatgg aaggatggag                                               20

<210> SEQ ID NO 152
<211> LENGTH: 20
<212> TYPE: DNA
<213> ORGANISM: Artificial
<220> FEATURE:
<223> OTHER INFORMATION: HDGF AntisensePrimer

<400> SEQUENCE: 152
taggcagctg ggataatagg                                               20

<210> SEQ ID NO 153
<211> LENGTH: 20
<212> TYPE: DNA
<213> ORGANISM: Artificial
<220> FEATURE:
<223> OTHER INFORMATION: HDGF TaqManProbe

<400> SEQUENCE: 153
cacaggaggg cggcctcctt                                               20

<210> SEQ ID NO 154
<211> LENGTH: 20
<212> TYPE: DNA
<213> ORGANISM: Artificial
<220> FEATURE:
<223> OTHER INFORMATION: HDGF SensePrimer

<400> SEQUENCE: 154
gagacctgaa gggttgactt                                               20

<210> SEQ ID NO 155
<211> LENGTH: 20
<212> TYPE: DNA
<213> ORGANISM: Artificial
<220> FEATURE:
<223> OTHER INFORMATION: HDGF AntisensePrimer

<400> SEQUENCE: 155
tgactataag ctggccttga                                               20

<210> SEQ ID NO 156
<211> LENGTH: 22
<212> TYPE: DNA
<213> ORGANISM: Artificial
<220> FEATURE:
<223> OTHER INFORMATION: HDGF TaqManProbe

<400> SEQUENCE: 156
tcaacactcc cacccaaatg gg                                            22

<210> SEQ ID NO 157
<211> LENGTH: 19
```

```
<212> TYPE: DNA
<213> ORGANISM: Artificial
<220> FEATURE:
<223> OTHER INFORMATION: HSPCA SensePrimer

<400> SEQUENCE: 157
tacacatctg cctctggtg                                              19

<210> SEQ ID NO 158
<211> LENGTH: 20
<212> TYPE: DNA
<213> ORGANISM: Artificial
<220> FEATURE:
<223> OTHER INFORMATION: HSPCA AntisensePrimer

<400> SEQUENCE: 158
gttagctacc tggtccttgg                                             20

<210> SEQ ID NO 159
<211> LENGTH: 25
<212> TYPE: DNA
<213> ORGANISM: Artificial
<220> FEATURE:
<223> OTHER INFORMATION: HSPCA TaqManProbe

<400> SEQUENCE: 159
tctggttctc cttcattctg gtgca                                       25

<210> SEQ ID NO 160
<211> LENGTH: 20
<212> TYPE: DNA
<213> ORGANISM: Artificial
<220> FEATURE:
<223> OTHER INFORMATION: HSPCA SensePrimer

<400> SEQUENCE: 160
aaatcggaag aagctttcag                                             20

<210> SEQ ID NO 161
<211> LENGTH: 20
<212> TYPE: DNA
<213> ORGANISM: Artificial
<220> FEATURE:
<223> OTHER INFORMATION: HSPCA AntisensePrimer

<400> SEQUENCE: 161
ctggttctcc ttcattctgg                                             20

<210> SEQ ID NO 162
<211> LENGTH: 26
<212> TYPE: DNA
<213> ORGANISM: Artificial
<220> FEATURE:
<223> OTHER INFORMATION: HSPCA TaqManProbe

<400> SEQUENCE: 162
ccatctcatc accagaggca gatgtg                                      26

<210> SEQ ID NO 163
<211> LENGTH: 20
<212> TYPE: DNA
<213> ORGANISM: Artificial
<220> FEATURE:
<223> OTHER INFORMATION: HSPCA SensePrimer

<400> SEQUENCE: 163
tggtgatgag atggtttctc                                             20
```

```
<210> SEQ ID NO 164
<211> LENGTH: 19
<212> TYPE: DNA
<213> ORGANISM: Artificial
<220> FEATURE:
<223> OTHER INFORMATION: HSPCA AntisensePrimer

<400> SEQUENCE: 164
ctaagccatg tttccgaag                                                  19

<210> SEQ ID NO 165
<211> LENGTH: 24
<212> TYPE: DNA
<213> ORGANISM: Artificial
<220> FEATURE:
<223> OTHER INFORMATION: HSPCA TaqManProbe

<400> SEQUENCE: 165
cctggtcctt ggtctcacct gtga                                            24

<210> SEQ ID NO 166
<211> LENGTH: 20
<212> TYPE: DNA
<213> ORGANISM: Artificial
<220> FEATURE:
<223> OTHER INFORMATION: IL13RA1 SensePrimer

<400> SEQUENCE: 166
ctcattgttc cagtcatcgt                                                 20

<210> SEQ ID NO 167
<211> LENGTH: 20
<212> TYPE: DNA
<213> ORGANISM: Artificial
<220> FEATURE:
<223> OTHER INFORMATION: IL13RA1 AntisensePrimer

<400> SEQUENCE: 167
tcattctggt ctccaaacat                                                 20

<210> SEQ ID NO 168
<211> LENGTH: 23
<212> TYPE: DNA
<213> ORGANISM: Artificial
<220> FEATURE:
<223> OTHER INFORMATION: IL13RA1 TaqManProbe

<400> SEQUENCE: 168
ccctccaatt cctgatcctg gca                                             23

<210> SEQ ID NO 169
<211> LENGTH: 20
<212> TYPE: DNA
<213> ORGANISM: Artificial
<220> FEATURE:
<223> OTHER INFORMATION: IL13RA1 SensePrimer

<400> SEQUENCE: 169
gtcaaggata atgcaggaaa                                                 20

<210> SEQ ID NO 170
<211> LENGTH: 20
<212> TYPE: DNA
<213> ORGANISM: Artificial
<220> FEATURE:
<223> OTHER INFORMATION: IL13RA1 AntisensePrimer
```

```
<400> SEQUENCE: 170
gtcatcattg tggaaggaga                                              20

<210> SEQ ID NO 171
<211> LENGTH: 23
<212> TYPE: DNA
<213> ORGANISM: Artificial
<220> FEATURE:
<223> OTHER INFORMATION: IL13RA1 TaqManProbe

<400> SEQUENCE: 171
cccgtgtgaa acctgatcct cca                                          23

<210> SEQ ID NO 172
<211> LENGTH: 20
<212> TYPE: DNA
<213> ORGANISM: Artificial
<220> FEATURE:
<223> OTHER INFORMATION: IL13RA1 SensePrimer

<400> SEQUENCE: 172
acctaagcaa acccagtgtc                                              20

<210> SEQ ID NO 173
<211> LENGTH: 20
<212> TYPE: DNA
<213> ORGANISM: Artificial
<220> FEATURE:
<223> OTHER INFORMATION: IL13RA1 AntisensePrimer

<400> SEQUENCE: 173
aacaatccct ggttgaagac                                              20

<210> SEQ ID NO 174
<211> LENGTH: 23
<212> TYPE: DNA
<213> ORGANISM: Artificial
<220> FEATURE:
<223> OTHER INFORMATION: IL13RA1 TaqManProbe

<400> SEQUENCE: 174
cccttcatct gggcactgaa ggg                                          23

<210> SEQ ID NO 175
<211> LENGTH: 20
<212> TYPE: DNA
<213> ORGANISM: Artificial
<220> FEATURE:
<223> OTHER INFORMATION: LRMP SensePrimer

<400> SEQUENCE: 175
gagcacgctg aattagaaga                                              20

<210> SEQ ID NO 176
<211> LENGTH: 20
<212> TYPE: DNA
<213> ORGANISM: Artificial
<220> FEATURE:
<223> OTHER INFORMATION: LRMP AntisensePrimer

<400> SEQUENCE: 176
ggcttggagt ttagagaagc                                              20

<210> SEQ ID NO 177
<211> LENGTH: 27
```

```
<212> TYPE: DNA
<213> ORGANISM: Artificial
<220> FEATURE:
<223> OTHER INFORMATION: LRMP TaqManProbe

<400> SEQUENCE: 177
tcctcttgaa gatgatgatg actgcca                                          27

<210> SEQ ID NO 178
<211> LENGTH: 20
<212> TYPE: DNA
<213> ORGANISM: Artificial
<220> FEATURE:
<223> OTHER INFORMATION: LRMP SensePrimer

<400> SEQUENCE: 178
gagcacgctg aattagaaga                                                  20

<210> SEQ ID NO 179
<211> LENGTH: 20
<212> TYPE: DNA
<213> ORGANISM: Artificial
<220> FEATURE:
<223> OTHER INFORMATION: LRMP AntisensePrimer

<400> SEQUENCE: 179
ttcgtagaga agatggcttg                                                  20

<210> SEQ ID NO 180
<211> LENGTH: 27
<212> TYPE: DNA
<213> ORGANISM: Artificial
<220> FEATURE:
<223> OTHER INFORMATION: LRMP TaqManProbe

<400> SEQUENCE: 180
tcctcttgaa gatgatgatg actgcca                                          27

<210> SEQ ID NO 181
<211> LENGTH: 20
<212> TYPE: DNA
<213> ORGANISM: Artificial
<220> FEATURE:
<223> OTHER INFORMATION: LRMP SensePrimer

<400> SEQUENCE: 181
aggaagccaa gtctttctga                                                  20

<210> SEQ ID NO 182
<211> LENGTH: 20
<212> TYPE: DNA
<213> ORGANISM: Artificial
<220> FEATURE:
<223> OTHER INFORMATION: LRMP AntisensePrimer

<400> SEQUENCE: 182
ggccttatta gcctttctga                                                  20

<210> SEQ ID NO 183
<211> LENGTH: 25
<212> TYPE: DNA
<213> ORGANISM: Artificial
<220> FEATURE:
<223> OTHER INFORMATION: LRMP TaqManProbe

<400> SEQUENCE: 183
tgggcaacaa atctcaagtc ctcca                                            25
```

```
<210> SEQ ID NO 184
<211> LENGTH: 20
<212> TYPE: DNA
<213> ORGANISM: Artificial
<220> FEATURE:
<223> OTHER INFORMATION: LRPPRC SensePrimer

<400> SEQUENCE: 184
cctgttactt gtgcttggtc                                              20

<210> SEQ ID NO 185
<211> LENGTH: 20
<212> TYPE: DNA
<213> ORGANISM: Artificial
<220> FEATURE:
<223> OTHER INFORMATION: LRPPRC AntisensePrimer

<400> SEQUENCE: 185
ccgagactca atttcagaga                                              20

<210> SEQ ID NO 186
<211> LENGTH: 20
<212> TYPE: DNA
<213> ORGANISM: Artificial
<220> FEATURE:
<223> OTHER INFORMATION: LRPPRC TaqManProbe

<400> SEQUENCE: 186
tgccgaagag cctccaggca                                              20

<210> SEQ ID NO 187
<211> LENGTH: 20
<212> TYPE: DNA
<213> ORGANISM: Artificial
<220> FEATURE:
<223> OTHER INFORMATION: LRPPRC SensePrimer

<400> SEQUENCE: 187
ttgattgaca gcatgagtga                                              20

<210> SEQ ID NO 188
<211> LENGTH: 20
<212> TYPE: DNA
<213> ORGANISM: Artificial
<220> FEATURE:
<223> OTHER INFORMATION: LRPPRC Antisense Primer

<400> SEQUENCE: 188
tggtagcttt ccaggagatt                                              20

<210> SEQ ID NO 189
<211> LENGTH: 24
<212> TYPE: DNA
<213> ORGANISM: Artificial
<220> FEATURE:
<223> OTHER INFORMATION: LRPPRC TaqManProbe

<400> SEQUENCE: 189
tctcaaatgc tcctccttgg cctg                                         24

<210> SEQ ID NO 190
<211> LENGTH: 20
<212> TYPE: DNA
<213> ORGANISM: Artificial
<220> FEATURE:
<223> OTHER INFORMATION: LRPPRC SensePrimer
```

```
<400> SEQUENCE: 190
cagctggaga agatgaatgt                                               20

<210> SEQ ID NO 191
<211> LENGTH: 20
<212> TYPE: DNA
<213> ORGANISM: Artificial
<220> FEATURE:
<223> OTHER INFORMATION: LRPPRC AntisensePrimer

<400> SEQUENCE: 191
ctctcaacca acaagtgagc                                               20

<210> SEQ ID NO 192
<211> LENGTH: 27
<212> TYPE: DNA
<213> ORGANISM: Artificial
<220> FEATURE:
<223> OTHER INFORMATION: LRPPRC TaqManProbe

<400> SEQUENCE: 192
tctcctggaa agctaccatg ttcctga                                       27

<210> SEQ ID NO 193
<211> LENGTH: 19
<212> TYPE: DNA
<213> ORGANISM: Artificial
<220> FEATURE:
<223> OTHER INFORMATION: NOV SensePrimer

<400> SEQUENCE: 193
taccgcagtg gagagaaat                                                19

<210> SEQ ID NO 194
<211> LENGTH: 20
<212> TYPE: DNA
<213> ORGANISM: Artificial
<220> FEATURE:
<223> OTHER INFORMATION: NOV AntisensePrimer

<400> SEQUENCE: 194
agttaggctc aggcagtagc                                               20

<210> SEQ ID NO 195
<211> LENGTH: 20
<212> TYPE: DNA
<213> ORGANISM: Artificial
<220> FEATURE:
<223> OTHER INFORMATION: NOV TaqManProbe

<400> SEQUENCE: 195
tgcccatctc tgcaggtgca                                               20

<210> SEQ ID NO 196
<211> LENGTH: 20
<212> TYPE: DNA
<213> ORGANISM: Artificial
<220> FEATURE:
<223> OTHER INFORMATION: NOV SensePrimer

<400> SEQUENCE: 196
cagatgagga ggattcactg                                               20

<210> SEQ ID NO 197
<211> LENGTH: 19
```

```
<212> TYPE: DNA
<213> ORGANISM: Artificial
<220> FEATURE:
<223> OTHER INFORMATION: NOV AntisenseProbe

<400> SEQUENCE: 197
tctgtggtct gttcaatgc                                               19

<210> SEQ ID NO 198
<211> LENGTH: 22
<212> TYPE: DNA
<213> ORGANISM: Artificial
<220> FEATURE:
<223> OTHER INFORMATION: NOV TaqManProbe

<400> SEQUENCE: 198
caggccagaa gccaccctag ga                                           22

<210> SEQ ID NO 199
<211> LENGTH: 20
<212> TYPE: DNA
<213> ORGANISM: Artificial
<220> FEATURE:
<223> OTHER INFORMATION: NOV SensePrimer

<400> SEQUENCE: 199
attgaggttc attgggaaga                                              20

<210> SEQ ID NO 200
<211> LENGTH: 20
<212> TYPE: DNA
<213> ORGANISM: Artificial
<220> FEATURE:
<223> OTHER INFORMATION: NOV AntisensePrimer

<400> SEQUENCE: 200
gtcatgttga agagctgcat                                              20

<210> SEQ ID NO 201
<211> LENGTH: 24
<212> TYPE: DNA
<213> ORGANISM: Artificial
<220> FEATURE:
<223> OTHER INFORMATION: NOV TaqManProbe

<400> SEQUENCE: 201
ccagctctga acttccaagc tcca                                         24

<210> SEQ ID NO 202
<211> LENGTH: 20
<212> TYPE: DNA
<213> ORGANISM: Artificial
<220> FEATURE:
<223> OTHER INFORMATION: PDK4 SensePrimer

<400> SEQUENCE: 202
cctttgagtg ttcaaggatg                                              20

<210> SEQ ID NO 203
<211> LENGTH: 20
<212> TYPE: DNA
<213> ORGANISM: Artificial
<220> FEATURE:
<223> OTHER INFORMATION: PDK4 AntisensePrimer

<400> SEQUENCE: 203
agagcatatg atggaggtga                                              20
```

<210> SEQ ID NO 204
<211> LENGTH: 25
<212> TYPE: DNA
<213> ORGANISM: Artificial
<220> FEATURE:
<223> OTHER INFORMATION: PDK4 TaqManProbe

<400> SEQUENCE: 204
tccagaccaa ccaattcaca tcgtg                                    25

<210> SEQ ID NO 205
<211> LENGTH: 20
<212> TYPE: DNA
<213> ORGANISM: Artificial
<220> FEATURE:
<223> OTHER INFORMATION: PDK4 SensePrimer

<400> SEQUENCE: 205
cctttgagtg ttcaaggatg                                          20

<210> SEQ ID NO 206
<211> LENGTH: 20
<212> TYPE: DNA
<213> ORGANISM: Artificial
<220> FEATURE:
<223> OTHER INFORMATION: PDK4 AntisensePrimer

<400> SEQUENCE: 206
gagcatatga tggaggtgag                                          20

<210> SEQ ID NO 207
<211> LENGTH: 25
<212> TYPE: DNA
<213> ORGANISM: Artificial
<220> FEATURE:
<223> OTHER INFORMATION: PDK4 TaqManProbe

<400> SEQUENCE: 207
tccagaccaa ccaattcaca tcgtg                                    25

<210> SEQ ID NO 208
<211> LENGTH: 20
<212> TYPE: DNA
<213> ORGANISM: Artificial
<220> FEATURE:
<223> OTHER INFORMATION: PDK4 SensePrimer

<400> SEQUENCE: 208
cctttgagtg ttcaaggatg                                          20

<210> SEQ ID NO 209
<211> LENGTH: 20
<212> TYPE: DNA
<213> ORGANISM: Artificial
<220> FEATURE:
<223> OTHER INFORMATION: PDK4 AntisensePrimer

<400> SEQUENCE: 209
agcatatgat ggaggtgaga                                          20

<210> SEQ ID NO 210
<211> LENGTH: 25
<212> TYPE: DNA
<213> ORGANISM: Artificial
<220> FEATURE:
<223> OTHER INFORMATION: PDK4 TaqManProbe

```
<400> SEQUENCE: 210
tccagaccaa ccaattcaca tcgtg                                      25

<210> SEQ ID NO 211
<211> LENGTH: 18
<212> TYPE: DNA
<213> ORGANISM: Artificial
<220> FEATURE:
<223> OTHER INFORMATION: PF4 SensePrimer

<400> SEQUENCE: 211
actgatagcc acgctgaa                                              18

<210> SEQ ID NO 212
<211> LENGTH: 20
<212> TYPE: DNA
<213> ORGANISM: Artificial
<220> FEATURE:
<223> OTHER INFORMATION: PF4 AntisensePrimer

<400> SEQUENCE: 212
atagcaaatg cacacacgta                                            20

<210> SEQ ID NO 213
<211> LENGTH: 21
<212> TYPE: DNA
<213> ORGANISM: Artificial
<220> FEATURE:
<223> OTHER INFORMATION: PF4 TaqManProbe

<400> SEQUENCE: 213
tttgcttgga cctgcaagcc c                                          21

<210> SEQ ID NO 214
<211> LENGTH: 20
<212> TYPE: DNA
<213> ORGANISM: Artificial
<220> FEATURE:
<223> OTHER INFORMATION: PF4 SensePrimer

<400> SEQUENCE: 214
ctgtgtgtga agaccacctc                                            20

<210> SEQ ID NO 215
<211> LENGTH: 18
<212> TYPE: DNA
<213> ORGANISM: Artificial
<220> FEATURE:
<223> OTHER INFORMATION: PF4 AntisensePrimer

<400> SEQUENCE: 215
cttcagcgtg gctatcag                                              18

<210> SEQ ID NO 216
<211> LENGTH: 20
<212> TYPE: DNA
<213> ORGANISM: Artificial
<220> FEATURE:
<223> OTHER INFORMATION: PF4 TaqManProbe

<400> SEQUENCE: 216
ccgtcccagg cacatcacca                                            20

<210> SEQ ID NO 217
<211> LENGTH: 19
```

```
<212> TYPE: DNA
<213> ORGANISM: Artificial
<220> FEATURE:
<223> OTHER INFORMATION: PF4 SensePrimer

<400> SEQUENCE: 217
aactgatagc cacgctgaa                                                 19

<210> SEQ ID NO 218
<211> LENGTH: 21
<212> TYPE: DNA
<213> ORGANISM: Artificial
<220> FEATURE:
<223> OTHER INFORMATION: PF4 AntisensePrimer

<400> SEQUENCE: 218
atagcaaatg cacacacgta g                                              21

<210> SEQ ID NO 219
<211> LENGTH: 21
<212> TYPE: DNA
<213> ORGANISM: Artificial
<220> FEATURE:
<223> OTHER INFORMATION: PF4 TaqManProbe

<400> SEQUENCE: 219
tttgcttgga cctgcaagcc c                                              21

<210> SEQ ID NO 220
<211> LENGTH: 20
<212> TYPE: DNA
<213> ORGANISM: Artificial
<220> FEATURE:
<223> OTHER INFORMATION: RPS6KA2 SensePrimer

<400> SEQUENCE: 220
gaccgagtga gatcgaagat                                                20

<210> SEQ ID NO 221
<211> LENGTH: 20
<212> TYPE: DNA
<213> ORGANISM: Artificial
<220> FEATURE:
<223> OTHER INFORMATION: RPS6KA2 AntisensePrimer

<400> SEQUENCE: 221
ggaagtccag gatcaggtag                                                20

<210> SEQ ID NO 222
<211> LENGTH: 24
<212> TYPE: DNA
<213> ORGANISM: Artificial
<220> FEATURE:
<223> OTHER INFORMATION: RPS6KA2 TaqManProbe

<400> SEQUENCE: 222
agctttcctt ccgtctgaaa ggca                                           24

<210> SEQ ID NO 223
<211> LENGTH: 20
<212> TYPE: DNA
<213> ORGANISM: Artificial
<220> FEATURE:
<223> OTHER INFORMATION: RPS6KA2 SensePrimer

<400> SEQUENCE: 223
gcttcattat gcctttcaga                                                20
```

<210> SEQ ID NO 224
<211> LENGTH: 20
<212> TYPE: DNA
<213> ORGANISM: Artificial
<220> FEATURE:
<223> OTHER INFORMATION: RPS6KA2 AntisensePrimer

<400> SEQUENCE: 224
tgaacatgac ctctttggag                                              20

<210> SEQ ID NO 225
<211> LENGTH: 21
<212> TYPE: DNA
<213> ORGANISM: Artificial
<220> FEATURE:
<223> OTHER INFORMATION: RPS6KA2 TaqManProbe

<400> SEQUENCE: 225
cccgcaggaa gtccaggatc a                                            21

<210> SEQ ID NO 226
<211> LENGTH: 20
<212> TYPE: DNA
<213> ORGANISM: Artificial
<220> FEATURE:
<223> OTHER INFORMATION: RPS6KA2 SensePrimer

<400> SEQUENCE: 226
tgagatcgaa gatggagaga                                              20

<210> SEQ ID NO 227
<211> LENGTH: 20
<212> TYPE: DNA
<213> ORGANISM: Artificial
<220> FEATURE:
<223> OTHER INFORMATION: RPS6KA2 AntisensePrimer

<400> SEQUENCE: 227
agtccaggat caggtagagc                                              20

<210> SEQ ID NO 228
<211> LENGTH: 27
<212> TYPE: DNA
<213> ORGANISM: Artificial
<220> FEATURE:
<223> OTHER INFORMATION: RPS6KA2 TaqManProbe

<400> SEQUENCE: 228
ccttccgtct gaaaggcata atgaagc                                      27

<210> SEQ ID NO 229
<211> LENGTH: 20
<212> TYPE: DNA
<213> ORGANISM: Artificial
<220> FEATURE:
<223> OTHER INFORMATION: SERPINE1 SensePrimer

<400> SEQUENCE: 229
atgagatcag caccacagac                                              20

<210> SEQ ID NO 230
<211> LENGTH: 20
<212> TYPE: DNA
<213> ORGANISM: Artificial
<220> FEATURE:
<223> OTHER INFORMATION: SERPINE1 AntisensePrimer

```
<400> SEQUENCE: 230
ttgatgatga atctggctct                                              20

<210> SEQ ID NO 231
<211> LENGTH: 20
<212> TYPE: DNA
<213> ORGANISM: Artificial
<220> FEATURE:
<223> OTHER INFORMATION: SERPINE1 TaqManProbe

<400> SEQUENCE: 231
tggtccaggg cttcatgccc                                              20

<210> SEQ ID NO 232
<211> LENGTH: 20
<212> TYPE: DNA
<213> ORGANISM: Artificial
<220> FEATURE:
<223> OTHER INFORMATION: SERPINE1 SensePrimer

<400> SEQUENCE: 232
aatgactggg tgaagacaca                                              20

<210> SEQ ID NO 233
<211> LENGTH: 19
<212> TYPE: DNA
<213> ORGANISM: Artificial
<220> FEATURE:
<223> OTHER INFORMATION: SERPINE1 AntisensePrimer

<400> SEQUENCE: 233
ttgaagtaga gggcattca                                               19

<210> SEQ ID NO 234
<211> LENGTH: 20
<212> TYPE: DNA
<213> ORGANISM: Artificial
<220> FEATURE:
<223> OTHER INFORMATION: SERPINE1 TaqManProbe

<400> SEQUENCE: 234
ccagctgaca cggctggtgc                                              20

<210> SEQ ID NO 235
<211> LENGTH: 20
<212> TYPE: DNA
<213> ORGANISM: Artificial
<220> FEATURE:
<223> OTHER INFORMATION: SERPINE1 SensePrimer

<400> SEQUENCE: 235
gcagctatgg gattcaagat                                              20

<210> SEQ ID NO 236
<211> LENGTH: 20
<212> TYPE: DNA
<213> ORGANISM: Artificial
<220> FEATURE:
<223> OTHER INFORMATION: SERPINE1 AntisensePrimer

<400> SEQUENCE: 236
gtgctgatct catccttgtt                                              20

<210> SEQ ID NO 237
<211> LENGTH: 20
```

```
<212> TYPE: DNA
<213> ORGANISM: Artificial
<220> FEATURE:
<223> OTHER INFORMATION: SERPINE1 TaqManProbe

<400> SEQUENCE: 237
ccgccctccg gcatctgtac                                              20

<210> SEQ ID NO 238
<211> LENGTH: 20
<212> TYPE: DNA
<213> ORGANISM: Artificial
<220> FEATURE:
<223> OTHER INFORMATION: SERPING1 SensePrimer

<400> SEQUENCE: 238
cataagggac acctttgtga                                              20

<210> SEQ ID NO 239
<211> LENGTH: 20
<212> TYPE: DNA
<213> ORGANISM: Artificial
<220> FEATURE:
<223> OTHER INFORMATION: SERPING1 AntisensePrimer

<400> SEQUENCE: 239
gctgatcttg ttgttggtgt                                              20

<210> SEQ ID NO 240
<211> LENGTH: 21
<212> TYPE: DNA
<213> ORGANISM: Artificial
<220> FEATURE:
<223> OTHER INFORMATION: SERPING1 TaqManProbe

<400> SEQUENCE: 240
tcatcaacac ctgggtggcc a                                            21

<210> SEQ ID NO 241
<211> LENGTH: 20
<212> TYPE: DNA
<213> ORGANISM: Artificial
<220> FEATURE:
<223> OTHER INFORMATION: SERPING1 SensePrimer

<400> SEQUENCE: 241
ctctgctctg acttggagag                                              20

<210> SEQ ID NO 242
<211> LENGTH: 20
<212> TYPE: DNA
<213> ORGANISM: Artificial
<220> FEATURE:
<223> OTHER INFORMATION: SERPING1 AntisensePrimer

<400> SEQUENCE: 242
atgttggtct ccaccttctt                                              20

<210> SEQ ID NO 243
<211> LENGTH: 23
<212> TYPE: DNA
<213> ORGANISM: Artificial
<220> FEATURE:
<223> OTHER INFORMATION: SERPING1 TaqManProbe

<400> SEQUENCE: 243
cccaacacgg cctctgttga atg                                          23
```

-continued

```
<210> SEQ ID NO 244
<211> LENGTH: 20
<212> TYPE: DNA
<213> ORGANISM: Artificial
<220> FEATURE:
<223> OTHER INFORMATION: SERPING1 SensePrimer

<400> SEQUENCE: 244
ctctctgctc tgacttggag                                              20

<210> SEQ ID NO 245
<211> LENGTH: 20
<212> TYPE: DNA
<213> ORGANISM: Artificial
<220> FEATURE:
<223> OTHER INFORMATION: SERPING1 AntisensePrimer

<400> SEQUENCE: 245
atgttggtct ccaccttctt                                              20

<210> SEQ ID NO 246
<211> LENGTH: 23
<212> TYPE: DNA
<213> ORGANISM: Artificial
<220> FEATURE:
<223> OTHER INFORMATION: SERPING1 TaqManProbe

<400> SEQUENCE: 246
cccaacacgg cctctgttga atg                                          23

<210> SEQ ID NO 247
<211> LENGTH: 20
<212> TYPE: DNA
<213> ORGANISM: Artificial
<220> FEATURE:
<223> OTHER INFORMATION: SETBP1 SensePrimer

<400> SEQUENCE: 247
cagatcttgt cctgttccag                                              20

<210> SEQ ID NO 248
<211> LENGTH: 20
<212> TYPE: DNA
<213> ORGANISM: Artificial
<220> FEATURE:
<223> OTHER INFORMATION: SETBP1 AntisensePrimer

<400> SEQUENCE: 248
tcttgccaat gtagatggtt                                              20

<210> SEQ ID NO 249
<211> LENGTH: 21
<212> TYPE: DNA
<213> ORGANISM: Artificial
<220> FEATURE:
<223> OTHER INFORMATION: SEPTBP1 TaqManProbe

<400> SEQUENCE: 249
tgctttcaat ggctgctgcc c                                            21

<210> SEQ ID NO 250
<211> LENGTH: 20
<212> TYPE: DNA
<213> ORGANISM: Artificial
<220> FEATURE:
<223> OTHER INFORMATION: SETBP1 SensePrimer
```

```
<400> SEQUENCE: 250
tcaagatgga ggaggtacaa                                              20

<210> SEQ ID NO 251
<211> LENGTH: 20
<212> TYPE: DNA
<213> ORGANISM: Artificial
<220> FEATURE:
<223> OTHER INFORMATION: SETBP1 AntisensePrimer

<400> SEQUENCE: 251
gggtttggta tggtctgact                                              20

<210> SEQ ID NO 252
<211> LENGTH: 20
<212> TYPE: DNA
<213> ORGANISM: Artificial
<220> FEATURE:
<223> OTHER INFORMATION: SETBP1 TaqManProbe

<400> SEQUENCE: 252
ccacctacgg tgggcagcaa                                              20

<210> SEQ ID NO 253
<211> LENGTH: 20
<212> TYPE: DNA
<213> ORGANISM: Artificial
<220> FEATURE:
<223> OTHER INFORMATION: SETBP1 SensePrimer

<400> SEQUENCE: 253
tcaagatgga ggaggtacaa                                              20

<210> SEQ ID NO 254
<211> LENGTH: 20
<212> TYPE: DNA
<213> ORGANISM: Artificial
<220> FEATURE:
<223> OTHER INFORMATION: SETBP1 AntisensePrimer

<400> SEQUENCE: 254
gtctgggttt ggtatggtct                                              20

<210> SEQ ID NO 255
<211> LENGTH: 20
<212> TYPE: DNA
<213> ORGANISM: Artificial
<220> FEATURE:
<223> OTHER INFORMATION: SETBP1 TaqManProbe

<400> SEQUENCE: 255
ccacctacgg tgggcagcaa                                              20

<210> SEQ ID NO 256
<211> LENGTH: 20
<212> TYPE: DNA
<213> ORGANISM: Artificial
<220> FEATURE:
<223> OTHER INFORMATION: TNF SensePrimer

<400> SEQUENCE: 256
atccctgaca tctggaatct                                              20

<210> SEQ ID NO 257
<211> LENGTH: 20
```

```
<212> TYPE: DNA
<213> ORGANISM: Artificial
<220> FEATURE:
<223> OTHER INFORMATION: TNF AntisensePrimer

<400> SEQUENCE: 257
ggaaacatct ggagagagga                                               20

<210> SEQ ID NO 258
<211> LENGTH: 21
<212> TYPE: DNA
<213> ORGANISM: Artificial
<220> FEATURE:
<223> OTHER INFORMATION: TNF TaqManProbe

<400> SEQUENCE: 258
tggccagaac caaaggctcc c                                             21

<210> SEQ ID NO 259
<211> LENGTH: 20
<212> TYPE: DNA
<213> ORGANISM: Artificial
<220> FEATURE:
<223> OTHER INFORMATION: TNF SensePrimer

<400> SEQUENCE: 259
atccctgaca tctggaatct                                               20

<210> SEQ ID NO 260
<211> LENGTH: 20
<212> TYPE: DNA
<213> ORGANISM: Artificial
<220> FEATURE:
<223> OTHER INFORMATION: TNF AntisensePrimer

<400> SEQUENCE: 260
aacatctgga gagaggaagg                                               20

<210> SEQ ID NO 261
<211> LENGTH: 21
<212> TYPE: DNA
<213> ORGANISM: Artificial
<220> FEATURE:
<223> OTHER INFORMATION: TNF TaqManProbe

<400> SEQUENCE: 261
tggccagaac caaaggctcc c                                             21

<210> SEQ ID NO 262
<211> LENGTH: 20
<212> TYPE: DNA
<213> ORGANISM: Artificial
<220> FEATURE:
<223> OTHER INFORMATION: TNF SensePrimer

<400> SEQUENCE: 262
acatctggaa tctggagacc                                               20

<210> SEQ ID NO 263
<211> LENGTH: 20
<212> TYPE: DNA
<213> ORGANISM: Artificial
<220> FEATURE:
<223> OTHER INFORMATION: TNF AntisensePrimer

<400> SEQUENCE: 263
gagagaggaa ggcctaaggt                                               20
```

<210> SEQ ID NO 264
<211> LENGTH: 21
<212> TYPE: DNA
<213> ORGANISM: Artificial
<220> FEATURE:
<223> OTHER INFORMATION: TNF TaqManProbe

<400> SEQUENCE: 264
tggccagaac caaaggctcc c                                              21

<210> SEQ ID NO 265
<211> LENGTH: 20
<212> TYPE: DNA
<213> ORGANISM: Artificial
<220> FEATURE:
<223> OTHER INFORMATION: TNFAIP6 SensePrimer

<400> SEQUENCE: 265
ggtgtgtacc acagagaagc                                                20

<210> SEQ ID NO 266
<211> LENGTH: 20
<212> TYPE: DNA
<213> ORGANISM: Artificial
<220> FEATURE:
<223> OTHER INFORMATION: TNFAIP6 AntisensePrimer

<400> SEQUENCE: 266
agcacagaca tgaaatccaa                                                20

<210> SEQ ID NO 267
<211> LENGTH: 20
<212> TYPE: DNA
<213> ORGANISM: Artificial
<220> FEATURE:
<223> OTHER INFORMATION: TNFAIP6 TaqManProbe

<400> SEQUENCE: 267
tttgaaggcg gccatctcgc                                                20

<210> SEQ ID NO 268
<211> LENGTH: 20
<212> TYPE: DNA
<213> ORGANISM: Artificial
<220> FEATURE:
<223> OTHER INFORMATION: TNFAIP6 SensePrimer

<400> SEQUENCE: 268
tatggtcagc gtattcacct                                                20

<210> SEQ ID NO 269
<211> LENGTH: 20
<212> TYPE: DNA
<213> ORGANISM: Artificial
<220> FEATURE:
<223> OTHER INFORMATION: TNFAIP6 AntisensePrimer

<400> SEQUENCE: 269
tccacagtat cttcccacaa                                                20

<210> SEQ ID NO 270
<211> LENGTH: 21
<212> TYPE: DNA
<213> ORGANISM: Artificial
<220> FEATURE:
<223> OTHER INFORMATION: TNFAIP6 TaqManProbe

<400> SEQUENCE: 270
tcagccaagc aacctgggtc a                                              21

<210> SEQ ID NO 271
<211> LENGTH: 20
<212> TYPE: DNA
<213> ORGANISM: Artificial
<220> FEATURE:
<223> OTHER INFORMATION: TNFAIP6 SensePrimer

<400> SEQUENCE: 271
tactgtggag atgagcttcc                                                20

<210> SEQ ID NO 272
<211> LENGTH: 20
<212> TYPE: DNA
<213> ORGANISM: Artificial
<220> FEATURE:
<223> OTHER INFORMATION: TNFAIP6 AntisensePrimer

<400> SEQUENCE: 272
acaggatcca ttgcaacata                                                20

<210> SEQ ID NO 273
<211> LENGTH: 24
<212> TYPE: DNA
<213> ORGANISM: Artificial
<220> FEATURE:
<223> OTHER INFORMATION: TNFAIP6 TaqManProbe

<400> SEQUENCE: 273
cctccagctg tcactgaagc atca                                           24

<210> SEQ ID NO 274
<211> LENGTH: 20
<212> TYPE: DNA
<213> ORGANISM: Artificial
<220> FEATURE:
<223> OTHER INFORMATION: WASF2 SensePrimer

<400> SEQUENCE: 274
atccctttgg tgagtatggt                                                20

<210> SEQ ID NO 275
<211> LENGTH: 20
<212> TYPE: DNA
<213> ORGANISM: Artificial
<220> FEATURE:
<223> OTHER INFORMATION: WASF2 AntisensePrimer

<400> SEQUENCE: 275
tgtcagggat agtttggtca                                                20

<210> SEQ ID NO 276
<211> LENGTH: 21
<212> TYPE: DNA
<213> ORGANISM: Artificial
<220> FEATURE:
<223> OTHER INFORMATION: WASF2 TaqManProbe

<400> SEQUENCE: 276
tcaggatgca ccaccaccac c                                              21

<210> SEQ ID NO 277
<211> LENGTH: 20

```
<212> TYPE: DNA
<213> ORGANISM: Artificial
<220> FEATURE:
<223> OTHER INFORMATION: WASF2 SensePrimer

<400> SEQUENCE: 277
ctgcggaagg taggattaga                                          20

<210> SEQ ID NO 278
<211> LENGTH: 20
<212> TYPE: DNA
<213> ORGANISM: Artificial
<220> FEATURE:
<223> OTHER INFORMATION: WASF AntisensePrimer

<400> SEQUENCE: 278
ggacttgcag atcattacca                                          20

<210> SEQ ID NO 279
<211> LENGTH: 25
<212> TYPE: DNA
<213> ORGANISM: Artificial
<220> FEATURE:
<223> OTHER INFORMATION: WASF2 TaqManProbe

<400> SEQUENCE: 279
agcacatcga aaccctagga ggtca                                    25

<210> SEQ ID NO 280
<211> LENGTH: 20
<212> TYPE: DNA
<213> ORGANISM: Artificial
<220> FEATURE:
<223> OTHER INFORMATION: WASF2 SensePrimer

<400> SEQUENCE: 280
ctttctgtag gctggtgttg                                          20

<210> SEQ ID NO 281
<211> LENGTH: 20
<212> TYPE: DNA
<213> ORGANISM: Artificial
<220> FEATURE:
<223> OTHER INFORMATION: WASF2 AntisensePrimer

<400> SEQUENCE: 281
agggatagtt tggtcatgga                                          20

<210> SEQ ID NO 282
<211> LENGTH: 20
<212> TYPE: DNA
<213> ORGANISM: Artificial
<220> FEATURE:
<223> OTHER INFORMATION: WASF2 TaqManProbe

<400> SEQUENCE: 282
tgcctccctc ccaggatccc                                          20
```